(12) United States Patent
Fitzgerald

(10) Patent No.: US 7,833,795 B2
(45) Date of Patent: Nov. 16, 2010

(54) ASSESSMENT OF CARDIOVASCULAR RISK USING ISOPROSTANE BIOMARKERS AND COX-2 SELECTIVE INHIBITORS

(75) Inventor: Garret A. Fitzgerald, Wayne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1341 days.

(21) Appl. No.: 11/210,378

(22) Filed: Aug. 24, 2005

(65) Prior Publication Data

US 2006/0051873 A1 Mar. 9, 2006

Related U.S. Application Data

(60) Provisional application No. 60/603,953, filed on Aug. 24, 2004, provisional application No. 60/604,087, filed on Aug. 24, 2004, provisional application No. 60/626,257, filed on Nov. 9, 2004, provisional application No. 60/683,380, filed on May 18, 2005.

(51) Int. Cl.
  *G01N 33/92* (2006.01)
(52) U.S. Cl. .......................................... 436/71; 436/173
(58) Field of Classification Search .................. None
  See application file for complete search history.

(56) References Cited

U.S. PATENT DOCUMENTS

| | | | |
|---|---|---|---|
| 5,891,622 A | 4/1999 | Morrow et al. | |
| 6,727,075 B2 | 4/2004 | Fitzgerald et al. | |
| 6,939,718 B2 * | 9/2005 | Singh et al. | 436/129 |

OTHER PUBLICATIONS

Mukherjee et al. "Risk of Cardiovascular Events Associated With Selective COX-2 Inhibitors", Journal of American Medical Association, 2001, v. 286, No. 8, pp. 954-959.*
Zhang et al. "COX-2-Dependent Cardiac Failure in Gh/tTG Transgenic Mice", Circulation Research, Apr. 2003, v. 92, pp. 1153-1161.*
Hennan et al. "Effect of Selective of Cyclooxygenase-2 Inhibiiton on Vascular Responses and Thrombosis in Canine Coronary Arteries", Circulation, 2001, v. 104, pp. 820-825.*
Knott et al. "Routine Prostaglanding Assya by DC-MS in Multiwell Tissue Culture Plates: Application to Human Synoviocytes and Chondrocytes", Anal. Biochem., 1993, v. 210, No. 2, pp. 360-365, Abstract.*
Mizugaki "Establishment of microanalysis of prostaglandin metabolites by GC/MS and its clincal application", Yakugaku Zasshi, 1999, v. 119, No. 1, pp. 61-80, Abstract.*
Domanski, "Cardiovascular risk assessment using pulse pressure in the first national health and nutrition examination survey (NHANES I)", Hypertension, Oct. 1, 2001; 38(4): pp. 793-797.*

(Continued)

*Primary Examiner*—Yelena G Gakh
(74) *Attorney, Agent, or Firm*—Drinker Biddle & Reath LLP

(57) ABSTRACT

The instant invention is drawn to methods and compositions useful for the assessment of cardiovascular risk in a mammal. The methods utilize biomarkers including prostanoid metabolites and isoprostanes as sensitive and stable markers of cardiovascular risk. The methods are particularly useful in a mammal that is contemplating undergoing coxib therapy, is undergoing coxib therapy, is undergoing antioxidant therapy, has ceased coxib therapy or has never undergone coxib therapy. The invention also includes kits useful for the assessment of cardiovascular risk in a mammal.

12 Claims, 42 Drawing Sheets

OTHER PUBLICATIONS

Fitzpatrick et al. "Cardiovascular responses to PGI2 (prostacyclin) in the dog", Circ. Res. 1978, v. 42, pp. 192-194.*

Schwedhelm et al. "Application of Gas Chromatography-Mass Spectrometry for Analysis of Isoprostanes: Their Role in Cardiovascular Disease", Clin Chem Lab Med 2003; v. 41, No. 12, pp. 1552-1561.*

McAdam et al. "Systemic biosynthesis of prostacyclin by cyclooxygenase (COX)-2: The human pharmacology of a selective inhibitor of COX-2", Proc. Natl. Acad. Sci. USA, Jan. 1999, vol. 96, pp. 272-277.*

Frishman, "Cyclooxygenase Inhibition in Patients With Coronary Artery Disease", J. Am. Coll. Cardiol., Feb. 2004, v. 43, No. 4, pp. 532-533.*

Audoly, L. P., et al., "Cardiovascular Responses to the Isoprostanes iPF$_{2\alpha}$-III and iPE$_2$-III are Mediated via the Thromboxane A$_2$ Receptor In Vivo," *Circulation*, vol. 101, pp. 2833-2840, 2000.

Awad, J. A., et al., "Identification Of Non-Cyclooxygenase-Derived Prostanoid (F$_2$-Isoprostane) Metabolites in Human Urine And Plasma," *J. Biol. Chem.*, vol. 268, pp. 4161-4169, 1993.

Basu, S., "Radioimmunoassay of 8-Iso-Prostaglandin F2 Alpha: an Index for Oxidative Injury Via Free Radical Catalysed Lipid Peroxidation,," *Prost. Leuk. Ess. Fatty Acids.*, vol. 58, pp. 319-325, 1998.

Basu, S., "Oxidative Injury Induced Cyclooxygenase Activation in Experimental Hepatotoxicity," *Biochem. Biophys. Res. Commun.*, vol. 254, pp. 764-767, 1999.

Bombardier, C., et al., "Comparison of Upper Gastrointestinal Toxicity of Rofecoxib and Naproxen in Patients With Rheumatoid Arthritis," *N. Engl. J. Med.*, vol. 343, pp. 1520-1528, 2000.

Bourassa, P. A. K., et al., "Estrogen Reduces Atherosclerotic Lesion Development in Apolipoprotein E-Deficient Mice," *Proc. Natl. Acad. Sci. USA*, vol. 93, p. 10022-10027, 1996.

Carlson, S. H., et al., "Long-Term Telemetric Recording of Arterial Pressure and Heart Rate in Mice Fed Basal and High NaCl Diets," *Hypertension*, vol. 35, pp. 1-5, 2000.

Carlson, S. H., et al., "Blood Pressure and NaC1-Sensitive Hypertension Are Influenced by Angiotensin-Converting Enzyme Gene Expression in Transgenic Mice," *Hypertension*, vol. 39, pp. 214-218, 2002.

Catella, F., et al., "Paired Analysis of Urinary Thromboxane B2 Metabolites in Humans," *Thromb. Res.*, vol. 47(6), pp. 647-656, 1987.

Catella, F., et al.,"11-Dehydrothromboxane B$_2$: a Quantitative Index of Thromboxane A$_2$ Formation in the Human Circulation," *PNAS*, vol. 83, pp. 5861-5865, 1986.

Catella-Lawson, F., et al., "Effects of Specific Inhibition of Cyclooxygenase-2 on Sodium Balance, Hemodynamics, and Vasoactive Eicosanoids," *J. Pharmacol. Exp. Ther.*, vol. 289, pp. 735-741, 1999.

Catella-Lawson, F., et al., "Cyclooxygenase Inhibitors and the Antiplatelet Effects of Aspirin," *N. Engl. J. Med.*, vol. 345, pp. 1809-1817, 2001.

Cayatte, A. J., et al., "The Thromboxane Receptor Antagonist S18886 but not Aspirin Inhibits Atherogenesis in Apo E-Deficient Mice Evidence That Eicosanoids Other Than Thromboxane Contribute to Atherosclerosis," *Arterioscler. Thromb. Vasc. Biol.*, Vo. 20, pp. 1724-1728, 2000.

Cesari, M., et al., "Inflammatory Markers and Onset of Cardiovascular Events Results from the Health ABC Study," *Circulation*, vol. 108, pp. 2317-2322, 2003.

Cheng, Y., et al., "Role of Prostacyclin in the Cardiovascular Response to Thromboxane A$_2$," *Science*, vol. 296, pp. 539-541, 2002.

Cheng, H. F., et al., "Cyclooxygenases, the Kidney, and Hypertension," *Hypertension*, vol. 43, pp. 525-530, 2004.

Collins, P., et al., "17β-Estradiol Attenuates Acetylcholine-Induced Coronary Arterial Constriction in Women but Not Men With Coronary Heart Disease," *Circulation*, vol. 92, pp. 24-30 1995.

Crofford, L. J., et al., "Thrombosis in Patients With Connective Tissue Diseases Treated With Specific Cyclooxygenase 2 Inhibitors. A Report of Four Cases," *Arthritis & Rheumatism*, vol. 43(8), pp. 1891-1896, 2000.

Cullen, L., et al., "Selective Cyclooxygenase-2 Inhibition by Nimesulide in Man[1]," *J. Pharmacol. Exp. Ther.*, vol. 287, pp. 578-582, 1998.

Dannhardt, G., et al., , "Cyclooxygenase Inhibitors—Current Status And Future Prospects," *Eur. J. Med. Chem.*, vol. 36, pp. 109-126, 2001.

De Zwart, L. L., et al., "Biomarkers of Free Radical Damage Applications in Experimental Animals and in Humans," *Free Radic. Biol. Med.*, vol. 26(1-2), pp. 202-226, 1999.

Dietrich, H., et al., "Mouse Model of Transplant Arteriosclerosis Role of Intercellular Adhesion Molecule-1," *Arterioscler. Thromb. Vasc. Biol.*, vol. 20, pp. 343-352, 2000.

Dowd, N. P., et al., "Inhibition of Cyclooxygenase-2 Aggravates Doxorubicin-Mediated Cardiac Injury In Vivo," *J. Clin. Invest.*, vol. 108, pp. 585-590, 2001.

Egan, K. M., et al., "COX-2-Derived Prostacyclin Confers Atheroprotection on Female Mice," *Science*, vol. 306, pp. 1954-1957, 2004.

Egan, K. M., et al., "Cyclooxygenases, Thromboxane, and Atherosclerosis Plaque Destabilization by Cyclooxygenase-2 Inhibition Combined With Thromboxane Receptor Antagonism," *Circulation*, vol. 111, pp. 334-342, 2005.

Emery, J. D., et al., "Whole-Blood Platelet Aggregation Predicts In Vitro and In Vivo Primary Hemostatic Function in the Elderly," *Arterioscler. Thromb. Vasc. Biol.*, vol. 15, pp. 748-753, 1995.

Evans, W. E., et al., "Pharmacogenomics—Drug Disposition, Drug Targets, and Side Effects," *N. Engl. J. Med.*, vol. 348, pp. 538-549, 2003.

Fabre, J. E., et al., "Activation of the Murine EP3 Receptor for PGE$_2$ Inhibits Camp Production And Promotes Platelet Aggregation," *J. Clin. Invest.*, vol. 107, pp. 603-610, 2001.

Fitzgerald, G., et al., "The Coxibs, Selective Inhibitors of Cyclooxygenase-2," *N. Engl. J. Med.*, vol. 345, pp. 433-442, 2001.

Fitzgerald, G., et al., "Analysis of Prostacyclin and Thromboxane Biosynthesis in Cardiovascular Disease," *Circulation*, vol. 67(6), pp. 1174-1177, 1983.

Fitzgerald, G., et al., "The Choreography of Cyclooxygenases in the Kidney," *J. Clin. Invest.*, vol. 110, pp. 33-34, 2002.

Fitzgerald, G., et al., "Cox-2 and Beyond: Approaches to Prostaglandin Inhibition in Human Disease," *Nat. Rev. Drug Discov.*, vol. 2, pp. 879-890, 2003.

Fitzgerald, G., "Coxibs and Cardiovascular Disease," *N. Engl. J. Med.*, vol. 351, pp. 1709-1711, 2004.

Folkow, B., "Structure and Function of The Arteries in Hypertension," *Am. Heart Journal*, vol. 114, pp. 938-948, 1987.

Francois, H., et al., "Role for Thromboxane Receptors in Angiotensin-II- Induced Hypertension," *Hypertension*, vol. 43, pp. 364-369, 2004.

Francois, H., et al., "Prostacyclin Protects Against Elevated Blood Pressure and Cardiac Fibrosis," *Cell Metab.*, vol. 2(3), pp. 201-207, 2005.

Fulton, D., et al., "Quantification of Enos and Mrna in the Canine Cardiac Vasculature by Competitive PCR," *Am. J. Physiol. Heart Circ. Physiol.*, vol. 278, pp. H658-H665, 2000.

Furberg, C. D., et al., "Parecoxib, Valdecoxib, and Cardiovascular Risk," *Circulation*, vol. 111(3), p. 249, 2005.

Goeptar, A. R., et al., "Oxygen and Zenobiotic Reductase Activities of Cytochrome P450," *Crit. Rev. Toxicol.*, vol. 25, pp. 25-65, 1995.

Halushka, M. K., et al., "Genetic Variation in Cyclooxygenase 1: Effects on Response to Aspirin," *Clin. Pharmacol. Ther.*, vol. 73, pp. 122-130, 2003.

Harmon, K. J., et al., "Strain-Dependent Vascular Remodeling Phenotypes in Inbred Mice," *Am. J. Pathol.*, vol. 156, pp. 1741-1748, 2000.

Harris, H. A., et al., "Characterization of the Biological Roles of the Estrogen Receptors, ERα and ERβ, in Estrogen Target Tissues in Vivo through the Use of an ERα-Selective Liquid," *Endocrinology*, vol. 143, pp. 4172-4174, 2002.

Hsu, P. Y., et al., "Expression, Purification, and Spectroscopic Characterization of Human Thromboxane Synthase," *J. Bio. Chem.*, vol. 274(2), pp. 762-769, 1999.

Huang, A., et al., "EDHF Mediates Flow-Induced Dilation in Skeletal Muscle Arterioles of Female Enos-KO Mice," *Am. J. Physiol. Heart Circ. Physiol.*, vol. 280, pp. H2462-H2469, 2001.

Huo, Y., et al., "Circulating activated platelets exacerbate atherosclerosis in mice deficient in apolipoprotein E," *Nat. Med.*, vol. 9, pp. 61-67, 2003.

Ihionkhan, C. E., et al., "Estrogen Causes Dynamic Alterations in Endothelial Estrogen Receptor Expression," *Circ. Res.*, vol. 91, pp. 814-820, 2002.

Kadiiska, M. B., et al., "Biomarkers of Oxidative Stress Study: Are Plasma Antioxidants Markers of Cci(4) Poisoning?," *Free Radic. Biol. Med.*, vol. 28, pp. 838-845, 2000.

Kadiiska, M. B., et al., "Biomarkers of Oxidative Stress Study II: Are Oxidation Products Of Lipids, Proteins, and Dna Markers of Cci4 Poisoning?," *Free Radic. Biol. Med.*, vol. 38, pp. 698-710, 2005.

Klein, T., et al., "Generation of the Isoprostane 8-Epi-Prostaglandin $F_{2\alpha}$ In Vitro and In Vivo via the Cyclooxygenases[1]," *J. Pharmacol. Exp. Ther.*, vol. 282, pp. 1658-1665, 1997.

Kobayashi, T., et al., "Roles of Thromboxane $A_2$ and Prostacyclin in the Development of Atherosclerosis in Apoe-Deficient Mice," *J. Clin. Invest.*, vol. 114, pp. 784-794, 2004.

Korshunov, V. A., et al., "Strain-Dependent Vascular Remodeling the "Glagov Phenomenon" is Genetically Determined," *Circulation*, vol. 110, pp. 220-226, 2004.

Kowala, M. C., et al., "Prostacyclin Agonists Reduce Early Atherosclerosis in Hyperlipidemic Hamsters," *Arterioscler. Thromb.*, vol. 13, 435-444, 1993.

Lawson, J. A., et al., "Isoprostanes: Formation, Analysis and Use as Indices of Lipid Peroxidation In Vivo," *J. Biol. Chem.*, vol. 274, pp. 24441-24444, 1999.

Lawson, J. A. et al., "Measurement of Urinary 2,3-Dinor-Thromboxane B2 and Thromboxane B2 Using Bonded-Phase Phenylboronic Acid Columns and Capillary Gas Chromatography—Negative-Ion Chemical Ionization Mass Spectrometry," *Anal Biochem.*, vol. 150, pp. 463-470, 1985.

Lawson, J. A., et al., "Identification of Two Major $F_2$ Isoprostanes, 8,12-Iso- and 5-epi-8, 12-Iso-isoprostane $F_{2\alpha}$-VI, in Human Urine," *J. Biol. Chem.*, vol. 273, pp. 29295-29301, 1998.

Li, H. et al., "Quantitative High Performance Liquid Chromatography/Tandem Mass Spectrometric Analysis of the Four Classes of $F_2$-Isoprostanes in Human Urine," *Proc. Natl. Acad. Sci.*, vol. 96, pp. 13381-13386, 1999.

Lim, T. T. et al., "Role of Compensatory Enlargement and Shrinkage in Transplant Coronary Artery Disease," *Circulation*, vol. 95, pp. 855-859, 1997.

Lubahn, D. B. et al., "Alteration of Reproductive Function but not Prenatal Sexual Development After Insertional Disruption of the Mouse Estrogen Receptor Gene," *Proc. Natl. Acad. Sci. USA*, vol. 90, pp. 11162-11166, 1993.

Marnett, L. J. et al., "Arachidonic Acid Oxygenation by COX-1 and COX-2," *J Biol. Chem.*, vol. 274, pp. 22903-22906, 1999.

Marsh, M. M. et al., "Protection Against Atherosclerosis by Estrogen is Independent of Plasma Cholesterol Levels in LDL Receptor-Deficient Mice," *J. Lipid Res.*, vol. 40, pp. 893-900, 1999.

McAdam, B. F. et al., "Systemic Biosynthesis of Prostacyclin by Cyclooxygenase (Cox)-2: The Human Pharmacology of a Selective Inhibitor of Cox-2," *Proc. Natl. Acad. Sci. USA*, vol. 96, pp. 272-277, 1999.

McAdam, B.F. et al., "Effect of Regulated Expression of Human Cyclooxygenase Isoforms on Eicosanoid and Isoeicosanoid Production in Inflammation," *J. Clin. Invest.*, vol. 105, pp. 1473-1482, 2000.

Müller, B. et al, "Assembly of U7 Small Nuclear Ribonucleoprotein particle and Histone RNA 3' Processing in *Xenopus* Egg Extracts," *The Journal of Biological Chemistry*, vol. 275 pp. 24284-24293, 2000.

Morishita, H. et al., "Increased Hydrolysis of Cholesteryl Ester with Prostacyclin Is Potentiated by High Density Lipoprotein through the Prostacyclin Stabilization," *J. Clin. Invest.* 86: 1885-1891 (1990).

Morrow, J. D. et al., "Mass Spectrometric Quantification of F2-Isoprostanes in Biological Fluids and Tissues as Measure of Oxidant Stress," *Methods Enzymol.*, vol. 300, pp. 3-12, 1999.

Morrow, J. D. et al., "Non-Cyclooxygenase-Derived Prostanoids ($F_2$-Isoprostanes) are Formed In Situ on Phospholipids," *Proc. Natl. Acad. Sci. USA*, vol. 89, pp. 10721-10725, 1992.

Morrow, J. D. et al., "The Isoprostanes: Their Quantification as an Index Of Oxidant Stress Status In Vivo," *Drug. Metab. Rev.*, vol. 32(3-4), pp. 377-385, 2000.

Myers, D. L. et al., "Improved Analysis of the Vascular Response to Arterial Ligation Using a Multivariate Approach," *Am. J. Pathol.*, vol. 164, pp. 43-48, 2004.

Panara, M. R., et al., "Dose-Dependent Inhibition of Platelet Cyclooxygenase-1 and Monocyte Cyclooxygenase-2 by Meloxicam in Healthy Subjects," J. Pharmacol. Exp. Ther. 290: 276-280 (1999).

Papafili, A., et al., "Common Promoter Variant in Cyclooxygenase-2 Represses Gene Expression Evidence of Role in Acute-Phase Inflammatory Response," *Arterioscler. Thromb. Vasc. Biol.*, vol. 22, pp. 1631-1636, 2002.

Pare, G., et al., "Estrogen Receptor-$\alpha$ Mediates the Protective Effects of Estrogen Against Vascular Injury," *Circ. Res.*, vol. 90, pp. 1087-1092, 2002.

Park, J. B., et al., "Correlation of Endothelial Function in Large and Small Arteries in Human Essential Hypertension," *J. Hypertens.*, vol. 19(3), pp. 415-420, 2001.

Patrignani, P., et al., "Selective Cumulative Inhibition of Platelet Thromboxane Production by Low-dose Aspirin in Healthy Subjects," *J. Clin. Invest.*, vol. 69, pp. 1366-1372, 1982.

Patrono, C., et al., "Isoprostanes: Potential Markers of Oxidant Stress in Atherothrombotic Disease," *Arter. Throm. Vas. Biol.*, vol. 17, pp. 2309-2315, 1997.

Pini, B., et al., "Prostaglandin E Synthases in Zebrafish," *Arterioscler. Thromb. Vasc. Biol.*, vol. 25, pp. 315-320, 2005.

Pratico, D., et al., "Cyclooxygenase-dependent Formation of the Isoprostane, 8-Epi Prostaglandin $F_{2\alpha}$," *J. Biol. Chem.*, vol. 270, No. 17, pp. 9800-9808, 1995.

Pratico, D., et al., "Local Amplification of Platelet Function by 8-Epi Prostaglandin $F_{2\alpha}$ Is Not Mediated by Thromboxane Receptor Isoforms," *J. Biol. Chem.*, vol. 271, pp. 14916-14924, 1996.

Pratico, D., et al., "Vitamin E Suppresses Isoprostane Generation In Vivo and Reduces Atherosclerosis in Apoe-Deficient Mice," *Nat. Med.*, vol. 4, No. 10, pp. 1189-1192, 1998.

Pratico, D., et al., "$Ipf_{2\alpha}$-I: An Index of Lipid Peroxidation in Humans," *Proc. Natl. Acad. Sci. USA*, vol. 95, pp. 3449-3454, 1998.

Pratico, D., et al., "Endogenous Biosynthesis Of Thromboxane And Prostacyclin In 2 Distinct Murine Models Of Atherosclerosis," Blood 96 No. 12: 3823-3826 (2000).

Pratico, D., et al., "Acceleration of Atherogenesis by Cox-1-Dependent Prostanoid Formation in Low Density Lipoprotein Receptor Knockout Mice," *Proc. Natl. Acad. Sci. USA*, vol. 98, pp. 3358-3363, 2001.

Pratico, D., et al., "$F_2$-Isoprostanes as Indices of Lipid Peroxidation in Inflammatory Diseases," *Chem. Phys. Lipids.*, vol. 128(1-2), pp. 165-171, 2004.

Pratico, D. et al., "Novel Indices of Oxidant Stress in Cardiovascular Disease: Specific Analysis of $F_2$—Isoprostanes," (in) *Prostaglandins and Control of Vascular Smooth Muscle Cell Proliferation*, pp. 26-41, 1997.

Pryor, W. A., et al., "Noninvasive Measures of Oxidative Stress Status in Humans," *Free Radic. Biol. Med.* 10(3-4): 177-184 (1991).

Reilly, M., et al., "Modulation of Oxidant Stress In Vivo in Chronic Cigarette Smokers," *Circulation*, 94: 19-25 (1996).

Ridker, P.M., "High Sensitivity C-Reactive Protein Potential Adjunct for Global Risk Assessment in the Primary Prevention of Cardiovascular Disease," *Circulation*, vol. 103, pp. 1813-1818, 2001.

Rudic, R.D., et al., "Direct Evidence for the Importance of Endothelium-derived Nitric Oxide in Vascular Remodeing," *J. Clin. Invest.* vol. 101, pp. 731-736, 1998.

Rudic, R. D., et al., "Temporal Events Underlying Arterial Remodeling After Chronic Flow Reduction in Mice: Correlation of Structural Changes With a Deficit in Basal Nitric Oxide Synthesis," *Circ. Res.*, vol. 86, pp. 1160-1166, 2000.

Rudic, R. D., et al., "BMAL1 and CLOCK, Two Essential Components of the Circadian Clock, Are Involved in Glucose Homeostasis," *PLoS Biol.*, vol. 2, pp. 1893-1899, 2004.

Sharrett, A. R., et al., "Coronary Heart Disease Prediction From Lipoprotein Cholesterol Levels, Triglycerides, Lipoprotein(a), Apolipoproteins A-I and B, and HDL Density Subfractions," *Circulation*, vol. 104, pp. 1108-1113, 2001.

Sun, D., et al., "Enhanced Release of Prostaglandins Contributes to Flow-Induced Arteriolar Dilation in eNOS Knockout Mice," *Circ. Res.*, vol. 85, pp. 288-293, 1999.

Tang, C., et al., "Major Role of Human Liver Microsomal Cytochrome P450 2C9 (CYP2C9) in the Oxidative Metabolism of Celecoxib, a Novel Cyclooxygenase-II Inhibitor," *J. Pharmacol. Exp. Ther.*, vol. 293, No. 2, pp. 453-459, 2000.

Tangirala, R. K., et al., "Quantitation of Atherosclerosis in Murine Models: Correlation Between Lesions in The Aortic Origin and in the Entire Aorta, and Differences in the Extent of Lesions Between Sexes in LDL Receptor-Deficient and Apolipoprotein E-Deficient Mice," *J. Lipid. Res.*, vol. 36, pp. 2320-2328, 1995.

Thomas, D. W., et al., "Coagulation Defects and Altered Hemodynamic Responses in Mice Lacking Receptors for Thromboxane $A_2$," *J. Clin. Invest.*, vol. 102, pp. 1994-2001, 1998.

Topper, J. N, et al., "Identification of Vascular Endothelial Genes Differentially Responsive to Fluid Mechanical Stimuli: Cyclooxygenase-2, Manganese Superoxide Dismutase, and Endothelial Cell Nitric Oxide Synthase are Selectively up-Regulated by Steady Laminar Shear Stress," *Proc. Natl. Acad. Sci. USA*, vol. 93, pp. 10417-10422, 1996.

Trebino, C. E., et al., "Impaired Inflammatory and Pain Responses in Mice Lacking an Inducible Prostaglandin E Synthase," *Proc. Natl. Acad. Sci. U.S.A.* vol. 100, pp. 9044-9049, 2003.

Trebino, C. E., et al., "Redirection of Eicosanoid Metabolism in mPGES-1-deficient Macrophases," *J. Biol. Chem.*, vol. 280, pp. 16579-16585, 2005.

Ulrich, C. M., et al., "Cyclooxygenase 1 (COX1) Polymorphisms in African-American and Caucasian Populations," *Hum. Mutat.*, vol. 20, 409-410, 2002.

Watanabe, H., et al., "Effects of Salt Loading on Blood Pressure in Mice Lacking the Prostanoid Receptor Gene," *Circ. J.*, vol. 69, pp. 124-126, 2005.

Wilson, P. W. F., et al., "Prediction of Coronary Heart Disease Using Risk Factor Categories," *Circulation*, vol. 97, pp. 1837-1847, 1998.

Wiltshire, T., et al., "Genome-Wide Single-Nucleotide Polymorphism Analysis Defines Haplotype Patterns in Mouse," *Proc. Natl. Acad. Sci. U S A*, vol. 100, pp. 3380-3385, 2003.

Xiao, C. Y., et al., "Roles of Prostaglandin $I_2$ and Thromboxane $A_2$ in Cardiac Ischemia-Reperfusion Injury A Study Using Mice Lacking Their Respective Receptors," *Circulation*, vol. 104, pp. 2210-2215, 2001.

Yu, et al., "Differential Impact of Prostaglandin H Synthase 1 Knockdown on Platelets and Parturition," *J. Clin. Invest.*, vol. 115, pp. 986-295, 2005.

U.S. Food and Drug Administration, FDA News [online]. FDA Announces Series of Changes to the Class of Marketed Non-steroidal Anti-inflammatory Drugs (NDAIDs), Apr. 2005 [retrieved Nov. 28, 2005]. Retrieved from the Internet: < URL:http://www.fda.gov/bbs/topics/news/2005/new01171.html >.

U.S. Dept. of Health and Services, National Institutes of Health, NIH News [online]. NIH Halts Use of COX-2 Inhibitor in Large Cancer Prevention Trial, Dec. 2004 [retrieved Nov. 28, 2005]. Retrieved from the Internet:< URL:htpp://www.nih.gov/news/pr/dec2004/od-17.htm >.

Fries et al. "The Cardiovascular Pharmacology of COX-2 Inhibition", Hematology, 2005, v. 1, pp. 445-451.

Hennan et al. "Effect of Selective Cyclooxygenase-2 Inhibition on Vascular Responses and Thrombosis in Canine Coronary Arteries", Circulation, 2001, v. 104, pp. 820-825.

Knott et al. "Routine Prostaglandin Assay by GC-MS in Multiwell Tissue Culture Plates: Application to Human Synoviocytes and Chondrocytes", Anal. Biochem., 1993, v. 210, No. 2, pp. 360-365, Abstract.

Mizugaki. "Establishment of Microanalysis of Prostaglandin Metabolites by GC/MS and Its Clinical Application", Yakugaku Zasshi, 1999, v. 119, No. 1, pp. 61-80, Abstract.

White. "Cardiovascular Aspects of Prostaglandin Inhibition: Focus on the COX-2 Specific Inhibitors", CVR&R, 2003, v. 24, No. 4, pp. 214-219.

* cited by examiner

Figures 23A-23C
A.
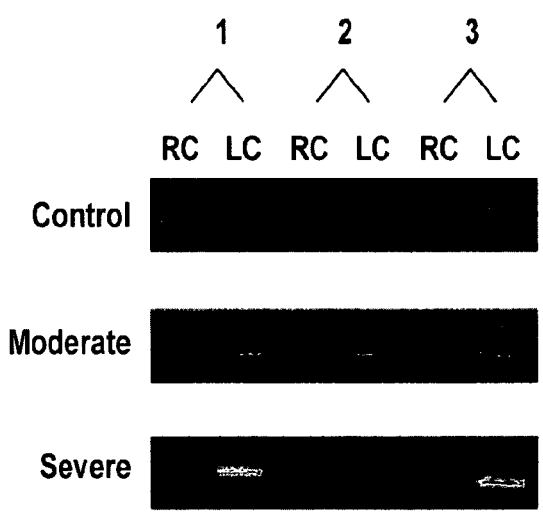
B.
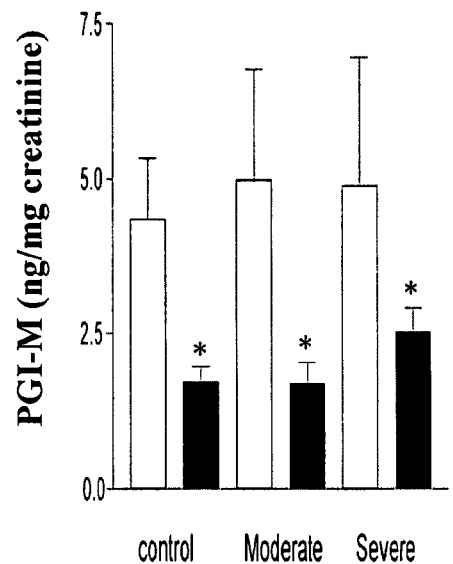
C.
i. 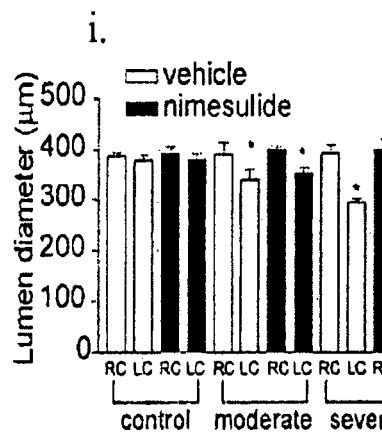
ii. 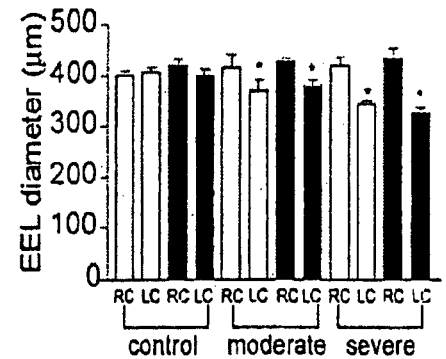

Figures 25A-25C
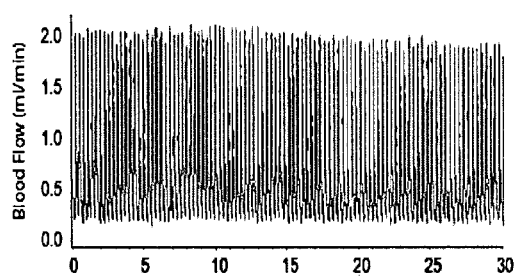
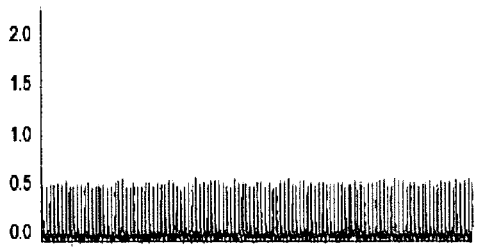
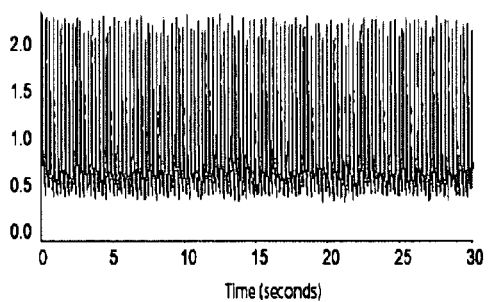
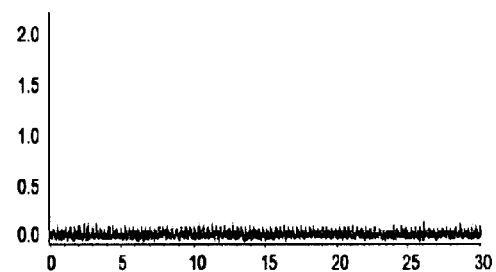
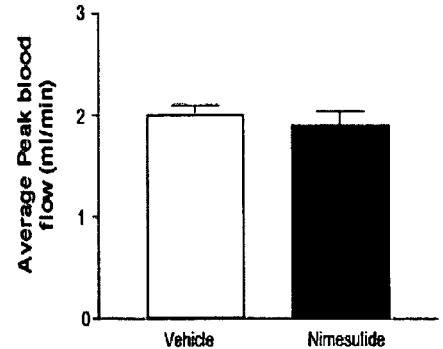
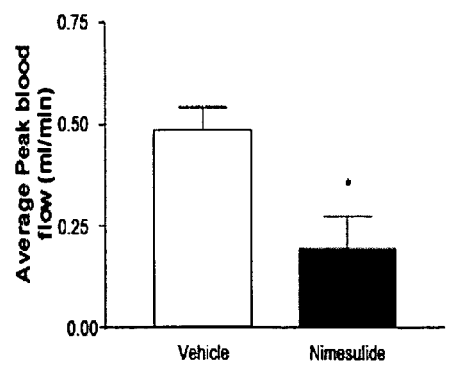

A.

B.

C.

A.

B.

C.

D.

E.

F.

G.

H.

I.

J.

K.

L.

A.

B.

C.

D.

ASSESSMENT OF CARDIOVASCULAR RISK USING ISOPROSTANE BIOMARKERS AND COX-2 SELECTIVE INHIBITORS

STATEMENT REGARDING FEDERALLY SPONSORED RESEARCH OR DEVELOPMENT

This invention was supported in part by funds obtained from the U.S. Government (National Heart Lung and Blood Institute Grant Numbers HL62250, HL70128, GM063130 and HL54500, and National Center for Research Resources Grant Number MO 1RR00040), and the U.S. Government may therefore have certain rights in the invention.

CROSS REFERENCE TO RELATED APPLICATIONS

This application is entitled to priority pursuant to 35 U.S.C. §119(e) to U.S. provisional patent application 60/603,953, which was filed on Aug. 24, 2004, U.S. provisional patent application 60/604,087, which was filed on Aug. 24, 2004, U.S. provisional patent application 60/626,257, which was filed on Nov. 9, 2004 and U.S. provisional patent application 60/683,380, which was filed on May 18, 2005.

BACKGROUND OF THE INVENTION

Cyclooxygenase (COX) is the enzyme that mediates biosynthesis of prostaglandins (PGs) and thromboxanes from arachidonic acid, and whose inhibition underlies the effectiveness of a variety of anti-inflammatory drugs (Sharma and Sharma, 1997, Indian J. Exp. Biol. 35: 1025-1031; Morteau, 2000, Arch. Immunol. Ther. Exp. 48: 473-480; Llorens, 2002, J. Mol. Graph Model. 20: 359-371; Smith et al., 2000, Annu. Rev. Biochem. 69: 145-182; FitzGerald and Patrono, 2001, N. Engl. J. Med. 345: 433-442; Vane and Botting, 1998, Inflamm. Res. 47: S78-S87). COX activity originates from two distinct and independently regulated isozymes, COX-1 and COX-2 (Dannhardt and Kiefer, 2001, Eur. J. Med. Chem. 36: 109-126; Otto and Smith, 1995, J. Lipid Mediat. Cell. Signal. 12: 139-156; Oberle et al., 1998, Circ. Res. 82: 1016-1020). Cyclooxygenase-2 is the dominant source of PGs which mediate pain and inflammation, while COX-1 catalyzes the formation of PGs that subserve housekeeping functions, such as the maintenance of gastrointestinal (GI) integrity. Traditional non-steroidal anti-inflammatory drugs (NSAIDs) inhibit both COX-1 and COX-2. As a consequence of COX-1 inhibition, however, traditional NSAIDs have been found to have adverse gastrointestinal effects, including both direct and indirect irritation of the gastrointestinal tract.

The coxibs, selective inhibitors of COX-2, were designed to inhibit the major enzymatic source of the PGs which mediate pain and inflammation, while sparing COX-1-derived PGs, which contribute dominantly to gastric cytoprotection (FitzGerald and Patrono, 2001, N. Engl. J. Med. 345: 433-42). Two coxibs, rofecoxib (Bombardier et al., 2000, N. Engl. J. Med. 343:1520-8, 2 p following 8) and lumiracoxib (Schnitzer et al., 2004, Lancet 364:665-74) have been shown in controlled trials to reduce the incidence of serious gastrointestinal (GI) adverse effects when compared with traditional NSAIDs. Rofecoxib, however, has been associated with an excess of heart attack and stroke in patients receiving this drug (25 mg/day) in the Adenomatous Polyp Prevention on VIOXX® (APPROVe) trial, and has recently been withdrawn from the market (FitzGerald, 2004, N. Engl. J. Med. 351:1709-11). A similar excess in cardiovascular events has recently been reported with celecoxib, again in a trial designed to prevent colonic adenomas (www(dot)nih(dot)gov/news/pr/dec2004/od-17(dot)htm). Furthermore, evidence has emerged to link a structurally distinct coxib, valdecoxib, to a cardiovascular hazard (Ott et al., 2003, J. Thorac. Cardiovasc. Surg. 125: 1481-92), suggesting strongly that this increased cardiovascular risk is a class effect. Indeed, valdecoxib has also been recently withdrawn from the market (www(dot)fda(dot)gov/bbs/topics/news/2005/NEW01171(dot)html).

All of the coxibs depress substantially prostacyclin ($PGI_2$), leaving platelet COX-1-derived thromboxane $A_2$ ($TxA_2$) unaffected (McAdam et al., 1999, Proc. Natl. Acad. Sci. USA 96: 272-7; Catella-Lawson et al., 1999, J. Pharmacol. Exp. Ther. 289; 735-41). $PGI_2$ is a COX-2-derived molecule. $PGI_2$, the dominant product of arachidonic acid in macrovascular endothelial cells, is formed by prostacyclin synthase (PGIS) action on prostaglandin endoperoxide intermediates, which are produced catalytically by COX-2 (Moncada et al., 1976, Nature 263: 663-5). $PGI_2$ exhibits properties of potential relevance to atheroprotection. Specifically, it inhibits platelet aggregation, vascular smooth muscle contraction and proliferation (Cheng et al., 2002, Science 296: 539-541), leukocyte-endothelial cell interactions (Della Bella et al., 2001, Prostaglandins 65: 73-83) and cholesteryl ester hydrolase (Gryglewski et al., 1995, Ann. N.Y. Acad. Sci. 748: 194-206; discussion 206-7). It also activates reverse cholesterol transport (Morishita et al., 1990, J. Clin. Invest. 86: 1885-91). Indirect evidence suggests that $PGI_2$ protects against oxidant-induced tissue injury. Deletion of the $PGI_2$ receptor (IP) or suppression of $PGI_2$ biosynthesis augments cardiac injury caused by ischemia/reperfusion (Xiao et al., 2001, Circulation 104: 2210-5) or the anthracycline, doxarubacin (Dowd et al., 2001, J. Clin. Invest. 108: 585-90). $PGI_2$ also limits the cardiovascular effects of thromboxane $A_2$ ($TxA_2$), the major COX-1 product of platelets (Cheng et al., 2002, Science 296: 539-541). The cardiovascular effects of $TxA_2$ include: platelet aggregation (Thomas et al., 1998, J. Clin. Invest. 102: 1994-2001), elevation of blood pressure (Qi et al., 2002, J. Clin. Invest. 110: 61-9; Francois et al., 2004, Hypertension 43:364-9) and acceleration of atherogenesis (Kobayashi et al., 2004, J. Clin. Invest. 114:784-94; Cayatte et al., 2000, Arterioscler. Thromb. Vasc. Biol. 20: 1724-8; Huo et al., 2003, Nat. Med. 9: 61-7). This last effect may be particularly pertinent to the "latent period" before the emergence of cardiovascular risk in the APPROVe study. Indeed, urinary thromboxane (Tx) metabolites increase during lesion development (Pratico et al., 2000, Blood 96: 3823-6) and thromboxane receptor (TP) antagonism retards atherogenesis in mice (Cayatte et al., 2000, Arterioscler. Thromb. Vasc. Biol. 20: 1724-8). Deletion of the IP accelerates the initiation and early development of atherosclerosis in two mouse models (Kobayashi et al., 2004, J. Clin. Invest. 114: 784-94; Egan et al., 2004, Science 360: 1954-7). In this context, COX-2-derived $PGI_2$ acts to limit the interactions of leucocytes and platelets with the vasculature and the attendant oxidant stress, thereby disrupting atherogenesis (Kobayashi et al., 2004, J. Clin. Invest. 114: 784-94; Egan et al., 2004, Science 360: 1954-7). Furthermore, in contrast to laminar shear stress, turbulent flow, which can be caused by atherosclerotic lesions, fails to increase endothelial expression of COX-2 (Topper et al., 1996, Proc. Natl. Acad. Sci. USA 93: 10417-22). Thus, defective expression of COX-2/PGIS-dependent $PGI_2$ may predispose to focal atherogenesis in vivo.

This last effect may be particularly pertinent to the "latent period" before the emergence of cardiovascular risk in the APPROVe study. Although blood pressure was elevated by 3-4 mm Hg as early as one month in patients receiving rofecoxib in APPROVe, the increase in cardiovascular risk evolved slowly over time, becoming first evident after 18 months of treatment, in only 1-2% of patients. Thus, a small minority of the patients, apparently initially at low risk of cardiovascular disease, proceeded to increase that risk to a point that culminated in clinical events (FitzGerald, 2004, N. Engl. J. Med. 351:1709-11). Suppression of the COX-2-derived $PGI_2$ pathway would afford a mechanism by which the hazard of drug-induced thrombosis would relate to the patient's underlying risk of cardiovascular disease (FitzGerald, 2003, Nat. Rev. Drug Discov. 2: 879-90). Indeed, this is consistent with evidence of a cardiovascular hazard in two placebo controlled trials of valdecoxib, another member of the class, in patients undergoing coronary artery bypass grafting (Furberg et al., 2005, Circulation 111:249 Epub 2005 Jan. 17), a setting of hemostatic activation (Anderson et al., 2003, Scand. Cardiovasc. J. 37: 356-62).

Therefore, evaluating initial cardiovascular risk in patients contemplating COX-2 selective inhibitor therapy, and on-going evaluation of cardiovascular risk in patients undergoing COX-2 selective inhibitor therapy would be of great value in the continued use of COX-2 selective inhibitor compounds. Assessing the plateau or decrease in cardiovascular risk by non-invasive means after cessation of COX-2 inhibitor therapy, or in patients on antioxidant therapy, would also be of great value.

In general, interest in assessing cardiovascular risk has been increasing in recent years. Early identification of cardiovascular risk is a high priority to medical doctors, because it would allow early treatment intervention in the hope of precluding a cardiovascular event. Historically and currently, cardiovascular risk assessment has relied substantially on measures of certain molecules in the blood. For instance, Wilson et al. (1998, Circulation 97:1837-1847) developed an algorithm using total cholesterol, LDL cholesterol and blood pressure to predict coronary heart disease (CHD). Sharrett et al. (2001, Circulation 104:1108-1113) identified the combination of LDL cholesterol, HDL cholesterol, triglycerides and lipoprotein (a) for predicting degree of risk of CHD. In recent years, research has demonstrated that inflammation plays a major role in atherothrombosis. Consequently, markers of inflammation, such as C-reactive protein (CRP), interleukin-6 (IL-6) and tumor necrosis factor-$\alpha$ (TNF-$\alpha$), have also recently been identified as predictors of cardiovascular risk (Ridker, 2001, Circulation 103:1813-1818; Cesari et al., 2003 Circulation 108:2317-2322). Disadvantageously, relying on blood tests requires drawing blood, an invasive procedure. Ideally, cardiovascular risk assessment would rely on non-invasive measures of biological compounds that correlate with cardiovascular risk. Furthermore, the identification of new, independent measures of cardiovascular risk may lead to increased accuracy in risk stratification.

Isoprostanes (iP) are PG isomers that are produced by free radical attack on arachidonic acid in situ in membrane phospholipids (Morrow et al., 1992, Proc. Natl. Acad. Sci. USA 89:10721-5). Isoprostanes are chemically stable end-products of lipid peroxidation that are released by phospholipases, circulate in plasma and are excreted in urine (Awad et al., 1993, J. Biol. Chem. 268:4161-4169). U.S. Pat. No. 5,891, 622 to Morrow et al. teaches a method of assessing oxidative stress by measuring the isoprostane, 8-epi-$PGF_{2\alpha}$ in a biological sample, including urine. It is noted in the background section of this patent that 8-epi-$PGF_{2\alpha}$ may have diagnostic potential for atherosclerosis. U.S. Pat. No. 6,727,075 to FitzGerald et al. teaches a method of measuring isoprostane biomarkers in a mammal suspected of having Alzheimer's disease. The isoprostane biomarkers disclosed include 8,12-iso-$iPF_{2\alpha}$-VI.

There is an unmet need in the art for compositions and methods of assessing cardiovascular risk using noninvasive assays to assess cardiovascular risk. This need is particularly apparent for subjects contemplating or already undergoing COX-2 selective inhibitor therapy; subjects who have ceased such therapy; subjects who are undergoing antioxidant therapy; or subjects lacking clinical evidence of cardiovascular disease. The present invention meets this need.

SUMMARY OF THE INVENTION

In one aspect of the invention, a method of assessing cardiovascular risk in a subject contemplating therapy with a COX-2 selective inhibitor compound is provided, the method comprising the steps of measuring the level of a $PGI_2$ metabolite in the urine of the subject prior to administration of the compound, measuring the level of $PGI_2$ metabolite in the urine of the subject at about four hours after administration of the compound, and determining a ratio by dividing the level of $PGI_2$ metabolite in the urine of the subject at about four hours after administration of the compound by the level of $PGI_2$ metabolite in the urine of the subject prior to administration of the compound, wherein the subject has not been administered a non-steroidal anti-inflammatory drug or a COX-2 selective inhibitor compound for at least two weeks prior to administration of the compound, and wherein a ratio of the level of $PGI_2$ metabolite at about four hours after compound administration to the level of $PGI_2$ metabolite prior to compound administration in the lower quartile is indicative of increased cardiovascular risk in the subject. In one embodiment, the method further comprises measuring the level of at least one of a thromboxane metabolite and 8,12-iso-$iPF_{2\alpha}$ in the urine of the subject. In another embodiment of this and other aspects of the invention, the method further comprises assessing at least one additional parameter of cardiovascular risk in the subject, wherein the parameter is selected from the group consisting of: blood pressure, blood level of C-reactive protein, blood level of interleukin-6 (IL-6), blood level of soluble intracellular adhesion molecule-1 (sICAM-1), blood level of monocyte chemoattractant protein-1 (MCP-1), blood level of homocysteine, blood level of $iPF_{2\alpha}$-III, presence or extent of atherosclerotic plaques, and presence of one or more genetic predispositions for elevated cardiovascular risk. In another embodiments of this and other aspects of the invention, measuring the level of $PGI_2$ metabolite in the urine comprises assessing the ratio of $PGI_2$ metabolite to a known quantity of synthetic $PGI_2$ metabolite homologous internal standard added thereto using gas chromatography and mass spectrometry, thereby measuring the level of the $PGI_2$ metabolite in the urine of the subject. In yet another embodiment of this and other aspects of the invention, the $PGI_2$ metabolite is 2,3-dinor-6-keto $PGF_{1\alpha}$.

In another aspect, the invention features a method of assessing cardiovascular risk in a subject contemplating therapy with a COX-2 selective inhibitor compound is provided, the method including the steps of measuring the level of thromboxane metabolite in the urine of the subject prior to administration of the compound, measuring the level of thromboxane metabolite in the urine of the subject about four hours after administration of the compound, and determining a ratio by dividing the level of thromboxane metabolite at about four hours after administration of the compound by the level of thromboxane metabolite prior to administration of the compound, wherein the subject has not taken a non-steroidal anti-inflammatory drug or a COX-2 selective inhibitor compound for at least two weeks prior to administration of the compound, and wherein a ratio of the level of thromboxane metabolite about four hours after compound administration to the level of thromboxane metabolite prior to compound administration in the upper quartile is indicative of increased cardiovascular risk in the subject. In one embodiment, the method further comprises measuring the level of at least one of a $PGI_2$ metabolite and 8,12-iso-iPF$_{2\alpha}$ in the urine of the subject. In an embodiment of this and other aspects of he invention, measuring the level of thromboxane metabolite in the urine comprises assessing the ratio of thromboxane metabolite to a known quantity of synthetic thromboxane metabolite homologous internal standard added thereto using high pressure liquid chromatography and tandem mass spectrometry, thereby measuring the level of the thromboxane metabolite in the urine of the subject. In another embodiment of this and other aspects of the invention, the thromboxane metabolite is 11-dehydro $TxB_2$.

The invention additionally provides, in another aspect, a method of assessing cardiovascular risk in a subject contemplating therapy with a COX-2 selective inhibitor compound, the method comprising the steps of measuring the level of 8,12-iso-iPF$_{2\alpha}$-VI in the urine of the subject prior to administration of the compound, measuring the level of 8,12-iso-iPF$_{2\alpha}$-VI in the urine of the subject at about four hours after administration of the compound, and determining a ratio by dividing the level of 8,12-iso-iPF$_{2\alpha}$-VI in the urine of the subject at about four hours after administration of the compound by the level of 8,12-iso-iPF$_{2\alpha}$-VI in the urine of the subject prior to administration of the compound, wherein the subject has not taken a non-steroidal anti-inflammatory drug or a COX-2 selective inhibitor compound for at least two weeks prior to administration of the compound, and wherein a ratio of the level of 8,12-iso-iPF$_{2\alpha}$-VI about four hours after compound administration to the level of 8,12-iso-iPF$_{2\alpha}$-VI prior to compound administration in the upper quartile is indicative of increased cardiovascular risk in the subject. In one embodiment, the method further comprises measuring the level of at least one of a thromboxane metabolite and a $PGI_2$ metabolite in the urine of the subject. In an embodiment of this aspect and other aspects of the invention, measuring the level of 8,12-iso-iPF$_{2\alpha}$-VI in the urine comprises assessing the ratio of 8,12-iso-iPF$_{2\alpha}$-VI to a known quantity of a synthetic 8,12-iso-iPF$_{2\alpha}$-VI homologous internal standard added thereto using gas chromatography and mass spectrometry, thereby measuring the level of the 8,12-iso-iPF$_{2\alpha}$-VI in the urine of the subject.

In another aspect, the invention provides a method of assessing cardiovascular risk in a subject contemplating therapy with a COX-2 selective inhibitor compound, the method including the steps of measuring the concentration of a COX-2 selective inhibitor compound in the plasma of the subject contemplating therapy with the compound at about four hours after administration of the compound, wherein the subject has not taken aspirin, any non-steroidal anti-inflammatory drug or any COX-2 selective inhibitor compound for at least two weeks prior to administration of the compound, and wherein a plasma COX-2 selective inhibitor compound concentration level in the upper quartile is indicative of increased cardiovascular risk in the subject. In an embodiment of this and other aspects of the invention, the method further include measuring the level of at least one of a $PGI_2$ metabolite, a thromboxane metabolite and 8,12-iso-iPF$_{2\alpha}$ in the urine of the subject. In another embodiment, measuring the level of plasma compound concentration includes assessing the ratio of the COX-2 selective inhibitor compound to a known quantity of a synthetic COX-2 selective inhibitor compound homologous internal standard added thereto using liquid chromatography and tandem mass spectrometry, thereby measuring the level of the a COX-2 selective inhibitor compound in the plasma of the subject.

In another aspect, the invention provides a method of assessing cardiovascular risk in a subject contemplating therapy with a COX-2 selective inhibitor drug, the method including the steps of determining the identity of a polymorphism in at least one of PTGS1 and CYP2C9 in a subject contemplating therapy with a COX-2 selective inhibitor drug, wherein the presence of a Pro17Leu variant of PTGS1 or the presence the minor allele of CYP2C9*2 is indicative of increased cardiovascular risk in the subject.

In another aspect of the invention, a method of assessing an increase in cardiovascular risk in a subject undergoing therapy with a COX-2 selective inhibitor compound is provided, the method including the steps of measuring the level of a $PGI_2$ metabolite in the urine of the subject undergoing therapy with a COX-2 selective inhibitor compound on at least a first and a second point in time to produce at least a first level of $PGI_2$ metabolite and a second level of $PGI_2$ metabolite, wherein the at least first and second points in time are separated from each other by an interval of at least about one month, and wherein a decrease in the second level of $PGI_2$ metabolite compared to the first level of $PGI_2$ metabolite is indicative of increased cardiovascular risk in the subject. In other aspects and embodiments of the invention, the level of a thromboxane metabolite or 8,12-iso-iPF$_{2\alpha}$-VI is measured, rather than, or in addition to, a $PGI_2$ metabolite. In an embodiment of this aspect and others, the at least first point in time is within about 18 months from the commencement of therapy with a COX-2 selective inhibitor. In another embodiment of this aspect and others, the method further comprises assessing at least one additional parameter of cardiovascular risk in the subject on the first and second time points, and the at least first point in time is within about 18 months from the commencement of therapy with a COX-2 selective inhibitor. In another embodiment of this aspect, as well as other aspects of the invention, the method further includes measuring the level of a $PGI_2$ metabolite in the urine of the subject on at least a third point in time to produce an at least third level of $PGI_2$ metabolite, calculating at least a first and a second rate of change of $PGI_2$ metabolite as a function of time, and comparing the first and second rates to evaluate the rate of change in cardiovascular risk.

The invention further provides, in another aspect, a method of assessing atherosclerotic plaque burden in a subject undergoing therapy with a COX-2 selective inhibitor compound and having an increased cardiovascular risk, the method including the steps of determining that a subject undergoing therapy with a COX-2 selective inhibitor compound is at an increased cardiovascular risk using a method of the invention, and assessing atherosclerotic plaque burden, wherein the assessing step comprises measuring atherosclerotic plaque burden on at least two points in time to produce at least a first and a second measure of atherosclerotic plaque burden, wherein the at least two points in time are separated by an interval of approximately three months in a patient, and calculating the rate of change of atherosclerotic plaque burden as a function of time wherein a positive rate of change is indicative of rapidly increasing cardiovascular risk.

In another aspect, the invention provides a method of assessing an increase in cardiovascular risk in a subject having no clinical evidence of cardiovascular disease, the method including the steps of measuring the level of a $PGI_2$ metabolite in the urine of a subject having no clinical evidence of cardiovascular disease on at least a first and a second point in time to produce at least a first level of $PGI_2$ metabolite and a second level of $PGI_2$ metabolite, wherein the at least first and second points in time are separated from each other by an interval of at least about one month, and wherein a decrease in the second level of $PGI_2$ metabolite compared to the first level of $PGI_2$ metabolite in urine is indicative of increased cardiovascular risk in the subject. In other aspects and embodiments of the invention, the level of a thromboxane metabolite or 8,12-iso-iPF$_{2\alpha}$-VI is measured, rather than, or in addition to, a $PGI_2$ metabolite.

A method of assessing a change in cardiovascular risk in a subject subsequent to cessation of COX-2 selective inhibitor compound therapy is provided in another aspect of the invention, the method comprising the steps of measuring the level of a $PGI_2$ metabolite in the urine of the subject who has ceased therapy with a COX-2 selective inhibitor compound on at least a first and a second point in time to produce at least a first level of $PGI_2$ metabolite and a second level of $PGI_2$ metabolite, wherein the at least first and second points in time are separated from each other by an interval of at least about one month, and wherein an increase in the second level of $PGI_2$ metabolite compared to the first level of $PGI_2$ metabolite is indicative of decreased cardiovascular risk in the subject. In other aspects and embodiments of the invention, the level of a thromboxane metabolite or 8,12-iso-iPF$_{2\alpha}$-VI is measured, rather than, or in addition to, a $PGI_2$ metabolite.

In yet another aspect, the invention provides a method of assessing a change in cardiovascular risk in a subject undergoing antioxidant therapy, the method comprising the steps of measuring the level of a $PGI_2$ metabolite in the urine of the subject who is undergoing antioxidant therapy on at least a first and a second point in time to produce at least a first level of $PGI_2$ metabolite and a second level of $PGI_2$ metabolite, wherein the at least first and second points in time are separated from each other by an interval of at least about one month, and wherein an increase in the second level of $PGI_2$ metabolite compared to the first level of $PGI_2$ metabolite is indicative of decreased cardiovascular risk in the subject. In other aspects and embodiments of the invention, the level of a thromboxane metabolite or 8,12-iso-iPF$_{2\alpha}$-VI is measured, rather than, or in addition to, a $PGI_2$ metabolite.

The invention provides, in another aspect, a kit for assessing cardiovascular risk in a mammal, the kit comprising i) an instructional material and ii) at least one component selected from the group consisting of a negative control solution of a biomarker of cardiovascular risk at a concentration of about the concentration of the biomarker present in a tissue or body fluid sample of a mammal not at risk for a cardiovascular event; a positive control solution of a biomarker of cardiovascular risk at a concentration of about the concentration of the biomarker present in a tissue or body fluid sample of a mammal at increased risk for a cardiovascular event; and a detector molecule for a biomarker of cardiovascular risk. In one embodiment, the biomarker of cardiovascular risk is selected from the group consisting of 8,12-iso-iPF$_{2\alpha}$-VI, a $PGI_2$ metabolite and a thromboxane metabolite. In another embodiment, the kit further includes at least a second component selected from the group consisting of a negative control solution of a second biomarker of cardiovascular risk at a concentration of about the concentration of the biomarker present in a tissue or body fluid sample of a mammal not at risk for a cardiovascular event; a positive control solution of a second biomarker of cardiovascular risk at a concentration of about the concentration of the biomarker present in a tissue or body fluid sample of a mammal at increased risk for a cardiovascular event; and a detector molecule for a second biomarker of cardiovascular risk, and further wherein the second biomarker is different from the first biomarker. In another embodiment, the second biomarker of cardiovascular risk is selected from the group consisting of 8,12-iso-iPF$_{2\alpha}$-VI, a $PGI_2$ metabolite and a thromboxane metabolite.

In another aspect, the invention provides a kit assessing cardiovascular risk in a mammal, the kit including i) an instructional material and ii) at least one component selected from the group consisting of a negative control solution of a $PGI_2$ metabolite at a concentration of about the concentration of the $PGI_2$ metabolite present in a tissue or body fluid sample of a mammal not at risk for a cardiovascular event; a positive control solution of a $PGI_2$ metabolite at a concentration of about the concentration of the $PGI_2$ metabolite present in a tissue or body fluid sample of a mammal at increased risk for a cardiovascular event; and a detector molecule for a $PGI_2$ metabolite.

In other aspects, the kit includes control solutions of a thromboxane metabolite or 8,12-iso-iPF$_{2\alpha}$-VI. In one embodiment, the detector molecule is an antibody. In another embodiment, the detector molecule is an homologous internal standard. In another embodiment, the kit further includes at least a second component, wherein the second component is selected from the group consisting of a negative control solution of a second biomarker at a concentration of about the concentration of the biomarker present in a tissue or body fluid sample of a mammal not at risk for a cardiovascular event; a positive control solution of a second biomarker at a concentration of about the concentration of the biomarker present in a tissue or body fluid sample of a mammal at increased risk for a cardiovascular event; and a detector molecule for a second biomarker, and further wherein the second biomarker is not the same as the first biomarker.

In another aspect, the invention provides a kit, the kit including i) a negative control solution of the $PGI_2$ metabolite at a concentration of about the concentration of the $PGI_2$ metabolite present in a tissue or body fluid sample of a mammal not at risk for a cardiovascular event; ii) a positive control solution of the $PGI_2$ metabolite at a concentration of about the concentration of the $PGI_2$ metabolite present in a tissue or body fluid sample of a mammal at increased risk of a cardiovascular event; iii) an antibody directed against the $PGI_2$ metabolite; and iv) an instructional material. In other aspects, the kit the kit includes control solutions of a thromboxane metabolite or 8,12-iso-iPF$_{2\alpha}$-VI.

BRIEF DESCRIPTION OF THE DRAWINGS

For the purposes of illustrating the invention, there are depicted in the drawings certain embodiments of the invention. However, the invention is not limited to the precise arrangements and instrumentalities of the embodiments depicted in the drawings.

FIG. 23A is a series of images of gels depicting semi-quantitative RT-PCR of COX-2 RNA electrophoresed on agarose gels and visualized with ethidium bromide. COX-2 RNA was obtained from control right (RC) and left (LC) common carotid arteries. Top panel-naïve mice; Middle panel-mice undergoing moderate flow reduction; and Bottom panel-mice undergoing severe flow reduction.

FIG. 23B is a graph depicting the effect of nimesulide on urinary 2,3-dinor 6-keto PGF$_{1\alpha}$ in control mice, mice undergoing moderate flow reduction, and mice undergoing severe flow reduction. (n=9 each group; *p<0.05).

FIG. 23C is a graph depicting the morphometric analysis of lumen diameter (i) and total vessel size (ii) measured as external elastic lamina diameter. In (i) RC vs. LC: moderate flow reduction n=11, *p<0.01; severe flow reduction n=11, *p<0.001).

FIG. 25A depicts a representative trace of blood flow as a function of time in carotid arteries of a mouse one week after LC ligation causing severe flow reduction without nimesulide. (i) control RC; (ii) experimental LC.

FIG. 25B depicts a representative trace of blood flow as a function of time in carotid arteries of a mouse one week after LC ligation causing severe flow reduction with nimesulide. (i) control RC; (ii) experimental LC.

FIG. 25C is a graph depicting the average peak blood flow in carotid arteries of mice one week after LC ligation causing severe flow reduction with nimesulide or without (vehicle). Control RC (left panel) and experimental LC (right panel). Mice were treated with nimesulide (n=11) versus vehicle alone (n=14). (*p<0.01).

FIGS. 31A-31D depict the average effects of the three treatments, shown as fitted means and standard error of the mean. There was inhibition of COX-2 by both drugs (31A), a minor degree of inhibition of COX-1 by celecoxib (31B), similar depression by both drugs of PGI-M (31C) and no effect of either on Tx-M (31D). FIGS. 31E-31H depict the variation of the responses in the whole study population by plotting all individual observations from which the average effects were derived. Individual observations are plotted on log scales. While the main effects, such as inhibition of COX-2 (31E) are evident, there is a striking variability within the population. FIGS. 31I-31L depict the variability of replicate measurements within five individuals (designated A to E on the ordinates) as repeatability-reproducibility plots. Data points of replicate measurements are connected by vertical lines. A box indicates the maximal range of observations for each drug treatment. A horizontal line in each box represents the average over all measurements within the box. There was also a striking intraindividual variability, which appears only slightly smaller than the variability of the whole population (31E-31H) and replicate measurements (31I-31L), which are plotted on the same scales.

DETAILED DESCRIPTION OF THE INVENTION

Figure 1:
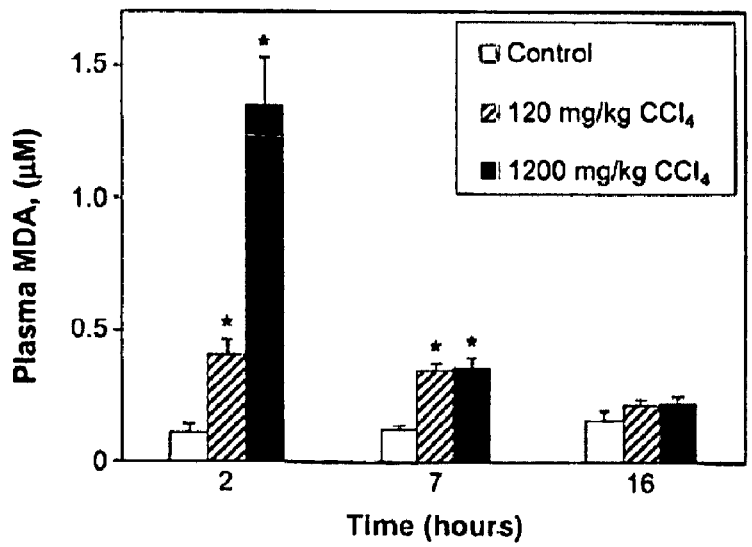
FIG. 1 is a graph depicting the effect of $CCl_4$ treatment on plasma MDA concentration measured by GC/MS. Values are the mean±SEM of n=5/group. Asterisks indicate a statistically significant ($p<0.05$) result relative to respective controls; statistical testing methods are described herein in the Detailed Description.

The present invention relates to compositions and methods useful in the assessment of cardiovascular risk in a mammal. The compositions and methods of the instant invention are intended for a mammal, preferably a human, that is: contemplating COX-2 selective inhibitor compound therapy; is undergoing COX-2 selective inhibitor compound therapy; has ceased COX-2 selective inhibitor compound therapy; is undergoing antioxidant therapy; or, is interested in monitoring cardiovascular risk in the absence of clinical evidence of cardiovascular disease.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "COX enzyme" is used herein to refer to an enzyme (EC 1.14.99.1) having cyclooxygenase activity. These enzymes catalyze the formation of prostaglandins and thromboxane from arachidonic acid by means of their cyclooxygenase and peroxidase activities. Alternative names include: fatty acid cyclooxygenase, prostaglandin-endoperoxide synthase, prostaglandin-endoperoxide synthetase, prostaglandin synthase, prostaglandin synthetase, PG synthetase, (PG)H synthase, and prostaglandin G/H synthase. There are two isoforms of cyclooxygenase, referred to as COX-1 and COX-2. Alternative names for these enzymes include PGHS-1 and PGHS-2, respectively.

A "non-steroidal anti-inflammatory drug" (NSAID) is used herein to refer to a drug which has analgesic, antipyretic and anti-inflammatory effects. Traditional NSAIDs are non-selective inhibitors of both COX-1 and COX-2. Examples of non-selective NSAID inhibitors include: aspirin, ibuprofen, naproxen, indomethacin, and meclofenamic acid. While acetaminophen (paracetamol) is sometimes listed as an NSAID, due to its inhibitory actions on cyclooxygenase, it lacks significant anti-inflammatory properties and is, therefore, not considered to be a true NSAID.

As used herein, "COX-2 selective inhibitor compound" or "COX-2 selective inhibitor" refers to a compound which inhibits COX-2 to a greater extent than it inhibits COX-1. Some non-limiting examples of COX-2 selective inhibitor compounds include: nimesulide, meloxicam, diclofenac, parecoxib (Dynastat®), celecoxib (Celebrex®), etoricoxib (Arcoxia®), lumiracoxib (Prexige®), rofecoxib (Vioxx®), and valdecoxib (Bextra®). The invention should not be construed as being limited solely to these examples, as other COX-2 selective inhibitor compounds which are at present unknown, once known, may also be relevant in the methods of the invention. Preferably, a COX-2 selective inhibitor compound has a selectivity ratio of cyclooxygenase-2 inhibition over cyclooxygenase-1 inhibition of at least about 5, more preferably about 10, and more preferably about 50. Inhibition is preferably assessed using a whole blood assay (FitzGerald and Patrono, 2001, N. Engl. J. Med. 345:433-442).

As used herein, "inhibits COX-2" or "inhibiting COX-2" should be construed to include: inhibiting the enzymatic activity of COX-2, inhibiting the transcription of the COX-2 gene, and inhibiting the translation of COX-2 mRNA. Inhibiting the enzymatic activity of COX-2 includes reducing the half-life of COX-2 enzyme, for instance, by increasing degradation of either COX-2 and/or the mRNA for COX-2. "Inhibiting" as used herein refers to a detectable reduction in an activity or process resulting from administration of a drug compared to the activity or process prior to the administration of the drug.

"COX-2 selective inhibitor compound therapy" is used herein to refer to any regular dosing of COX-2 selective inhibitor compound.

"Regular dosing" as used herein refers to a regimen of compound administration at regular intervals. A non-limiting example of regular dosing is daily dosing that continues for at least about two weeks. The intervals between doses can be more or less than a day, depending on the formulation of the COX-2 selective inhibitor compound. The minimum duration of dosing is two doses, and is preferably more than two doses. Other examples of regular dosing regimens include, but are not limited to, the following:

Typical dosage and administration for Celebrex®:
  a. osteoarthritis: 200 mg per day administered as a single dose or as 100 mg twice per day
  b. rheumatoid arthritis: 100 to 200 mg per day
  c. management of acute pain and treatment of primary dysmenorrheal: 400 mg daily followed by 200 mg if needed on the first day; subsequent days, dose is 200 mg twice daily as needed
  d. familial adenomatour polyposis (FAP); 400 mg twice daily to be taken with food.

Typical dosage and administration for Bextra®:
  a. osteoarthritis and adult rheumatoid arthritis: 10 mg daily
  b. primary dysmenorrheal: 20 mg twice daily as needed.

"Cardiovascular risk" is used herein to refer to the likelihood or possibility of a patient incurring or experiencing a cardiovascular event. A subject who is "not at risk for a cardiovascular event" is a subject who is considered to be at low cardiovascular risk using guidelines from the American College of Cardiology and the American Medical Association available as of the filing date of this application.

"Increased cardiovascular risk" is used herein to refer to an increase in the likelihood or possibility of incurring or experiencing a cardiovascular event. This risk can be assessed relative to a patient's own risk, or with respect to a population that does not have clinical evidence of a cardiovascular disease and/or is not at risk for a cardiovascular event. The population may be representative of the patient with regard to approximate age, age group and/or gender.

"Cardiovascular event" as used herein refers to a disorder or disease of the cardiovascular system having a sudden onset; it can also refer to a sudden worsening of such a disorder or disease. Examples of cardiovascular events include, without limitation: cardiac arrest, myocardial infarction, thrombosis, deep vein thrombosis, pulmonary thrombosis, atherogenesis, atherosclerosis, plaque fracture, ischemia, stroke, worsening of angina, and congestive heart failure.

As used herein "sudden" refers to a short period time encompassing a few minutes to several hours or days.

"Clinical evidence of cardiovascular disease" is used herein to refer to medical evidence indicative of cardiovascular disease, as established by American College of Cardiology guidelines current at the time of filing of this application. Such clinical evidence includes, but is not limited to, abnormal results from: blood pressure, blood tests including a lipid profile, high density cholesterol, low density, cholesterol, triglycerides, cardiac biomarkers (enzymes, proteins, and hormones, such as troponin, myoglobin, b-type natriuretic peptide and creatine phosphokinase, that are associated with heart function, damage or failure), electrocardiograms (ECG or EKG), stress tests, chest x-ray, MUGA scan, computed tomography (CT), nuclear scanning (nuclear heart scan), echocardiogram (heart ultrasound), cardiac catheterization (coronary angiography), duplex/doppler ultrasound, magnetic resonance angiography (MRA) and magnetic resonance imaging (MRI). Documented incidents of myocardial infarctions, heart attack or plaque-associated thrombus are also clinical evidence of cardiovascular disease.

As used herein, the term "antioxidant therapy" refers to treatment with one or more medicaments that prevent or reduce the oxidation of other molecules. Antioxidants include, but are not limited to: vitamin C (ascorbic acid), retinol (vitamin A), vitamin E (tocopherol), selenium, indole-3-propionic acid, melantonin, and enzymatic antioxidants such as superoxide dismutase, glutathione peroxidase and catalase.

"Blood level" is used herein to refer to the measure or concentration of a compound in whole blood or in a liquid component of blood, including plasma or serum.

"Isoprostane" as used herein refers to a free-radical-catalyzed prostaglandin isomer formed from arachidonic acid. An isoprostane is an isomer of a prostaglandin. Non-limiting examples include: iPF$_{2\alpha}$-III (also known as 8-iso-PGF$_{2\alpha}$; 8-epi-PGF$_{2\alpha}$; IPF$_{2\alpha}$-IV; and 15-F$_{2t}$-IsoP), iPF$_{2\alpha}$-IV (also known IPF$_{2\alpha}$-III), iPF$_{2\alpha}$-V (also known IPF$_{2\alpha}$-II), iPF$_{2\alpha}$-VI (also known as 5-F$_{2t}$-IsoP and IPF$_{2\alpha}$-I), and 8,12-iso-iPF$_{2\alpha}$-VI (also known as 8,12-iso-IPF$_{2\alpha}$-I and 5-F$_{2c}$-IsoP).

"PGI$_2$" is used herein to refer to prostacyclin, also known as epoprostenol.

"PGI$_2$ metabolite" as used herein refers to a byproduct of prostacyclin metabolism in an animal, preferably in a mammal. Non-limiting examples of PGI$_2$ metabolites are 2,3-dinor-6-keto PGF$_{1\alpha}$ and 15-keto-13,14-dihydro-2,3-dinor-6-keto-PGF$_{1\alpha}$. The most abundant PGI$_2$ metabolite in human urine is 2,3-dinor-6-keto PGF$_{1\alpha}$ (referred to herein as "PGI-M").

"Thromboxane metabolite" as used herein refers to a byproduct of thromboxane metabolism in an animal, preferably in a mammal. Non-limiting examples of thromboxane metabolites include: 2,3-dinor thromboxane B$_2$ (2,3-dinor-TxB$_2$), 11-dehydro-thromboxane B$_2$ (11-dehydro TxB$_2$; also referred to herein as "Tx-M"), 2,3,4,5-tetranor-thromboxane B$_1$ and 2,3-dinor-thromboxane B$_1$. 11-Dehydro TxB$_2$ is the most abundant thromboxane metabolite in human urine.

"MDA" is used herein to refer to malondialdehyde. An "MDA-like product" is used herein to refer to a substance that reacts with a nucleophilic reagent to yield the same product that is observed following reaction of the same reagent with MDA. Thus, the final product in an MDA assay may represent an unknown substance rather than MDA.

As used herein, "8-OHdG" refers to 8-hydroxy-2'-deoxyguanosine.

"Oxidative stress" or "oxidant stress" is used here to refer to the consequences of free radical dependent damage to proteins, DNA and/or lipids without regard to the specific free radical involved or the relative preponderance of the targets. "Oxidant stress" or "oxidative stress" implies radical generation in excess of that which can be quenched (i.e. coped with) by the endogenous antioxidant defenses of a mammal, and implies tissue or organ dysfunction in the mammal, and is thus a potential mechanism of disease. "Oxidative stress" and "oxidant stress" are used interchangeably herein.

"Genetic predisposition for elevated cardiovascular risk" as used herein refers to having at least one genetic mutation that is correlated with increased risk of a cardiovascular event. Such genetic predispositions include, but are not limited to: familiar hypercholesterolemia and hypercoagulable disorders including Factor V Leiden, prothrombin gene mutation, antithrombin III deficiency, protein C deficiency, protein S deficiency and homocystinuria.

Blood component parameters that are correlated with cardiovascular risk include, but are not limited to: total cholesterol, LDL cholesterol, homocysteine, triglycerides, C-reactive protein (CRP), monocyte chemoattractant protein-1 (MCP-1) and certain cytokines. Cytokines correlated with cardiovascular risk include, but are not limited to, soluble intracellular adhesion molecule-1 (sICAM-1), interleukin-6 (IL-6) and tumor necrosis factor-α (TNFα).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, a "detector molecule" is a molecule that may be used to detect a compound of interest. Non-limiting examples of a detector molecule are a molecule that binds specifically to a compound of interest, such as, but not limited to, an antibody, a receptor, or a small molecule, and a homologous internal standard.

As used herein, an "instructional material" includes a publication, a recording, a diagram, or any other medium of expression which can be used to communicate the usefulness of the kit component(s) in practicing a method of the invention. The instructional material of the kit of the invention may, for example, be affixed to a container which contains a component needed for practicing a method of the invention or be shipped together with a container which contains the composition. Alternatively, the instructional material may be shipped separately from the container with the intention that the instructional material and the composition be used cooperatively by the recipient.

Description

The invention includes compositions and methods for assessing whether or not a patient is at high risk for a cardiovascular event, whether or not the patient has undergone therapy with a coxib, is undergoing coxib therapy, is contemplating undergoing coxib therapy or will never undergo coxib therapy.

The compositions and methods of the invention are designed to assess various biochemical and/or physiological markers that, either alone or in combination, provide a measure of whether or not the patient is at risk for a cardiovascular event. These biochemical and/or physiological markers include biomarkers of mechanistic effects resulting from the inhibition of COX-2-catalyzed formation of PGs. These biomarkers include: prostanoid metabolites, such as $PGI_2$ metabolites and thromboxane $A_2$ metabolites, and markers of oxidant stress, such as isoprostanes. Assessment of cardiovascular risk includes measurement of a marker, preferably in a sample of urine taken from the patient.

In each of the methods and compositions of the invention described herein, the subject can be any mammal, and is preferably a human. The methods of the invention can be performed either on a subject which manifests a symptom or symptoms of cardiovascular risk or disease, or on a subject which does not manifest a symptom or symptoms of cardiovascular risk or disease. Furthermore, the methods of the invention may be performed on the subject at any stage in the progression of cardiovascular risk or disease. Additionally, the methods of the invention may be performed on a subject suspected of having a change, either an increase or a decrease, in cardiovascular risk or disease.

Cardiovascular risk assessment according to the instant invention comprises measurement of at least one urinary marker. Preferably, cardiovascular risk assessment further comprises measurement of at least a second marker of cardiovascular risk, wherein the second marker is a second urinary component, a blood component or determination of a genetic predisposition in the patient. More preferably, risk assessment comprises measurements of more than one parameter, comprising measurement of any combination of a urinary component, a blood component and assessing one or more genetic predispositions. For instance, if a urinary diagnostic test indicates elevated cardiovascular risk, one can test one or more additional parameters of cardiovascular risk in order to confirm and/or further stratify the degree of risk. In one embodiment, cardiovascular risk assessment is made based on measurement of two urinary components, preferably an isoprostane and either a prostacyclin metabolite or a thromboxane metabolite. More preferably, cardiovascular risk assessment is made based on urinary 8,12-iso-iPF$_{2\alpha}$-VI and at least one of urinary 11-dehydro-TxB$_2$ and 2,3-dinor-6-keto PGF$_{1\alpha}$.

In the methods and compositions of the invention described herein, measurements made using a tissue sample can be made using any tissue sample obtained from any type of tissue. Measurements made using a sample of body fluid can be made in any type of body fluid. Preferably the body fluid sample is a sample obtained from the group consisting of plasma and urine. Most preferably, the body fluid sample is urine.

Urine is collected in sterile containers, preferably 30 minutes after voiding. Alternatively, urine is collected as a time integrated sample. For instance, after voiding, urine is collected for a time period, for instance 2, 4 or 6 hours. At the end of the time period, the bladder is voided again and the sample collection is then complete. If the urine sample is not analyzed immediately, the sample is stored in such a way as to prevent or reduce breakdown of the component(s) to be measured in the urine. One method of storage to prevent or reduce breakdown is to freeze the sample on dry ice immediately after collection and store the frozen sample at $-70°$ C.

Marker levels in urine are generally normalized to another urine component. Typically, the other urine component is creatinine. Creatinine is measured is preferably measured using an automated colorimetric assay (Sigma-Aldrich Co., St Louis, Mo.).

One skilled in the art knows how to draw blood and how to process it (e.g., obtain serum or obtain plasma) for use in measuring conventional blood component measures for cardiovascular risk.

Assays of the present invention include various immunoassays, for example, immunohistochemistry assays, immunocytochemistry assays, ELISA, capture ELISA, sandwich assays, enzyme immunoassay, radioimmunoassay, fluorescent immunoassay, and the like, all of which are known to those of skill in the art. See e.g. Harlow et al., 1988, Antibodies: A Laboratory Manual, Cold Spring Harbor, N.Y.; Harlow et al., 1999, Using Antibodies: A Laboratory Manual, Cold Spring Harbor Laboratory Press, NY.

In some embodiments of the invention, risk assessment is determined by comparison of the level of a marker to a database for that marker for which cardiovascular risk has been evaluated. In these embodiments, a ratio of the level of the marker before and after administration of a COX-2 selective inhibitor compound is calculated. The cardiovascular risk indicated by the ratio is interpreted by comparison to a database of such ratios, divided into quartiles. The database is generated by measuring the same marker under the same conditions in a representative population. Typically the representative population does not have clinical evidence of cardiovascular disease and has not taken a COX-2 selective inhibitor compound for a period of time prior to the test. This period is preferably at least about two weeks. The database of ratios is, optionally, sub-divided by age and/or gender. A quartile is the value of the boundary at the 25th, 50th, or 75th percentiles of a frequency distribution divided into four parts, each containing a quarter of the population. For instance, in a database comprising these values: 2.0, 2.2, 2.04, 1.99, 1.8, 1.8, 1.78, 1.75, 1.65, 1.6, 1.58, 1.45, 1.26, 1.1, 1.05 and 1, the first quartile is 1.4, the second quartile is 1.7 and the third quartile is 1.85. A ratio of 1.56 is therefore within the second quartile. As used here, "lower quartile" or "first quartile" refers to a value within the quartile demarcated by the $25^{th}$ percentile.

Details of the methods and compositions of the invention with regard to the various biochemical and/or physiological markers are now described.

Isoprostanes

In one embodiment, the methods and compositions of the invention employ a class of molecules termed isoprostanes as biomarkers of oxidative stress and thus, cardiovascular risk. Specifically, the methods and compositions of the invention assess levels of one or more isoprostane biomarkers in biological sample of a mammal as a means of identifying mammal at risk of elevated cardiovascular risk. The biological sample is preferably urine and the mammal is preferably human.

The isoprostane biomarker for assessment of cardiovascular risk is preferably an isoprostane selected from the group consisting of iPF$_{2\alpha}$-III (8-iso-PGF$_{2\alpha}$), iPF$_{2\alpha}$-VI and 8,12-iso-iPF$_{2\alpha}$-VI. Most preferably, the isoprostane is 8,12-iso-iPF$_{2\alpha}$-VI. U.S. Pat. No. 5,891,622 mentions that 8-epi-PGF$_{2\alpha}$ (iPF$_{2\alpha}$-III) may have diagnostic potential for atherosclerosis. However, the patent neither teaches nor suggests measuring 8,12-iso-iPF$_{2\alpha}$-VI in urine as a possible diagnostic for atherosclerosis. Measuring 8,12-iso-iPF$_{2\alpha}$-VI in mammals has been previously disclosed, for use in mammals suspected of having Alzheimer's disease (U.S. Pat. No. 6,727,075). This reference does not disclose measuring urinary 8,12-iso-iPF$_{2\alpha}$-VI as a diagnostic marker for cardiovascular risk.

The isoprostane biomarker can be isolated from the sample and the level measured using any method known to the skilled artisan for isolating a prostaglandin molecule and are described herein by way of example. Such methods are described, for example, in Pratico et al., 1995, J. Biol. Chem. 270:9800-9808, Pratico et al., 1998, Proc. Natl. Acad. Sci. USA 95:3449-3454 and Lawson et al. (1999, J. Biol. Chem., 374(35) 24441-24444). These methods include, by way of example, and not by limitation, solvent extractions, solid phase extractions, centrifugation and sedimentation methods, quantitative and semi-quantitative methods such as chromatographic methods including thin layer chromatography, low, medium, and high pressure liquid chromatography methods, mass spectrometry methods, gas chromatography methods, gas chromatography/mass spectrometry methods, and immunological methods.

An exemplary method comprises obtaining a sample of a tissue or body fluid from the mammal. Briefly, the isoprostane biomarker is isolated by first, in the case of a tissue sample, homogenizing the tissue sample. In the case of a body fluid sample, no homogenization step is necessary. Total lipids are then extracted from the sample using ice-cold Folch solution, chloroform/methanol (2:1,v/v). The solution is then centrifuged briefly, and the organic phase, which contains the extracted lipids, is dried under nitrogen. Lipids are then hydrolyzed using aqueous potassium hydroxide to release the isoprostane biomarker.

The isoprostane biomarker isolated as described above is then measured using an assay method for an isoprostane. Preferably, the assay is a quantitative assay. The level of the isoprostane biomarker is then quantified based on the assay results using, for example, peak area or peak height ratios. An example of a preferred quantitative assay for an isoprostane is described herein in the Examples. (See also Pratico et al., 1998, Proc. Natl. Acad. Sci. USA 95:3449-3454 and U.S. Pat. No. 6,727,075).

For example, the isoprostane biomarker isolated as described above can be measured as follows. Briefly, after potassium hydroxide hydrolysis, the sample which contains an isoprostane is spiked with a known amount of a synthetic homologous internal standard. A non-limiting example of an internal standard includes a radio-labeled synthetic homologous isoprostane molecule. The samples are then subjected to solid phase extraction, derivatized, and purified using thin layer chromatography. After thin layer chromatography, each sample is analyzed for isoprostane content using gas chromatography-mass spectrometry, and quantitation is performed using peak area or peak height ratios of the radio-labeled synthetic homologous isoprostane molecule and the isoprostane molecule of interest.

The preferred isoprostane to be measured in the methods of the invention is 8,12-iso-iPF$_{2\alpha}$-VI. Along with its epimer 5-epi-8,12-iso-iPF$_{2\alpha}$-VI, 8,12-iso-iPF$_{2\alpha}$-VI is the most prevalent PGF-ring isoprostane in human urine. The level of urinary 8,12-iso-iPF$_{2\alpha}$-VI can be measured using several different assays. Advantageously, these assays for 8,12-iso-iPF$_{2\alpha}$-VI are highly reproducible, sensitive, specific and applicable to stored specimens.

In one assay, 8,12-iso-iPF$_{2\alpha}$-VI and its epimer 5-epi-8,12-iso-iPF$_{2\alpha}$-VI, are measured by addition of a tetradeuterated internal standard to the urine sample followed by solid phase extraction and quantitation using liquid chromatography and tandem mass spectroscopy (LC/MS/MS) (Li et al., 1999, Proc. Natl. Acad. Sci. USA 96: 13381-13386).

Another method of measuring the level of 8,12-iso-iPF$_{2\alpha}$-VI is the use of an immunoassay which employs an antibody against 8,12-iso-iPF$_{2\alpha}$-VI. Preferably, the anti-8,12-iso-iPF$_{2\alpha}$-VI antibody is monoclonal. While any known immunoassay can be utilized to test for 8,12-iso-iPF$_{2\alpha}$-VI in urine, the preferred immunoassay is an ELISA.

While measurement in urine is a preferred embodiment, in another embodiment of the invention, the level of 8,12-iso-iPF$_{2\alpha}$-VI is measured in plasma. Free 8,12-iso-iPF$_{2\alpha}$-VI concentration in plasma is determined by gas chromatography/negative ion chemical ionization mass spectrometry (GC/NICI-MS) by the method of Morrow et al. (Morrow and Roberts, 1999, Methods Enzymol. 300: 3-12). Briefly, [$^2$H$_4$] 8,12-iso-iPF$_{2\alpha}$-VI internal standard is added to plasma and F$_2$-isoprostanes are extracted with a C$_{18}$ Sep-Pak® Cartridge (Waters Associates, Milford, Mass.). The extracted F$_2$-isoprostanes are converted to pentafluorobenzyl ester and purified by TLC after which they are converted to a trimethylsilyl ether derivative and subsequently analyzed by GC-MS.

Another isoprostane that is useful in the methods of the invention is iPF$_{2\alpha}$-III (8-iso-PGF$_{2\alpha}$). Urinary iPF$_{2\alpha}$-III can be measured using the same methods as used for measuring urinary 8,12-iso-iPF$_{2\alpha}$-VI Free iPF$_{2\alpha}$-III concentrations in plasma is determined by gas chromatography/negative ion chemical ionization mass spectrometry (GC/NICI-MS) by the method of Morrow et al. (Morrow and Roberts, 1999, Methods Enzymol. 300: 3-12). Briefly, [$^2$H$_4$] iPF$_{2\alpha}$-III internal standard is added to plasma and F$_2$-isoprostanes are extracted with a C$_{18}$ Sep-Pak® Cartridge (Waters Associates, Milford, Mass.). The extracted F$_2$-isoprostanes are converted to pentafluorobenzyl ester and purified by TLC after which they are converted to a trimethylsilyl ether derivative and subsequently analyzed by GC-MS.

To assess cardiovascular risk in the methods and compositions of the invention, the level of an isoprostane biomarker is measured in a first and a second biological sample. The first and second samples are obtained from the same mammal at two separate points in time, such that the second sample is obtained at a time after the first sample is obtained. The level of the isoprostane biomarker present in the second sample is preferably assessed by the same method used in assessing the level of the isoprostane biomarker in the first sample. The level of isoprostane is preferably normalized to another urine component, typically creatinine, by dividing the amount of isoprostane by the amount of creatinine in the sample.

In a mammal contemplating therapy with a COX-2 selective inhibitor compound, the first sample is obtained prior to a first dose of COX-2 selective inhibitor therapy and after at least a two week period during which no NSAIDs or COX-2 selective inhibitor compound is administered. The second sample is obtained after an initial dose of COX-2 selective inhibitor compound. Preferably the second sample is obtained at about four hours after the initial dose of COX-2 selective inhibitor compound. The level of isoprostane biomarker in the second sample is divided by the level of isoprostane biomarker in the first sample to determine a ratio. The ratio determined is then compared to a database of such ratios to ascertain which quartile the ratio falls into, thereby determining risk. For instance, a ratio that falls within the upper quartile is indicative of increased cardiovascular risk in the mammal.

Alternatively, in order to assess on-going cardiovascular risk in a mammal, the samples are collected at two separate points in time and the level of isoprostane biomarker is determined. Additional samples (third, fourth, etc) may be additionally obtained as a function of time in order to monitor cardiovascular risk in a on-going fashion. Cardiovascular risk in a subject is determined by comparing the level of isoprostane biomarker in the second sample to the level in the first sample. If the second level is greater than the level in the first sample, this is indicative of an increased cardiovascular risk in the subject. In an alternate embodiment, the level of isoprostane biomarker at each time point is compared to a database of such levels for which ranges of risk have been determined, to determine the risk relative a population. In either embodiment, advantageously, one can identify if there is a trend of increasing levels of the isoprostane biomarker, even if the levels are still within an average or low risk range. For instance, one can compare levels of isoprostane biomarker in three samples collected once every three months to determine if cardiovascular risk has increased from an average risk to an elevated risk, which might indicate the need for a change in therapy. Similarly, the levels of the three samples may remain within the same risk category but may be steadily increasing, indicating a growing chance of progression into an elevated risk category.

Furthermore, one can determine the rate of change of the cardiovascular risk. This knowledge can inform the decision on the subsequent frequency of cardiovascular assessment. For instance, the urine levels of an isoprostane of a subject are measured at three different time points, taken every three months, are 80 pg isoprostane/mg creatinine, 110 pg isoprostane/mg creatinine and 200 pg isoprostane/mg creatinine. The first rate of change in isoprostane level, from the first time point level to the second time point level, is 10 pg isoprostane/mg creatinine per month. The second rate of change in isoprostane level, from the second time point level to the third time point level, is 30 pg isoprostane/mg creatinine per month. Both rates of change are positive, indicating increasing cardiovascular risk. The second rate of change is, however, greater than the first rate of change. This increase in rate of change of the isoprostane biomarker, and thus in cardiovascular risk, would suggest the need for more frequent monitoring, as well as other possible intervention, including cessation of COX-2 selective inhibitor compound therapy.

These assessments have value for many patient populations. In particular, these assessments are useful for mammals undergoing COX-2 selective inhibitor therapy to determine if there is an increasing cardiovascular risk that might indicate the need to cease COX-2 selective inhibitor therapy. These assessments are also useful in assessing if cardiovascular risk decreases after cessation of COX-2 selective inhibitor therapy. Likewise, these are useful in mammals undergoing antioxidant drug therapy to assess if cardiovascular risk is decreasing on the therapy.

As described elsewhere herein, a kit is envisaged for every method disclosed. The following description of a kit useful for assessing cardiovascular risk in a mammal by measuring an isoprostane biomarker in urine therefore is not intended to be limiting and should not be construed that way.

The kit comprises a negative control solution containing an isoprostane biomarker at a concentration of about the concentration of the isoprostane biomarker which is present in a tissue or body fluid sample of a mammal which is not at increased cardiovascular risk. Preferably, the isoprostane biomarker is suspended in an ethanol solution.

The kit also includes a positive control solution containing an isoprostane biomarker at a concentration of about the concentration of the isoprostane biomarker which is present in a tissue or body fluid sample of a mammal which is at increased risk of cardiovascular risk. Preferably, the isoprostane biomarker is suspended in an ethanol solution.

Additionally, the kit includes an antibody directed against an isoprostane biomarker for cardiovascular risk. Methods for the preparation and purification of antibodies are known in the art, and are described, for example, in Harlow et al., 1988, Antibodies: A Laboratory Manual, Cold Spring Harbor, N.Y. The antibody can be any type of antibody known in the art.

The kit optionally can include at least one sample container for containing a tissue or body fluid sample obtained from the mammal. The kit also can optionally include a solution useful in the extraction of an isoprostane biomarker for cardiovascular risk from the tissue or body fluid sample obtained from the mammal. Preferably, the solution is an ethanol solution.

The kit can, optionally include a secondary antibody directed against the antibody specific for the isoprostane molecule.

Furthermore, the kit includes an instructional material for use in the assessment of cardiovascular risk in a mammal. The instructional material can be a publication, a recording, a diagram, or any other medium of expression which can be used to communicate the usefulness of the method of the invention in the kit for assessment of cardiovascular risk in a mammal. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

In another embodiment, the kit comprises a dipstick or means for a chromatographic immunoassay for measuring an isoprostane biomarker.

Prostanoid Metabolites

In other embodiments, the methods and compositions of the invention employ metabolites of a class of molecules called prostanoids. Prostanoids are derived from arachidonic acid, which is a fatty acid derivative, by the action of COX enzymes, and include prostaglandins, prostacylins and thromboxanes. Specifically, the methods and compositions of the invention assess levels of one or more prostanoid metabolites in biological sample of a mammal as a means of identifying mammal at risk of elevated cardiovascular risk. The biological sample is preferably urine and the mammal is preferably human. In one embodiment, the methods and compositions employ a product of prostacyclin metabolism to assess cardiovascular risk. In yet another embodiment, the methods and compositions of the invention employ a product of thromboxane metabolism to assess cardiovascular risk.

The prostanoid metabolite can be isolated from the biological sample and the level measured using any method known to the skilled artisan for isolating a prostaglandin molecule and are described herein by way of example. Techniques and methods for measuring a prostanoid metabolite are known to the skilled artisan. Such methods include, but are not limited to, solvent extractions, solid phase extractions, centrifugation and sedimentation methods, quantitative and semi-quantitative methods such as chromatographic methods including thin layer chromatography, low, medium, and high pressure liquid chromatography methods, mass spectrometry methods, gas chromatography methods, gas chromatography/mass spectrometry methods, and immunological methods.

a. Prostacylin Metabolites

Prostacyclin metabolites are found in urine and in blood. As the most abundant $PGI_2$ metabolite in human urine, 2,3-dinor-6-keto $PGF_{1\alpha}$ is the preferred $PGI_2$ metabolite in the methods and compositions of the instant invention.

A preferred method of measuring the level of urinary 2,3-dinor-6-keto $PGF_{1\alpha}$ is described herein in the Examples. In brief, urinary 2,3-dinor-6-keto $PGF_{1\alpha}$ is measured by a stable isotope dilution method, using gas chromatography/mass spectrometry (GC/MS). Briefly, the isoprostane biomarker is isolated by first, in the case of a tissue sample, homogenizing the tissue sample. In the case of a body fluid sample, no homogenization step is necessary. Total lipids are then extracted from the sample using ice-cold Folch solution, chloroform/methanol (2:1,v/v). The solution is then centrifuged briefly, and the organic phase, which contains the extracted lipids, is dried under nitrogen. Lipids are then hydrolyzed using aqueous potassium hydroxide to release the prostacyclin metabolite. Briefly, after potassium hydroxide hydrolysis, the sample which contains an prostacyclin metabolite is spiked with a known amount of a synthetic homologous internal standard. A non-limiting example of an internal standard includes a radio-labeled synthetic homologous prostacyclin metabolite. The samples are then subjected to solid phase extraction, derivatized, and purified using thin layer chromatography. After thin layer chromatography, each sample is analyzed for prostacyclin metabolite using gas chromatography-mass spectrometry, and quantitation is performed using peak area or peak height ratios of the radio-labeled synthetic homologous prostacyclin metabolite and the prostacyclin metabolite of interest.

b. Thromboxane Metabolites

Thromboxane metabolites are found in both blood and urine. The preferred thromboxane metabolite in human urine is 11-dehydro-thromboxane $B_2$. A preferred method of measuring the level of 11-dehydro-$TxB_2$ in urine is described herein in the Examples. In brief, a sample of urine is spiked with a known quantity of an internal standard, for instance, $[^2H_4]$ 11-dehydro-$TxB_2$. The sample is allowed to equilibrate for 15 min, and 20 µl of formic acid is added. After one hour at room temperature, the sample is extracted by solid phase extraction (SPE) techniques, dried, and analyzed by liquid chromatography/tandem mass spectrometry using reverse phase chromatography and selected reaction monitoring (SRM) techniques. Transitions monitored are m/z 567→m/z 305 for the endogenous 11-dehydro-$TxB_2$ and m/z 571→m/z 309 for the internal standard.

In another embodiment, the level of urinary 2,3-dinor $TxB_2$ is measured by stable dilution isotope reverse phase (C18) HPLC/MS/MS assay. In brief, a sample of urine is spiked with a known quantity of an internal standard, for instance, $[^{18}O_2]$ $dTxB_2$. The sample is allowed to equilibrate for 15 min, and 50 µl of methoxyamine HCl in $H_2O$, 1 g/ml, is added. After 5 minutes, the sample is subjected to SPE and analyzed by liquid chromatography/tandem mass spectrometry using reverse phase chromatography and selected reaction monitoring (SRM) techniques. Transitions monitored are m/z 370→m/z 155 for the endogenous 2,3-dinor $TxB_2$ and m/z 374→m/z 155 for the internal standard.

Thromboxane metabolites in the blood can be measured using capillary gas chromatography/negative-ion chemical ionization mass spectrometry as taught by Catella et al (1986 PNAS 83:5861-5865).

To assess cardiovascular risk in the methods and compositions of the invention, the level of a prostanoid metabolite is measured in at least a first and second biological sample. The at least first and second samples are obtained from the same mammal at two separate points in time, wherein the second sample is obtained at time after the first sample is obtained. The level of the prostanoid metabolite present in the second sample is preferably assessed by the same method used in assessing the level of the prostanoid metabolite in the first sample. The level of prostanoid metabolite is preferably normalized to another urine component, typically creatinine, by dividing the amount of prostanoid metabolite by the amount of creatinine in the sample.

To assess cardiovascular risk in a mammal contemplating therapy with a COX-2 selective inhibitor compound, the first sample is obtained prior to a first dose of COX-2 selective inhibitor therapy and after at least a two week period during which no NSAIDs or COX-2 selective inhibitor compound is administered. The second sample is obtained after an initial dose of COX-2 selective inhibitor compound. Preferably the second sample is obtained at about four hours after the initial dose of COX-2 selective inhibitor compound. The level of prostanoid metabolite in the second sample is divided by the level of prostanoid metabolite in the first sample to determine a ratio. The ratio determined is then compared to a database of such ratios to ascertain which quartile the ratio falls into, thereby determining risk. For a thromboxane metabolite, a ratio that falls within the upper quartile is indicative of increased cardiovascular risk in the mammal. For a $PGI_2$ metabolite, a ratio that falls within the lower quartile is indicative of increased cardiovascular risk in the mammal.

In another embodiment of the invention, the ratio of a thromboxane metabolite is divided by the ratio of a $PGI_2$ metabolite. This ratio of ratios reflects the in vivo selectivity of a subject for a COX-2 selective inhibitor compound. If this ratio of ratios is in the lower quartile, it is indicative of increased cardiovascular risk in the subject.

Alternatively, in order to assess on-going cardiovascular risk in a mammal, the samples are collected at two separate points in time and the level of prostanoid metabolite is determined. Additional samples (third, fourth, etc) may be additionally obtained as a function of time in order to monitor cardiovascular risk in an on-going fashion. Cardiovascular risk in a subject is determined by comparing the level of a prostanoid metabolite in the second sample to the level of the metabolite in the first sample. For a prostacyclin metabolite, if the second level is less than the level in the first sample, this is indicative of an increased cardiovascular risk in the subject. For a thromboxane metabolite, if the second level is greater than the level in the first sample, this is indicative of an increased cardiovascular risk. In an alternate embodiment, the level of prostanoid metabolite at each time point is compared to a database of such levels for which ranges of risk have been determined, to determine the risk relative a population. In either embodiment, advantageously, one can identify if there is a trend of increasing cardiovascular risk, based on the level of the prostanoid metabolite, even if the levels are still within an average or low risk range. Such a trend might indicate the need for a change in the frequency of monitoring as well as possible change in therapy. Measurements of a prostanoid metabolite that show a change in cardiovascular risk category, for instance, from average risk to elevated risk, may indicate the need for increased frequency in monitoring, as well as additional cardiovascular risk assessment, including but not limited to, atherosclerotic plaque burden.

Furthermore, one can determine the rate of change of the cardiovascular risk. This knowledge can impact the frequency of cardiovascular assessment, as well as other treatment or intervention. For instance, the urine levels of a $PGI_2$ metabolite of a subject are measured at three different time points, taken every three months, are 600 pg $PGI_2$ metabolite/mg creatinine, 570 pg $PGI_2$ metabolite/mg creatinine and 510 pg $PGI_2$ metabolite/mg creatinine. The first rate of change in $PGI_2$ metabolite level, from the first time point level to the second time point level, is −10 pg $PGI_2$ metabolite/mg creatinine per month. The second rate of change in $PGI_2$ metabolite level, from the second time point level to the third time point level, is −20 pg $PGI_2$ metabolite/mg creatinine per month. Both rates of change are negative, indicating increasing cardiovascular risk. The second rate of change is, however, greater than the first rate of change. This elevation in the rate of decrease of the $PGI_2$ metabolite, and thus in cardiovascular risk, would suggest the need for more frequent monitoring, as well as other possible intervention, including cessation of COX-2 selective inhibitor compound therapy. Note that for a thromboxane metabolite, positive rates of change are indicative of increasing cardiovascular risk.

These on-going assessments have value for many patient populations. In particular, these assessments are useful for mammals undergoing COX-2 selective inhibitor therapy to determine if there is an increasing cardiovascular risk that might indicate the need to cease COX-2 selective inhibitor therapy. These assessments are also useful in assessing if cardiovascular risk decreases after cessation of COX-2 selective inhibitor therapy. Likewise, they are useful in mammals undergoing antioxidant drug therapy to assess if cardiovascular risk is decreasing on the therapy.

As described elsewhere herein, a kit is envisaged for every method disclosed. The following description of a kit useful for assessing cardiovascular risk in a mammal by measuring a prostanoid metabolite in urine therefore is not intended to be limiting and should not be construed that way.

The kit comprises a negative control solution containing a prostanoid metabolite at a concentration of about the concentration of the prostanoid metabolite which is present in a tissue or body fluid sample of a mammal which is not at increased cardiovascular risk.

The kit also includes a positive control solution containing a prostanoid metabolite at a concentration of about the concentration of the prostanoid metabolite which is present in a tissue or body fluid sample of a mammal which is at increased risk of cardiovascular risk. Preferably, the prostanoid metabolite is suspended in an ethanol solution.

Additionally, the kit includes an antibody directed against a prostanoid metabolite for cardiovascular risk. Methods for the preparation and purification of antibodies are known in the art, and are described, for example, in Harlow et al., 1988, Antibodies: A Laboratory Manual, Cold Spring Harbor, N.Y. The antibody can be any type of antibody known in the art.

The kit can, optionally include a secondary antibody directed against the antibody specific for the prostanoid metabolite.

The kit can optionally include at least one sample container for containing a tissue or body fluid sample obtained from the mammal. The kit also optionally includes a solution useful in the extraction of a prostanoid metabolite for cardiovascular risk from the tissue or body fluid sample obtained from the mammal.

Furthermore, the kit includes an instructional material for use in the assessment of cardiovascular risk in a mammal. The instructional material can be a publication, a recording, a diagram, or any other medium of expression which can be used to communicate the usefulness of the method of the invention in the kit for assessment of cardiovascular risk in a mammal. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

In another embodiment, the kit comprises a dipstick or means for a chromatographic immunoassay for measuring an prostanoid metabolite.

The present invention also includes embodiments which are particularly useful for subjects contemplating COX-2 selective inhibitor therapy. Assessing cardiovascular risk in these embodiments provides an early measure of baseline cardiovascular risk that is useful in determining if the contemplated COX-2 selective inhibitor therapy should initiated or, if initiated, the frequency at which on-going cardiovascular risk is monitored.

Plasma COX-2 Selective Inhibitor Concentration

For a subject contemplating COX-2 selective inhibitor therapy, the methods and compositions of the invention assess cardiovascular risk by measuring plasma COX-2 selective inhibitor compound concentration in plasma after being administered an initial dose. A preferred method of measuring COX-2 selective inhibitor compound concentration in plasma is described herein in the Examples. In brief, plasma samples are analyzed by liquid chromatography tandem mass spectrometry (Micromass Quattro Ultima, Micromass, Beverly, Mass.) using the appropriate internal standard for the COX-2 selective inhibitor compound being analyzed. For instance, L755100 (Merck Frosst, Point Claire, Canada) and SC58125 (Cayman, Ann Arbor, Mich.) are appropriate internal standards for celecoxib and rofecoxib, respectively. Samples are separated on a Luna 3μ $C_{18}$ (150×2.0 mm) column (Phenomenex, Torrance, Calif.) and quantitated using negative atmospheric pressure ionization and multiple reaction monitoring of m/z 380.2→316.1 (celecoxib), 384.2→305.1 (SC58125), 314.2→215.1 (rofecoxib) and 328.2→313.1 (L755100).

For this embodiment, a blood sample is obtained at about four hours after a first dose of COX-2 selective inhibitor compound in a mammal who has not been administered an NSAID or COX-2 selective inhibitor compound in at least the two weeks prior to administration of the COX-2 selective inhibitor compound contemplated for therapy. The level of plasma COX-2 selective inhibitor concentration is compared to a database of plasma COX-2 selective inhibitor concentrations to ascertain which quartile the observed concentration falls into. A concentration that falls within the upper quartile is indicative of increased cardiovascular risk in the mammal. Identifying increased cardiovascular risk prior to starting COX-2 selective inhibitor compound therapy may indicate that such therapy should not be undertaken, or if undertaken, frequent and on-going monitoring of cardiovascular risk should be pursued. The on-going monitoring of cardiovascular risk may be done by the methods and compositions of the instant invention, or by conventional measures.

Genetic Predisposition

In another embodiment, for a subject contemplating COX-2 selective inhibitor therapy, the methods and compositions of the invention assess cardiovascular risk by determining the identity of a polymorphism in at least one of PTGS1 and CYP2C9. Determining the identity of a polymorphism can be done by any method known to the skilled artisan. Non-limiting examples of such methods include: mass spectrometry, 5' nuclease assay, TaqMan® (Applied Biosystems, Foster City, Calif.), primer extension assay, invasive cleavage assay, allele-specific oligonucleotide ligation, differential hybridization, single-strand conformational polymorphism (SSCP), denaturing gradient gel electrophoresis (DGGE), oligonucleotide arrays, as well as direct DNA sequencing.

A preferred method of determining the identity of a polymorphism in at least one of PTGS1 and CYP2C9 is described herein in the Examples. In brief, single nucleotide polymorphism (SNP) assays are performed using Sequenom® MassARRAY® system (Sequenom, San Diego, Calif.) (Wiltshire et al., 2003, Proc. Natl. Acad. Sci. USA 100: 3380-5) and appropriate primers for the polymorphism of interest. Testing is done using genetic material obtained from the mammal. The genetic material can be obtained from a specimen of blood, urine, saliva, stool, body tissues, bone, or hair. Cells in these samples are isolated and the DNA within them is extracted and examined for possible mutations or alterations.

In the gene encoding human COX-1, PTGS1, nucleotide 50 of the coding sequence (SEQ ID NO: 1; 5'-atgagccg-gagtctcttgctctggttcttgctgttcctgctcctgc tcccgccgctccccgtcct-gctcgcggacccaggggcgcccacgc-cagtgaatccctgttgttactatccatgccagcacc agggcatctgtgtccgcttcggcct-tgaccgctaccagtgtgactgcacccg-cacgggctattccggccccaactgcacca tccctggcctgtggacctggctccg-gaattcactgcggcccagcccctcttcacccacttcctgctcactcacgggcgctg gttctgggagttgtcaatgccacct-tcatccgagagatgctcatgcgcctggtactcacagtgcgctccaaccttatcccca gtccccccacctacaactcagcacat-gactacatcagctgggagtcttttccaacgtgagctattacactcgtattctgcct ctgtgcctaaagattgccccacac-ccatgggaaccaaagggaagaagcagt-tgccagatgcccagctcctggcccgccg cttcctgctcaggaggaagttcatac-ctgacccccaaggcaccaacctcatgtttgccttcttgcacaacacttcacccacc agttcttcaaaacttctggcaa-gatgggtcctggcttcaccaaggcct-tgggccatggggtagacctcggccacattatgg agacaatctggagcgtcagtat-caactgcggctcttaaggatgggaaactcaagtaccaggtgctggatggagaaatgta cccgccctcggtagaagaggcgcctgt-gttgatgcactaccccgaggcatcccgccccagagccagatggctgtgggc caggaggtgttgggctgcttcctgggct-catgctgtatgccacgctctggctacgtgagcacaaccgtgtgtgacctgct gaaggctgagcaccccacctggggcgat-gagcagctttccagacgaccgcctcatcctcataggggagaccatcaag attgt-catcgaggagtacgtgcagcagct-gagtggctatttcctgcagctgaaattgacccagagctgctgttcggtgtcca gttccaataccgcaaccgcattgccatg-gagttcaaccatctctaccactggcacccctcatgcctgactccttcaaggtgg gctcccaggagtacagctacgagcagt-tcttgttcaacacctccatgttggtggactatggggttgaggccctggtggatgc cttctctcgccagattgctggccg-gatcggtgggggcaggaacatggaccac-cacatcctgcatgtggctgtggatgtcat cagggagtctcgggagatgcggctg-cagcccttcaatgagtaccgcaagaggtttggcatgaaacccacacctccttcca ggagctcgtaggagagaaggagatg-gcagcagagttggaggaattgtatggagacattgatgcgttggagttctaccctg gactgcttcttgaaaagtgccatc-caaactctatctttggggagagtat-gatagagattggggctcccttcccctcaagggtct cctagggaatcccatctgt-tctccggagtactggaagccgagcacattggcggcgaggtgggcttaacattgtcaagac ggccacactgaagaagctggtctgcct-caacaccaagacctgtccctacgtccttccgtgtgccggatgccagtcaggat gatgggcctgctgtggagcgaccatccacagagctctga-3') is the site of a SNP (Accession No: rs3842787 in NCBI's Entrez SNP database; nucleotides 25-75 of SEQ ID NO: 1). This position is the middle nucleotide of codon 17. This nucleotide position is a C in the major allele, encoding Pro, and a T in the minor allele, encoding Leu.

In the gene encoding human cytochrome P450, CYP2C9, nucleotide 430 of the coding sequence (SEQ ID NO: 2; 5'-atg-gattctcttgtggtccttgtgctctgtctctca tgtgcttctcctcactctggagaca-gagctctgggagaggaaaactccctcctggccccactcctctcccagtgattgga aatatcctacagataggtattaagga-catcagcaaatccttaaccaatctctcaaaggtctatggccctgtgttcactctgtattt tggcctgaaacccatagtggtgctg-catggatatgaagcagtgaaggaagccctgattgatcttggagaggagttctgga agaggcattttcccactggctgaaa-gagctaacagaggattggaattgtttcagcaatggaaagaaatggaaggagatcc ggcgtttctccctcatgacgctgcg-gaatttgggatggggaagaggagcattgaggaccgtgttcaagaggaagcccgct gccttgtggaggagttgagaaaaac-caaggcctcaccctgtgatcccacttcatcctgggctgtgctccctgcaatgtgatc tgctccattattttccat-aaacgttttgattataaagatcag-caatttcttaacttaatggaaaagttgaatgaaaacatcaagattt tgagcagc-ccctggatccagatctgcaataatttctcctatcattgattacttcccgggaactcacaa caaattacttaaaaa cgttgcttttatgaaaagttatattttg-gaaaaagtaaaagaacaccaagaatcaatggacatgaacaaccctcaggacttatt gattgcttcctgatgaaaatggagaag-gaaaagcacaaccaaccatctgaattactattgaaagcttggaaaacactgcag ttgacttgttggagctgggacagagac-gacaagcacaaccctgagatatgctctccttctcctgctgaagcacccagaggt cacagctaaagtccaggaagagat-tgaacgtgtgattggcagaaaccggagc-ccctgcatgcaagacaggagccacatg ccctacacagatgctgtggtgcacgag-gtccagagatacattgaccttctccccaccagcctgccccatgcagtgacctgt gacattaaattcagaaactatctcattc-ccaagggcacaaccatattaattccctgacttctgtgctacatgacaacaaagaat ttcccaacccagagatgtttgaccct-catcacttttggatgaaggtggcaatttaagaaaagtaaatacttcatgcctttctca gcaggaaaacggatttgtgtgg-gagaagccctggccggcatggagctg-mttmattcctgacctccatttacagaacttaac ctgaaatctctggttgacccaaa-gaaccttgacaccactccagttgtcaatggattgcctctgtgccgcccttctaccagct g tgcttcattcctgtctga-3') is the site of a SNP. This SNP is referred to herein as "CYP2C9*2" (Accession No. rs1799853 in NCBI's Entrez SNP database; nucleotides 405-455 of SEQ ID NO: 2). This position is the first nucleotide of codon 144. This nucleotide position is a C in the major allele, encoding Arg, and a T in the minor allele, encoding Cys.

Known genetic predispositions for elevated cardiovascular risk include: Factor V Leiden, prothrombin gene mutation, antithrombin III deficiency, protein C deficiency, protein S deficiency and homocystinuria. Determination of any of these genetic predispositions is known to the skilled artisan.

Additional Parameters of Cardiovascular Risk

As discussed above, some embodiments of the instant invention also include measurement of known parameters of cardiovascular risk.

a. Blood Components

Conventional parameters of cardiovascular risk include, but are not restricted to, measuring the blood levels of C-reactive protein, homocysteine, sICAM-1, IL-6, MCP-1, TNF-α, LDL cholesterol, HDL cholesterol, triglycerides and lipoprotein (a), and measuring blood pressure. The specific techniques and methods for measuring each of these parameters are known to the skilled artisan. Such methods include, but are not restricted to: immunoassay, ELISA, immunochemiluminometric assay, allele-specific polymerase chain reaction (PCR) and gel electrophoresis.

b. Atherosclerotic Plaque Burden

Assessment of atherosclerotic plaque burden is also a known method of cardiovascular risk assessment. Techniques and methods for measuring atherosclerotic plaque burden are known to the skilled artisan. Such methods include, but are not restricted to: Doppler ultrasound, duplex ultrasound, magnetic resonance imaging (MRI), computed tomography (CT), multidetector CT, and digital subtraction X-ray angiography, and electron beam computerized tomography (EBCT). Plaque burden assessed is assessed preferably in coronary arteries or in carotid arteries.

c. Urinary 8-OHdG

Urinary 8-OHdG is measured using an immunoassay. In brief, 8-OHdG is determined using a microtiter ELISA method where the test analyte competes with monoclonal antibody against 8-OHdG for 8-OHdG bound to the plate. After incubation and washing, an anti-mouse second antibody conjugated to horseradish peroxidase is used to determine the bound monoclonal antibody. The color yield is directly proportional to the analyte concentration. Data reduction was by 4-parameter logistic curve fit.

d. Urinary MDA

Urinary MDA is measured by HPLC with spectrophotometry. For instance, to 500 μl urine samples, 25 μl BHT and 750 μl 0.5% TBA solution are added, in this order. Samples are incubated at 60° C. for 60 min. After cooling, chloroform (750 μl) is added and mixed well. Following centrifugation, the aqueous layer is removed and used for HPLC analysis (column 250×46 mm; mobile phase, 6:4(v/v) 0.04 M acetate buffer (pH 5.5)/MeOH; detection, 532 nm).

e. Plasma MDA

Plasma MDA can be measured using a calorimetric assay. For instance, the Bioxytech® LPO-586™ colorimetric assay is based upon the reaction of the chromogenic reagent N-methyl-2-phenylindole (NMPI) with MDA at 45° C. One molecule of free MDA combines with 2 molecules of the chromogenic agent to produce a stable chromophore with a maximal absorbance at 586 nm. The concentration of MDA is then determined with 3rd derivative spectroscopy.

Another method to measure plasma MDA concentrations uses gas chromatography/negative ion chemical ionization mass spectroscopy (GC/NICI-MS) as described by Yeo et al. (Yeo et al., 1994, Anal. Biochem. 220: 391-396). The stable isotope internal standard [$^2H_2$] MDA and an antioxidant (2,6-tert-butyl-4-methylphenol) are added to the plasma samples. The samples are then incubated at room temperature in 6.6 mol $H_2SO_4$ for 10 min to hydrolyze the aldehydes from the proteins. Plasma MDA is converted to a stable pentafluorophenyl hydrazine derivative which is quantified by using the GC-MS in the negative chemical ionization mode.

Kits

All of the methods disclosed herein, or flowing from the disclosure herein, should be construed as being adaptable to a kit. That is, for each method, a corresponding kit derived therefrom is envisaged. In general, a kit will comprise at least one component useful for practicing a method of the invention and will also include an instructional material for the use of the kit.

An example of a component useful for practicing a method of the invention is a control solution. The control solution may comprise a biomarker, such as an isoprostane, a prostacyclin metabolite or a thromboxane metabolite, a homologous internal standard, or a COX-2 selective inhibitor. The concentration of the biomarker in the control solution may be indicative of cardiovascular risk. As a non-limiting example, the control solution may contain 8,12-iso-iPF$_{2\alpha}$-VI at a concentration that is associated with an increased cardiovascular risk. As another non-limiting example, the control solution may contain 2,3-dinor-6-keto PGF$_{1\alpha}$ at about the concentration of 2,3-dinor-6-keto PGF$_{1\alpha}$ present in a tissue or body fluid sample of a mammal not at risk for a cardiovascular event.

Other examples of components useful for practicing a method of the invention include, but are not limited to, a detector molecule, materials for quantitating urinary creatinine; an antibody specific for an isoprostane, a prostacyclin metabolite or a thromboxane metabolite; a secondary antibody that recognizes the first antibody; a solvent useful for extracting an isoprostane, a prostacyclin metabolite or a thromboxane metabolite from a tissue or body fluid sample; nucleic acid, such as primer pairs and/or probes for SNP analysis of CYP2C9 or PTGS1 or any other loci associated with predisposition to cardiovascular risk; a tool or implement useful in practicing a method of the invention, such as a solid phase extraction device or a multi-well plate pre-coated for EIA; a tracer; a container for holding a tissue or body fluid sample; a dipstick designed to detect a specific isoprostane, prostacyclin metabolite or thromboxane metabolite in a body fluid sample; and a second control solution. Such a second control solution may contain a different biomarker than the first solution, or it may contain the same biomarker at a different concentration. As a non-limiting example, a kit may contain a control solution of 8,12-iso-iPF$_{2\alpha}$-VI and a control solution of 2,3-dinor-6-keto PGF$_{1\alpha}$. This kit may be used, for instance, in a method of assessing cardiovascular risk using these two urinary components. A kit may contain any combination of the above components, as well as any other component, useful in practicing a method of the invention.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Experimental Example 1

Identifying Oxidation Products of Lipids Proteins and DNA Useful as Markers of Oxidative Stress In the field of oxidative stress, one of the greatest needs has been to assess reliably oxidative stress in animal models and in humans (Pryor and Godber, 1991, Free Radic. Biol. Med. 10: 177-184). A variety of methods for the measurement of oxidative stress have been proposed and a number of review articles addressing this issue have been written (Morrow et al., 1992, Proc. Natl. Acad. Sci. USA 89: 10721-10725; Pratico et al., 2004, Chem. Phys. Lipids. 128: 165-171; Hensley et al., 2000, Free Radic. Biol. Med. 28: 520-528; Davies et al., 1999, Free Radic. Biol. Med. 27: 1151-1163; Risby and Sehnert, 1999, Free Radic. Biol. Med. 27: 1182-1192; De Zwart et al., 1999, Free Radic. Biol. Med. 26: 202-226). Currently however, there is no consensus on which methods are the most useful, reliable, accurate, or specific, for different types of oxidative insults (Pryor, 1999, Free Radic. Biol. Med. 27: 1135-1136). There has been little direct comparison between the different methods using identical samples (De Zwart et al., 1998, Toxicol. Appl. Pharmacol. 148: 71-82). Therefore, it is extremely difficult to provide absolute reference values for the specific markers in different living systems (Pryor and Godber, 1991, Free Radic. Biol. Med. 10: 177-184; Pryor, 1999, Free Radic. Biol. Med. 27: 1135-1136).

Acute carbon tetrachloride poisoning in rats has become a model for studying oxidative stress. During the last decades, application of this compound has been shown to be an excellent tool for the study of experimental oxidative injury due to its rapid metabolism in the liver by cytochrome P450 to a trichloro-methyl radical metabolite ($*CCl_3$). Upon exposure to oxygen, this radical is converted to a peroxy radical ($*OOCCl_3$), which can abstract hydrogen from different molecules, thus initiating oxidation of lipids, proteins and DNA (Recknagel, 1983, Life Sci. 33: 401-408; Recknagel et al., 1989, Pharmacol. Ther. 43: 139-154; Reinke et al., 1992, Toxicol. Appl. Pharmacol. 112: 17-23; Goeptar et al., 1995, Crit. Rev. Toxicol. 25: 25-65).

In the present example, the time and dose-dependent effects of $CCl_4$ on the oxidation products of lipids, proteins and DNA were measured in blood, plasma and urine collected from rats treated under the same protocol as the previous study (Kadiiska et al., 2000, Free Radic. Biol. Med. 28: 838-845). The criterion used to identify a reliable marker for the measurement of oxidative stress was that the marker responded significantly at more than one dose of $CCl_4$ and at more than one time point when measurements were taken.

The materials and methods used in the experiments presented in Experimental Example 1 are now described. These material and methods also apply to Example B discussed elsewhere herein.

Chemicals and reagents: Carbon tetrachloride ($CCl_4$), indomethacin (1-[p-chlorobenzoyl]-5-methoxy-2-methylindole-3-acetic acid), meclofenamic acid (2-[2,6-dichloro-3-methyl-phenyl)amino]benzoic acid), and all other chemicals and reagents used in Experimental Examples 1 and 2 were obtained from Sigma-Aldrich Corporation (St. Louis, Mo.).

Animals and treatment protocol: Male Fisher 344 rats (260-280 g) obtained from Charles River Laboratories (Raleigh, N.C.) were used in all experiments. The animals were housed three to a cage. Autoclaved hardwood bedding was used in solid-bottom polycarbonate cages with filter tops. Animal rooms were maintained at 20-25° C. with 35-70% relative humidity with alternating 12-hour light and dark cycles. The rats had free access to deionized, reverse-osmosis-treated water and received autoclaved NIH 31 rodent chow (Zeigler Bros., Gardners, Pa.) ad libitum. For all experiments, rats were fasted overnight and then administered intraperitoneal injections of carbon tetrachloride in canola oil. Control rats received an equal volume of canola oil. Fasting continued throughout the experiment. Rats were anesthetized with Nembutal (0.1 ml/100 g body weight) and 5 ml blood was removed from the dorsal aorta proximal to its bifurcation into the common iliac arteries.

Indomethacin pretreatment: The indomethacin regimen used has been previously shown to inhibit COX activity in rats by 90% (dose of 5 mg/kg s.c. 24 hours, 12 hours, and 2 hours prior to the injection of $CCl_4$) (Jackson, 1989, J. Pharmacol. Exp. Ther. 250: 9-21). An additional booster dose was injected 8 hours after the last injection of $CCl_4$ for the measurements performed 16 hours after treatment with $CCl_4$.

Meclofenamic acid pretreatment: Meclofenamic acid was injected at a dose of 5 mg/kg i.p. 12 h and 2 h prior to the injection of $CCl_4$.

Carbon tetrachloride ($CCL_4$) treatment: Animals from each of the three dose groups (Control-canola oil, 120 mg/kg $CCl_4$ i.p. and 1200 mg/kg $CCl_4$ i.p.) were investigated at three time points (2, 7, and 16 hours after $CCl_4$ injection). Indomethacin-pretreated rats were also investigated at the same three time points, and the meclofenamic acid-pretreated rats were investigated at one time point (7 hours). Each group consisted of five rats for each analysis, except the meclofenamic acid pretreatment group which consisted of six rats. Animal treatment, sample preparation, assessment of liver histology and serum enzyme activities are described elsewhere (Kadiiska et al., 2000, Free Radic. Biol. Med. 28: 838-845; Jackson, 1989, J. Pharmacol. Exp. Ther. 250: 9-21) and were carried out at NIEHS, Research Triangle Park, N.C.

Specimen Collection

Each sample of blood and of urine was marked with a code number so that those conducting the assays were not aware of the treatment status of the animals.

Whole blood sample preparation: Blood (5 ml) was drawn through single draw Vacutainer® needles of 21 G into open Vacutainer® blood collection tubes containing heparin. The tubes were gently inverted 2-3 times for mixing. Samples were collected so as to prevent hemolysis and stored on ice for immediate use. Blood samples were frozen immediately on dry ice and stored at −70° C.

Plasma sample preparation: Blood (5 ml) was drawn through single draw Vacutainer® needles (21 Gauge) into open Vacutainer® blood collection tubes containing heparin. The tubes were gently inverted 2-3 times for mixing and immediately placed on ice. Blood was centrifuged (2,000 rpm for 10 minutes at 4° C.) no more than 30 minutes after collection, and the plasma was collected, frozen on dry ice and stored at −70° C.

Urine sample preparation: The day prior to treatment, both experimental and control animals were placed in stainless steel metabolic cages especially designed for urine collection. For Experimental Example 2, animals were placed in metabolic cages immediately after the last injection of indomethacin or meclofenamic acid. Urine was collected (in dark vials) from the animals during the following intervals: 2 to 7 hours and 7 to 16 hours after $CCl_4$ or canola oil (controls) treatment. Urine samples from indomethacin-pretreated rats were collected from 2 to 7 hours and 7 to 16 hours after the injection of $CCl_4$, whereas samples from meclofenamic-acid-pretreated rats were collected only from 2 to 7 hours after the injection. All urine samples were immediately frozen on dry ice and stored at −70° C.

Oxidation Products of Lipids in Plasma

Two assays were used to measure the effect of $CCl_4$ on lipid hydroperoxides. A lipid hydroperoxide assay kit (Catalog No. 705002) from Cayman Chemical Company (Ann Arbor, Mich.) was used to measure hydroperoxides directly, utilizing the redox reaction with ferrous ion. Hydroperoxides were extracted into chloroform and reacted with ferrous ions to produce ferric ions. The resulting ferric ions were detected using thiocyanate ion as the chromogen. The hydroperoxide concentration was determined based on the absorption at 504 nm using a Beckman DU-7 spectrophotometer at room temperature. The experiments were performed at National Institute of Environmental Health Sciences (NIEHS), Research Triangle Park, N.C.

The second assay of plasma lipid hydroperoxides used iodometric spectrophotometric determination. Concentrations of lipid hydroperoxides were measured according to a slightly modified procedure of Cramer et al. (1991, Anal. Biochem. 193: 204-211) where plasma was treated to enzymatically hydrolyze lipids, and nonesterified fatty acid peroxides were then extracted with ethyl acetate. Extracted lipids were reacted with potassium iodide in citric acid and methylene chloride, and the resulting triiodide ion ($I_3^-$) was measured spectrophotometrically. All measurements were done at the United States Environmental Protection Agency (EPA), Research Triangle Park, N.C.

Malondialdehyde (MDA) in plasma was measured using several different assays. In one assay in Experimental Example 1, free MDA and other thiobarbituric acid-reactive substances (TBARS) (MDA-protein adducts) were measured with the thiobarbituric acid (TBA assay) (Draper et al., 1993, Free Radic. Biol. Med. 15: 353-363). One ml of biological sample was combined with 2.0 ml of 1:1 TCA/TBA (30% trichloracetic acid and 0.67% thiobarbituric acid) in the presence of 200 mM butylated hydroxytoluene (BHT) for spectrophotometric readings (Porter et al., 1976, Biochim. Biophys. ACTA 441: 506-512). The incubation mixture was heated for 20 minutes in boiling water. The samples were centrifuged (2,000 rpm for 10 minutes at 4° C.), and the TBARS concentration was determined based on the absorbance at 532 nm measured with a Beckman DU-7 spectrophotometer at room temperature. Measurements were done at NIEHS, Research Triangle Park, N.C. in the case of Experimental Example 1.

Two colorimetric-based assays, using third derivative spectroscopy, were also used to measure MDA in plasma. The TBA colorimetric assay is designed to measure free MDA and MDA-protein adducts (Schiff base), and therefore includes mild acid hydrolysis. The Bioxytech® LPO-586™ colorimetric assay is based upon the reaction of the chromogenic reagent N-methyl-2-phenylindole (NMPI) with MDA at 45° C. One molecule of free MDA combines with 2 molecules of the chromogenic agent to produce a stable chromophore with a maximal absorbance at 586 nm. In both assays, the concentration of MDA was determined with 3rd derivative spectroscopy. Both assays were developed by OXIS Research Inc., Portland, Oreg., and were performed at OXIS and at Loyola University Medical Center, Maywood, Ill.

Plasma MDA concentrations were also measured by using gas chromatography/negative ion chemical ionization mass spectroscopy (GC/NICI-MS) as described by Yeo et al. (Yeo et al., 1994, Anal. Biochem. 220: 391-396). The stable isotope internal standard [$^2H_2$] MDA and an antioxidant (2,6-tert-butyl-4-methylphenol) were added to the plasma samples. The samples were then incubated at room temperature in 6.6 mol $H_2SO_4$ for 10 minutes to hydrolyze the aldehydes from the proteins. Plasma MDA was converted to a stable pentafluorophenyl hydrazine derivative which was quantified by using the GC-MS in the negative chemical ionization mode. The assay was performed at Children's Hospital Oakland Research Institute, Oakland, Calif.

In Experimental Example 2, plasma MDA was measured using a colorimetric-based assay and the GC-MS assay only.

Two slightly different methods developed in two different laboratories were used to measure the effect of $CCl_4$ on the plasma levels of free 8-iso-$PGF_{2\alpha}$, and the sum of free plus esterified 8-iso-$PGF_{2\alpha}$ (also known as 8-epi-$PGF_{2\alpha}$ and $iPF_{2\alpha}$-III and 15-$F_{2t}$-IsoP). Free 8-iso-$PGF_{2\alpha}$ concentrations in plasma were determined by gas chromatography/negative ion chemical ionization mass spectrometry (GC/NICI-MS) by the method of Morrow et al. (1999, Methods Enzymol. 300: 3-12). Briefly, [$2H_4$] 8-iso-$PGF_{2\alpha}$ internal standard was added to plasma and $F_2$-isoprostanes were extracted with a $C_{18}$ Sep-Pak® Cartridge (Waters Associates, Milford, Mass.). The extracted $F_2$-isoprostanes were converted to pentafluorobenzyl ester and purified by TLC after which they were converted to a trimethylsilyl ether derivative and subsequently analyzed by GC-MS. The assay was developed and performed at Vanderbilt University, Nashville, Tenn.

Measurement of the sum of free plus esterified 8-iso-$PGF_{2\alpha}$ in plasma were performed using an improved GC/MS-based analysis for the quantitation of this isoprostane in plasma. A detailed protocol for this extraction and quantitation has been published (Parker et al., 2001, Mol. Biotechnol. 18: 105-118). Measurements of the sum of free plus esterified 8-iso-$PGF_{2\alpha}$ in plasma were performed at NIEHS, Research Triangle Park, N.C.

Oxidation Products of Lipids in Urine

Urinary MDA was analyzed using high pressure liquid chromatography (HPLC). To 500 μl urine samples, 25 μl BHT and 750 μl 0.5% TBA solution were added, in this order. Samples were incubated at 60° C. for 60 minutes. After cooling, chloroform (750 μl) was added and mixed well. Following centrifugation, the aqueous layer was removed and used for HPLC analysis (column 250×46 mm; mobile phase, 6:4 (v/v) 0.04 M acetate buffer (pH 5.5)/MeOH; detection, 532 nm). The procedure was developed and performed by OXIS Research, Portland, Oreg.

Urinary 8-iso-$PGF_{2\alpha}$ concentrations were measured by the competitive immunoassay procedure in which 8-iso-$PGF_{2\alpha}$ conjugated to alkaline phosphatase competed with the test analyte for antibody specific for the isoprostane. The anti-8-iso-$PGF_{2\alpha}$ antibody was captured by anti-Fc antibodies immobilized on a microtiter plate. The assay was developed by Assay Designs, Inc., Ann Arbor, Mich. and performed at OXIS Research, Portland, Oreg.

In Experimental Example 2, urine samples were also analyzed for free 8-iso-$PGF_{2\alpha}$, without any extraction, by radioimmunoassay (Basu, 1998, Prost. Leuk. Ess. Fatty Acids. 58: 319-325). The measurements were performed at Uppsala University, Uppsala, Sweden.

Analysis of 8,12-iso-$iPF_{2\alpha}$-VI, which is, along with its epimer 5-epi-8,12-iso-$iPF_{2\alpha}$-VI, the most prevalent PGF-ring isoprostane in human urine, was accomplished by addition of a tetradeuterated analog, solid phase extraction and quantitation using liquid chromatography and tandem mass spectroscopy (LC/MS/MS) (Li et al., 1999, Proc. Natl. Acad. Sci. USA 96: 13381-13386). The measurements were performed at the University of Pennsylvania, Philadelphia, Pa.

Oxidation Products of Proteins in Plasma

Several different assays for oxidation products of proteins were employed. The protein carbonyl content (Agarwal and Sohal, 1995, Mech. Ageing Develop. 85: 55-63), indicative of plasma protein oxidative damage, was measured according to the method of Levine et al. (Levine et al., 1994, Meth. Enzymol. 233: 346-357), based on derivatization of carbonyls with tritiated borohydride, as described in detail by Yan and Sohal (2000, Current Protocols Protein Science 144: 105-128). The isolated protein was counted in a Beckman scintillation counter and calculated using a standard curve. The measurements were performed at the University of Southern California, Los Angeles.

Methionine sulfoxidation was measured according to Levine et al. (1996, Proc. Natl. Acad. Sci. USA 93: 15036-15040). In brief, serum samples were hydrolyzed with HCl. The methionine sulfoxide residue was converted to methionine, which represents the methionine sulfoxide level in the protein. The samples were analyzed on a Beckman Model 7300 amino acid analyzer. The methionine concentrations were measured at Weill Medical College of Cornell University, New York, N.Y., USA.

Determination of tyrosine products employed a method of sample preparation wherein tyrosine analogs were enzymatically hydrolyzed from protein without the need for sample extraction, concentration or derivatization (Henley et al., 1997, Analytical Biochem. 251: 187-195). High performance liquid chromatography was applied in conjunction with coulometric electrochemical array (HPLC-EC) detection to allow ultrasensitive determination of protein-bound 3-nitrotyrosine and 3,4-dihydroxyphenylalanine (3-hydroxytyrosine) as specific in situ biomarkers of protein exposure to reactive nitrating or oxidizing species (Henley et al., 1997, Analytical Biochem. 251: 187-195). Tyrosine and derivatives were analyzed simultaneously, with practical detection limits for tyrosine, 3-nitrotyrosine, and 3,4-Dopa being 10, 50 and 2 pmol respectively, in as little as 20 µL of sample. The measurements were conducted at the Oklahoma Medical Research Foundation (OMRF), Oklahoma City, Okla.

Oxidation Products of Proteins in Urine

Dityrosine concentration was assayed by isolating amino acids from urine using solid-phase extraction on a C-18 column, elution of amino acids to n-propyl-heptafluorobutyryl derivatives, and quantification of o,o'-dityrosine by isotope dilution GC/MS with selected ion monitoring in the negative ion electron capture mode (Heinecke et al., 1999, Meth. Enzym. 300: 124-144). The measurement was performed at Washington University School of Medicine, St. Louis, Mo.

Oxidation Products of DNA in Blood

The "Comet assay", a microgel electrophoretic technique, was used for the detection of DNA damage and repair in individual cells (Tice, 1995, The single cell gel/Comet assay: a microgel electrophoretic technique for the detection of DNA damage and repair in individual cells. In: Environmental Mutagenesis, D. H. Phillis and S. Venitt, eds. Bios Scientific Publishers, Ltd Oxford, U.K. pp. 315-339). Slides were prepared in situ immediately after blood collection. The assay was performed at ILS, Integrated Laboratory Systems, Inc., Research Triangle Park, N.C.

$M_1G$, a pyrimidopurinone adduct, was measured in rat leukocytes. Rat leukocyte DNA was purified from whole blood using Qiagen® Genomic tips (Leuratti et al., 1998, Carcinogenesis 19: 1919-1924). $M_1G$ levels were analyzed by immunoslot blot analysis as described previously, employing propidium iodide staining of membranes to normalize for the quantity of immobilized DNA (Leuratti et al., 1998, Carcinogenesis 19: 1919-1924; Plastaras et al., 2000, Chem. Res. Toxicol. 13: 1235-1242). The assay was performed at Vanderbilt University, Nashville, Tenn.

Oxidation Products of DNA in Urine

8-Hydroxy-2'-deoxyguanosine (8-OHdG) was measured using an immunoassay. In brief, 8-OHdG was determined using a microtiter ELISA method where the test analyte competed with monoclonal antibody against 8-OHdG for 8-OHdG bound to the plate. After incubation and washing, an anti-mouse second antibody conjugated to horseradish peroxidase was used to determine the bound monoclonal antibody. The color yield is directly proportional to the analyte concentration. Data reduction was by 4-parameter logistic curve fit. The assay was developed and measurements were performed by Oxis Research, Portland, Oreg.

Liver Enzyme Activities, Histopathology and Other Clinical Parameters

Serum enzyme activities of lactic acid dehydrogenase (LDH), alanine aminotransferase (ALT), alkaline phosphatase (ALP), aspartate aminotransferase (AST), sorbitol dehydrogenase (SDH), 5'-nucleotidase (5'-NT), serum concentration of total bile acids (TBA), and liver histopathology were performed, as described (Kadiiska et al., 2000, Free Radic. Biol. Med. 28:838-845). In addition, other clinical parameters such as serum albumin, total protein, total iron, total iron binding capacity, nitrite/nitrate, and urinary creatinine were determined, using standard techniques known to those in the art.

Statistical Analysis of Data

Statistical comparisons were performed by analysis of variance (ANOVA), using pooled estimates of error. When the variance increased substantially with the mean, data were logarithmically transformed prior to analysis. For one assay in Experimental Example 1, one value was off the scale, so it was imputed to be just above the highest observed value. Where multiple urinary samples were obtained from the same animals, both the assay variance within animals and the variance between animals were taken into account in the analysis. In Experimental Example 1, dosed groups were compared to canola oil controls at the same time point. In Experimental Example 2, dosed groups were compared to canola oil controls at the same time point with the same pretreatment status. In addition, pretreated groups were compared to non-pretreated groups with the same $CCl_4$ treatment at the same time point. Values of $p<0.05$ were considered statistically significant. Statistical analyses were performed at NIEHS, Research Triangle Park, N.C.

The results of the experiments presented in Experimental Example 1 are now described.

Lipid Oxidation Products in Plasma

In plasma, the candidates for markers of free-radical induced oxidation were lipid hydroperoxides, malondialdehyde (MDA), and $F_2$-isoprostanes. Two assays for lipid hydroperoxides were tested: a lipid peroxidation assay kit and the iodometric assay. When measurements were performed with the kit, statistically significant increases in the levels of lipid hydroperoxides were found for both doses of $CCl_4$ 2 hour after the injection, with the high dose resulting a 3-fold increase compared to controls (Table 1). When lipid hydroperoxides were measured in the iodometric assay, only the higher dose of $CCl_4$ caused a similar significant increase (Table 1). Since neither measurement exhibited a significant change after 7 hour or 16 hour (Table 1), it was concluded that neither of these assays were useful for assessing plasma lipid hydroperoxides.

MDA was assessed spectrophotometrically using three variations of the TBA assay and using GC/NICI-MS. Spectrophotometric assays included thiobarbituric acid reactive substances (TBARS), the TBA calorimetric assay, and the Bioxytech LPO-586 calorimetric assay kit, with the latter two using 3rd derivative spectroscopy. When TBA was measured as TBARS, only one measurement out of six was affected. The higher dose of $CCl_4$ caused a significant decrease at 16 hours. When assessed using the colorimetric TBA method, the plasma level of MDA did not give rise to any consistent pattern: MDA was higher in rats 2 hours after the administration of both doses of $CCl_4$ (Table 1), 7 hours after the higher dose, and 16 hours after the lower dose. No significant effect on MDA was found for the low dose of $CCl_4$ at 7 hours or for the high dose at the 16 hour time point (Table 1). When the procedure for the measurement of MDA with LPO-586 reagents followed by 3rd derivative analysis was applied, a significant increase was found only for the early time points for both $CCl_4$ doses. When GC/NICI-MS was used to assess the effect of $CCl_4$ on MDA levels in plasma, MDA increased for both doses at the 2 hour and 7 hour time points (Table 1, FIG. 1). These increases were statistically significant. The plasma MDA concentrations were highest in rats 2 hours after $CCl_4$ treatment, especially in the plasma of rats injected with the higher dose of $CCl_4$, where a 12-fold

TABLE 1

Effect of $CCl_4$ on oxidation products of lipids and proteins in rat plasma

| Plasma | 2 h | | | 7 h | | | 16 h | | |
|---|---|---|---|---|---|---|---|---|---|
| Dose/Assay | Control | $CCl_4$ 120 mg/kg | $CCl_4$ 1200 mg/kg | Control | $CCl_4$ 120 mg/kg | $CCl_4$ 1200 mg/kg | Control | $CCl_4$ 120 mg/kg | $CCl_1$ 1200 mg/kg |
| 1. LOOH (µM) (by LPO assay kit) | 0.44 ± 0.06 | 0.96 ± 0.19* | 1.42 ± 0.14* | 1.04 ± 0.08 | 1.20 ± 0.04 | 1.35 ± 0.09 | 1.67 ± 0.21 | 1.60 ± 0.10 | 1.64 ± 0.17 |
| 2. LOOH (µM) (iodometric assay) | 0.47 ± 0.23 | 0.30 ± 0.11 | 1.42 ± 0.57* | 0.27 ± 0.07 | 0.30 ± 0.09 | 0.40 ± 0.13 | 0.43 ± 0.12 | 0.56 ± 0.13 | 0.39 ± 0.10 |
| 3. TBARS (µM) | 3.7 ± 0.1 | 4.1 ± 0.1 | 4.2 ± 0.3 | 10.5 ± 0.6 | 10.4 ± 0.6 | 9.4 ± 0.4 | 13.5 ± 0.4 | 13.0 ± 0.4 | 10.7 ± 0.3* |
| 4. MDA (µM) (by GC-MS) TBA $3^{rd}$ derivative) | 0.162 ± 0.020 | 0.268 ± 0.009* | 0.686 ± 0.034* | 0.202 ± 0.005 | 0.209 ± 0.010 | 0.274 ± 0.016* | 0.142 ± 0.055* | 0.214 ± 0.055* | 0.156 ± 0.004 |
| 5. MDA (µM) (by GC-M5) | 0.12 ± 0.03 | 0.41 ± 0.06* | 1.35 ± 0.18* | 0.12 ± 0.02 | 0.35 ± 0.03* | 0.36 ± 0.04* | 0.16 ± 0.03 | 0.22 ± 0.03 | 0.23 ± 0.03 |
| 6. Free plus esterified 8-iso-$PGF_{2\alpha}$ (by GC-MS) (ng/ml) | 0.43 ± 0.07 | 3.07 ± 0.80* | 6.63 ± 0.51* | 0.43 ± 0.05 | 1.79 ± 0.12* | 4.39 ± 0.31* | 0.41 ± 0.06 | 0.93 ± 0.16* | 1.68 ± 0.18* |
| 7. Free 8-iso-$PGF_{2\alpha}$ (ng/ml) (by GC-MS) | 0.10 ± 0.02 | 0.48 ± 0.05* | 1.80 ± 0.37* | 0.13 ± 0.03 | 0.34 ± 0.09 | 1.27 ± 0.32* | 0.10 ± 0.03 | 0.27 ± 0.11 | 0.74 ± 0.14* |
| 8. Protein carbonyls (nmol/mg protein) (by HPLC) | 0.42 ± 0.08 | 0.40 ± 0.08 | 0.53 ± 0.09 | 0.39 ± 0.06 | 0.42 ± 0.05 | 0.59 ± 0.10 | 0.46 ± 0.03 | 0.51 ± 0.07 | 0.48 ± 0.08 |
| 9. Methionine sulfoxide (% of total methionine) | 3.0 ± 0.5 | 2.3 ± 0.7 | 1.8 ± 0.3 | 1.8 ± 0.2 | 1.7 ± 0.3 | 1.1 ± 0.10 | 2.3 ± 0.8 | 3.1 ± 1.0 | 1.7 ± 0.6 |
| 10. 3-Nitrotyrosine, bound (µM) | 0.16 ± 0.08 | 0.24 ± 0.14 | 0.26 ± 0.14 | 0.35 ± 0.17 | 0.39 ± 0.17 | 0.42 ± 0.11 | 0.23 ± 0.09 | 0.43 ± 0.24 | 0.38 ± 0.11 |

Entries are Means ± SE. Sample size is n=5/group (except for free 8-iso-$PGF_{2a}$ n=4-5/group). Asterisks represent statistically significant ($p < 0.05$) values compared to the control at the same time point; statistical testing methods are described in the methods section. "LOOH" is an abbreviation for lipid hydroperoxides.

increase compared to controls was seen. The effect of $CCl_4$ on MDA levels declined with time after treatment, but remained significantly elevated at 7 hours, exhibiting a 3-fold increase, but resumed a level that was not altered significantly from the control at 16 hours (FIG. 1 and Table 1). The GC/NICI-MS assay was the most sensitive of the four assays for MDA presented here in tracking the effect of $CCl_4$ toxicity with respect to both time and dose.

Free plasma 8-iso-$PGF_{2\alpha}$ concentrations were increased after $CCl_4$ treatment at all three time points compared to their corresponding controls (Table 1). However, the 8-iso-$PGF_{2\alpha}$ concentrations were highest in plasma at 2 hours, with an 18-fold increase evident at the high dose, and subsequently decreased, with 10-fold and 7-fold increases at the high dose at 7 and 16 hours, respectively.

TABLE 2

Effect of $CCl_4$ on oxidation products of lipids and DNA in rat urine

| Urine Dose/Assay | 7 h | | | 16 h | | |
|---|---|---|---|---|---|---|
| | Control | $CCl_4$ 120 mg/kg | $CCl_4$ 1200 mg/kg | Control | $CCl_4$ 120 mg/kg | $CCl_4$ 1200 mg/kg |
| 1. MDA (nmol/mg creatinine) (by HPLC with spectrophotometry) | 0.81 ± 0.16 | 2.01 ± 0.12* | 2.61 ± 0.20* | 0.82 ± 0.12 | 1.54 ± 0.10 | 2.16 ± 0.15* |
| 2. Free plus esterified 8-iso $PGF_{2\alpha}$ (ng/mgcreatinine) (by immunoassay) | 5.9 ± 0.4 | 25.7 ± 2.3* | 57.0 ± 5.1* | 5.1 ± 0.5 | 17.4 ± 1.6* | 30.4 ± 7.4* |
| 3. 8,12-iso-i$PF_{2\alpha}$-VI (ng/ml) (by LC/MS/MS) | 4.9 ± 0.8 | 36.8 ± 15* | 84.3 ± 26.1* | 11.9 ± 2.5 | 32.4 ± 3.3* | 78.5 ± 8.8* |
| 4. 8-OHdG (ng/mg creatinine) (by immunoassay) | 25 ± 2 | 42 ± 13 | 165 ± 133* | 18 ± 1 | 83 ± 29* | 60 ± 10* |

Entries are Means ± SE. Sample size is n=5/group. Asterisks represent statistically significant ($p < 0.05$) values compared to the control at the same time point; statistical testing methods are described in the methods section.

Figure 2:
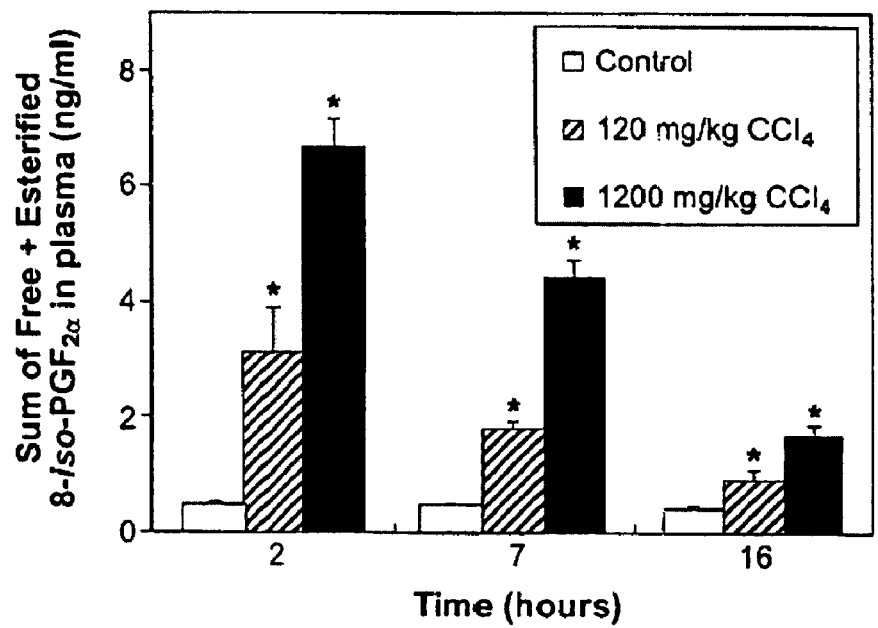
FIG. 2 is a graph depicting the effect of $CCl_4$ treatment on plasma free plus esterified 8-iso-$PGF_{2\alpha}$ concentration measured by GC/MS. Values are the mean±SEM of n=5/group. Asterisks indicate a statistically significant ($p<0.05$) result relative to respective controls; statistical testing methods are described herein in the Detailed Description.

Free plus esterified plasma 8-iso-PGF$_{2\alpha}$ concentrations exhibited statistically significant increases in a time- and dose-dependent manner; the high dose resulted in 15-fold, 10-fold, and 4-fold increases at the 3 successive time points (Table 1, FIG. 2). It is important to note that measurements of both free 8-iso PGF$_{2\alpha}$, and free plus esterified plasma 8-iso PGF$_{2\alpha}$ exhibited the same pattern of increase, even though the assays were performed on "blind" sets of samples in two different laboratories utilizing slightly different GC/NICI-MS procedures.

Lipid Oxidation Products in Urine

Figure 3:
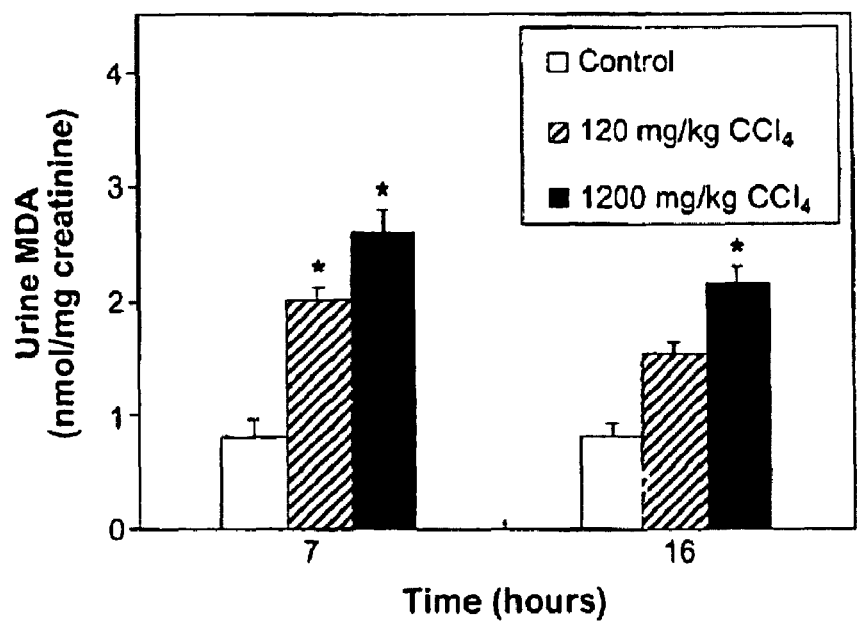
FIG. 3 is a graph depicting the effect of $CCl_4$ treatment on urinary MDA concentration measured by HPLC with spectrophotometry. Values are the mean±SEM of n=5/group. Asterisks indicate a statistically significant (p<0.05) result relative to respective controls; statistical testing methods are described herein in the Detailed Description.

When measured by HPLC with spectrophotometry, urinary MDA increased markedly following both doses of CCl$_4$ in urine collected at 7 hours and 16 hours after treatment (Table 2, FIG. 3). MDA concentrations in urine were highest in rats dosed with the higher dose of CCl$_4$ from urine collected 7 hours after treatment, when a 3-fold increase was observed.

Figure 4:
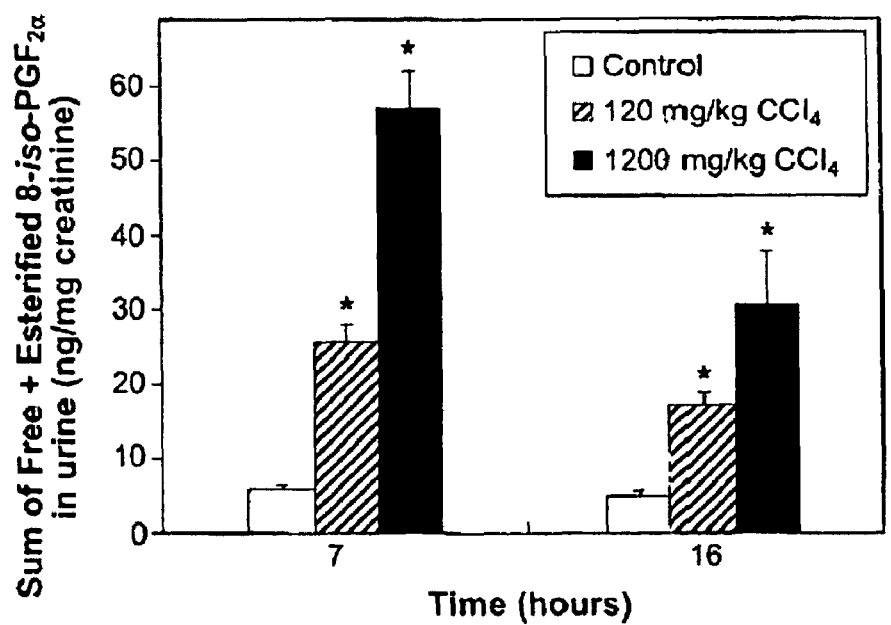
FIG. 4 is a graph depicting the effect of $CCl_4$ treatment on urinary free plus esterified 8-iso-$PGF_{2\alpha}$ concentration measured by an immunoassay. Values are the mean±SEM of n=5/group. Asterisks indicate a statistically significant (p<0.05) result relative to respective controls.
Figure 5:
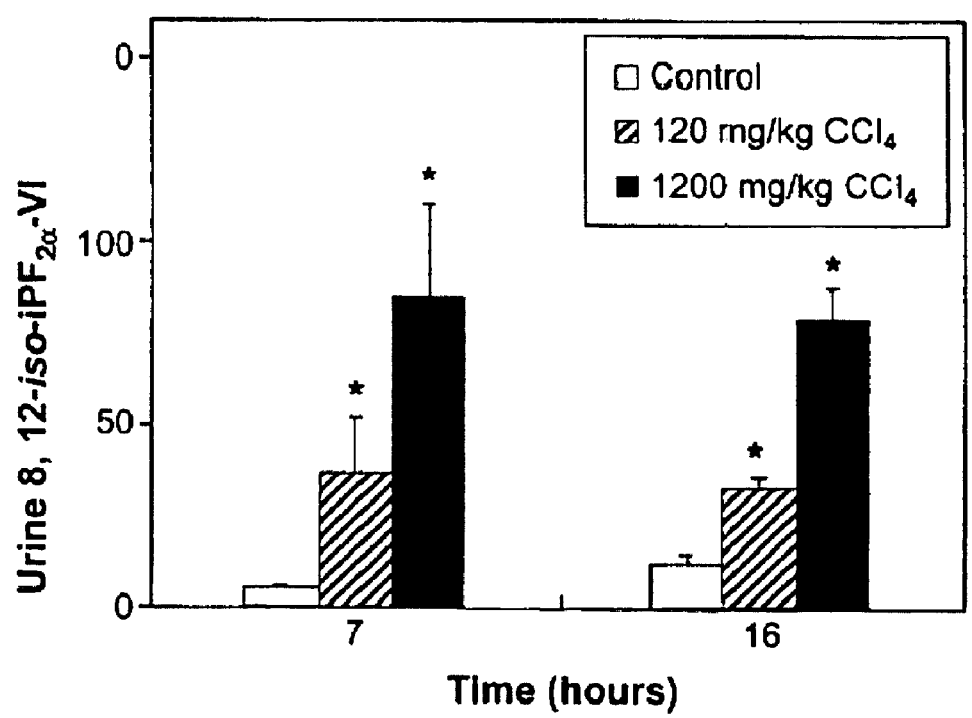
FIG. 5 is a graph depicting the effect of $CCl_4$ treatment on urinary 8,12-iso-$iPF_{2\alpha}$-VI concentration measured by LC/MS/MS. Values are the mean±SEM of n=5/group. Asterisks indicate a statistically significant (p<0.05) result relative to respective controls.

Urinary 8-iso-PGF$_{2\alpha}$, when measured by an immunoassay, exhibited statistically significant increases for both CCl$_4$ doses at both time points (Table 2, FIG. 4). The high dose resulted in 10-fold and 6-fold increases at the two successive time points. When measured by LC/MS/MS, urinary 8,12-iso-iPF$_{2\alpha}$-VI also exhibited a statistically significant increase at both CCl$_4$ doses at both time points (Table 2, FIG. 5). The high dose resulted in 17-fold and 7-fold increases at the two time points.

Protein Oxidation Products in Plasma and Urine

Several protein oxidation products were measured in plasma using a variety of methods. The plasma protein carbonyl content tended to increase only at the higher dose of CCl$_4$ at 2 hours and 7 hours after injection, but the differences were not statistically significant compared to controls (Table 1). The methionine sulfoxide levels in plasma proteins was not affected by either dose of CCl$_4$ at any time point studied (Table 1).

Various tyrosine products of oxidation measured in plasma (3-nitro-, di-, ortho-, meta-, 3-chloro-, 3-4 DOPA) were either difficult to detect or unchanged as, for example, bound 3-nitrotyrosine, which was not increased by either CCl$_4$ doses at any time point studied (Table 1).

An attempt was made to measure and quantify levels of o,o'-dityrosine in the urine. However, o,o'-[$^{14}$C] dityrosine added as an internal standard was also undetectable in the samples, indicating that something in the urine was interfering with the analysis. Because of this interference, it was not possible to interpret urinary levels of o,o'-dityrosine in these experiments.

DNA Oxidation Products in Blood and Urine

Three assays were used to measure changes in oxidation products of DNA: the Comet assay was utilized for leucocyte DNA strand breaks, GC/MS analysis for levels of leucocyte MDA-DNA adduct (M$_1$G), and urinary-8-OHdG was determined by an immunoassay.

The results of the Comet assay, presented as the percentage of migrated DNA, tail length (from the leading edge of the head) and tail moment (% migrated DNA×tail length) exhibited a statistically significant increase only at the low dose of CCl$_4$ at 16 hours. For the other time points, the Comet assay provided no evidence of DNA changes as a result of CCl$_4$ treatment.

Samples of leucocyte DNA proved insufficient to analyze the major product, malondialdehyde-deoxyguanosine adduct (MDA-M$_1$G). Therefore, individual samples were pooled and one measurement was made for each dose and time point. Statistics were thus not applicable; however, there was no discernible pattern in the pooled results.

Significant differences in urinary excretion of 8-OHdG were observed between the control and CCl$_4$-treated animals for the low dose at 16 hours and high dose at both times after treatment (Table 2). The high dose resulted in a 7-fold and 3-fold increase at the two successive time points.

Clinical Parameters

Determination of serum enzyme activities has been used for decades as an index of liver toxicity. The activities of liver enzymes in serum have been found to correlate the biomarker concentration in plasma/urine with the toxic effect of CCl$_4$ on the liver (Kadiiska et al., 2000, Free Radic. Biol. Med. 28: 838-845). A significant increase in many of the enzyme activities studied was observed at the high dose at 2 hours and for both doses at 7 and 16 hours (Kadiiska et al., 2000, Free Radic. Biol. Med. 28: 838-845). It was also found that plasma iron concentrations and total iron binding capacity were significantly increased only at the high dose at 16 hours.

The hepatic effects of treatment with both doses of CCl$_4$ were histologically apparent by diffuse hepatocyte degeneration and infiltration of inflammatory cells associated with necrosis. This was evident at each time point after treatment, particularly after the high dose was administered (Kadiiska et al., 2000, Free Radic. Biol. Med. 28: 838-845). The time course of changes in plasma nitrite/nitrate concentration after CCl$_4$ administration was evaluated to determine if evidence of inflammation coincident with CCl$_4$-induced liver injury was apparent. Nitrite/nitrate levels were significantly increased only at the high dose at all three time points, whereas the lower CCl$_4$ dose did not result in any significant changes.

In summary, the time-dependent (2, 7, and 16 hours) and dose-dependent (120 and 1200 mg/kg ip) effects of CCl$_4$ on concentrations of lipid hydroperoxides, TBARS, malondialdehyde (MDA), isoprostanes, protein carbonyls, methionine sulfoxidation, tyrosine products, 8-hydroxy-2'-deoxyguanosine (8-OHdG), leucocyte DNA-MDA adducts and DNA-strand breaks, were investigated to determine whether the oxidative effects of CCl$_4$ would result in increased generation of these oxidation products. Plasma concentrations of MDA and isoprostane 8-iso-PGF$_{2\alpha}$ (both measured by GC/MS), and urinary concentrations of isoprostanes (measured as 8-iso-PGF$_{2\alpha}$ by immunoassay or as 8,12-iso-iPF$_{2\alpha}$-VI by LC/MS/MS) were increased in both low-dose and high-dose CCl$_4$-treated rats, at more than one time point. The other urinary markers (MDA and 8-OHdG) exhibited significant elevation with treatment at 3 of the 4 conditions tested. It is concluded that measurements of MDA and isoprostane in plasma and urine as well as 8-OHdG in urine are potential candidates for general biomarkers of oxidative stress. All other products were not changed by CCl$_4$ or exhibited sufficiently fewer significant effects so as not to be useful as biomarker for oxidative stress.

Experimental Example 2

Effects of the Non-Steroidal Anti-Inflammatory Agents Indomethacin and Meclofenamic Acid on Measurements of Oxidative Products of Lipids in CCl$_4$ Poisoning MDA is a product of both free radical-initiated lipid peroxidation and the enzymatic activity of thromboxane synthase. The latter converts the COX-generated unstable endoperoxide intermediate prostaglandin (PG)H$_2$ in equimolar quantities to thromboxane A$_2$ and to 15-hydroxyheptadecatrienoate and MDA (Dejana et al., 1980, Br. J. Haematol. 46: 465-469; Hsu et al., 1999, J. Bio. Chem. 274(2):762-769;

Dannhardt et al., 1998, Archiv der Pharmazie 331(11):359-364). There is evidence for COX participation in the production of one of the isoprostanes, 8-iso-PGF$_{2\alpha}$ (Pratico et al., 1995, J. Biol. Chem. 270: 9800-9808; Bachi et al., 1997, Br. J. Pharmacol. 121: 1770-1774; Klein et al., 1997, J. Pharmacol. Exp. Ther. 282: 1658-1665; Schweer et al., 1997, J. Mass Spectrometry 32: 1362-1370; Basu, 1999, Biochem. Biophys. Res. Commun. 254: 764-767). In this regard, it has been previously reported that the COX enzyme can catalytically generate small amounts of the isoprostane 8-iso-PGF$_{2\alpha}$, although the majority of studies suggest that COX does not significantly contribute to the formation of this compound in urine in normal humans or animals (Vatella et al., 1995, Adv. Prostaglandin, Thromboxane, Leucotriene Res. 23: 233-235; Morrow, 2000, Drug. Metab. Rev. 32: 377-385; Pratico et al., 1996, J. Biol. Chem. 271: 14916-14924; McAdam et al., 2000, J. Clin. Invest. 105: 1473-1482; Reilly et al., 1996, Circulation 94: 19-25).

Plasma and urinary levels of malondialdehyde-like products (MDA) and isoprostanes were identified in Experimental Example 1 as markers of in vivo lipid peroxidation in an animal model of CCl$_4$ poisoning.

In Experimental Example 2, experiments were designed to determine the extent to which the formation of these oxidation products was influenced by inhibition of the COX enzymes which catalytically generate pro-inflammatory lipid peroxidation products known as prostaglandin and thromboxane. Specifically, the effects of indomethacin and meclofenamic acid on the formation of MDA and isoprostanes in a rodent model of CCl$_4$-induced oxidant stress (Kadiiska et al., 2005, Free Radic. Biol. Med. 38: 698-710). Based on previous reports, the free radical-mediated formation of isoprostanes and MDA occurs via non-enzymatic mechanisms. However, MDA and the specific isoprostane 8-iso-PGF$_{2\alpha}$ can also be generated under certain conditions via the catalytic activity of the cyclooxygenases. Because NSAIDs are widely used as anti-inflammatory agents, the experiments in this example were designed to determine the effect of NSAIDs on oxidant stress as quantified by the formation of isoprostanes and MDA. The experimental design also included examination of whether inhibition of the formation of these products was due to blockade of the catalytic activity of COX or was related to a decrease of free radicals formed via these enzymes.

Materials, experimental treatment of the animals, specimen collection, and methods for Experimental Example 2 are described herein in Experimental Example 1.

In an additional method not recited in Example 1, an immunoassay was used to measure the sum of free plus esterified 8-iso-PGF$_{2\alpha}$. The immunoassay used anti-8-iso-PGF$_{2\alpha}$ antibody was developed by Assay Designs, Inc., Ann Arbor, Mich., and performed at Oxis Research, Portland, Oreg.

The results of the experiments presented in this Experimental Example are now described.

Oxidation Products of Lipids in Plasma

Figure 6:
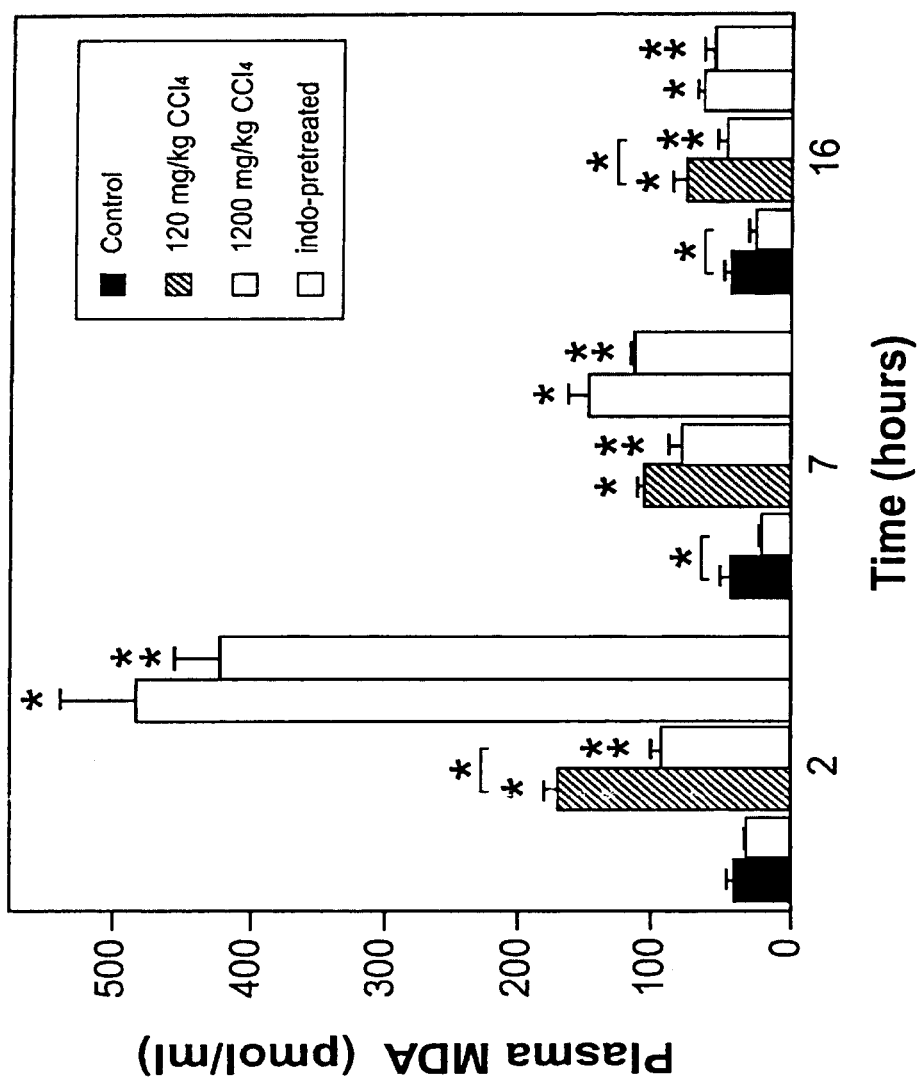
FIG. 6 is a graph depicting the effect of indomethacin pretreatment and $CCl_4$ treatment on plasma MDA concentration measured by GC/MS. Values are the mean±SEM of n=5/group. Asterisks indicate statistically significant (p<0.05) result relative to respective comparison groups. Differences between values marked * vs. control; ** vs. indomethacin pretreated controls; ⌐ non-pretreated vs. indomethacin-pretreated.

Compared to the corresponding controls, MDA plasma levels measured by GC/MS were significantly increased by CCl$_4$ in both indomethacin-pretreated and non-pretreated rats (FIG. 6). When pretreated rats were compared to non-pretreated rats, indomethacin caused a statistically significant decrease in both the controls measured at 7 and 16 hours, and also in the groups treated with the lower dose of CCl$_4$ measured at the 2 and 16 hour time points (FIG. 6). Levels were similarly decreased by indomethacin pretreatment when the method used to determine plasma MDA was third derivative spectroscopy.

Figure 7:
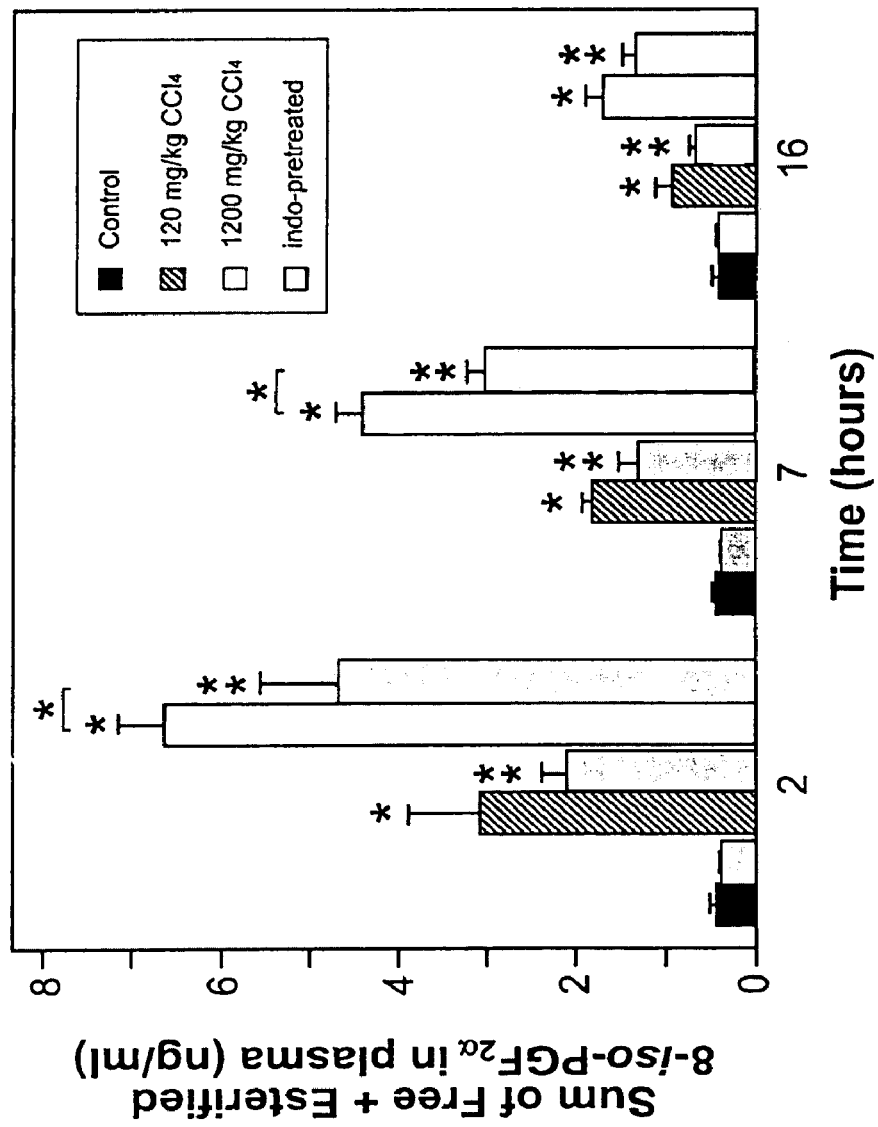
FIG. 7 is a graph depicting the effect of indomethacin pretreatment and $CCl_4$ treatment on plasma free plus esterified 8-iso-$PGF_{2\alpha}$ concentration measured by GC/MS. Values are the mean±SEM of n=5/group. Asterisks indicate statistically significant (p<0.05) result relative to respective comparison groups. Differences between values marked * vs. control; ** vs. indomethacin pretreated controls; ⌐ non-pretreated vs. indomethacin-pretreated.

The concentration of free plus esterified 8-iso-PGF$_{2\alpha}$ measured in plasma by GC/MS in the indomethacin pretreated animals had a similar time- and dose-dependent pattern to the non-pretreated animals (FIG. 7). Administration of indomethacin prior to treatment with CCl$_4$ resulted in statistically significant suppression of plasma levels of the compounds only at the higher CCl$_4$ dose measured at the 2 hour and 7 hour time points (FIG. 7). A similar suppression of free 8-iso-PGF$_{2\alpha}$ was observed at the high dose at all time points, although it was not statistically significant.

Figure 8:
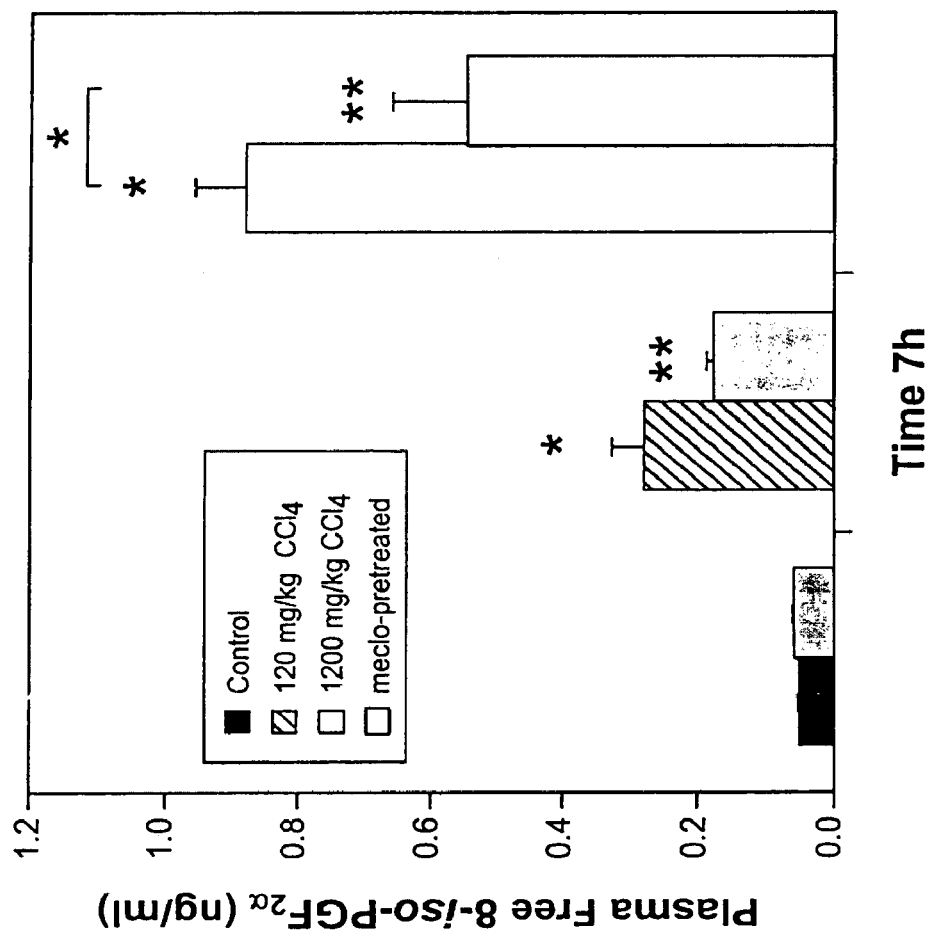
FIG. 8 is a graph depicting the effect of meclofenamic acid pretreatment and $CCl_4$ treatment on plasma free 8-iso-$PGF_{2\alpha}$ concentration measured by GC/MS 7 h after $CCl_4$. Values are the mean±SEM of n=6/group. Asterisks indicate statistically significant (p<0.05) result relative to respective comparison groups. Differences between values marked * vs. control; ** vs. meclofenamic acid pretreated controls; ⌐ non-pretreated vs. meclofenamic acid-pretreated.

Meclofenamic acid pretreatment caused a significant decrease of free 8-iso-PGF$_{2\alpha}$ only at the higher CCl$_4$ dose at 7 h for free 8-iso-PGF$_{2\alpha}$ (FIG. 8). The effect on free plus esterified 8-iso-PGF$_{2\alpha}$ was similar.

Oxidation Products of Lipids in Urine

Figure 9:
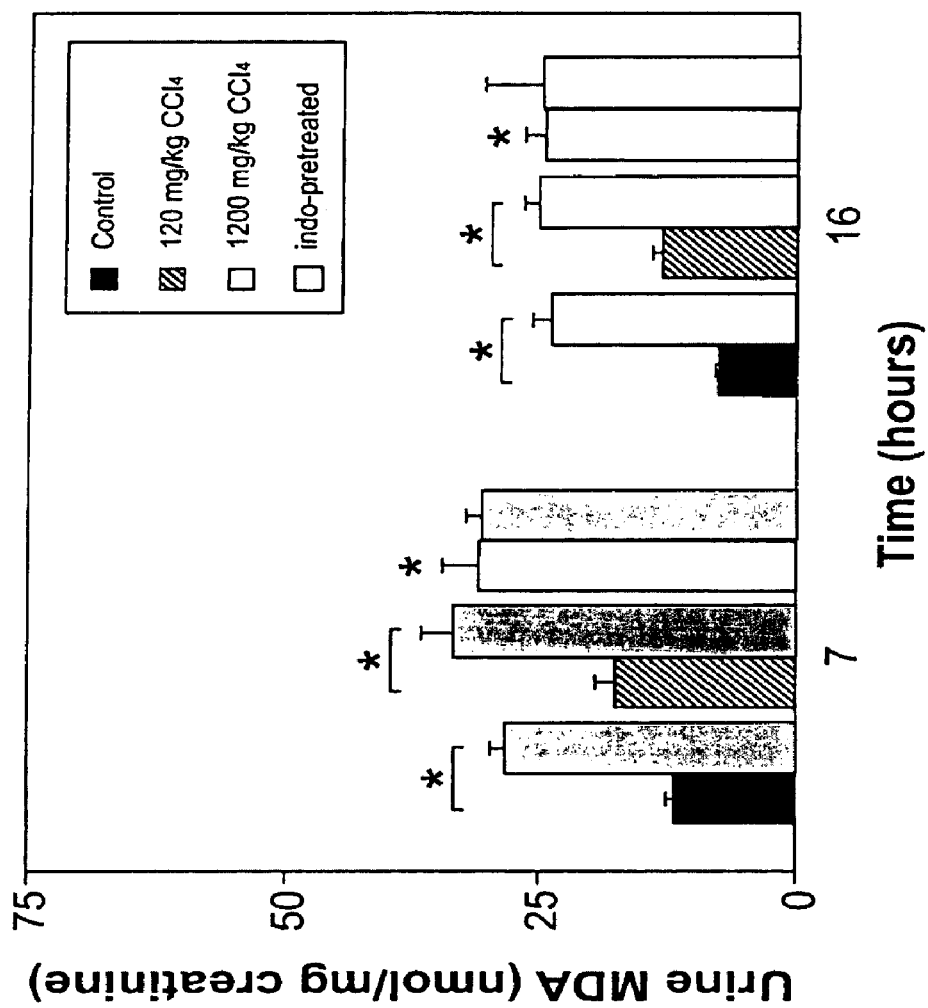
FIG. 9 is a graph depicting the effect of indomethacin pretreatment and $CCl_4$ treatment on urinary MDA concentration measured by HPLC with spectrophotometry. Values are the mean±SEM of n=5/group. Asterisks indicate statistically significant (p<0.05) result relative to respective comparison groups. Differences between values marked * vs. control; ** vs. indomethacin pretreated control; ⌐ non-pretreated vs. indomethacin-pretreated.
Figure 10:
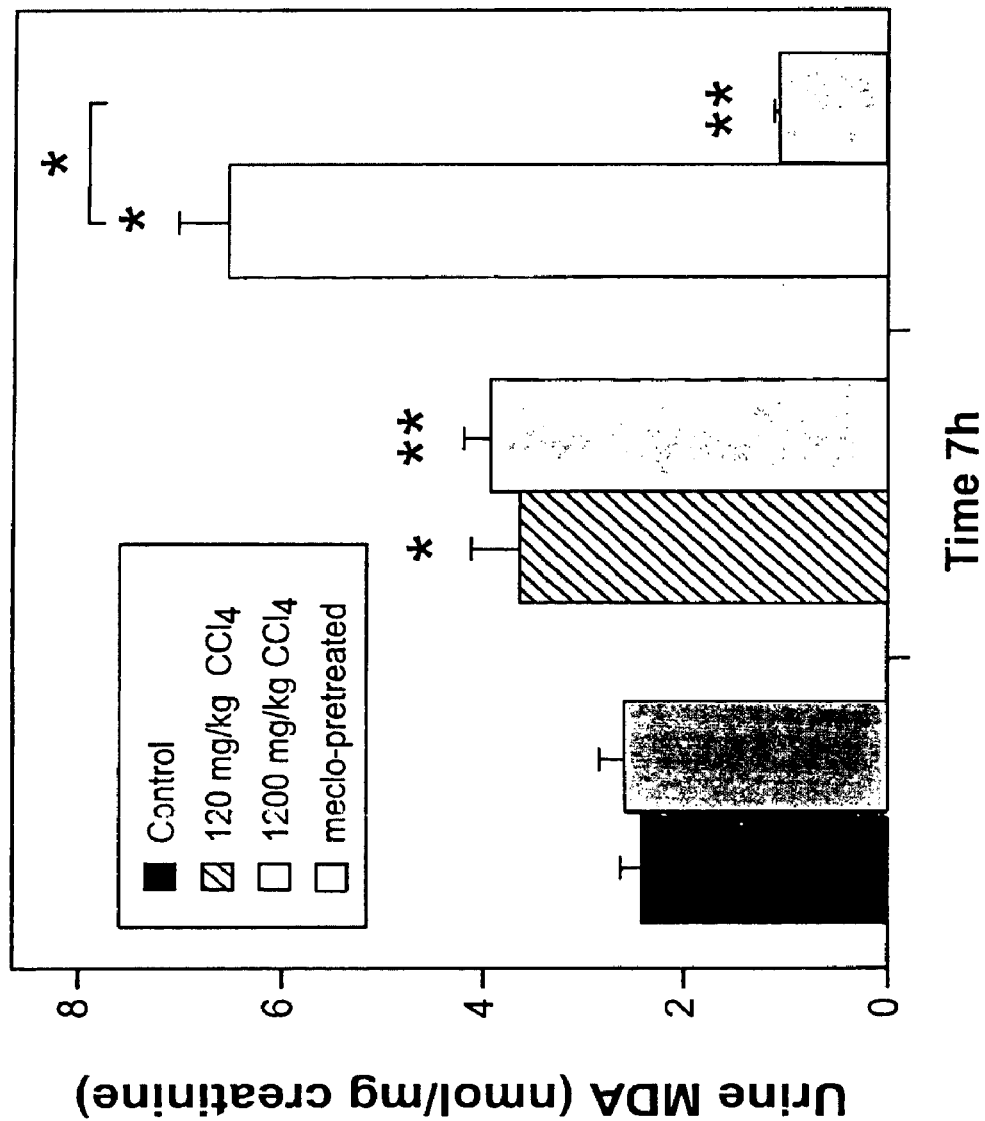
FIG. 10 is a graph depicting the effect of meclofenamic acid pretreatment and $CCl_4$ treatment on urinary MDA concentration measured by HPLC with spectrophotometry 7 h after $CCl_4$. Values are the mean±SEM of n=6/group. Asterisks indicate statistically significant (p<0.05) result relative to respective comparison groups. Differences between values marked * vs. control; ** vs. meclofenamic acid pretreated controls; ⌐ non-pretreated vs. meclofenamic acid-pretreated.

The concentration of MDA increased in urine collected at 7 hours and 16 hours after administration of high doses of CCl$_4$ to the rats (FIG. 9). The highest MDA levels were observed in rats dosed with the higher dose of CCl$_4$ in urine excreted 7 hours after treatment. Unexpectedly, indomethacin pretreatment of the controls and low-dose CCl$_4$ treated rates resulted in an increase in MDA excretion in the urine at both time points compared to animals not treated with indomethacin (FIG. 9). Thus, CCl$_4$ did not result in any statistically significant changes in urinary MDA after indomethacin pretreatment (FIG. 9). Following meclofenamic acid pretreatment, urinary MDA increased only at the low dose of CCl$_4$, whereas the higher dose caused significant inhibition in urinary MDA (FIG. 10).

Figure 11:
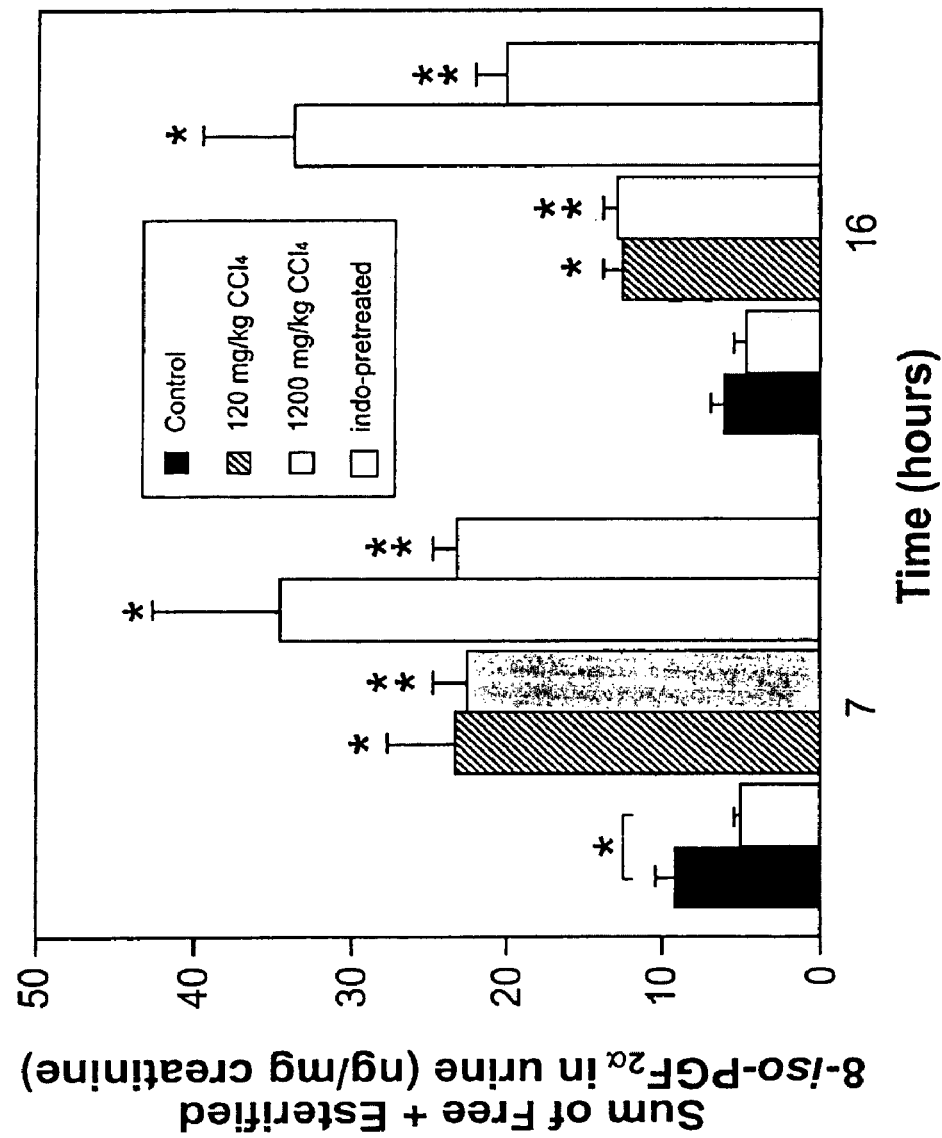
FIG. 11 is a graph depicting the effect of indomethacin pretreatment and $CCl_4$ treatment on urinary free plus esterified 8-iso-$PGF_{2\alpha}$ concentration measured by immunoassay. Values are the mean±SEM of n=5/group. Asterisks indicate statistically significant (p<0.05) result relative to respective comparison groups. Differences between values marked * vs. control; ** vs. indomethacin pretreated control; ⌐ non-pretreated vs. indomethacin-pretreated.
Figure 12:
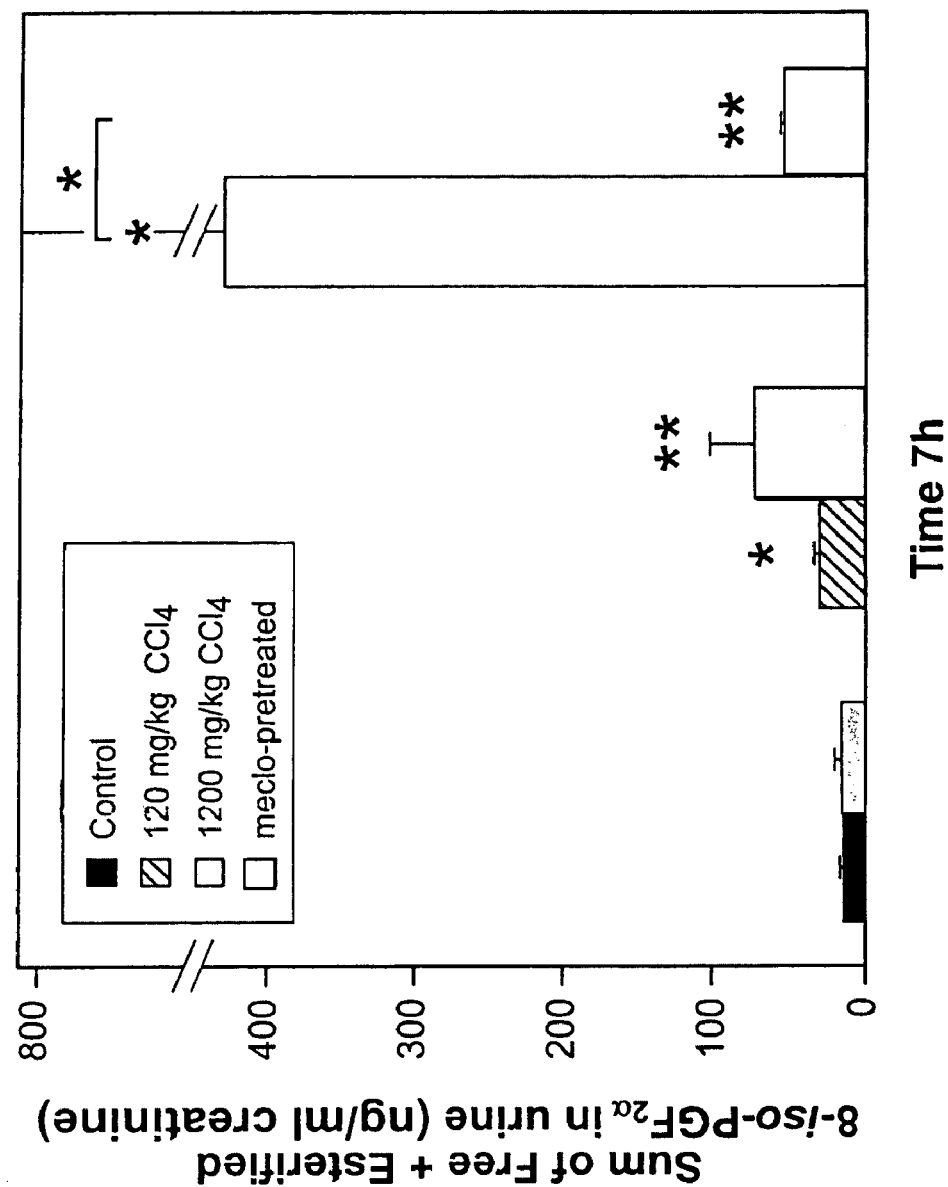
FIG. 12 is a graph depicting the effect of meclofenamic acid pretreatment and $CCl_4$ treatment on urinary free plus esterified 8-iso-$PGF_2$ concentration measured by immunoassay 7 h after $CCl_4$. Values are the mean±SEM of n=6/group. Asterisks indicate statistically significant (p<0.05) result relative to respective comparison groups. Differences between values marked * vs. control; ** vs. meclofenamic acid pretreated controls; ⌐ non-pretreated vs. meclofenamic acid-pretreated.

FIG. 11 illustrates the pattern and extent of the effect of CCl$_4$ on urinary free plus esterified 8-iso-PGF$_{2\alpha}$ as measured in an immunoassay. Significant increases were observed at both CCl$_4$ doses at both time points with or without indomethacin pretreatment as compared to the corresponding controls (FIG. 11). Suppression of this urinary index of isoprostane formation by indomethacin pretreatment was evident in both the controls at the 7 hour time point and at the higher dose of CCl$_4$ at both time points (FIG. 11). Pretreatment with meclofenamic acid also resulted in a significant decrease at the high dose at the 7 hour time point (FIG. 12).

Figure 13:
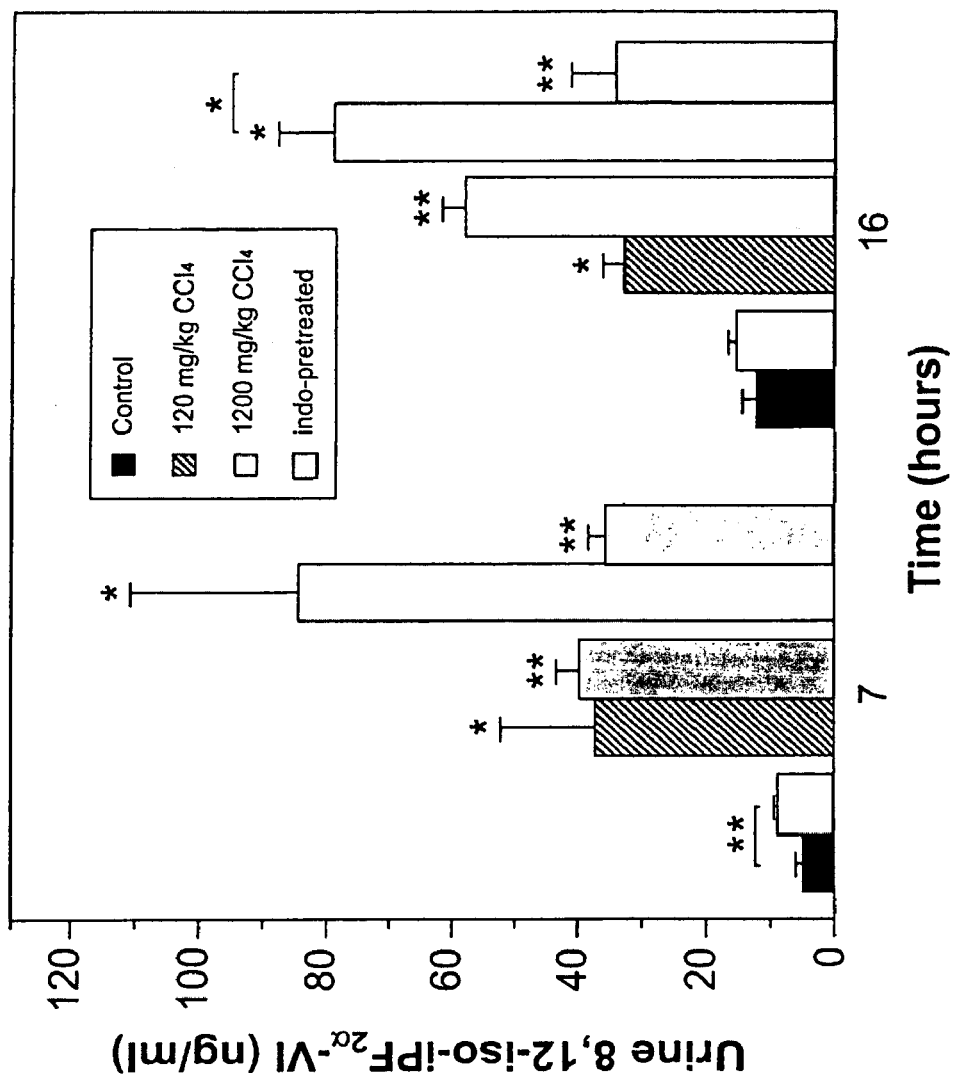
FIG. 13 is a graph depicting the effect of indomethacin pretreatment and $CCl_4$ treatment on urinary 8,12-iso-$iPF_{2\alpha}$-VI concentration measured by LC/MS/MS. Values are the mean±SEM of n=5/group. Asterisks indicate statistically significant (p<0.05) result relative to respective comparison groups. Differences between values marked * vs. control; ** indomethacin-pretreated vs. pretreated control; ⌐ non-pretreated vs. indomethacin-pretreated.
Figure 14:
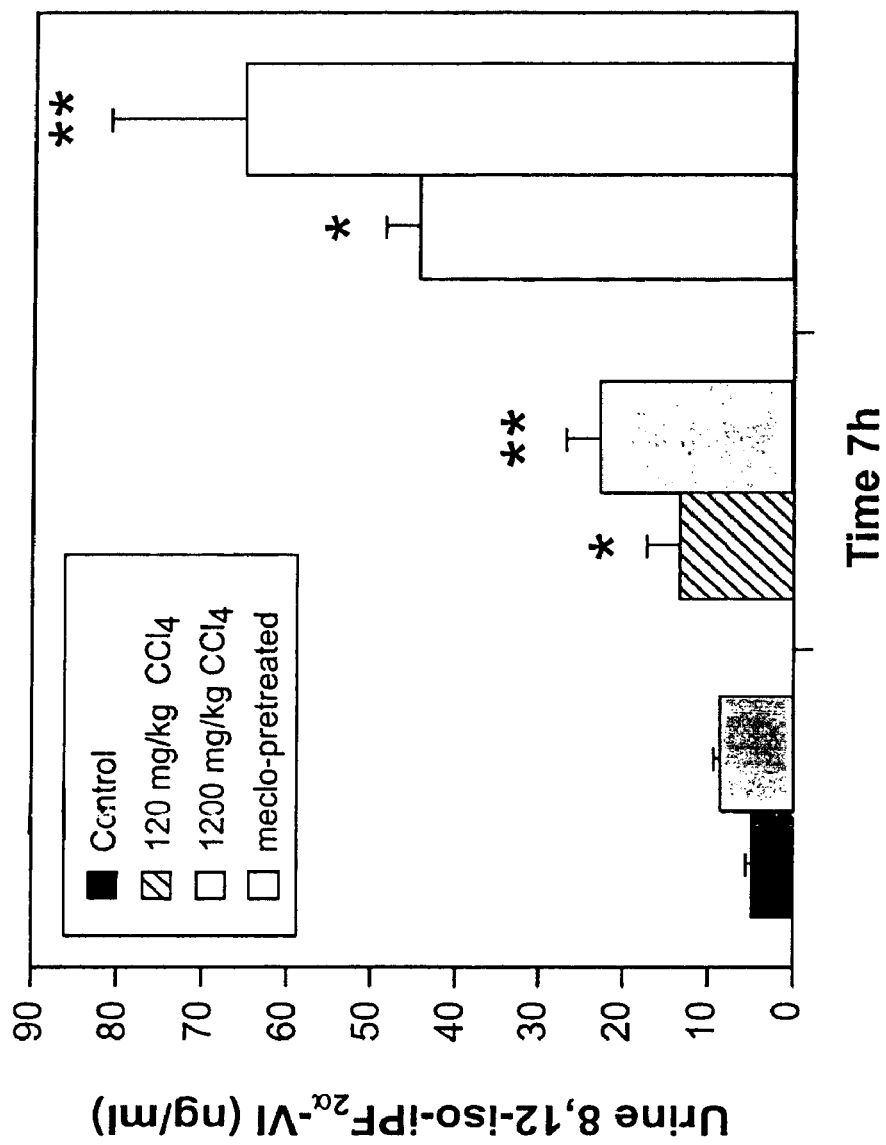
FIG. 14 is a graph depicting the effect of meclofenamic acid pretreatment and $CCl_4$ treatment on urinary 8,12-iso-$iPF_{2\alpha}$-VI concentration measured by LC/MS/MS 7 h after $CCl_4$. Values are the mean±SEM of n=6/group. Asterisks indicate statistically significant (p<0.05) result relative to respective comparison groups. Differences between values marked * vs. control; ** meclofenamic acid-pretreated vs. pretreated control.

As measured by LC/MS/MS, both CCl$_4$ doses at both time points resulted in enhanced excretion of urinary 8,12-iso-iPF$_{2\alpha}$-VI (FIGS. 13 and 14). Indomethacin pretreatment had no effect after low dose CCl$_4$ was administered, but it markedly inhibited excretion of the isoprostane induced by the higher dose of the oxidant (FIG. 13). In the controls at the earlier time point, excretion of 8,12-iso-iPF$_{2\alpha}$-VI was increased. Meclofenamic acid pretreatment, by contrast, increased CCl$_4$-induced 8,12-iso-iPF$_{2\alpha}$-VI in urine (FIG. 14).

Figure 15:
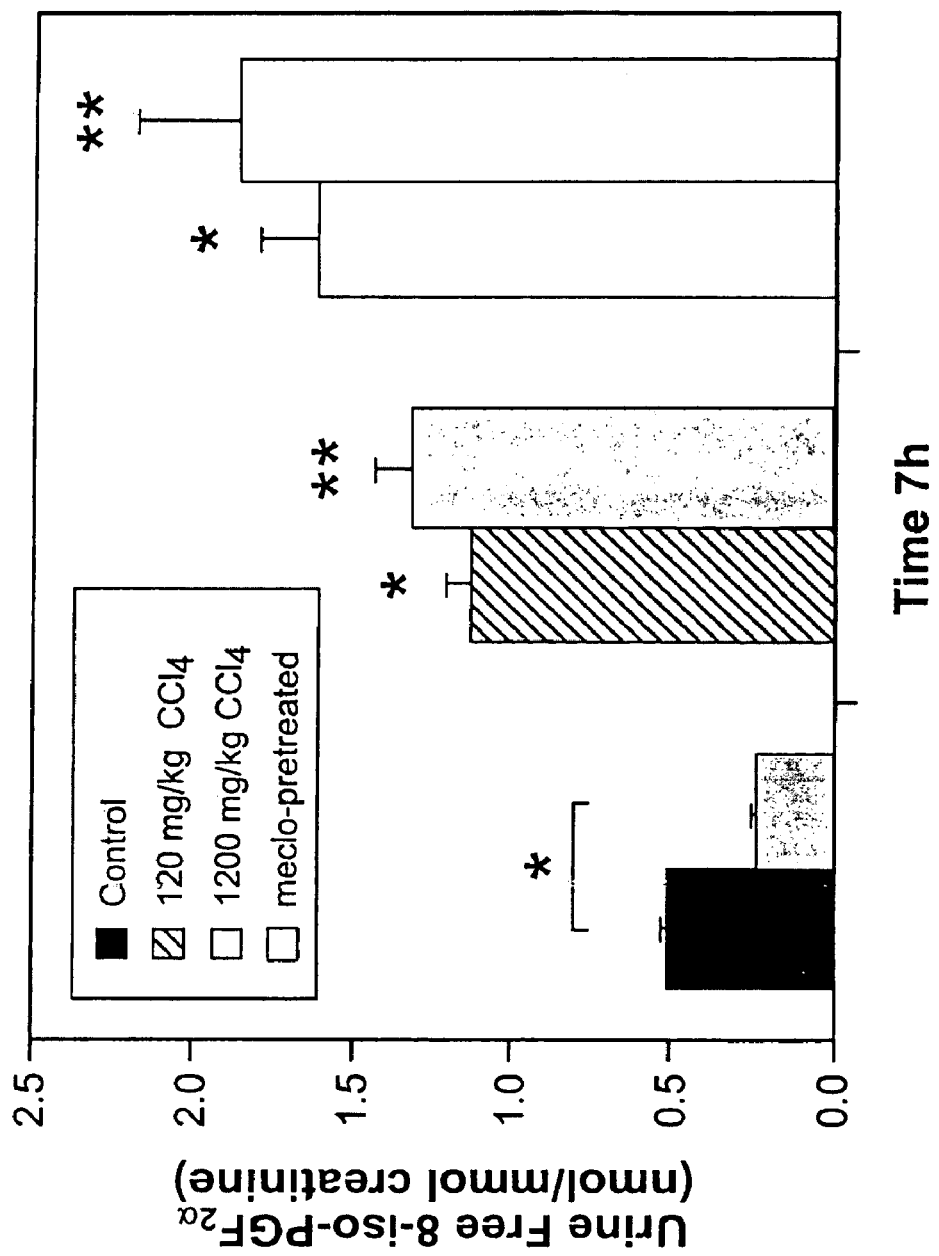
FIG. 15 is a graph depicting the effect of meclofenamic acid pretreatment and $CCl_4$ treatment on urinary free 8-iso-$PGF_{2\alpha}$ concentration measured by radioimmunoassay 7 h after $CCl_4$. Values are the mean±SEM of n=6/group. Asterisks indicate statistically significant (p<0.05) result relative to respective comparison groups. Differences between values marked * vs. control; ** vs. meclofenamic acid pretreated controls; ⌐ non-pretreated vs. meclofenamic acid-pretreated.

A dose-dependent increase in free 8-iso-PGF$_{2\alpha}$ in urine measured by radioimmunoassay was observed after administration of both doses of CCl$_4$ (FIG. 15). Meclofenamic acid-treated rats had lower basal levels of free 8-iso-PGF$_{2\alpha}$ compared to the control group. Enhanced excretion of urinary free 8-iso-PGF$_{2\alpha}$ was found to be statistically significant for both CCl$_4$ doses at the 7 hour time point. Meclofenamic pretreatment increased free 8-iso-PGF$_{2\alpha}$ in urine at both doses of CCl$_4$ (FIG. 15).

In summary, the data in this Experimental Example demonstrate that after induction of oxidant stress in rats with CCl$_4$, the lipid peroxidation products plasma MDA and F$_2$-isoprostanes are significantly decreased by pretreatment with cyclooxygenase inhibitors. However, even after pretreatment, these markers still respond significantly, related to both the dose and timing of $CCl_4$. The results of experiments assessing these markers measured in urine were more variable.

While not wishing to be bound by theory, it is noted that lowering of isoprostane and MDA formation by either NSAID may not be due primarily to the diminution of COX-catalyzed generation of isoprostanes or MDA. Rather, it may be the result of the suppression of nonenzymatic lipid peroxidation. This possibility is suggested because 8,12-iso-iPF$_{2\alpha}$-VI is also reduced by indomethacin, yet, unlike other isoprostanes and MDA, it is not generated catalytically by the cyclooxygenase. Thus, although the two COX inhibitors tested result in statistically significant effects on the measurements of both isoprostanes and MDA in this study, the results provide evidence that these lipid-degradation products primarily constitute markers of oxidative stress. This result thus supports their use as reliable biomarkers of oxidative stress.

Experimental Example 3

Prostacyclin Confers Atheroprotection on Female Mice

Age-dependent increases in cardiovascular disease are less pronounced in women than in men, but this difference narrows after the menopause (Godsland et al., 1987, Am. Heart J. 114: 1467-503). Estrogen (17-β-Estradiol) treatment retards atherogenesis (Bourassa et al., 1996, Proc. Natl. Acad. Sci. USA 93: 10022-7) and limits the response to vascular injury in animal models (Pare et al., 2002, Circ. Res. 90: 1087-92) and improves impaired endothelial function in hyperlipidemic women (Collins et al., 1995, Circulation 92: 24-30). These observations suggest that estrogens confer atheroprotection. However, the mechanisms involved are largely unknown.

COX-2 catalyzes the formation of PG endoperoxide intermediates which are transformed by prostacyclin synthase (PGIS) to prostacyclin (PGI$_2$), the dominant product of arachidonic acid in macrovascular endothelial cells (Moncada et al., 1976, Nature 263: 663-5). PGI$_2$ inhibits: platelet aggregation, vascular smooth muscle contraction and proliferation (Cheng et al., 2002, Science 296: 539-541), leukocyte-endothelial cell interactions (Della Bella et al., 2001, Prostaglandins 65: 73-83) and cholesteryl ester hydrolase (Gryglewski et al., 1995, Ann. N.Y. Acad. Sci. 748: 194-206; discussion 206-7). These properties are of potential relevance to atheroprotection.

Turbulent flow, in contrast to laminar shear stress, fails to increase endothelial expression of COX-2 (Topper et al., 1996, Proc. Natl. Acad. Sci. USA 93: 10417-22). Thus, defective expression of COX-2/PGIS dependent PGI$_2$ may predispose to focal atherogenesis in vivo. This may have particular relevance to atheroprotection in females as estrogen increases expression of COX-2 in vascular tissues and augments PGI$_2$ production (Akarasereenont et al., 2000, Inflamm. Res. 49: 460-5).

The materials and methods used in the experiments presented in this Experimental Example are now described.

Generation and use of LDL receptor and PGI$_2$ receptor double knock out (DKO) mice: The protocol was approved by the Institutional Animal Care and Usage Committee. PGI$_2$ receptor knock outs (IPKOs) were generated as described (Collins et al., 1995, Circulation 92: 24-30). Female LDL receptor KOs (LDLR KOs) were obtained from Jackson Laboratories (Bar Harbor, Me.; 10th generation back-crossed from 129/B6F1 heterozygous to C57 B1/6). DKO mice were generated using a simple breeding strategy and were fed a high fat, Western-type diet (0.2% cholesterol, 21% saturated fat; formula TD88137, Harlan Teklad, Madison, Wis.) from six weeks of age. The diet was replaced every three days.

After three months, half of the mice were euthanized by overexposure to $CO_2$. Those remaining were fed for a further three months to examine the role of PGI$_2$ at both early and late stages of atherosclerosis. Samples were collected at baseline and approximately every four weeks until sacrifice. Mice were bled from the abdominal vena cava to collect blood for cholesterol and HDL measurements. Total cholesterol (mg/dL) and HDL (mg/dL) levels were determined by colorimetric assays (Sigma-Aldrich, St. Louis, Mo.).

Quantitation of atherosclerosis: The aorta was perfused for 10 minutes with PBS by inserting a cannula into the left ventricle and allowing free efflux from an incision in the vena cava. The vessel was opened longitudinally from the aortic root to the iliac bifurcation after removal of the surrounding adventitial tissue and fixed overnight at 4° C. in 10% phosphate buffered formalin (Fisher Scientific, Atlanta, Ga.). Finally, aortas were stained with Sudan IV (Sigma-Aldrich, St. Louis, Mo.). The extent of atherosclerosis was determined using the en face method (Morishita et al., 1990, J. Clin. Invest. 86: 1885-91). Aortic images were captured with a Dage-MTI 3CCD three-chips color video camera connected to a Leica MZ12 dissection microscope (Morishita et al., 1990, J. Clin. Invest. 86: 1885-91).

Urinary 2,3-dinor thromboxane B$_2$, Urinary 2,3-dinor-6-keto PGF$_{1\alpha}$ and 8,12-iso-iPF$_{2\alpha}$-VI: Urine was collected over a 24 hour period in metabolic cages (Nalgene Labware, Deepwater, N.J.) with water ad libitum. The 2,3-dinor thromboxane B$_2$ (2,3-dinor TxB$_2$) metabolite was measured by stable dilution isotope reverse phase (C18) HPLC/MS/MS assay. Urinary 2,3-dinor-6-keto PGF$_{1\alpha}$ was also measured by a stable isotope dilution method using gas chromatography/mass spectrometry (GC/MS) (Murata et al., 1997, Nature 388: 678-82). Urinary 8,12-iso-iPF$_{2\alpha}$-VI was measured by GC/MS (Kowala et al., 1993, Arterioscler. Thromb. 13: 435-44). A urine aliquot (0.1 mL) was used for measurement of creatinine by an automated colorimetric assay (Sigma-Aldrich Co., St Louis, Mo.).

Mouse aortic smooth muscle cells (MASMCs): Primary aortic smooth muscle cells were prepared. Animals were euthanized by overexposure to $CO_2$, the thorax opened and a section of aorta dissected and excised. The adventitia and endothelium were removed and placed smooth muscle side down on tissue culture plates at 37° C. Explants of smooth muscle cell were evident within one week. Cells were cultured in Dulbecco's Modified Eagles medium (DMEM)/Ham's F12 (50/50) (Gibco BRL, Grand Island, N.Y.; with 15 mM HEPES and 2 mM glutamine) supplemented with 20% fetal bovine serum. Cells were routinely passaged using 0.05% trypsin/0.53 mM EDTA, seeded onto six well plates and used at 80-90% confluence, between passages five to nine.

Human Embryonic Kidney (HEK) cells: HEK 293 cells (American Type Tissue Culture Collection, Rockville, Md.) were maintained in Dulbecco's modified Eagles medium (DMEM) (Gibco BRL, Grand Island, N.Y.) supplemented with 10% fetal bovine serum, 50 units/ml penicillin, 50 μg/ml streptomycin, 25 mM HEPES, and 2 mM glutamine. Cells were routinely passaged using 0.05% trypsin/0.53 mM EDTA, seeded onto six well plates and used at 80-90% confluence. HEK were transfected with the human IP as previously described (Smyth et al., 2000, J. Biol. Chem. 275: 32037-45). Stably-transfected cells were selected in G418 (1.5 mg/ml, Gibco BRL, Grand Island, N.Y.), expanded and expression maintained in 1 mg/ml G418. Cells were lysed in RIPA (RIPA: 50 mM Tris, 5 mM EDTA, pH 8.0, containing 150 mM NaCl, 1% Nonidet P-40, 0.1% SDS, 0.5% deoxycholic acid, 1 tablet/50 ml complete protease inhibitor mixture) by drawing them through a 23 gauge needle six times and the resultant lysed cell solution was centrifuged at 14,000 rpm at 4° C. Protein concentration was determined by Micro BCA protein assay (Pierce, Rockford, Ill.). Cells were washed twice with RPMI serum free, phenol red free medium and then pre-incubated in 1 ml RPMI serum free medium for 1 hour.

Hydrogen peroxide and cicaprost treatments: Hydrogen peroxide ($H_2O_2$) (Sigma-Aldrich, St. Louis, Mo.) was added to the pre-incubation medium to a final concentration of 100 µM and after incubation for 30 minutes at 37° C., 1 ml samples were removed and stored at –80° C. until time of analysis. Cells were lysed in RIPA and protein concentration determined by Micro BCA protein assay as described. Cicaprost (100 nM, Schering A G, Berlin, Germany by agreement) was added to MASMC medium just prior to addition of $H_2O_2$.

Dichlorofluorescein (DCFH) fluorescence: DCFH is a fluorescent probe used to detect reactive oxygen species in cultured cells (Dowd et al., 2001, J. Clin. Invest. 108: 585-90). Cells were pre-loaded with DCHF for 30 minutes and then challenged with $H_2O_2$ (100 µM) for a further 30 minutes. Thereafter, they were washed in PBS and viewed under microscope.

Heme oxygenase 1 (HO 1) Western Blotting: A polyclonal rabbit anti-heme oxygenase 1 (HO 1, ~32 kDa) was purchased from Stressgen Biotechnologies, Victoria, BC, Canada. MASMCs were treated with 100 nM cicaprost for 8 hours in RPMI vehicle at 37° C. Control cells were treated with vehicle for the same time period. Cells were lysed in RIPA and protein concentration determined by Micro BCA protein assay as described. Protein isolated from aortae of high fat fed mice was quantitated by the BioRad DC assay for Western Blotting.

COX-2 and IP detection: Proteins from MASMC lysates (50 mM Tris/5 mM EDTA, pH 8.0, containing 150 mM NaCl, 1% NP40, 0.1% SDS, 0.5% deoxycholic acid, Complete Protease Inhibitor cocktail) were resolved by SDS-PAGE and transferred to nitrocellulose. COX-2 and IP were visualized by immunoblotting with specific polyclonal primary antibodies (Cayman Chemicals, Ann Arbor, Mich.). Antibody/antigen complexes were revealed with an anti-rabbit antibody conjugated to horse radish peroxidase (Jackson Laboratories). b-actin staining (Novus Biologicals, Littleton, Colo.) was used as an internal loading control.

Treatment of Cells with $E_2$ (17-β-Estradiol)

Short term treatment with $E_2$: Cells were washed twice rinsing with RPMI serum free medium and then pre-incubated in 1 ml RPMI serum free medium for 1 hour. $E_2$ was added to the pre-incubation medium to a final concentration of $10^{-8}$ M. $E_2$ incubations were performed in the absence or presence of 100 µM $H_2O_2$ for 30 minutes at 37° C. Samples were removed and stored at –80° C. until time of analysis. Cells were lysed in RIPA buffer as described and the protein concentration determined by Micro BCA assay.

Long term treatment with $E_2$: Cells were washed twice with RPMI serum free medium and treated with or without $E_2$ at a final concentration of 1-8 M. After 18 hours at 37° C., samples were removed and stored at –80° C. until time of analysis. Cells were lysed in RIPA buffer as described and the protein concentration determined by Micro BCA assay.

The stable hydrolysis product of $PGI_2$, 6-keto-$PGF_{1\alpha}$, was measured in conditioned medium by stable dilution isotope reverse phase HPLC/MS/MS assay (Huo et al., 2003, Nat. Med. 9: 61-7). The 8,12-iso-$iPF_{2\alpha}$-VI was analyzed in 1 ml conditioned medium, adjusted to pH 3, using the same method described for urine samples.

In vivo estrogen administration studies: Ovariectomized mice (C57 B16 and LDLR KO, obtained from Jackson Laboratories, Bar Harbor, Me.), were implanted with subcutaneous slow-release hormone pellets (Innovative Research of America, Toledo, Ohio) designed to release 2, 3 and 8 µg/day of exogenous $E_2$ as 17-β-estradiol. Animals were allowed two weeks to recover from the ovariectomy surgery and then a baseline urine sample was collected prior to pellet administration. After approximately eight days of hormone release, a urine sample was collected for 2,3-dinor-6-keto $PGF_{1\alpha}$ and 8,12-iso-$iPF_{2\alpha}$-VI analyses.

For atherosclerosis studies, LDLR KO and DKO mice were bilaterally ovariectomized at approximately six weeks of age. Approximately seven to ten days after surgery, mice began high fat diet feeding in the absence or presence of exogenous $E_2$ (17-β-Estradiol; 8 µg/day) as above. After three months of high fat feeding, aortae were harvested and prepared for en face analysis.

Estrogen receptor (ER) selective agonists: Selective agonists for the ERα (Propyl Pyrazole Triol, PPT) (Huo et al., 2003, Nat. Med. 9: 61-7) and ERβ (WAY-200070) (Pratico et al., 2000, Blood 96: 3823-6) were a gift from Dr. C. Richard Lyttle and Dr. Heather Harris at Wyeth, Collegeville, Pa. MASMCs were washed twice with RPMI serum free, phenol red free medium and then incubated with either agonist (0.5 µM and 1.0 µM) in RPMI serum free medium (as vehicle). After 24 hours at 37° C., conditioned medium samples were removed and stored at –80° C. until time of analysis. Cells were lysed in RIPA as described and protein concentration determined by Micro BCA protein assay.

ER knock out (ER KO) mice: ER KO mice (ERα KO and ERβ KO) were a kind gift from Dr. Richard Lyttle and Dr. Heather Harris at Wyeth, Collegeville, Pa. ERα KO mice were generated in a C57B16/129 background as described (Lubahn et al., 1993, Proc. Natl. Acad. Sci. USA 90, 11162-6) and ERβ KO were generated in a 129 background (Shughrue, et al., 2002, Endocrinology 143, 1643-50). Ovariectomized females of each genotype, and their respective ovariectomized wild-type controls, were given daily injections of $E_2$ (17-β-Estradiol, 0.4 µg/day for eight days, in a corn oil/aqueous vehicle) or vehicle alone. After seven days, overnight urine samples were collected and samples stored at –80° C. for analysis.

Statistics: Data are expressed as the mean±SEM. Comparisons of multiple groups were performed initially by one or two way analysis of variance (ANOVA), as appropriate. If ANOVA (Kruskal-Wallis) was significant, subsequent pairwise comparisons were performed using Dunn's Multiple Comparisons. When only two groups were compared, a Student's t test was performed, with pairwise analysis when appropriate. Differences were considered statistically significant at $P<0.05$.

The results of the experiments presented in this Experimental Example are now described.

IP Deletion Accelerates Atherogenesis in Female LDLR KOs

Male mice lacking the LDL receptor (LDLR KO) develop atherosclerosis more rapidly on a high-fat diet than female LDLR KO mice (Tangirala et al., 1995, J. Lipid. Res. 36: 2320-8). These mice were used in this Experimental Example to address the role of $PGI_2$ in gender-dependent atheroprotection. No differences in body weight, plasma total or HDL cholesterol were observed among the four experimental groups of mice employed in this Experimental Example (Table 3). Neither total cholesterol nor HDL cholesterol differed significantly in animals at 3 vs. 6 months of age. Body weight increased as the animals aged, but there were no significant differences as a function of genotype.

Figures 16A, 16B, 16C, 16D:
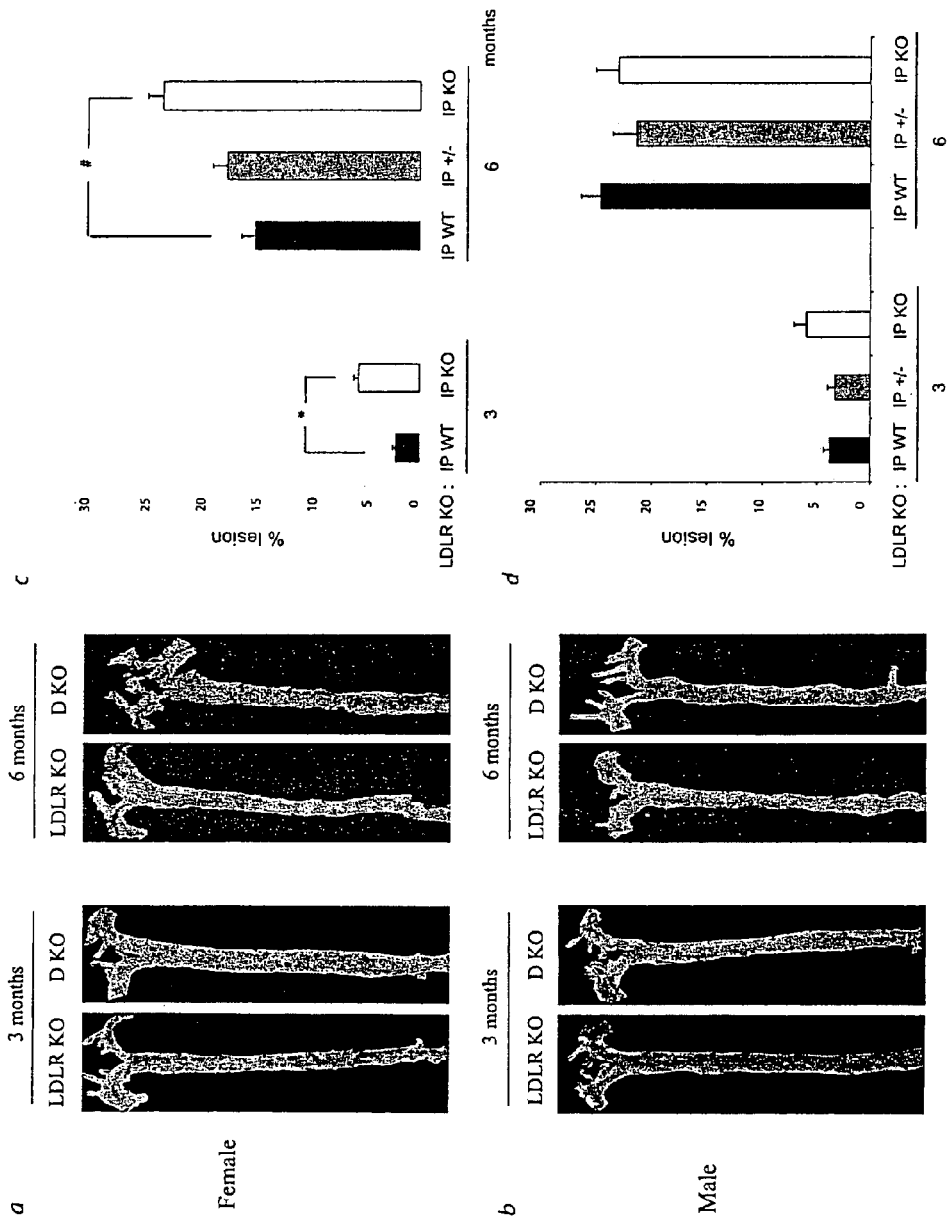
FIG. 16A is a series of images of en face aorta preparations in female LDL receptor (LDLR) knock out (KO) and double knock out (DKO) mice fed a Western-type diet for 3 or 6 months. A DKO mouse is one in which both the LDL receptor and the prostacyclin receptor (IP) have been rendered completely non-functional.
FIG. 16B is a series of images of en face aorta preparations in male LDLR KO and DKO mice fed a Western-type diet for 3 or 6 months. For both FIGS. 16A and 16B, representative en face aortas were chosen that were approximately equal to the mean % lesion area for each treatment group.
FIG. 16C is a graph depicting the percentage of total aortic-lesion areas in female LDLR KO and DKO mice fed a Western-type diet for 3 or 6 months. (*P<0.001 compared to LDLR KO at 3 months; # P<0.05 and 6 months). Data are the mean±SEM, n=10-13 per group.
FIG. 16D is a graph depicting the percentage of total aortic-lesion areas in male LDLR KO and DKO mice fed a Western-type diet for 3 or 6 months. IP +/− indicates one of the two alleles of the gene for the prostacyclin receptor is knocked out.

Analysis of aortas en face revealed that the extent of atherosclerosis was significantly greater at 3 and 6 months in male vs. female LDLR KOs (FIGS. 16A and 16B). IP/LDLR DKO females developed significantly greater aortic lesion areas than LDLR KO females at 3(5.6±1.1% vs. 2.2±0.2%) and 6(23.2±1.4% vs. 15.0±1.2%) months. Furthermore, this effect was gene dose dependent (FIG. 16C). While coincidental deletion of the IP accelerated atherosclerosis in female mice, it did not significantly alter the rate of lesion progression in male LDLR KO mice (FIGS. 16C and 16D). At the early timepoint, there was a trend of greater lesion area in the IP/LDLR DKO males than LDLR KO males (5.95±1.1%, n=12 vs. 3.83±0.5%, n=12), however, this did not reach statistical significance and no such increase was evident at the later timepoint.

Platelet Activation During Atherogenesis

Figures 17A, 17B:
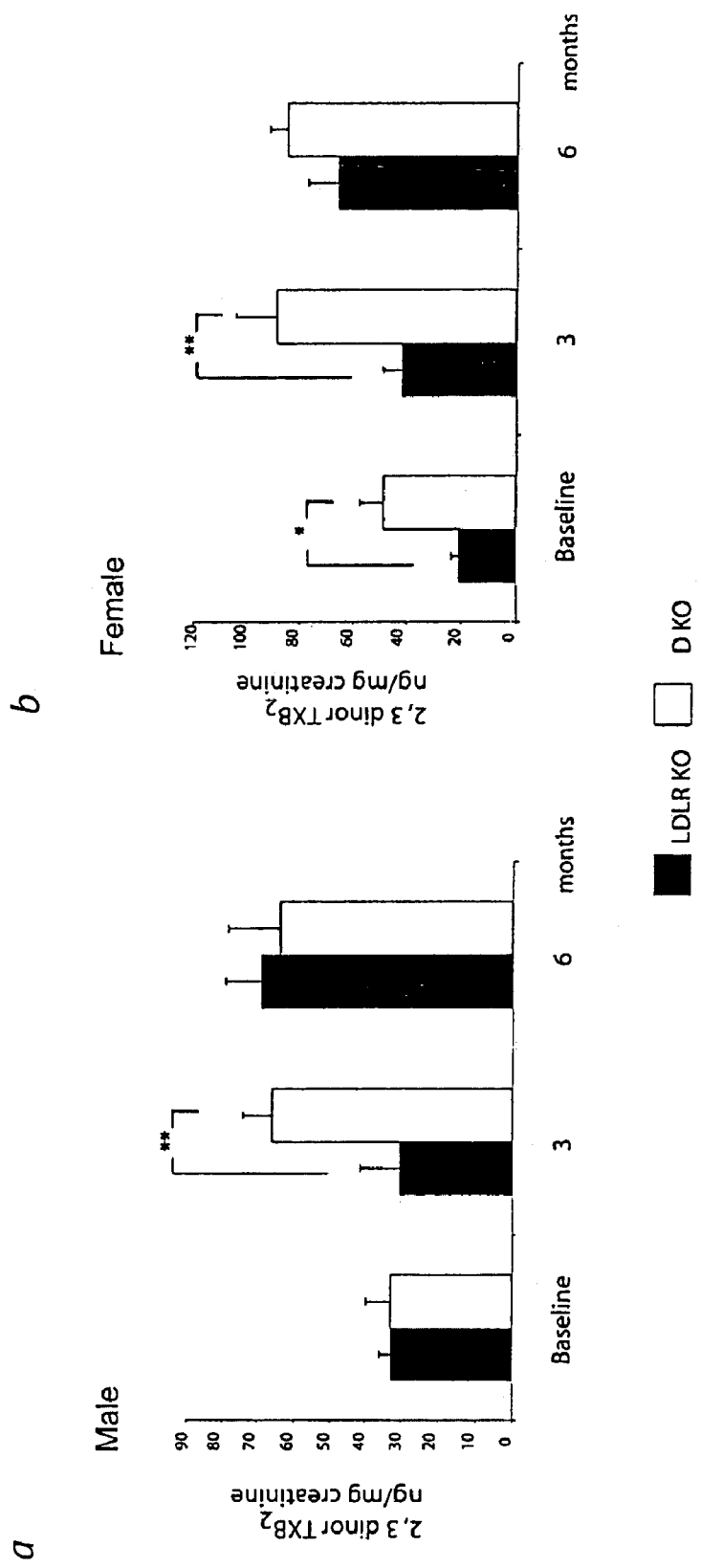
FIG. 17A is a graph depicting the effect of IP deletion on thromboxane biosynthesis in LDLR KO male mice at baseline and after 3 and 6 months feeding on the Western-type diet. (**P<0.01). Data are the mean±SEM.
FIG. 17B is a graph depicting the effect of IP deletion on thromboxane biosynthesis in LDLR KO female mice at baseline and after 3 and 6 months feeding on the Western-type diet. Pairwise comparisons reveal significant differences at baseline (*P<0.05) and at 3 months (**P<0.01). Data are the mean±SEM.

Urinary 2,3-dinor $TxB_2$ reflects platelet activation in vivo. Deletion of the IP augments the excretion of urinary 2,3-dinor $TxB_2$ in response to carotid vascular injury (Cheng et al., 2002, Science 296: 539-541). Consistent with these observations, analysis of variance revealed that deletion of the IP augmented the increase in 2,3-dinor $TxB_2$ (FIGS. 17A and 17B) that coincides with atherogenesis in LDLR KOs (Pratico et al., 2000, Blood 96: 3823-6). This effect was evident in both genders at 3, but not at 6, months of age. Male IP/LDLR DKO mice do not have elevated Tx biosynthesis at baseline. However, upon high fat feeding a significant increase in Tx biosynthesis was observed in the IP/LDLR DKO mice (all males: F=6.14; P<0.01, all females: F=8.17; P<0.01). This is accounted for by a difference after 3 months. While urinary 2,3-dinor $TxB_2$ was higher in male than female LDLR KOs (32.8±3.2 vs. 20.5±3.0 ng/mg creatinine, respectively), deletion of the IP significantly elevated 2,3-dinor $TxB_2$ excretion in the females, so that levels exceeded those in male DKOs at baseline. Pairwise comparisons reveal significant differences at baseline and at 3 months. Thus, prostacyclin modulates, particularly in female mice, the increment in platelet activation that accompanies the early stages of atherogenesis, as reflected by urinary 2,3-dinor $TxB_2$.

Oxidant Stress During Atherogenesis

Figures 18A, 18B:
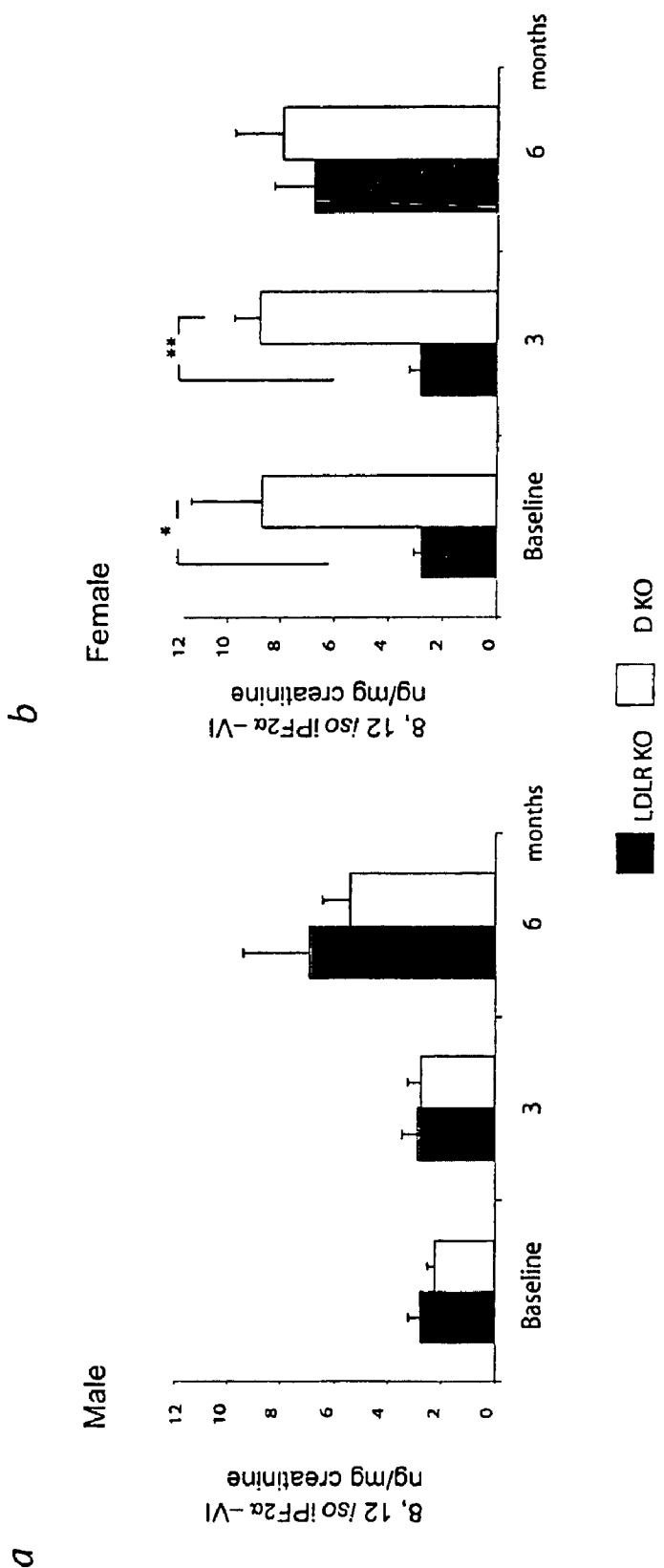
FIG. 18A is a graph depicting the 8,12-iso-$iPF_{2\alpha}$-VI levels in male LDLR KO and DKO mice at baseline and after 3 and 6 months feeding on the Western-type diet. Data are the mean values±SEM.
FIG. 18B is a graph depicting the 8,12-iso-iPF$_{2\alpha}$-VI levels in female LDLR KO and DKO mice at baseline and after 3 and 6 months feeding on the Western-type diet. (* P<0.05 and ** P<0.01). Data are the mean values±SEM.

Urinary isoprostanes (iPs), reflective of lipid peroxidation in vivo, are increased during atherogenesis (Pratico et al., 1998, Nat. Med. 4: 1189-92). 8,12-iso-iPF$_{2\alpha}$-VI, the most abundant $F_2$-iP in urine, increased in LDLR KOs during atherogenesis (FIGS. 18A and 18B). There was no significant effect of coincidental IP deletion in male LDLR KOs (F=1.77; p=0.2) (FIG. 18A). However, deletion of the IP augmented lipid peroxidation in female LDLR KOs (F=15.8; P<0.0005), but not male LDLR KO mice (F=2.70; P=0.01082). This different was particularly evident at baseline (8.7±2.6 vs. 2.8±0.3 ng/mg creatinine; p<0.05) and 3 months (8.8±1.1 vs. 2.8±0.4 ng/mg creatinine; p<0.001) (FIG. 18B). Thus, $PGI_2$ subserves an antioxidant function in female LDLR KOs. This function is most evident at baseline and at the early stages of atherogenesis.

Prostacyclin Mediates an Antioxidant Effect in Vitro

Figures 19A, 19B, 19C, 19D, 19E, 19F:
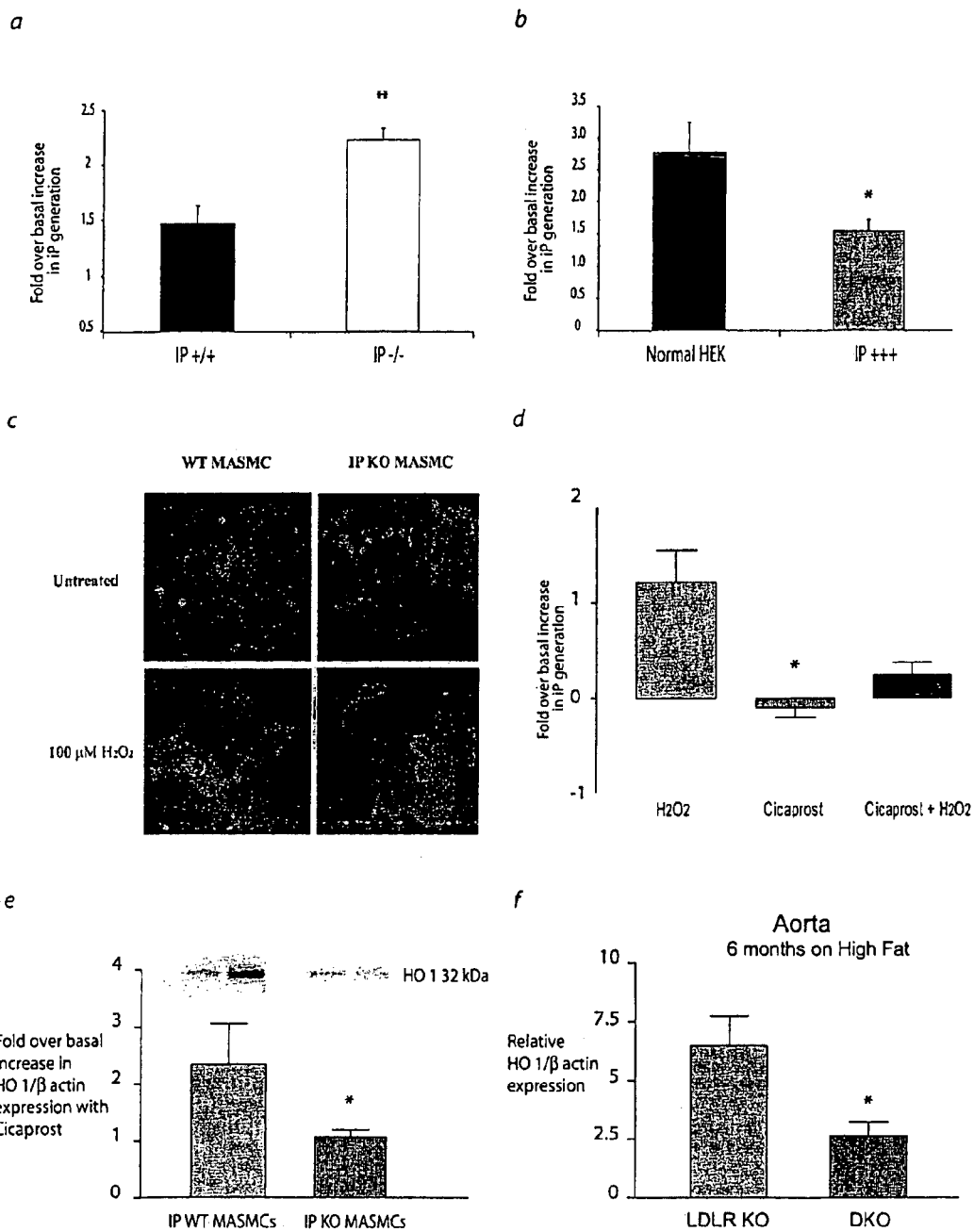
FIG. 19A is a graph depicting the effect of hydrogen peroxide ($H_2O_2$) exposure on isoprostane generation in mouse aortic smooth muscle cells (MASMC) isolated from wild-type (IP +/+) mice and IP KO (IP −/−) mice. (**P<0.001 compared to MASMCs isolated from wild-type mice). "Fold over basal increase" is the ratio of the isoprostane released in cells exposed to $H_2O_2$ to the isoprostane released in cells not exposed to $H_2O_2$, where the isoprostane measured is 8,12-iso-iPF$_{2\alpha}$-VI (ng/mg creatinine).
FIG. 19B is a graph depicting the effect of $H_2O_2$ on isoprostane (iP) generation in normal human embryonic cells (HEK) and HEK stably expressing IP (IP+++). isolated from wild-type (IP +/+) mice and IP KO (IP −/−) mice. (*P<0.05 compared to normal HEK cells. "Fold over basal increase" is the ratio of the isoprostane released in cells exposed to $H_2O_2$ to the isoprostane released in cells not exposed to $H_2O_2$, where the isoprostane measured is 8,12-iso-iPF$_{2\alpha}$-VI (ng/mg creatinine).
FIG. 19C is a series of images of the fluorescence of wild-type MASMC and IP KO MASMC before and after stimulation with $H_2O_2$ using the fluorescent probe, dichlorofluorescein (DCFH).
FIG. 19D is a graph depicting the effects of IP agonist, cicaprost, on MASMC response to $H_2O_2$, as measured by 8,12-iso-iPF$_{2\alpha}$-VI generation. (*P<0.05 compared to $H_2O_2$).
FIG. 19E is a graph depicting the effect of cicaprost treatment on heme oxygenase 1 (HO 1) protein expression in wild-type MASMC and IP KO MASMC. (*P<0.05).
FIG. 19F is a graph depicting the relative expression of HO 1 protein expression in atherosclerotic aortas from LDLR KO mice and from DKO mice, fed a high-fat diet for 6 months.

Exposure of MASMC to $H_2O_2$ results in augmented $PGI_2$ synthesis and, as expected, increased generation of 8,12-iso-iPF$_{2\alpha}$-VI detected in the culture medium. Free radical dependent formation of 8,12-iso-iPF$_{2\alpha}$-VI was greatly augmented by deletion of the IP (FIG. 19A). Overexpression of the IP, by contrast, reduced levels of the 8,12-iso-iPF$_{2\alpha}$-VI generated by unstimulated HEK cells (6.4±1.2 ng/mg vs. 2.5±0.2 ng/mg respectively) which express extremely low levels of endogenous IP. Similarly, overexpression of the IP in these cells significantly diminished the oxidant response to $H_2O_2$ stimulation (FIG. 19B).

Dichlorofluorescein is a fluorescent probe used to detect reactive oxygen species in cultured cells. Chemically, fluorescence is achieved by the oxidation of 2',-7'-dichlorodihydrofluorescein (DCFH) to 2',-7'-dichlorofluorescein (DCF) Munzel et al., 2002, Arterioscler. Thromb. Vasc. Biol. 22: 1761-8). MASMCs challenged with $H_2O_2$ displayed greater fluorescence than untreated cells. IPKO MASMCs exhibited greater fluorescence than wild-type MASMCs (FIG. 19C). These results suggest a role for the IP in modulating oxidant stress under basal conditions. Following stimulation with $H_2O_2$, this distinction from wild-type cells was increased further (FIG. 19C). The addition of cicaprost (100 nM), an IP agonist, limits the response of MASMCs to $H_2O_2$ with subsequent reduction of iP generation (FIG. 19D). Cicaprost does not significantly reduce iP generation from unstimulated cells. There is evidence that iloprost, a $PGI_2$ analog, increases expression of the antioxidant gene, heme oxygenase 1 (HO 1) (Meyer-Kirchrath et al., 2004, Biochem. Pharmacol. 67: 757-65). Addition of 100 nM cicaprost to MASMCs increased expression of HO 1 protein in an IP-dependent manner (FIG. 19E). IP deletion decreased HO 1 expression in the aortae of fat-fed female LDLR KOs (FIG. 19F).

Figures 20A, 20B, 20C, 20D, 20E, 20F:
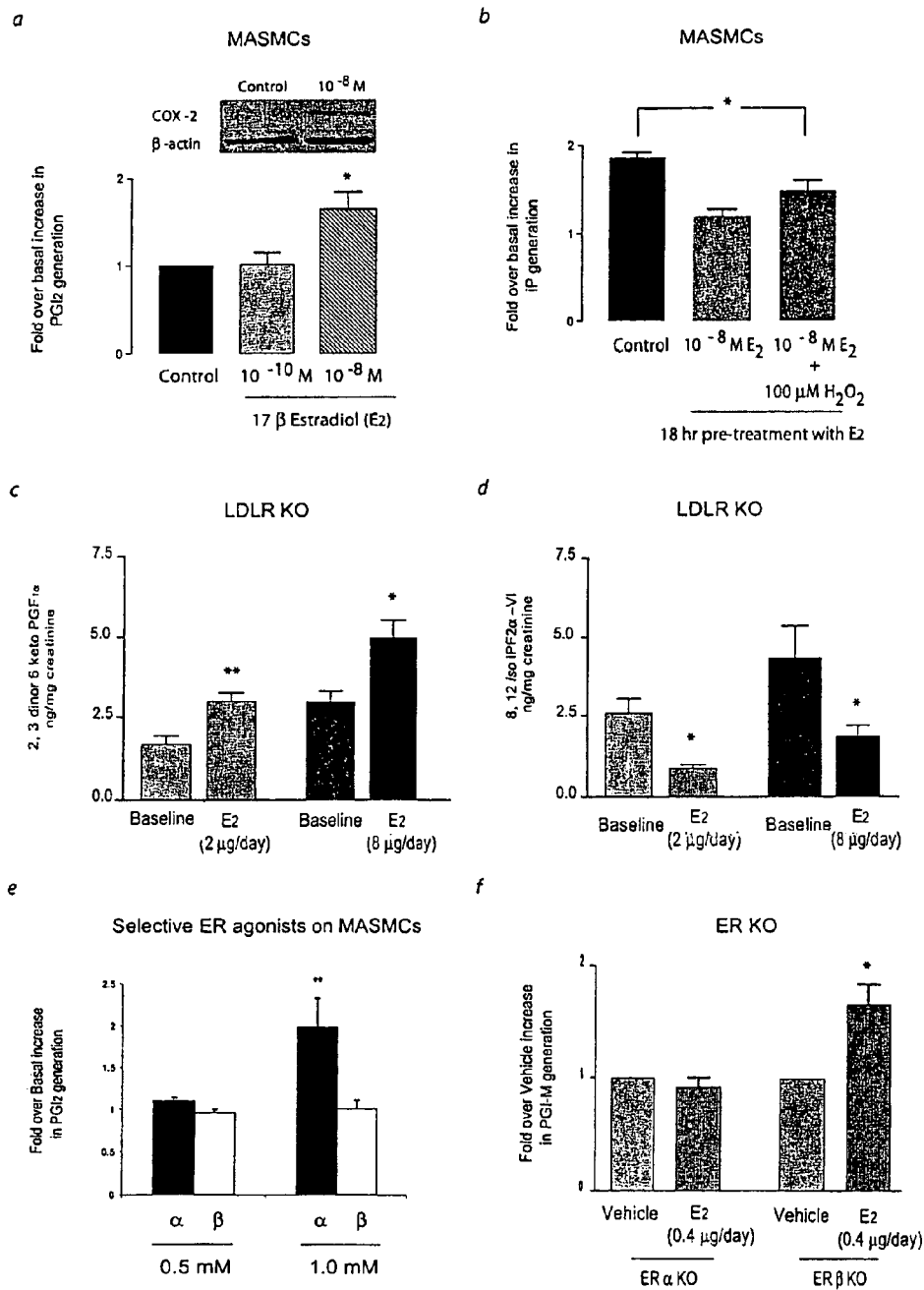
FIG. 20A is a graph depicting the prostacyclin (PGI$_2$) generation in wild-type MASMC in response to E$_2$ (17-β-Estradiol). PGI$_2$ production was measured in the conditioned medium as 6-keto PGF$_{1\alpha}$. Values are expressed as a fold over basal increase in 6-keto-PGF$_{1\alpha}$ (pg/mg protein). (*P<0.05).
FIG. 20B is a graph depicting the effect of pre-treatment with E$_2$ on isoprostane production in wild-type MASMC in response to $H_2O_2$. (*P<0.05).
FIG. 20C is a graph depicting the PGI$_2$ generation in ovariectomized LDLR KO mice in response to sub-cutaneous E$_2$ administration. PGI$_2$ generation is measured as the urinary PGI$_2$ metabolite, 2,3-dinor 6-keto PGF$_{1\alpha}$. (**p<0.01 and *p<0.05, respectively vs. their own baseline controls).
FIG. 20D is a graph depicting the isoprostane generation in ovariectomized LDLR KO mice in response to sub-cutaneous E$_2$ administration. Isoprostane generation was measured as urinary 8,12-iso-iPF$_{2\alpha}$-VI. (*P<0.05 vs. baseline).
FIG. 20E is a graph depicting the PGI$_2$ biosynthesis in MASMCs in response to estrogen receptor (ER) selective agonists. (**P<0.05 fold over basal). PGI$_2$ biosynthesis was measured as 6-keto-PGF$_1$, in the medium.
FIG. 20F is a graph depicting the PGI$_2$ biosynthesis in ERα and ERβ KO mice in response to E$_2$. PGI$_2$ generation was measured as urinary 2,3-dinor 6-keto PGF$_{1\alpha}$. (*P<0.05).

Estrogen Stimulates $PGI_2$, which Limits the Response to Oxidants and Attenuates Oxidative Stress in Vivo Long term $E_2$ (17-β-Estradiol) exposure stimulated COX-2 expression and $PGI_2$ formation in MASMCs. Cells exposed to physiological concentrations of $E_2$ at $10^{-8}$ M (Ihionkhan et al., 2002, Circ. Res. 91: 814-20), for 18 hours, increased $PGI_2$ production (FIG. 20A). $E_2$ increased release of the $PGI_2$ hydrolysis product, 6-keto $PGF_{1\alpha}$, into the medium (from 2.4±0.33 to 3.8±0.38 ng/mg protein; *p<0.05).

Exposure of MASMC to $H_2O_2$ resulted in augmented $PGI_2$ synthesis and, as expected, increased release of 8,12-iso-iPF$_{2\alpha}$-VI into the culture medium, but had no effect on COX-2 expression. Acute treatment with $E_2$ did not alter the oxidant response. However, cells pre-treated with $E_2$ ($10^{-8}$ M) for 18 hours had an attenuated response to 30 minutes of 100 mM $H_2O_2$, reflected by diminished release of the isoprostane (FIG. 20B).

As previously reported, it was found that $E_2$ (8 μg/day) was atheroprotective in female LDLR KOs (Marsh et al., 1999, J. Lipid Res. 40: 893-900). In addition, administration of $E_2$ (2 μg/day and 8 μg/day) to female ovariectomized LDLR KOs increased $PGI_2$ biosynthesis, as reflected by urinary 2,3-dinor 6-keto $PGF_{1\alpha}$ (FIG. 20C) and depressed oxidant stress, as reflected by urinary 8,12-iso-iPF$_{2\alpha}$-VI (FIG. 20D). Similarly, $E_2$ (3 μg/day) administration to female ovariectomized wild-type mice (C 57B16) increased urinary 2,3-dinor 6-keto $PGF_{1\alpha}$ and depressed excretion of the iP. MASMCs were treated with agonists selective for the estrogen receptors, ERα (Propyl Pyrazole Triol, PPT) (Harris et al., 2002, Endocrinology 143: 41727) and ERβ (WAY-200070) (Malamas et al., 2004, J. Med. Chem. 47:5021-40). The ERα-selective agonist, but not ERβ-selective agonist, increased release of 6-keto $PGF_{1\alpha}$ into the medium (FIG. 20E, *P<0.05). Furthermore, this evidence is consistent with results obtained using mice deficient in the ERs (Lubahn et al., 1993, Proc. Natl. Acad. Sci. USA 90: 11162-6; Shughrue et al., 2002, Endocrinology 143: 1643-50). Thus, $E_2$ (20 μ/kg=0.4 μg/day) augmented urinary PGI-M in ERβ KOs, but not in ERα KOs (FIG. 20F), indicating that estrogen exerts its effect on biosynthesis of $PGI_2$ by activating ERα.

Figures 21A, 21B:
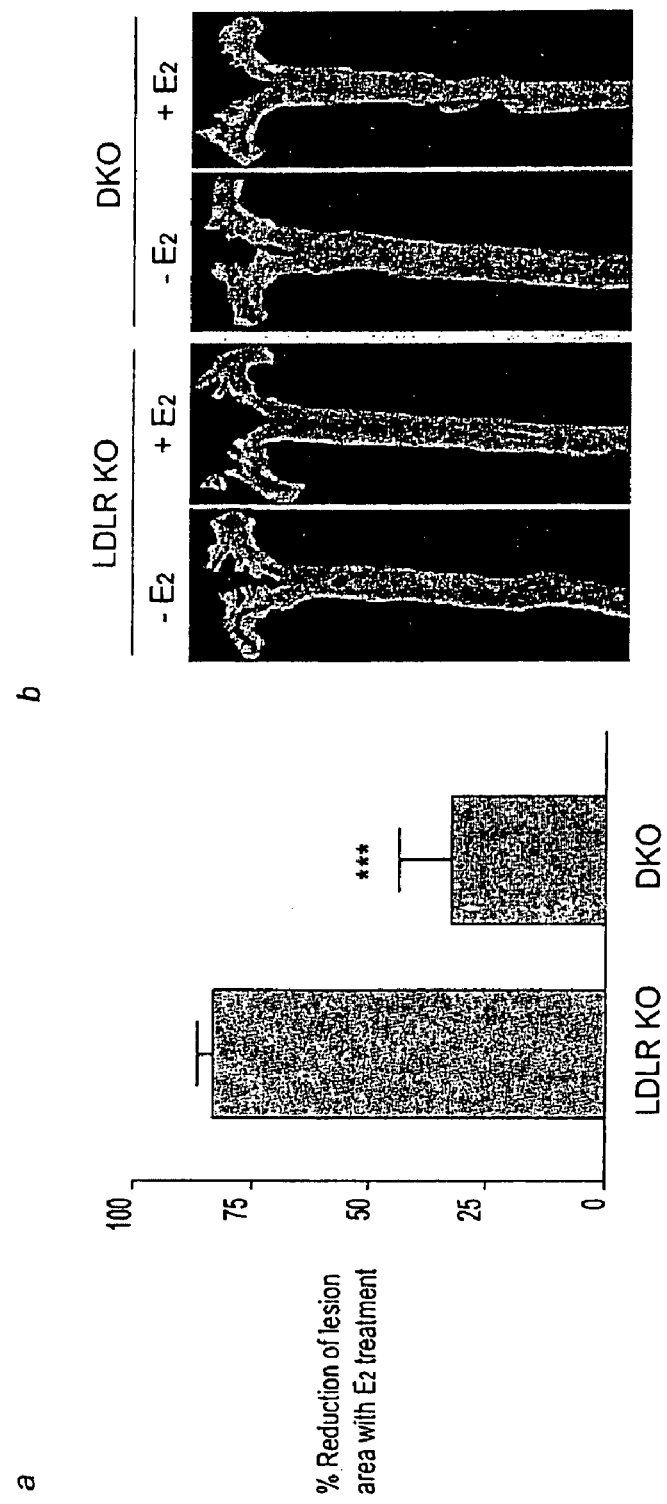
FIG. 21A is a graph depicting the effect of sub-cutaneous E$_2$ treatment on aortic lesions in ovariectomized LDLR KO and DKO females. (***P<0.0001). Values are expressed as % reduction of lesion area with E$_2$ (17-β-Estradiol) administration.
FIG. 21B is a series of images of en face aortas from ovariectomized LDLR KO and DKO females fed a high-fat diet±slow release sub-cutaneous E$_2$ treatment. Representative en face aortas were chosen that were approximately equal to the mean % lesion area for each treatment group.

Atheroprotective Effect of Estrogen is Significantly Diminished in the Absence of the IP LDLR KO and IP/LDLR DKO female mice were bilaterally ovariectomized at approximately 6 weeks of age. Approximately 7-10 days after surgery, mice were started on the high fat diet (in the absence or presence of a slow-release subcutaneous pellet of exogenous $E_2$ (8 µg/day). After 3 months of high fat feeding, aortic lesion area was significantly augmented in the DKO compared to the LDLR KO (7.89±1.0 vs. 3.58±0.39; p<0.05). $E_2$ significantly reduced lesion burden (~80%) in LDLR KO mice (FIG. 21A). However, coincidental deletion of the IP reduced this effect significantly (p<0.0001) with an average reduction of 32%.

In summary, atherogenesis proceeds faster in male LDLR knockouts compared to female LDLR KOs. However, deletion of the prostacyclin ($PGI_2$) receptor (IPKO) in females abolished this rate difference and increased generation of both 8,12-iso-$iPF_{2\alpha}$-VI, an index of oxidant stress (OS), and urinary 2,3-dinor $TxB_2$, reflecting platelet activation. Estrogen acts via ERα to evoke COX-2-dependent $PGI_2$ formation, and correspondingly, decrease OS in vascular cells and in vivo. Activation of the IP augments the antioxidant protein HO-1. In IPKOs, retardation of atherogenesis by estrogen was constrained. Activation of ERα confers atheroprotection via COX-2 dependent $PGI_2$, which limits platelet activation and decreases OS in vivo.

These findings indicate that $PGI_2$ contributes to the antioxidant effects of female gender. Isoprostane generation increases with atherogenesis in LDLR KOs in the present experiments. However, deletion of the IP augmented markedly the degree of lipid peroxidation in female, but not in male mice. Thus, estrogen exerts an antioxidant effect in vivo that is mediated substantially by $PGI_2$. Both in vitro and in vivo data are consistent with this model. Deletion of the IP in vascular cells exacerbated $H_2O_2$ induced 8,12-iso-$iPF_{2\alpha}$-VI generation. In addition, $H_2O_2$-induced fluorescence of DCF was increased in IPKOs, indicating an increase in reactive oxygen species. In contrast, overexpression of the IP in a cell line deficient in endogenous receptors and agonist activation of the receptor in vascular cells attenuated the oxidant response. This may result from induction of antioxidant gene expression by activation of the IP (Meyer-Kirchrath et al., 2004, Biochem. Pharmacol. 67: 757-65). In the present example, it was determined that cicaprost, a $PGI_2$ analog, induced expression of one such enzyme, heme oxygenase 1 (HO 1), in vascular cells and that deletion of the IP reduced HO 1 expression in the aortae of LDLR KOs. Other lines of evidence support an antioxidant action of $PGI_2$. For example, deletion of the IP increases cardiac reperfusion injury (Xiao et al., 2001, Circulation 104: 2210-5) and suppression of $PGI_2$ formation by COX-2 inhibition augments oxidant injury to myocardium by doxarubacin (Dowd et al., 2001, J.

TABLE 3

Plasma cholesterol and body weight in LDLR −/− mice on a high fat diet

| | Mon- ths | Male LDLR −/− | | Female LDLR −/− | |
|---|---|---|---|---|---|
| | | IP +/+ | IP −/− | IP +/+ | IP −/− |
| Total cholesterol (mg/dl) | 3 | 666 ± 61 | 610 ± 100 | 677 ± 81 | 516 ± 62 |
| | 6 | 664 ± 102 | 597 ± 83 | 731 ± 67 | 753 ± 38 |

TABLE 3-continued

Plasma cholesterol and body weight in LDLR −/− mice on a high fat diet

| | Mon- ths | Male LDLR −/− | | Female LDLR −/− | |
|---|---|---|---|---|---|
| | | IP +/+ | IP −/− | IP +/+ | IP −/− |
| HDL cholesterol (mg/dl) | 3 | 92 ± 12 | 106 ± 10 | 86 ± 9 | 75 ± 4 |
| | 6 | 90 ± 12 | 83 ± 11 | 110 ± 11 | 103 ± 12 |
| Body Weight (g) | 3 | 29.9 ± 2 | 31.5 ± 2 | 20.7 ± 1 | 21.8 ± 2 |
| | 6 | 33.0 ± 2 | 34.5 ± 2 | 26.9 ± 4 | 26.8 ± 2 |

Table 3 note: Cholesterol values are mg/dL (mean ± SEM).

Recent clinical trials of cardioprotection with hormone replacement therapy have been disappointing. Estrogens have often been combined with progestins in these trials. These clinical trials, however, differ from studies in rodents in both the route and duration of administration of estrogen and their delivery as conjugates rather than free hormone, which may alter their receptor specificity and tissue specific effects. The present example reveals a mechanism by which estrogen may act to retard atherogenesis in premenopausal females: ERα-dependent upregulation of COX-2-derived $PGI_2$ formation which limits platelet activation and attenuates oxidant stress. This finding may have relevance to the design of trials of supplemental estrogen. As disruption of this pathway impairs atheroprotection from estrogen, these results may also have implications for treatment of premenopausal women with selective inhibitors of COX-2.

Experimental Example 4

COX-2 Derived Prostacyclin Modulates Vascular Remodeling

Aside from initiation and early development of atherogenesis, little is known about how suppression of COX-2 dependent $PGI_2$ might condition the response of the vasculature to sustained stress, such as a rise in blood pressure, in the presence of intact endothelium. Using two models which distinctly perturb vascular homeostasis, but preserve the integrity of the endothelium, this Experimental Example was designed to examine whether deletion of the IP or administration of a COX-2 inhibitor induces intimal hyperplasia and remodeling of the vasculature to maintain luminal geometry. Such perturbation of the relationship between vascular hemodynamics and structure may interact with salt retention (Qi et al., 2002, J. Clin. Invest. 110: 61-9; Athirakul et al., 2001, Kidney Int. 60: 2324-9) and atherogenesis (Kobayashi et al., 2004, J. Clin. Invest. 114: 784-94; Egan et al., 2004, Science 306: 1954-7) to contribute to an emerging cardiovascular hazard in patients initially at low cardiovascular risk during extended therapy with selective inhibitors of COX-2.

The materials and methods used in the experiments presented in this Experimental Example are now described.

Animals: All animal studies were performed according to protocols approved by the Institutional Committee for Use and Care of Laboratory Animals. Male C57BL/6J mice, aged four to six weeks were used for the flow reduction models. The parental background strain of the male, four to six week old donor mice in the transplant studies was also C57BL/6J (H2b). The background of the recipient mice was C3H(H2k) (Taconic Farms Inc, Germantown, N.Y.). Donor mice were homozygous for deletion of the IP (IPKO), as previously described (Cheng et al., 2002, Science 296: 539-41) or homozygous littermate controls. Wild-type (WT) littermate controls were also used for studies involving mice deficient in the thromboxane receptor (TPKOs) (Thomas et al., 1998, J. Clin. Invest. 102: 1994-2001).

Urine was collected over a 24 hour period in metabolic cages (Nalgene Labware, Deepwater, N.J.) with vehicle or nimesulide allowed ad libitum. Urinary levels of prostanoid metabolites were measured by stable isotope dilution methods as previously described. The $PGI_2$ metabolite, 2,3-dinor-6-keto $PGF_{1\alpha}$ (PGI-M) was measured by GC/MS (Pratico et al., 2000, Blood 96: 3823-6) and 2,3-dinor $TxB_2$, the Tx metabolite, was measured by reverse phase (C18) HPLC/MS/MS (Pratico et al., 2000, Blood 96: 3823-6). The isoprostane, 8,12-iso-$iPF_{2\alpha}$-VI, was measured by GC/MS (Lawson et al., 1998, J. Biol. Chem. 273: 29295-301). A urine aliquot (0.1 ml) was used for measurement of creatinine by an automated colorimetric assay (Sigma-Aldrich Co., St Louis, Mo.).

Transplant Arteriosclerosis: Common carotid artery transplantations were performed (Dietrich et al., 2000, Arterioscler. Thromb. Vasc. Biol. 20: 343-52; Shi et al., 1994, Circ. Res. 75: 199-207). Briefly, the recipient mouse was prepared for transplantation via a midline cervical incision. The right common carotid artery (RC) was mobilized and divided midway from the innominate artery to the carotid bifurcation. The proximal and distal arteries were fashioned into arterial cuffs by passing the artery through autoclaved nylon tubing (0.63 mm O.D. and 0.5 mm I.D.), everting the arterial ends over the tubing and securing with a 9-0 nylon tie. The donor mouse was operated on via a similar cervical midline incision. The full length of the RC was harvested between 8-0 silk ties and flushed with normal saline to remove any remaining blood. The donor artery was immediately placed over the recipient arterial cuffs and secured with a 9-0 nylon tie. Total cerebral ischemia of the recipient mouse and ischemia of the donor carotid artery lasted for approximately 10-15 minutes. No heparin or antibiotics were used at any time.

Grafts were harvested at 3 weeks and 6 weeks post transplant. Graft harvest was undertaken by exposure of the donor artery, then median sternotomy and left ventricular puncture and an infusion of a 0.9% NaCl solution at 4° C. The donor carotid artery was then removed. The proximal half of the carotid artery was placed in 4% phosphate-buffered formaldehyde (pH 7.2), and the distal half placed in OTC medium (Triangle Biomedical Sciences, Durham, N.C.) and rapidly frozen in liquid nitrogen. Five separate sections 10 micrometer (μm) apart were sectioned from different layers of the carotid artery. Sections were then stained with hematoxylin and eosin and examined via a Sony 3CCD camera and television monitor and a Nikon microscope with images digitized with ImagePro®D analysis software (Media Cybernetics, Silver Springs Md.). The intima was defined as the region between the lumen and internal elastic lamina. The media was defined as the region between the internal and external elastic laminas.

Flow Dependent Vascular Remodeling: Left external carotid (EC) artery ligation (moderate) was performed (Rudic et al., 1998, J. Clin. Invest. 101: 731-6). Briefly, the distal left common carotid artery (LC) artery and its bifurcation into the external and internal carotid were exposed using blunt dissection. 9-0 nylon sutures (USSC Sutures, Norwalk, Conn.) were used to ligate the EC artery, incisions were closed (7-0 polypropylene) and mice were left to recover. Severe reduction in flow was achieved by ligating the LC artery just proximal to the external/internal carotid artery bifurcation. Five μm cross sections were used from parallel regions of RC and LC that were isolated in 5 millimeter (mm) blocks proximal to the ligation, until reaching a parallel point at the RC artery branchpoint with the right subclavian artery. Although different permutations of this model of severe flow reduction may result in formation of neointima, (Kumar and Lindner, 1997, Arterioscler. Thromb. Vasc. Biol. 17: 2238-44), dependent on the section of carotid artery analyzed (Myers and Liaw, 2004, Am. J. Pathol. 164: 43-8) and mouse strain (Harmon et al., 2000, Am. J. Pathol. 156: 1741-8; Korshunov and Berk, 2004, Circulation 110: 220-6), this was not observed in the present studies of severe flow reduction with complete LC ligation, unless the mice were also treated with a COX-2 selective inhibitor (vide infra). Mice that developed thrombosis were excluded from the analysis. Mice were administered nimesulide (Sigma-Aldrich Co., St. Louis, Mo.) in drinking water at a concentration of 40 mg/L containing 0.7% ethanol (changed tri-weekly) to achieve selective inhibition of COX-2, as previously described (Pratico et al., 2001, Proc. Natl. Acad. Sci. USA 98: 3358-63). Urine was collected from individual mice using metabolic cages at four weeks of age, and again after a four week period of treatment, subsequent to either moderate or severe flow reduction. Urine samples were frozen at −20° for analysis.

Semi-quantitative RT-PCR: RC and LC were harvested, flash frozen, and pulverized to a fine powder. Total RNA was extracted using Trizol® (Invitrogen® Life Technologies, Carlsbad, Calif.). Five hundred nanograms (ng) RNA from individual common carotid arteries was reverse transcribed (RT) (Fulton et al., 2000, Am. J. Physiol. Heart Circ. Physiol. 278: H658-65). The RT reaction (2 μl) was amplified using Taq DNA polymerase (Roche Boehringer Mannheim Diagnostics, Indianapolis, Ind.) and primers to murine COX-2 cDNA (sense: 5'-CCGGGTTGCTGGGGGAAGA-3', SEQ ID NO: 3; antisense: 5'-GTGGCTGTTTTGGTAGGCT-GTGGA-3', SEQ ID NO: 4). The PCR profile was set at 94° C. melting, 55° C. annealing, and 72° C. extension for 2 minutes and semi-quantitation was optimized to 27 cycles. The amplified transcripts were visualized on 1.5% agarose gels using ethidium bromide.

Blood Flow: Blood flow was measured in RC or LC at their midpoint, using an ultrasonic flow probe (0.5 mm PSB-series probe from Transonic Systems Inc., Ithaca, N.Y.). Despite severe conditions of flow restriction, with cessation of flow distal to the ligation, a net flow pulse was retained across the flow probe. Blood flow was recorded for 1 minute and a 30 second interval was used to determine and analyze peak blood flow using the PowerLab® data acquisition system and Chart 4.0 software (AD Instruments Pty Ltd, Colorado Springs, Colo.; www(dot)adinstruments(dot)com).

Statistical analysis: Statistical analyses were performed using a computerized software package (GraphPad Prism version 3.02, GraphPad Software Inc., San Diego, Calif.). The results presented are represented as mean±SEM. Intima/media ratios for the experimental and control groups were analyzed using analysis of variance with subsequent pairwise analysis by Student's t test, as appropriate.

The results of the experiments presented in this Experimental Example are now described.

Prostacyclin Receptor Deletion and Transplant Arteriosclerosis

Figure 22A:
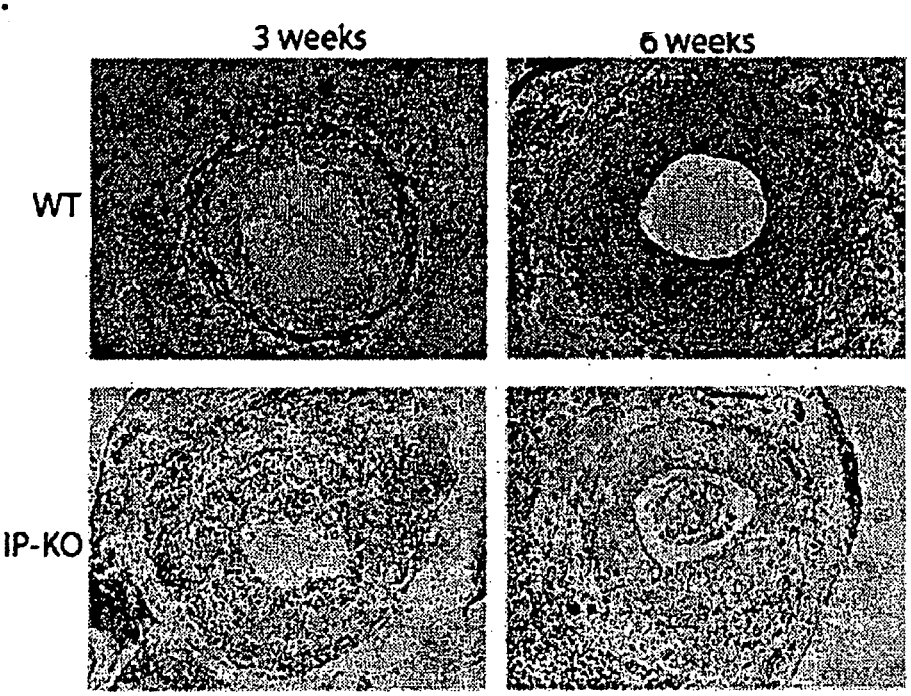
FIG. 22A is a series of images depicting sections of carotid artery transplants obtained from wild-type and IP KO mice, harvested at 3 and 6 weeks post-transplant. Sections were stained with hematoxyline and eosin.
Figure 22B:
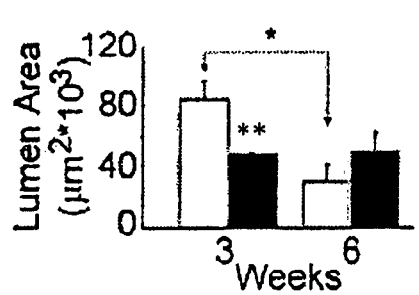
FIG. 22B is a graph depicting the quantitative morphometry data of the luminal area in carotid artery transplants obtained from wild-type (white boxes) and IP KO (black boxes) mice, harvested 3 and 6 weeks post-transplant. (*p<0.05; **p<0.01).
Figure 22C:
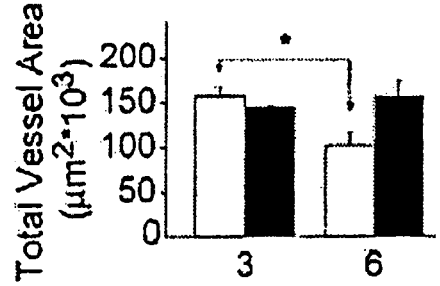
FIG. 22C is a graph depicting the quantitative morphometry data of the total vessel area in carotid artery transplants obtained from wild-type (white boxes) and IP KO (black boxes) mice, harvested 3 and 6 weeks post-transplant. (*p<0.05).
Figure 22D:
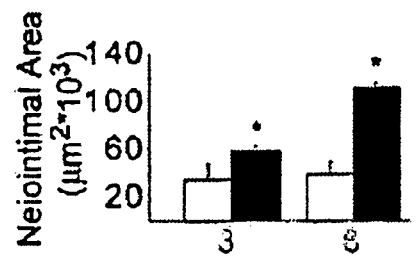
FIG. 22D is a graph depicting the quantitative morphometry data of the neointimal area in carotid artery transplants obtained from wild-type (white boxes) and IP KO (black boxes) mice, harvested 3 and 6 weeks post-transplant. (*p<0.05).
Figure 22E:
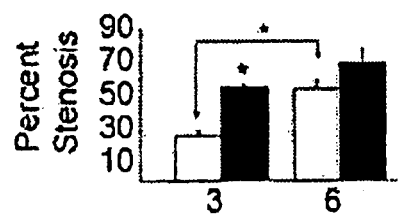
FIG. 22E is a graph depicting the percent stenosis in carotid artery transplants obtained from wild-type (white boxes) and IP KO (black boxes) mice, harvested 3 and 6 weeks post-transplant. (*p<0.05).

Transplant arteriosclerosis manifests as neointimal thickening (Shi et al., 1994, Circ. Res. 75: 199-207) and expansive luminal remodeling (Lim et al., 1997, Circulation 95: 855-9). Arteries allogenically transplanted from WT c57/black6 mice to the histoincompatible C3H background exhibited the typical arteriopathy of rejection (FIG. 22A, top panel), which progressed over time. Quantitative analysis of arterial geometry in transplanted arteries revealed a significant reduction in lumen area that occurred from 3 to 6 weeks post-transplant (FIG. 22B). Similarly, total vessel size quantified as cross-sectional area, declined in WT transplants from 3 to 6 weeks (FIG. 22C). These reductions in vessel caliber were accompanied by neointimal proliferation 3 weeks post-transplantation, as expected (FIG. 22D). Neointimal proliferation and a reduction in total vessel area increased stenosis from 3 to 6 weeks post transplantation, (FIG. 22E). Deletion of the IP modulated progression of the arteriopathy (FIG. 22A, bottom panel). Lumen area and total vessel area from transplanted IPKO arteries remained stable from 3 to 6 weeks (FIGS. 22B, 22C). However, the proliferative response was greater at 3 weeks in arteries lacking the IP and continued neointimal growth was evident 6 weeks after transplantation, a time when proliferation in the WT transplants had stabilized (FIG. 22D). Despite these disparate effects on neointimal proliferation, encroachment on luminal area by 6 weeks was comparable between WT and IPKO arteries (FIG. 22E). Thus, luminal geometry was preserved in IPKO transplants to an extent similar to WT's, by augmented, progressive neointimal proliferation.

COX-2 Inhibition and Flow-Induced Vascular Remodeling

The consequences of suppressing COX-2 dependent $PGI_2$ biosynthesis following surgically induced chronic flow reduction was examined. Left EC ligation results in a moderate reduction in blood flow along the LC and a consequent reduction in LC luminal diameter, cell death and endothelial dysfunction (Rudic et al., 2000, Circ. Res. 86: 1160-6). After seven days, expression of COX-2 mRNA was increased in response to the reduction in flow in the LC compared to the contralateral RC (FIG. 23A). Correspondingly, when the reduction in flow was severe, the increase in expression of COX-2 was more pronounced (FIG. 23A). A corresponding flow dependent increase in COX-2 protein was observed. Interestingly, both non-ligated RC and LC also exhibited detectable expression of COX-2.

Chronic administration of the COX-2 selective inhibitor, nimesulide, depressed urinary PGI-M (FIG. 23B) as expected (McAdam et al., 1999, Proc. Natl. Acad. Sci. USA 96: 272-7), but did not itself affect either the internal vascular geometry, as measured by lumen diameter (FIG. 23C i) or external structure, as reflected by the external elastic lamina (EEL) diameter (FIG. 23C ii) of RCs or LCs obtained from control mice. Nimesulide depressed PGI-M to a similar degree under conditions of moderate and severe reduction in flow (FIG. 23B). However, selective inhibition of COX-2 failed to alter the flow dependent reduction in vessel size, whether quantified as a reduction in luminal diameter (FIG. 23C i) or a reduction in EEL diameter (FIG. 23C ii). Lumen diameter was significantly reduced after moderate flow reduction (RC vs. LC, n=11, *p<0.01) and to a greater extent by severe flow reduction n=11, *p<0.001), but the absolute lumen diameter after flow induced remodeling was not different between vehicle and nimesulide treatment in moderate (LC vehicle vs. LC nimesulide, p=0.26) or severe flow reduced conditions (LC vehicle vs. LC nimesulide, p=0.59). Similarly, analysis of total vessel size (EEL) mirrored those observations in lumen diameter.

Figure 24A:
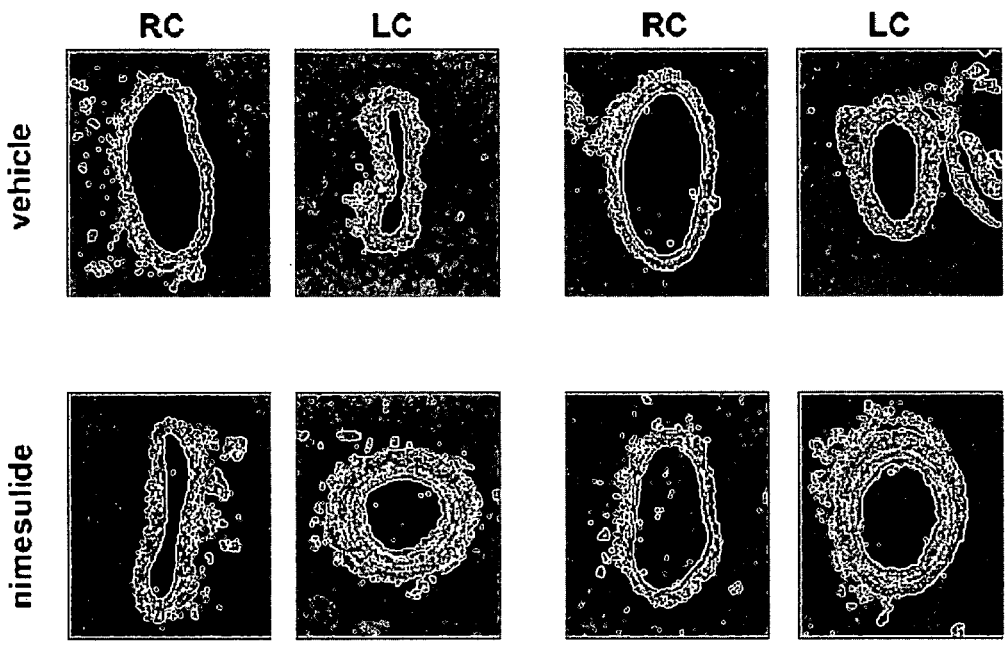
FIG. 24A is a series of images depicting sections of carotid arteries from mice which underwent severe flow reduction with or without nimesulide.
Figure 24B:
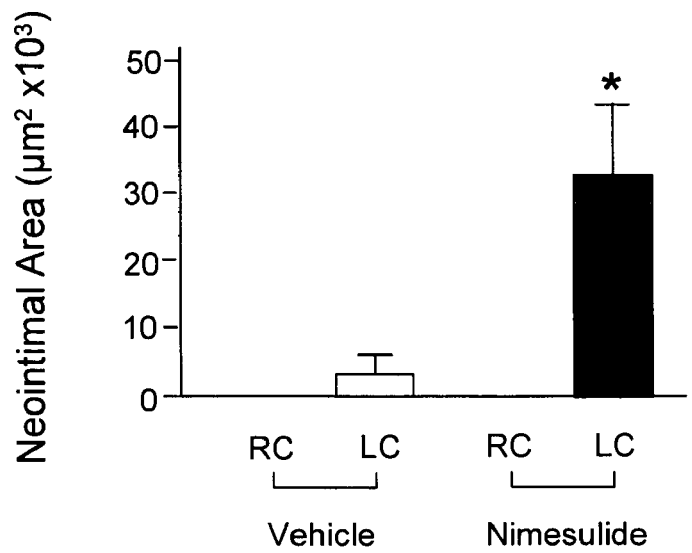
FIG. 24B is a graph depicting the neointimal area in mice which underwent severe flow reduction with or without nimesulide. (nimesulide RC vs. LC; n=10: *p<0.02).

This result contrasted with a marked augmentation effect of neointimal proliferation by nimesulide under conditions of severe flow reduction (FIGS. 24A and 24B). Severe flow caused narrowing of the LC due to inward remodeling (FIG. 24A, top panel), which was accompanied by neointima formation (FIG. 24A, bottom panel) in mice treated with nimesulide. Neointimal area did not alter significantly in the face of severe flow restriction alone (RC vs. LC; n=11: p=0.29). However, treatment with nimesulide markedly augmented the intimal hyperplastic response in the experimental (LC) artery (RC vs. LC; n=10: *p<0.02).

Nimesulide also caused the reduction in blood flow in the LC under ligation conditions of severe flow reduction. Comparing blood flow in the LC of nimesulide treated vs. the vehicle treated exhibits marked reduction (FIGS. 25A and 25B). Similarly, in contralateral controls (FIG. 25c), significant reduction in blood flow in the experimental LC (right panel) compared to the control RC (left panel) is observed when the mice were treated with nimesulide (n=11) versus vehicle alone (n=14; *p<0.01). Thus, consistent with the effects of IP deletion in transplant arteriosclerosis, suppression of $PGI_2$ biosynthesis with nimesulide, under conditions of severe flow restriction, resulted in neointimal proliferation and compensatory vascular remodeling that preserved luminal geometry.

Figure 26A:
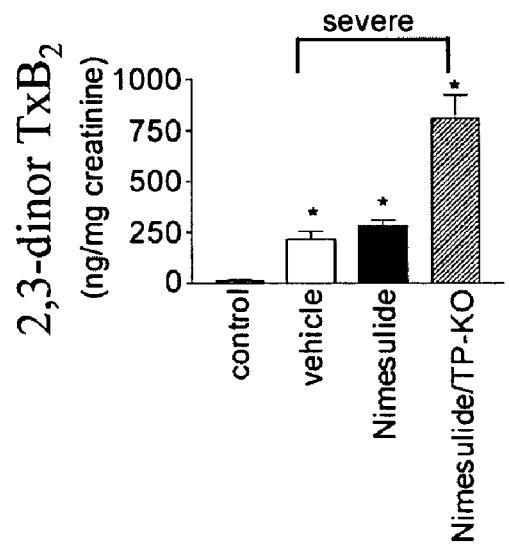
FIG. 26A is a graph depicting the urinary thromboxane metabolite quantity in control mice vs. mice undergoing severe flow reduction, and with nimesulide treatment or without (vehicle). Vehicle-treated mice: severe vs. control; n=10, *p<0.01. Nimesulide-treated mice: severe/nimesulide vs. control; n=10, *p<0.01. Mice with knock out of thromboxane receptor (TPKO) vs. severe/nimesulide and severe/vehicle; n=7, *†p<0.001. Statistical significance was determined by one-way ANOVA and Bonerroni's Multiple Comparison Test.
Figure 26B:
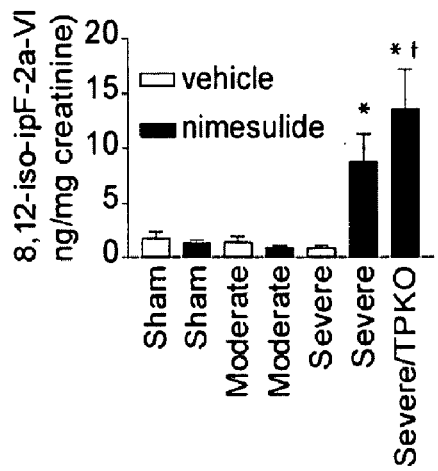
FIG. 26B is a graph depicting the urinary 8,12-iso iPF$_{2\alpha}$-VI quantity in control mice vs. mice undergoing moderate or severe flow reduction, and with nimesulide treatment or without (vehicle). Severe/nimesulide vs. severe/vehicle; n=9, 7 respectively, *p<0.05. Severe/nimesulide/TPKO vs. severe/vehicle; n=7, 7 respectively, *†p<0.001. Statistical significance was determined by one-way ANOVA and Bonerroni's Multiple Comparison Test.
Figure 26C:
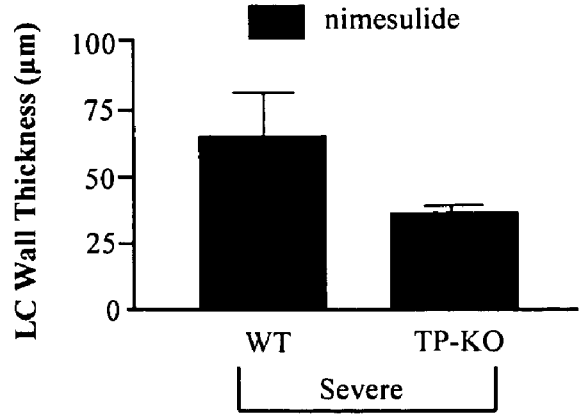
FIG. 26C is a graph depicting the LC wall thickness in wild-type vs. TPKO mice, undergoing severe flow reduction and nimesulide treatment. (n=7, *p<0.05) Statistical significance was determined by unpaired two-tailed Student's t-test.

Although selective inhibition of COX-2 with nimesulide failed to suppress 2,3-dinor $TxB_2$ excretion under control conditions (FIG. 26A), as expected (Famaery, 1997, Inflamm. Res. 46: 437-46), both platelet activation, as reflected by 2,3-dinor $TxB_2$ excretion (FIG. 26A) and oxidant stress, as reflected by urinary 8,12-iso-$iPF_{2\alpha}$-VI (FIG. 26B), were markedly augmented by nimesulide following severe flow reduction. Given that both $TxA_2$ and isoprostanes can bind to the TP, the experiments were repeated in TPKOs. Although deletion of the TP further augmented the increase in Tx and isoprostane generation with nimesulide (FIGS. 26A, 26B), the proliferative response to severe flow reduction was markedly reduced (FIG. 26C).

In summary, allogenic transplantation of the carotid artery results in a proliferative, progressively occlusive response—a model of human transplant arteriosclerosis. Deletion of the $PGI_2$ receptor (IP) augments intimal hyperplasia, but preserves luminal geometry following transplantation of the common carotid artery in mice. Similarly, suppression of $PGI_2$ with the selective COX-2 inhibitor, nimesulide, augments the effect of common carotid artery ligation in reducing blood flow in wild-type mice. Like IP deletion, COX-2 inhibition evokes an initial hyperplastic response, but maintains luminal geometry through vascular remodeling. Generation of both thromboxane ($TxA_2$) and the isoprostane, 8,12-iso-$iPF_{2\alpha}$-VI, are increased by nimesulide in the setting of flow reduction. Deletion of the $TXA_2$ receptor (TP) reduces the hyperplastic response to nimesulide and carotid ligation, despite further augmentation of TP ligand production.

While nimesulide did not influence Tx biosynthesis in the control mice, the increase in Tx formation in the setting of flow reduction was exacerbated by nimesulide. Such a COX-1 dependent source of Tx formation may reflect platelet activation in the face of hemodynamic perturbation. Exacerbation of an increase in Tx formation likely reflects the removal of $PGI_2$ as a constraint on platelets and is consistent with previous observations in vascular injury (Cheng et al., 2002, Science 296: 539-41). Similarly, $PGI_2$ acts as a constraint on oxidant stress, both in occlusion/reperfusion injury (Xiao et al., 2001, Circulation 104: 2210-5), and as atherogenesis proceeds (Egan et al., 2004, Science 306: 1954-7) in genetically predisposed mice. In the present example, nimesulide did not alter excretion of an isoprostane biomarker of lipid peroxidation in control mice. However, selective inhibition of COX-2 markedly augmented the increase in 8,12-iso-$iPF_{2\alpha}$-VI in the setting of severe flow reduction. Given that both isoprostanes and $TxA_2$ can activate the TP (Audoly et al., 2000, Circulation 101: 2833-40), and that coincidental deletion of the TP largely rescued the hyperplastic response to vascular injury in IPKOs (Cheng et al., 2002, Science 296:

539-41), vascular remodeling was examined in TPKOs. Hyperplasia induced by nimesulide in the setting of severe flow reduction was markedly diminished. This diminution was despite a further augmentation in both TP ligands when the TP was deleted. This apparent compensatory increase in ligand generation is consistent with recent observations made in atherosclerotic mice (Egan et al., 2004, Science 306: 1954-7). Here, Tx biosynthesis increases with atherogenesis and is further increased by a structurally distinct COX-2 selective inhibitor. Analogous to the experience with TP deletion, addition of a TP antagonist to the COX-2 selective inhibitor results in a marked augmentation of Tx biosynthesis and plaque destabilization (Egan et al., 2005, Circulation 111: 334-342 Epub 2005 Jan. 17).

These studies, which employ genetic and pharmacological approaches in two distinct models of stress-induced vascular remodeling, provide congruent information on the impact of COX-2-derived $PGI_2$ on the structural response of the vasculature to hemodynamic stress. Inhibition of this pathway augments intimal hyperplasia, similar to the response to vascular injury. However, remodeling in these studies tended to preserve luminal geometry. While not wishing to be bound by theory, this may reflect a compensatory role for mediators derived from endothelium, such as NO (nitric oxide). Evidence for such redundancy derives from eNOSKOs (epithelial nitric oxide synthase knock outs) in which flow-mediated vasodilatation is preserved by enhanced release of vasodilator prostaglandin, such as $PGI_2$ and endothelial hyperpolarizing factor (Sun et al., 1999, Circ. Res. 85: 288-93; Huang et al., 2001, Am. J. Physiol. Heart Circ. Physiol. 280: H2462-9).

Vascular modeling occurs in both hypertension (Safar et al., 1996, J. Hypertens. 14: 545-55; Folkow, 1987, Am. Heart. J. 114: 938-48; Park et al., 2001, J. Hypertens. 19: 415-20) and atherosclerosis (Lim et al., 1997, Circulation 95: 855-9), and deletion of the IP results in a rise in blood pressure (Francois and Coffmann, 2004, unpublished observations) and accelerates atherogenesis (Kobayashi et al., 2004, J. Clin. Invest. 114: 784-94; Egan et al., 2004, Science 306: 1954-7) in genetically prone mice. In the present example, a distinct impact on the remodeling response to hemodynamic stress was observed, mediated at least in part by removal of a biological constraint on TP ligands. These consequences of $PGI_2$ suppression—elevation of blood pressure, acceleration of atherogenesis and modulation of the vascular response to hemodynamic stress—may converge to alter vascular architecture and elevate cardiovascular risk during extended dosing with selective inhibitors COX-2.

Suppression of COX-2 derived $PGI_2$ influences profoundly the architectural response of the vasculature to hemodynamic stress. Mechanism based vascular remodeling may interact with a predisposition to hypertension and atherosclerosis in contributing to the gradual transformation of cardiovascular risk during extended periods of treatment with selective inhibitors of COX-2.

Experimental Example 5

Differential Effect of PG/H and mPGE Synthase Disruption on Cardiovascular Function in Vivo While the contribution of the two PGHS enzymes to urinary PG and Tx metabolites has been defined in humans, it has not been fully defined in mice. This Experimental Example was undertaken to ascertain whether PGHS-2 inhibition or disruption—as opposed to IP deletion (Murata et al., 1997, Nature 388:678)—alters the response to thrombogenic stimuli in mice and further, whether this hazard is mitigated by inhibition of PGHS-1 derived $TxA_2$. Since PGHS-2 may be coordinately regulated with the microsomal PGE synthase (mPGES)-1 (Thoren et al., 2003, J. Biol. Chem. 278:22199; Claveau et al., 2003, J. Immunol. 170:4738), and mPGES-1 deletion (KO) limits the inflammatory response in mice (Trebino et al., 2003, Proc. Natl. Acad. Sci. U.S.A. 100:9044), mPGES-1 deletion was also examined.

The materials and methods used in the experiments presented in this Experimental Example are now described.

Mice: In all cases, transgenic mice deficient in the indicated gene were compared with appropriate strain-, age-, and sex-matched control animals. The investigator was unaware of the genotype throughout the experiment. All procedures were approved and animal husbandry was overseen by the Institutional Animal Care and Usage Committee of the University of Pennsylvania.

Generation of PGHS-1 KD and PGHS-$2^{Y385F}$ mutant mice: Prostaglandin G/H synthases (PGHS) comprise a cyclooxygenase (COX) activity, which catalyzes the conversion of arachidonic acid to $PGG_2$ and a peroxidase (POX) activity which reduces $PGG_2$ to $PGH_2$. Traditional nonsteroidal anti-inflammatory drugs target both PGHS1 and PGHS2 by inhibition of COX activity, leaving POX activity intact (Smith et al. 2000, Annu. Rev. Biochem. 69: 145; Marnett et al., 1999, J. Biol. Chem. 274: 22903). Similarly, NSAIDs selective for PGHS-2 (COX-2 selective inhibitors) do not affect POX activity. Others have shown that Tyr385 in PGHS (ovine numbering) is critical for COX catalysis, but is uninvolved in POX activity (Smith et al., 2000, Annu. Rev. Biochem. 69: 145; Marnett et al., 1999, J. Biol. Chem. 274: 22903; Shimokawa et al., 1990, J. Biol. Chem. 265: 20073). PGHS-$2^{Y385F}$ mutant mice were generated, replacing Tyr385 with phenylalanine using a homologous recombination strategy (Yu et al., 2005, Submitted manuscript). Briefly, a 7.7 kb segment containing exons 1-9 was used as the 5' arm in the targeting construct cloned into a modified pPNT vector, upstream of a floxed neomycin cassette (Neo) using appropriate linkers. The mutation Phe385 to Tyr385 was induced with the QuickChange site-directed mutagenesis kit (QIAGEN®, Valencia, Calif.). A 3.5 kb fragment with exon 10 and 3' flanking sequence was then cloned downstream of the floxed Neo site to generate the final construct. TL1 ES cells were transfected with Not I-linearized targeting vector by electroporation, The targeted ES clones were injected into blastocysts derived from C57BL/6J mice, and germ-line transmission (PGHS2 Y385F$^{Neo}$) was confirmed first by Southern blot analysis and subsequently by genomic PCR and sequencing. All of these mice were maintained on a mixed C57BL/x 129/sv genetic background and the WT controls were generated from heterozygous PGHS-$2^{Y385F}$ mice.

Since insertion of a Neo within intronic sequences can generate a hypomorphic allele or "knock down" of gene expression (Meyers et al., 1998, Nat. Genet. 18: 136), PGHS-1 KD mice with Neo insertion in PGHS-1 intron 10 sequence, as described previously (Yu et al., 2005, J. Clin. Invest. 115: 986), were used.

IPKO and mPGES-1 KO mice: IPKO mice were backcrossed into a C57BL/6 genetic background (Cheng et al., 2002, Science 296: 539). IP$^{-/-}$, IP$^{+/-}$, and WT littermates were identified in litters generated by the intercross of IP$^{+/-}$ animals by polymerase chain reaction analysis (PCR) of genomic DNA isolated from tail biopsy samples. Southern blot analysis confirmed the IP gene copy number. mPGES-1 KO mice were kindly provided by Pfizer Inc (New York, N.Y.). They were generated and maintained on the DBA/1 lacJ genetic background (Trebino et al., 2003, Proc. Natl. Acad. Sci. U.S.A. 100: 9044). Heterozygous animals were intercrossed, and the litters were screened by PCR analysis to identify both mPGES-1 KO and wild-type controls. Biochemical and functional analyses in each case were performed on mutant mice and WT littermate controls.

Eicosanoid analyses: Urinary 2,3-dinor $TxB_2$ and 2,3-dinor 6-keto $PGF_{1\alpha}$ were measured in twenty four hour urines collected in metabolic cages. After extraction and purification by thin layer chromatography, they were analyzed by gas chromatography/mass spectrometry, as previously described (Egan et al., 2005, Circulation 111:334). Urinary PGE-M was measured by LC/MS/MS as follows: First, 10 ng of hexadeuterated PGE-M (9,15-dioxo-11α-hydroxy-2,3,4,5-tetranor-prostan-1,20-dioic-17,17,18,18,19,19-$d_6$ acid; Cayman Chemical Co., Ann Arbor, Mich.) was added to 0.1 ml of mouse urine. Next, 50 μL of methoxyamine HCl, 1 g/L, was added and the sample was mixed and allowed to stand at room temperature for 15 minutes. The sample was then diluted to 1.0 ml with water and extracted on a Strata™-X solid phase extraction (SPE) cartridge (Phenomenex Inc., Torrance, Calif.). The SPE was eluted with 1.0 mL of 5% acetonitrile in ethyl acetate, dried, dissolved in 200 μL 10% acetonitrile in water, and injected for LC/MS/MS analysis. Transitions monitored were m/z 385→336 for the endogenous PGE-M and 391→342 for the internal standard.

Models of Thrombogenesis (i) Photochemical vascular injury: This model is an adaptation of one previously described (Yu et al., 2005, J. Clin. Invest. 115:986; Bodary et al., 2002, JAMA 287:1706). Briefly, mice (12→16 weeks) were anesthetized with sodium pentobarbital (80 mg/kg, intraperitoneally). Following a midline cervical incision, the left common carotid artery was isolated and a Doppler flow probe (Model 0.5 VB, Transonic Systems Co., Ithaca, N.Y.) was applied. The probe was connected to a flowmeter (Transonic Model T105) and interpreted with Powerlab® (AD Instruments, Colorado Springs, Colo.), a computerized data acquisition program. Rose Bengal (Fisher Scientific, Fair Lawn, N.J.) was diluted to phosphate-buffered saline and then injected into the jugular vein in a volume of 0.12 ml at a concentration of 50 mg/kg. Immediately prior to injection, a 1.5-mW green light laser (540 nm) (Melles Griot, Carlsbad, Calif.) was applied to the desired site of injury from a distance of 5 cm carotid artery; blood flow was monitored for 120 minutes or until stable occlusion occurred, after which the mice still showing blood flow were assigned a value of 120 minutes. Stable occlusion was defined as a blood flow of 0 ml/min for 3 minutes. To confirm occlusive thrombosis, carotid arterial segments subjected to injury were excised and embedded in paraffin. Sections were then stained with hematoxylin and eosin.

(ii) Collagen induced platelet consumption: Briefly, mice (8 weeks old, 20-25 g) were weighed and anesthetized with sodium pentobarbital (80 mg/kg). 100 μl of a mixture of collagen (250 μg/ml) and epinephrine (15 μg/ml) in 0.9% NaCl was injected rapidly into the tail vain. Blood was collected from the inferior vena cava after 2 minutes and anticoagulated with $\frac{1}{6}^{th}$ vol of tripotassium EDTA. After thorough mixing, platelets were counted by automated multispecies hematology analyzers (CDC Technologies Inc., Oxford, Conn.), as previously described (Gresele et al., 1990, Thromb. Haemost. 64:80).

(iii) U46619 induced sudden death: This model was also based on a model established previously (Momi et al., 2000, Eur. J. Pharmacol. 397:177). Briefly, mice (3-4 months old) were anesthetized with sodium pentobarbital. Then they received a rapid intravenous injection of U46619 (0.2 mg/kg in PBS, Cayman Chemical) via the tail vein. Heart rate was monitored for 15 minutes prior to sacrifice. The mice which did not die within this time period were recorded as survivors.

(iv) Tail bleeding time: Bleeding time was measured by the tail clip method before and 6 hrs after 2 mg/kg LPS (Sigma-Aldrich, St. Louis, Mo.) or saline vehicle were administered intraperitoneally to mice that were 10 to 12 weeks of age.

(iv) Platelet aggregation assay: Blood was isolated from the inferior vena cava of anesthetized 10-12 weeks mice (80 mg/kg sodium pentobarbital) using a heparinized syringe (15 U/ml blood). 250 μl blood was mixed with 750 μl of sodium chloride at 37° C. Platelet aggregation was performed as described (Gresele et al., 1983, Thromb. Haemost. 50:852; Booth et al, 1998, Can. J. Physiol. Pharmacol. 76:811; Emery et al., 1995, Arterioscler. Thromb. Vasc. Biol. 15:748) using a 500 Whole Blood Lumi-Aggregometion System (Chrono-Log Corp, Havertown, Pa.). Samples were pretreated with or without 10 nM cicaprost for 1 minute, and aggregation was initiated by addition of 2 μg/ml collagen (Chrono-Log Corp).

Blood Pressure Measurements (i) Tail Cuff measurement: Resting systolic blood was measured in conscious mice (3-4 months old) using a computerized noninvasive tail-cuff system (Visitech Systems, Apex, N.C.). The validity of this system has been demonstrated previously (Tilley et al., 1999, J. Clin. Invest. 103: 1539; Kennedy et al., 1999, Nat. Med. 5:217). Mice were adapted to the system for 14 days; measurements of sessions 25 minutes in length were done once each day between 15:00 and 18:00. After that, blood pressure was recorded daily for 3 consecutive days in the same way. Data were collected and analyzed using updated BP 2000 software (http://www(dot)visitechsystems(dot)com/).

(ii) Telemetry: This approach is based on prior studies with minor modifications (Carlson et al., 2002, Hypertension 39:214; Carlson et al., 2000, Hypertension 35:E1). Briefly, male mice (3-4 months old) were anesthetized, using ketamine (100 mg/kg, intraperitoneally) and acepromazine (5 mg/kg, intraperitoneally) and were subject to surgery under strict sterile conditions. A horizontal incision (right blade to mid-scapular) was made on the back and the telemetry probe (TA11-PA20; Data Sciences International, St. Paul, Minn.) was inserted. The probe was secured by suturing the 3 suture holes on the probe to the skin, along with an additional suture which ran through the muscle and loops around the body of the probe and through the first suture hole. This prevented the probe from sliding laterally down the side of the mouse. A vertical incision was then made on the neck and the tips of fine hemostats were advanced underneath the skin to the incision on the back and externalized. The flexible tip of the transmitter catheter was gently grasped and pulled through, so that it protruded through the incision on the neck. The left common carotid artery was then isolated. The tip of the catheter was inserted into the common carotid lumen, and advanced until the catheter notch reaches the level of the carotid bifurcation. The transmitter signal was monitored with an AM radio tuned to the low end of the dial to verify the proper catheter placement. A pulsing tone indicated proper catheter placement. After surgery, mice were maintained on normal salt intake (0.6% NaCl; diet No. 8746, Harlan Teklad, Indianapolis, Ind.) for a 1-week period, after which the telemetry probes were turned on. The cage with the animal was placed on a receiver plate and the signal collected using the Dataquest LabPRO Acquisition System (version 3.01, Data Sciences international, Inc., Colorado Springs, Colo.). Mice were maintained on a 12 hour light: dark regimen, and in a sound attenuated room. 10 second waveforms of mean arterial pressure (MAP), diastolic arterial pressure (DAP), systolic arterial pressure (SAP), heart rate (HR), and locomotor activity were sampled every 5 minutes during the 4 day monitoring periods, and hourly averages and SD were then calculated, and then all data were expressed as values averaged from daytime (resting phase) and nighttime (active phase) measurements. After this baseline data collection, the probes were then turned off, and the mice were fed a high salt diet (8% NaCl; diet No. 5008, Harland Teklad) diet for 1 week, after which the probes were turned on and the data were collected for additional 4 days.

(iii) Direct measurement of blood pressure: Mice were anesthetized (ketamine 100 mg/kg, acepromazine 5 mg/kg) and placed on a temperature-controlled panel. The right internal jugular vein and left carotid artery were cannulated with PE-10 tubing. The arterial catheter was connected to a Capto SP844 pressure transducer (Capto, Horten, Norway), and blood pressure (BP) was monitored continuously with a Powerlab/8SP system (AD Instruments Inc.), as previously described (Hui et al., 2004, Circulation 110:3360; Rocca et al., 2000, Nat. Med. 6:219). Blood pressure and heart rate were continuously monitored for 20-40 minutes until stable values were obtained. After the equilibration period and the baseline BP was recorded, mice were injected via the right internal jugular vein with cicaprost (1 ug/kg in 4 mL/kg saline) as a bolus, and the same volume of saline was injected before cicaprost administration to exclude volume-mediated BP changes. The BP was continuously recorded until it returned to pretreatment baseline.

Statistical analysis: Statistical analyses were performed by one way ANOVA, followed by a pairwise comparison and/or adjustment for multiple comparisons, as appropriate and using a computerized software package (GraphPad Prism version 4.0, GraphPad Software, Inc., San Diego, Calif.). All values were expressed as mean±SEM. A value of $p<0.05$ was considered significant.

The results of the experiments presented in this Experimental Example are now described.

Figure 27A:
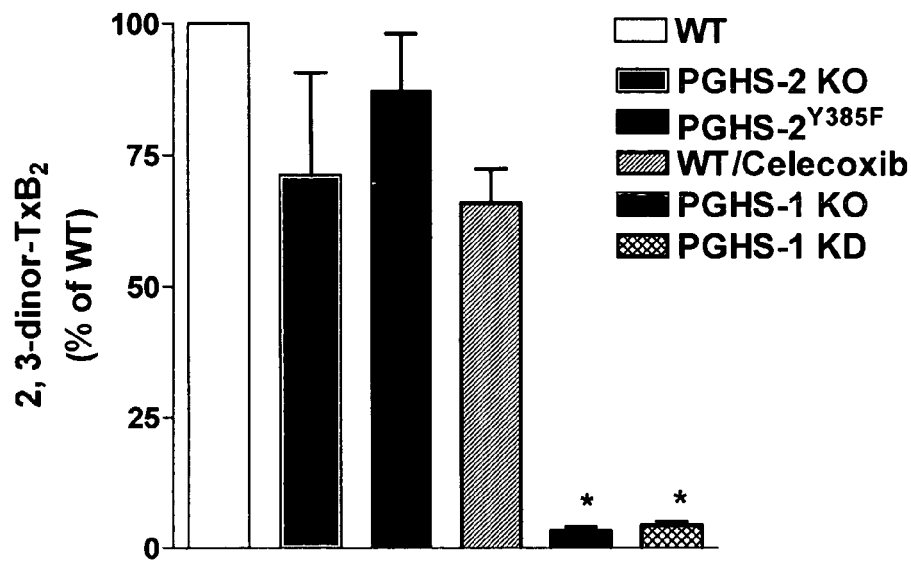
FIG. 27A is a series of graphs depicting the effect of knocked out, knocked down, mutant or inhibited PGHS enzymes on eicosanoid biosynthesis. (n=6 per group; *p<0.001).
Figure 27A:
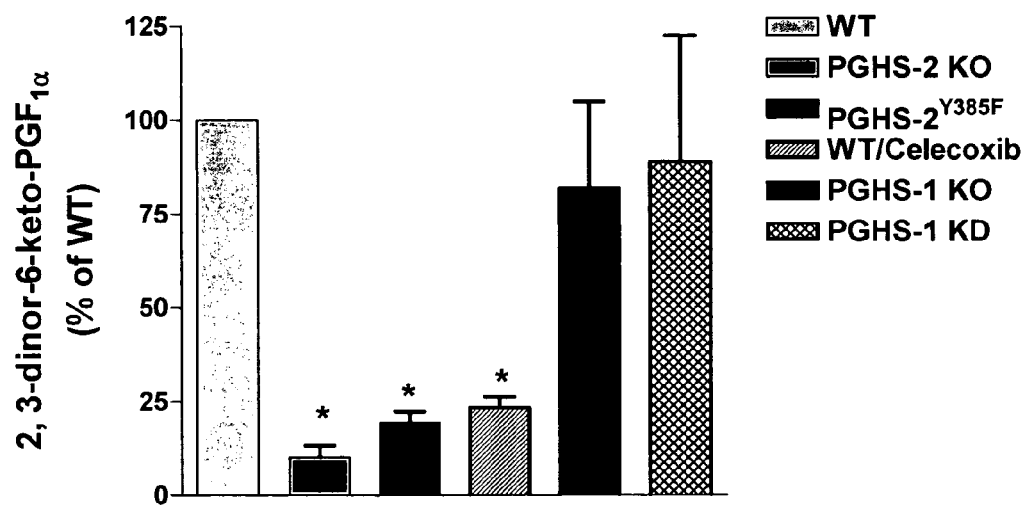
Figure 27B:
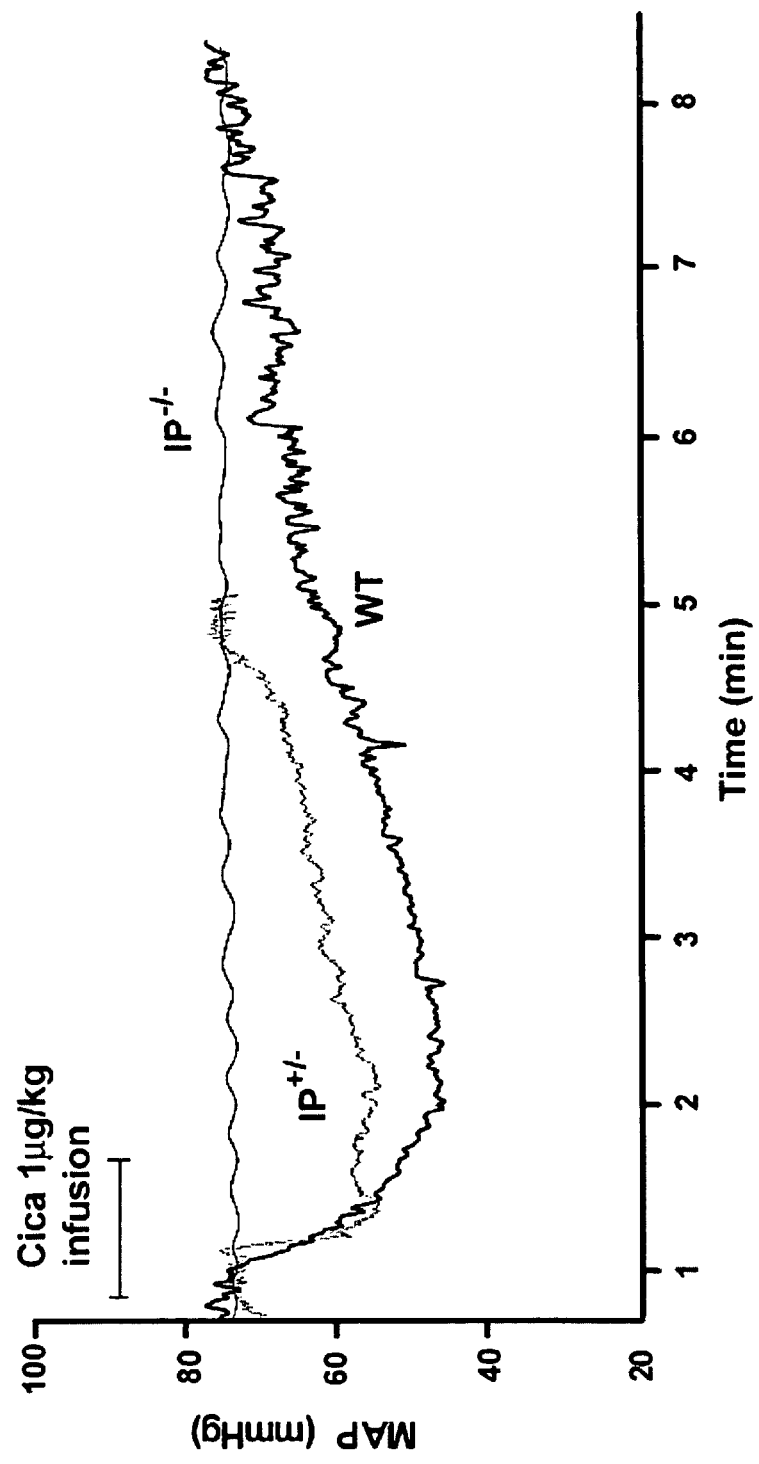
FIG. 27B is a graph depicting the effect of IP deletion on mean arterial pressure. A representative mean arterial pressure (MAP) tracing is shown, measured directly via by carotid artery catheterization in anesthetized WT, IP$^{+/-}$, and IP$^{-/-}$ littermates following administration of the IP agonist cicaprost (Cica) 1 µg/kg intravenously.

The relative contribution of the PGHS enzymes to urinary excretion of 2,3-dinor 6-keto $PGF_{1\alpha}$ and a major Tx metabolite, 2,3-dinor $TxB_2$ (Lawson et al., 1985, Anal Biochem. 150:463) was addressed using mice deficient in either PGHS enzyme or treated with celecoxib or 5,5-dimethyl-3-(3-fluorophenyl)-4-(4-methylsulphonyl)phenyl-2(5H)-furanone (DFU), highly selective PGHS-2 inhibitors (Penning et al., 1997, J. Med. Chem. 40:1347; Riendeau et al., 1997, Br. J. Pharmacol. 121:105). Also utilized were mice with a PGHS-1 knockdown (KD), which mimics the effect of low dose aspirin, achieving a mean 97% inhibition of platelet Tx formation (Yu et al., 2005, J. Clin. Invest. 115:986) and mice with mutant PGHS-$2^{Y385F}$ in which the cyclooxygenase, but not the peroxidase function of the enzyme is inactivated, thereby mimicking the effect of a selective PGHS-2 inhibitor (Yu et al., 2005, Nature (Submitted)). While 2,3-dinor $TxB_2$ is markedly depressed by PGHS-1 KO or KD, it is unaltered significantly in PGHS-2 KO or PGHS-$2^{Y385F}$ mice or by treatment with the PGHS-2 selective inhibitors (FIGS. 27A and 30A. 2,3-dinor 6-keto $PGF_{1\alpha}$, by contrast, is suppressed substantially by PGHS-2 inhibition or KO and in PGHS-$2^{Y385F}$ mice (FIGS. 27A and 27B). Thus, PGHS-1 is the dominant source of 2,3-dinor $TxB_2$, and PGHS-2 is the dominant source of 2,3-dinor 6-keto $PGF_{1\alpha}$ in mice, as in humans (McAdam et al., 1999, Proc. Natl. Acad. Sci. U.S.A. 96:272; Catella-Lawson et al., 1999, J. Pharmacol. Exp. Ther. 289: 735; Catella-Lawson et al., 2001, N. Engl. J. Med. 345:1809).

Figure 27C:
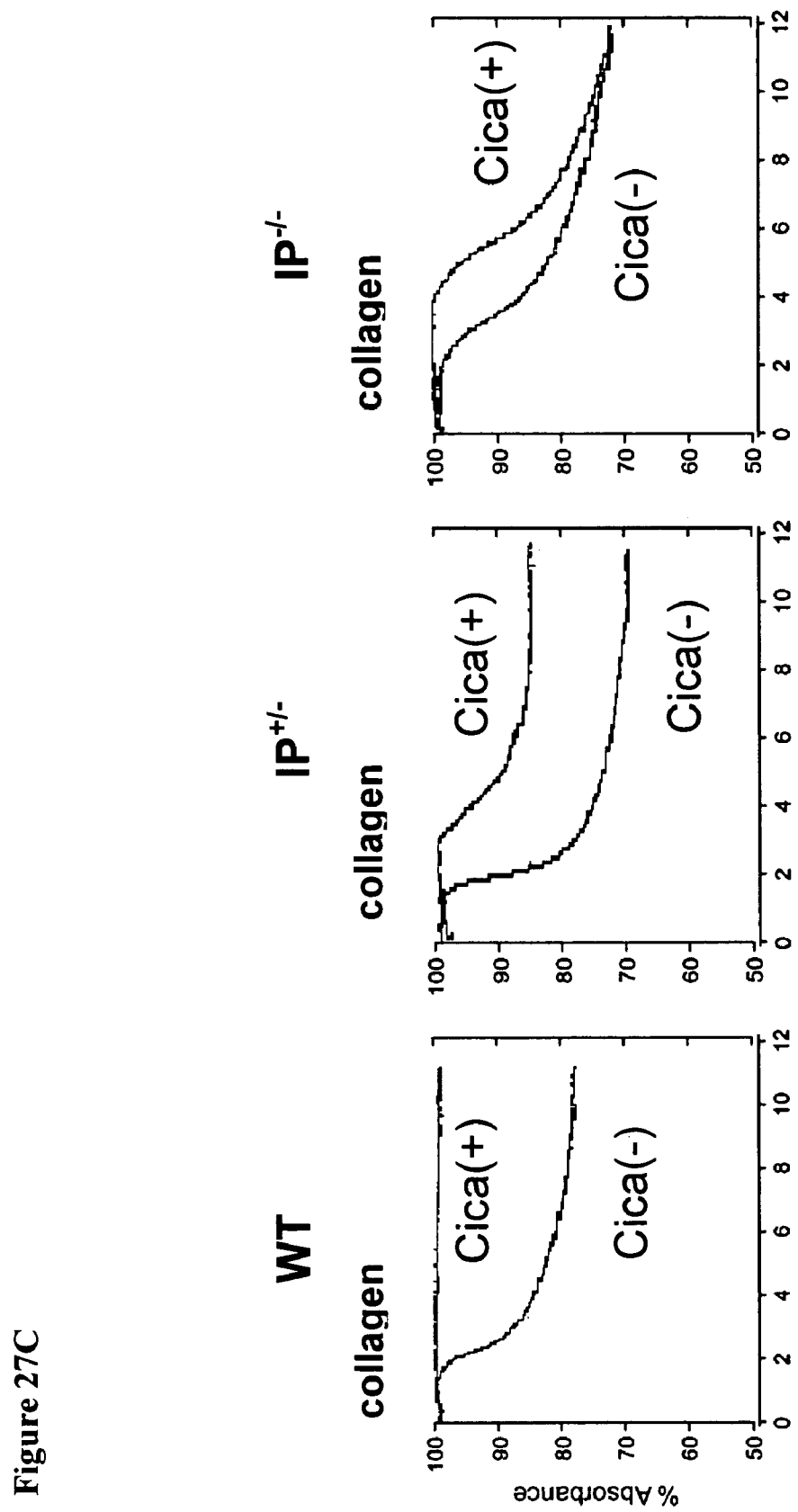
FIG. 27C is a series of graphs depicting the effect of IP deletion on platelet aggregation. A representative platelet aggregation tracing of whole blood is shown from WT (left panel), IP$^{+/-}$ (center panel), and IP$^{-/-}$ (right panel) littermates pretreated with (+) or without (−) 10 nM cicaprost (Cica) for 1 min. Platelet aggregation was initiated by the addition of 2 µg/ml collagen.
Figure 27D:
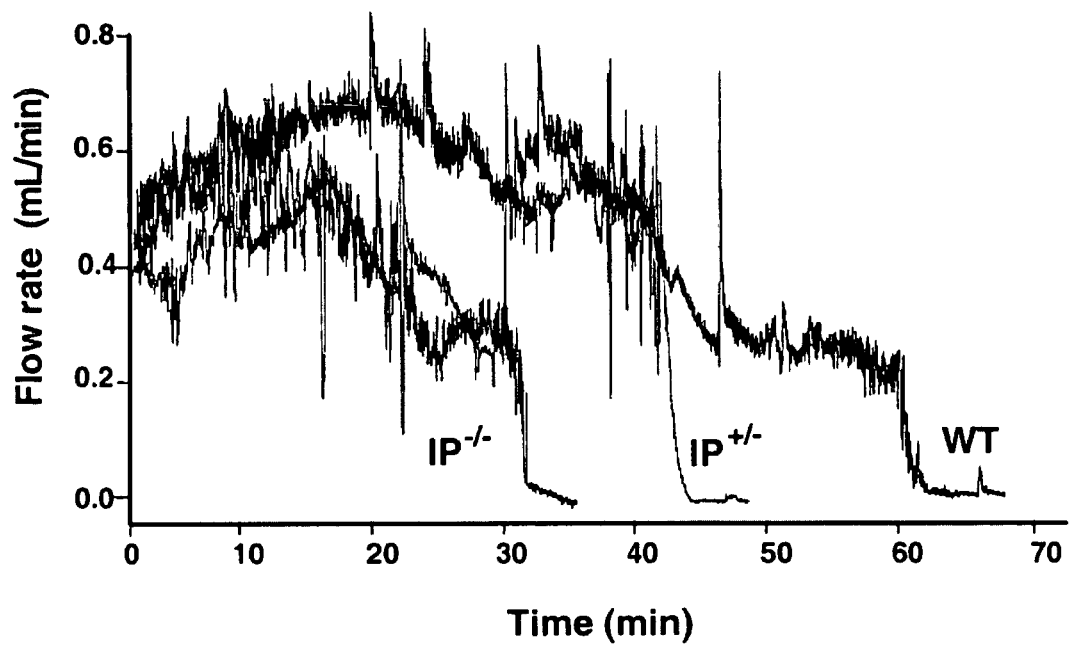
FIG. 27D is a series of graphs depicting the effect of PGHS-2 inhibition and IP deletion on thrombosis. Representative carotid artery blood flow recordings after photochemical injury in WT (black line), IP$^{+/-}$, IP$^{-/-}$ mice (top panel), and WT mice (bottom panel) treated with DFU (10 mg/kg/day for 3 days) or vehicle (black line) are shown. Rose Bengal dye was injected at time=0 min.
Figure 27D:
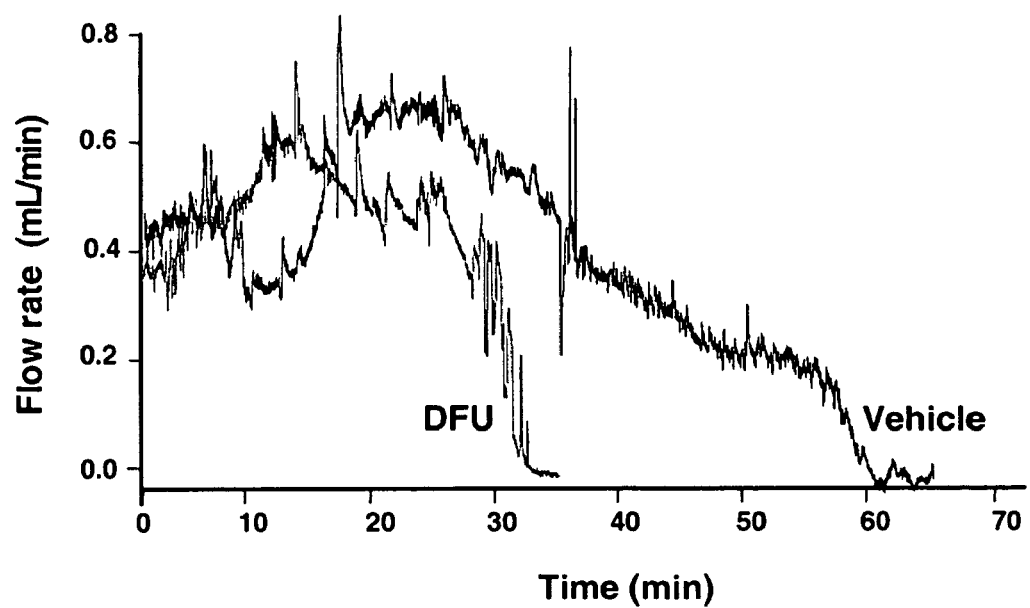

Given the substantial, but incomplete inhibition of $PGI_2$ attained on PGHS-2 inhibitors (COX-2 selective inhibitors), the cardiovascular consequences of deleting just one copy of the IP on cardiovascular function in vivo was studied. The blood pressure response to an IP agonist, cicaprost (Skuballa et al., 1986, J. Med. Chem. 29:313), was reduced in a gene dose dependent manner (FIG. 27B). The maximal decline evoked by cicaprost (1 μg/kg iv) in mean arterial pressure (MAP), measured directly via the carotid artery, was 36±3.5% from pretreatment baseline in WT, 24%±3.3% in $IP^{+/-}$ and 0% in $IP^{-/-}$ littermates (F=42; p<0.0001). Similarly, the duration of the depressor response fell from 10.8±2.5 min in WTs to 5.3±1.1 min in $IP^{+/-}$ animals; there was no change in MAP in $IP^{-/-}$ mice. A similar gene dose dependent effect of IP deletion was observed on the inhibitory effect of 10 nM cicaprost on platelet aggregation induced by collagen 2 μg/ml ex vivo (FIG. 27C). Here $IP^{+/-}$ mice attained 86.7% of the maximal inhibition observed in WTs, while 100% was achieved in $IP^{+/-}$ mice (F=744; p<0.0001). Next, the impact of IP deletion and PGHS-2 inhibition on the time to thrombogenic carotid arterial occlusion after green laser activation of Rose Bengal and consequent free radical catalyzed vascular injury was studied. Again, $IP^{+/-}$ mice exhibited an intermediate phenotype (FIG. 27D). The time to occlusion fell from 66.3±5.1 min in WTs to 44.4±7.0 min in $IP^{+/-}$ to 29.7±7.6 min in $IP^{-/-}$ mice (F=6.5; p<0.0055). Treatment with DFU also accelerated the time to vascular occlusion (FIG. 27D) from 59.4±10.4 min to 33.4±4.3 min (p<0.05). The mean impact of DFU on time to occlusion (56.2% of WT value) was intermediate between that of $IP^{+/-}$ (68.1% of WT) and $IP^{-/-}$ (45.5%) mice. Thus, loss of even one copy of the IP attenuates the response to a $PGI_2$ mimetic on both platelets and the vasculature and also augments the response to a thrombogenic stimulus. Inhibition of PGHS-2 also accelerates thrombogenesis, to a degree intermediate between $IP^{+/-}$ and $IP^{-/-}$ mice.

Figure 28A:
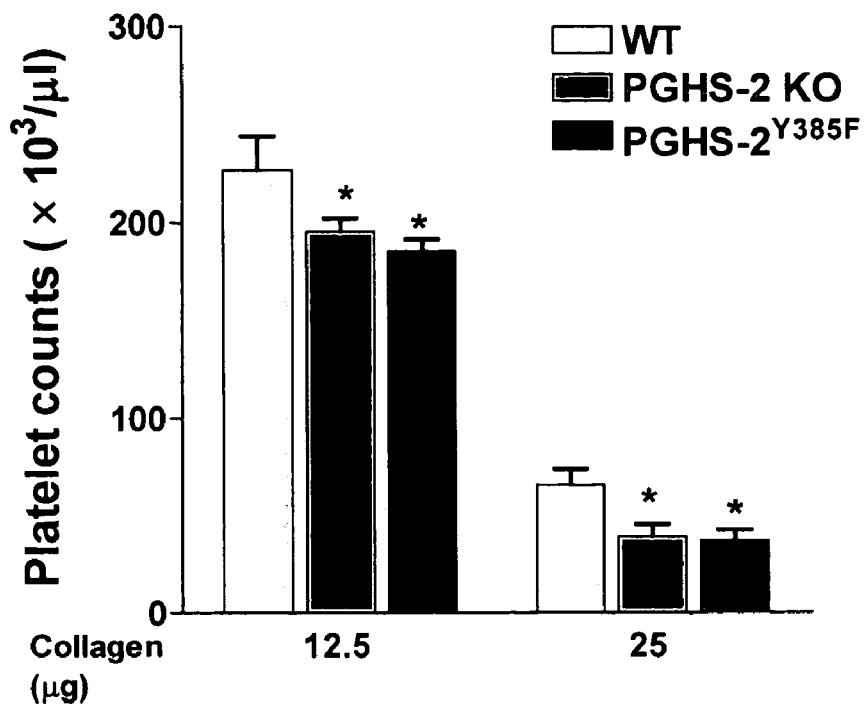
FIG. 28A is a series of graphs depicting the effect of PGHS-2 knock out or mutation on platelet consumption and sudden death. Circulating platelet number 2 minutes after i.v. injection of collagen (12.5 and 25 µg/kg) plus epinephrine (15 µg/ml) into 8-10 week old WTs, PGHS-2$^{Y385F}$, and PGHS-2 KO mice (top panel) is shown. (*p<0.01, n=4 per group). Sudden death (bottom panel) induced within 15 min by intravenous injection of 0.2 mg/kg of the TxA$_2$ analogue, U46619, into 8-10 week old WTs, PGHS-2$^{Y385F}$, and PGHS-2 KO mice (right panel) are shown. (*p<0.01, n=10-14).
Figure 28A:
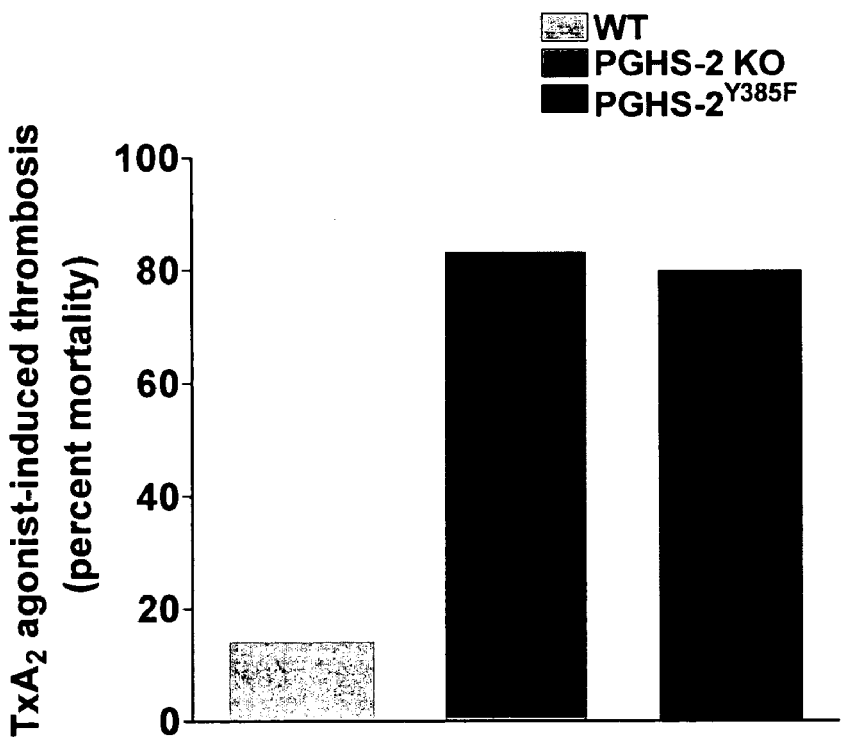
Figure 28B:
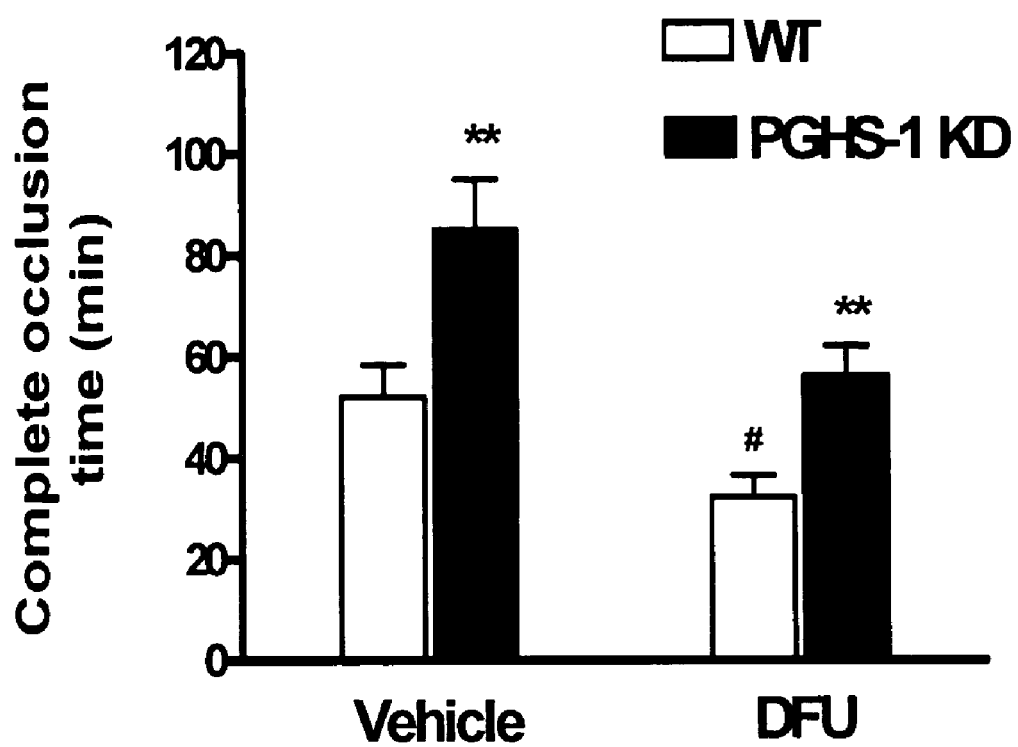
FIG. 28B is a graph depicting the effect of PGHS-2 inhibition on thrombosis in PGHS-1 knock outs. PGHS-2 inhibited with DFU (10 mg/kg) is shown. (**p<0.01; # p<0.05). Ten to 12 animals were used in each group.

The impact of PGHS-2 inhibition, deletion or mutation on the response to thrombogenic stimuli was investigated. Both the fall in platelet count following injection of the platelet agonist, collagen,—reflecting platelet consumption in a developing thrombus—and the frequency of sudden death induced by an intravenous dose of a TP agonist, U46619, were augmented in PGHS-2 KO and PGHS-$2^{Y385F}$ mice (FIG. 28A). Furthermore, the prolongation in bleeding time—an index of platelet vessel wall interactions—induced by LPS (2 mg/kg i.p.) administration to WT mice (2.0±0.2 min vs. 8.9±2.0 min, n=14; p<0.001), was abolished in PGHS-$2^{Y385F}$ mice (1.99±0.27 min vs. 2.3±0.78 min, n=6-7; p=NS). Acceleration of the time to thrombotic carotid vascular occlusion the PGHS-2 inhibitor, DFU (FIG. 28B) was attenuated by PGHS-1 KD, suggesting that the risk of thrombosis from selective inhibition of PGHS-2 would be attenuated by low dose aspirin.

Figure 28C:
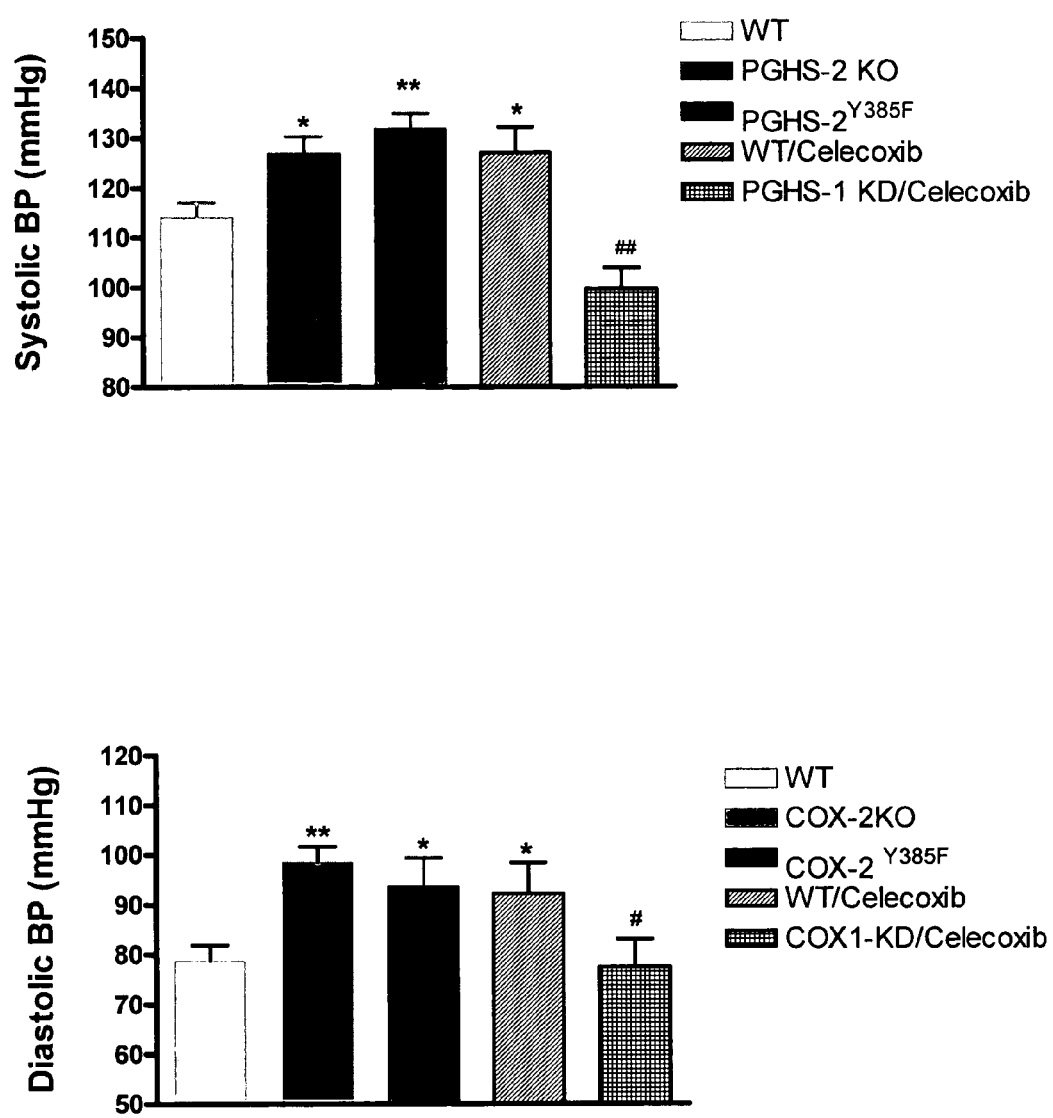
FIG. 28C is a series of graphs depicting the effect of PGHS-2 disruption or inhibition on blood pressure. Systolic blood pressure (top panel) and diastolic blood pressure (bottom panel) measured by tail cuff are shown. (*p<0.05; **p<0.01, n=6-12; # p<0.05; ## p<0.01).

Previous studies have raised the possibility that the risk of hypertension on nonsteroidal anti-inflammatory drugs (NSAIDs) might relate predominantly to inhibition of PGHS-2 and the selectivity with which it is attained (FitzGerald, 2002, J. Clin. Invest. 110:33). Although this hypothesis has not been addressed directly in humans, hypertension has been reported both in patients receiving traditional NSAIDs and in patients receiving NSAIDs selective for inhibition of PGHS-2 (Cheng et al., 2004, Hypertension 43:525; Brater, 2002, Semin. Arthritis Rheum. 32:33). Hypertension, reported as an adverse event, relates to dose in patients receiving either celecoxib or rofecoxib, with a more pronounced signal on the latter drug. While this reflects the relative degree of selectivity for inhibition of PGHS-2, it is confounded with the duration of drug exposure in this comparison (FitzGerald, 2003, Nat. Rev. Drug Discov. 2:879). Hypertension was more common in patients taking PGHS-2 selective drugs than traditional NSAIDs in an observational study (Aw et al., 2005, Arch. Intern. Med. 165:490). Here, blood pressure was elevated by PGHS-2 deletion or mutation or by treatment with the PGHS-2 inhibitor, celecoxib, compared to WT controls on a regular chow diet (FIG. 28C). Thus, selective disruption or deletion of PGHS-2, just like deletion of the IP (Francois et al., 2005, Cell Metab. (in press)), can result in an elevation of blood pressure in mice.

Figure 29A:
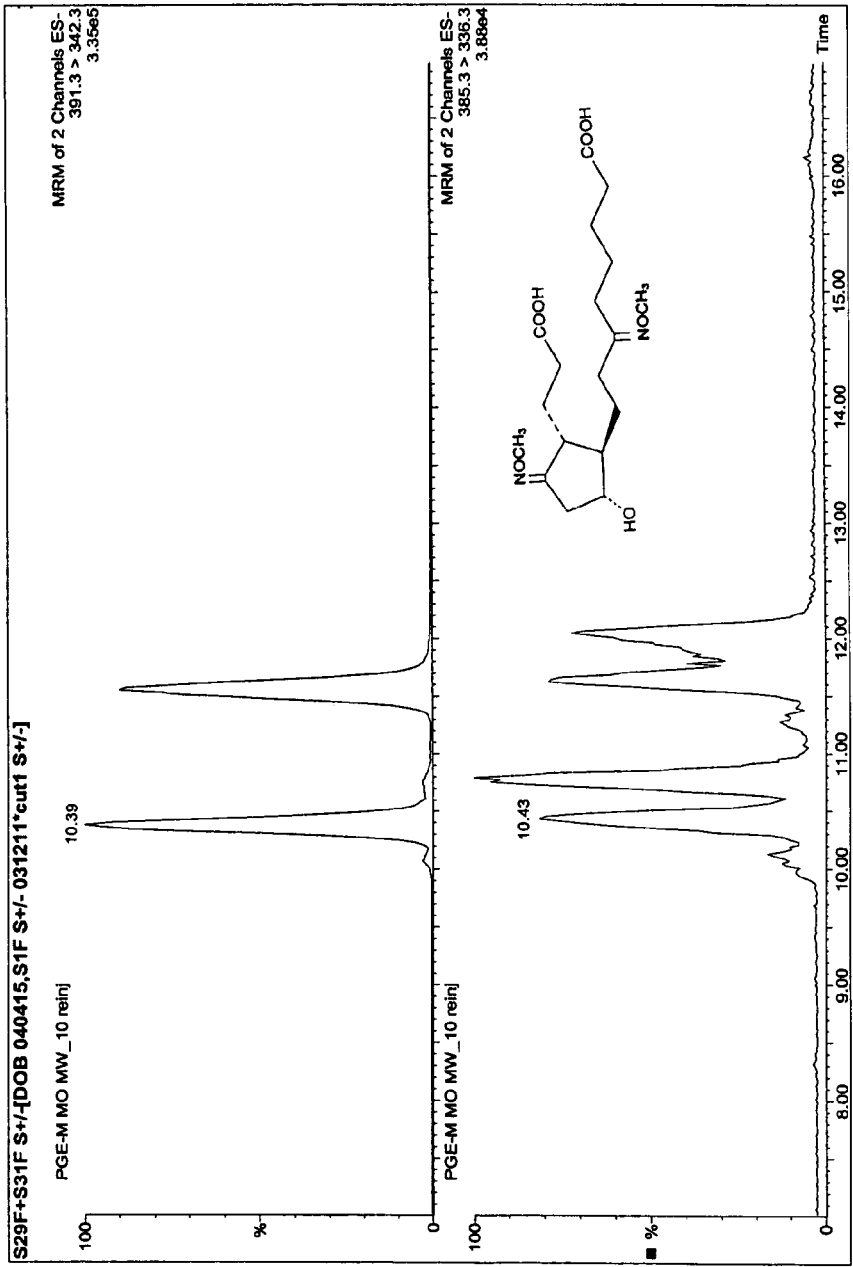
FIG. 29A is a series of images depicting selected ion monitoring traces of the methoximated derivative of endogenous PGE-M (9,15-dioxo-11α-hydroxy-2,3,4,5-tetranor-prostan-1,20-dioic-17,17,18,18,19,19-d$_6$ acid; bottom panel) and its hexadeuterated internal standard (top panel).
Figure 29B:
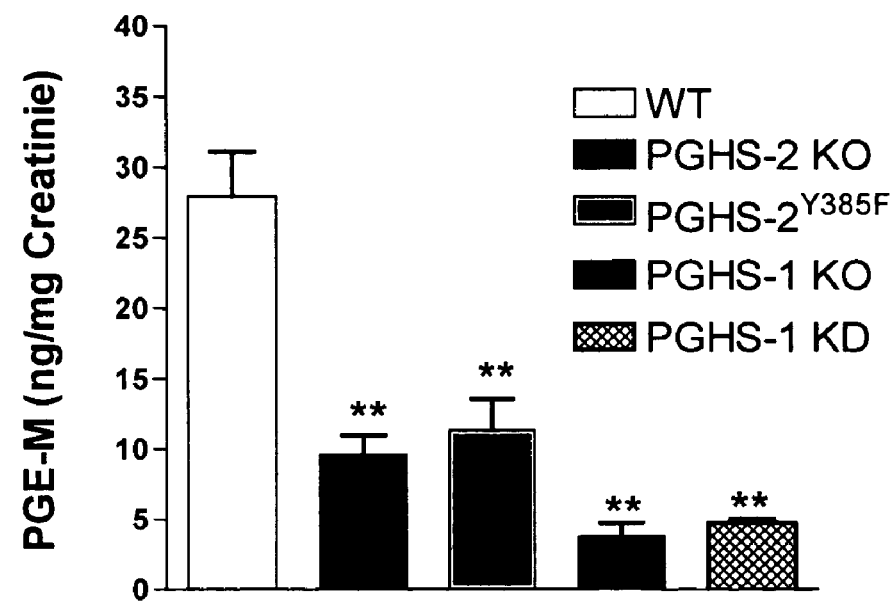
FIG. 29B is a series of graphs depicting the effect of knocked out, knocked down, mutant or inhibited PGHS enzymes on PGE-M biosynthesis in male (top panel) and female (bottom panel) mice. (**p<0.01; *p<0.05). Both PGHS-1 and PGHS-2 contribute to PGE$_2$ biosynthesis as reflected by excretion of its major urinary metabolite (PGE-M).
Figure 29B:
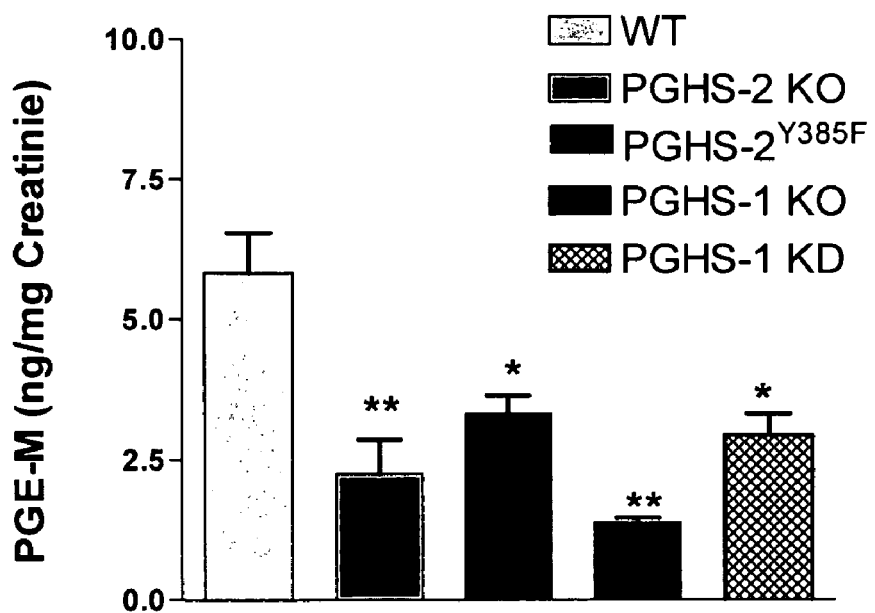
Figure 30A:
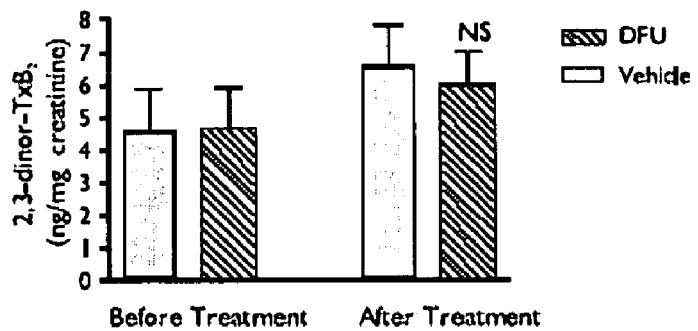
FIG. 30A is a graph depicting the effect of PGHS-2 suppression on 2,3-dinor TxB$_2$. 2,3-dinor TxB$_2$ was not significantly different as a result of DFU treatment in WT mice. (9 to 13 animals in each group).
Figure 30B:
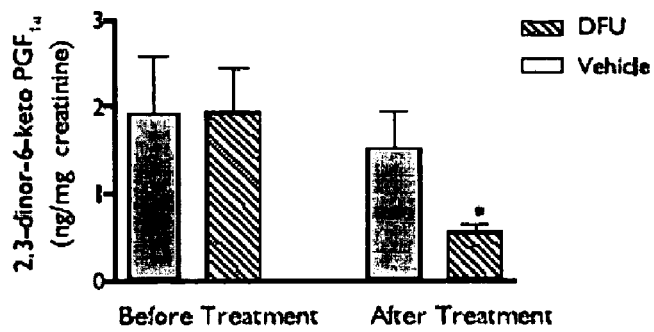
FIG. 30B is a graph depicting the effect of PGHS-2 suppression on 2,3-dinor 6-keto PGF$_{1\alpha}$. 2,3-dinor 6-keto PGF$_1$, was suppressed as a result of DFU treatment in WT mice. (*=p<0.05 compared with pretreatment values; 9 to 13 animals in each group).
Figure 30C:
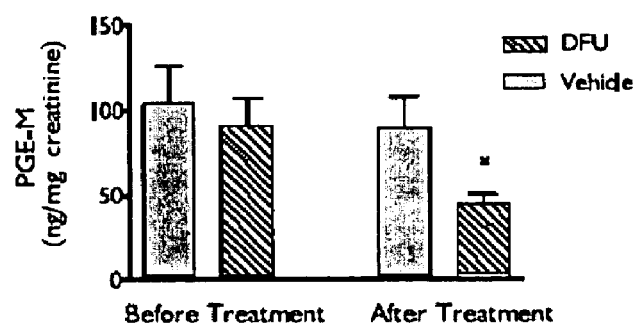
FIG. 30C is a graph depicting the effect of PGHS-2 suppression on PGE-M. PGE-M was suppressed as a result of DFU treatment in WT mice. (*=p<0.05 compared with pretreatment values; 9 to 13 animals in each group).

Besides $PGI_2$ (McAdam et al., 1999, Proc. Natl. Acad. Sci. U.S.A. 96:272; Catella-Lawson et al., 1999, J. Pharmacol. Exp. Ther. 289:735), PGHS-2 is also the predominant source of $PGE_2$ biosynthesis in humans (Murphey et al., 2004, Anal. Biochem. 334:266). Using a mass spectrometric assay (FIG. 29A) for the major PGE metabolite, 11α-hydroxy-9,15-dioxo-2,3,4,5-tetranor-prostan-1,20-dioic acid (PGE-M), it was observed that DFU depressed PGE-M by a mean 52.3% ($p<0.05$; FIG. 30C) and depressed 2,3-dinor 6-keto $PGF_{1\alpha}$ by a mean 71.2% ($p<0.05$; FIG. 30B), but did not depress 2,3-dinor $TxB_2$ (4.63±1.3 ng/mg creatinine vs. 6.0±1.1 ng/mg creatinine; $p=0.44$; FIG. 30A) from pretreatment values in WT mice. Urinary PGE-M in WT mice is strikingly higher in males (FIG. 29b, top panel) than in females (FIG. 29B, bottom panel). However in both genders, deletion or mutation of PGHS-2 to inactivate its cyclooxygenase property, and thereby mimic a PGHS-2 inhibitor, depresses PGE-M excretion. Similarly deletion (KO) or knock down (KD) of PGHS-1, such as to mimic genetically low dose aspirin, also depresses urinary PGE-M. Thus, although not exclusive to this enzyme, PGE-M may act as a biomarker of PGHS-2 activity or inhibition. While deletion of the IP augments the response to thrombogenic or hypertensive stimuli, depression of $PGE_2$ might also be expected to influence cardiovascular function. Thus, deletion of the EP2 receptor (Kennedy et al., 1999, Nat. Med. 5, 217), like the IP (Francois et al., 2005, Cell Metab. (in press); Watanabe et al., 2005, Circ. J. 69:124) increases salt sensitivity in mice. Additional to effects on blood pressure, low concentrations of $PGE_2$ activate platelets via the EP3, while higher concentrations inhibit platelet function by ligating the IP (Fabre et al., 2001, J. Clin. Invest. 107:603). Activation of PGHS-2-derived $PGE_2$, acting via EP4, has been proposed as a mechanism of destabilization of atherosclerotic plaque. Thus, unlike $PGI_2$, which is uniformly cardioprotective, $PGE_2$ may be harmful or protective of the cardiovascular system. Either way an estimate of its biosynthesis may reflect an evolving risk.

Figure 29C:
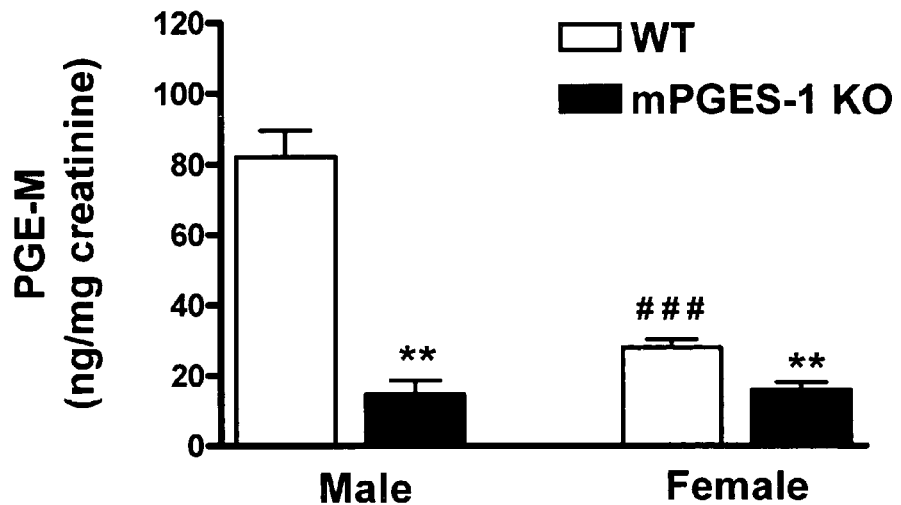
FIG. 29C is a graph depicting the effect of mPGES-1 KO on urinary PGE-M in male and female mice. (**p<0.01; ###p<0.001).

The unstable $PGH_2$ endoperoxide product of PGHS enzymes is further converted to $PGE_2$ by PGE synthases. One of them, mPGES-1, is regulated by inflammatory cytokines and mitogens, like PGHS-2, and colocalizes with it in certain inflammatory tissues (Thoren et al., 2003, J. Biol. Chem. 278:22199; Claveau et al., 2003, J. Immunol. 170:4738) and during development (Pini et al., 2005, Arterioscler. Thromb. Vasc. Biol. 25:315). Deletion of mPGES-1 attenuates inflammation to a degree indistinguishable from a traditional NSAID in mice, and mPGES-1 has emerged as an alternative drug target to PGHS-2 (Trebino et al., 2003, Proc. Natl. Acad. Sci. U.S.A. 100:9044). As depicted in FIG. 29C, urinary PGE-M is significantly lower in both male (82.1±7.5 ng/mg creatinine vs. 14.7±4.0 ng/mg creatinine; $p<0.01$) and female (28.0±2.3 ng/mg creatinine vs. 15.8±2.2 ng/mg creatinine; $p<0.01$) KO mice than in WT littermates. Urinary PGE-M was also significantly higher in WT males than in females (###$p<0.001$), as is the case in humans (Murphey et al., 2004, Anal. Biochem. 334:266). Thus, mPGES-1, rather than other PGES enzymes, such as cytosolic PGES (Tanioka et al., 2000, J. Biol. Chem. 275:32775) or mPGES-2 (Murakami et al., 2003, J. Biol. Chem. 278:37937) is the dominant source of PGE biosynthesis under physiological conditions in mice.

Figure 29D:
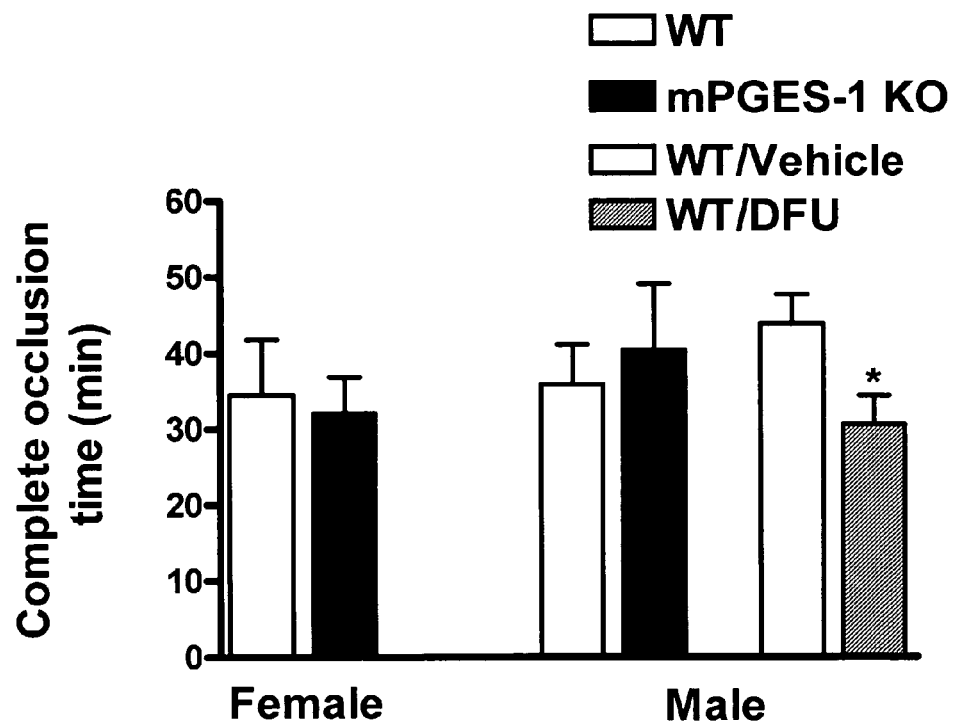
FIG. 29D is a graph depicting the effect of mPGES-1 KO on thrombogenesis in male and female mice. Carotid arterial thrombotic occlusion induced by photochemical injury, as described elsewhere herein, is shown. (p=0.85, n=6-10 per group).
Figure 29E:
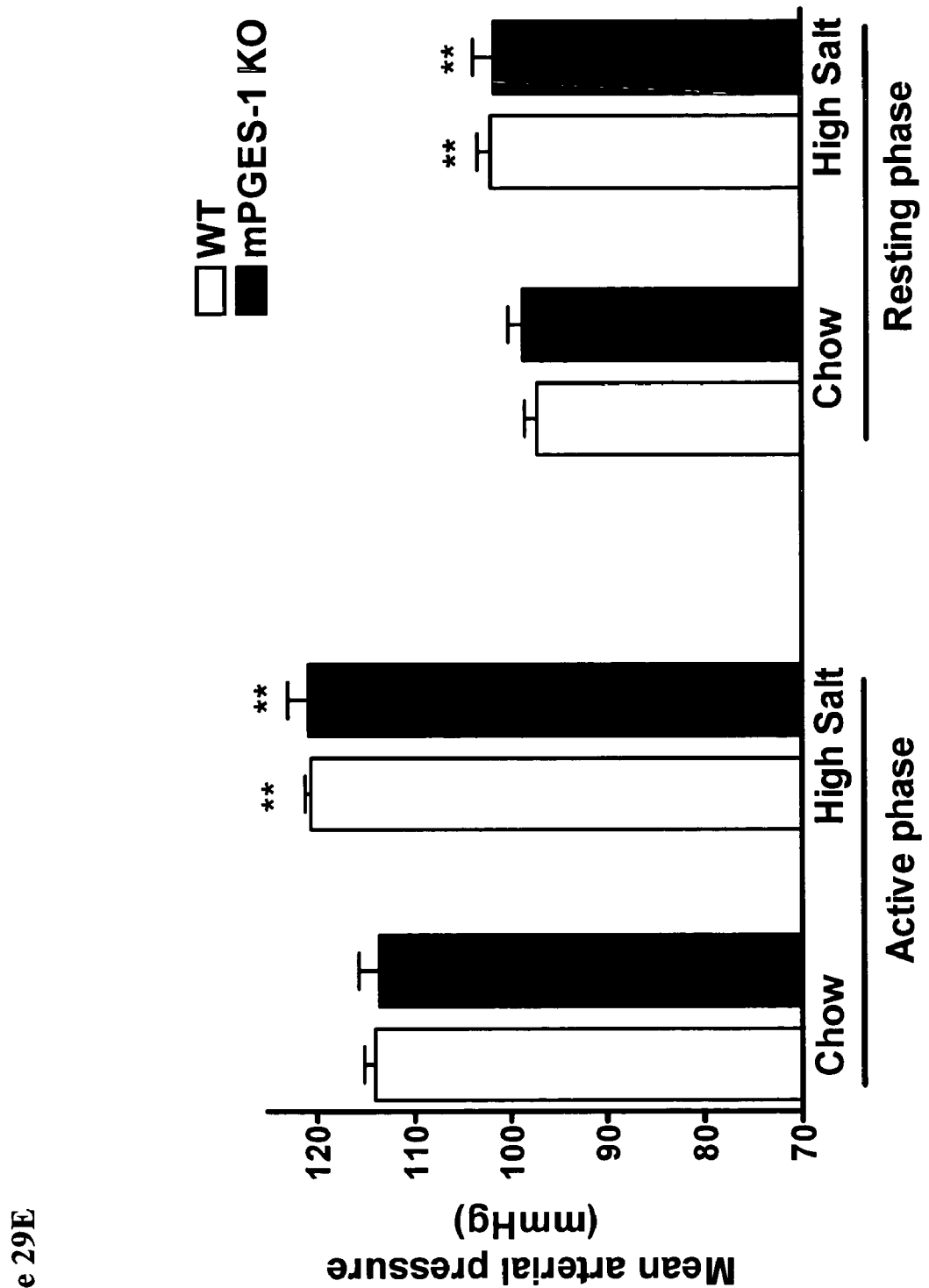
FIG. 29E is a series of graphs depicting the effect of mPGES-1 KO on blood pressure. Radio telemetry was used to measure continuously blood pressure. The recordings were of the 12 hour dark, "active" phase (left panel) and light periods, "resting" phrase (right panel). Blood pressure for each of these phases was averaged over consecutive four day periods for each mouse. (**p<0.01; n=6 per group).

Unlike disruption or inhibition of PGHS-2, deletion of mPGES-1 failed to alter the response to a thrombogenic stimulus in either male (40.4±8.7 min) or female (32.1±4.7 min) mice versus WTs littermates (35.9±5.3 min and 34.5±7.3 min, respectively (FIG. 29D). Tail cuff measurement of blood pressure also failed to reveal an impact of mPGES-1 deletion compared to WT controls (mean arterial pressure: 110.5±3.34 mmHg vs. 107.0±6.65 mmHg; $p=0.84$). The potential impact of mPGES-1 deletion was examined in more detail using a telemetric approach to continuous monitoring of blood pressure in male mice. Blood pressure was measured after an acclimatization period, both on a normal (0.6% NaCl) diet and a high salt (8% NaCl) diet. An impact of mPGES-1 deletion was not detected, either in the night time activity period (FIG. 29E, left panel) or in the day time rest period (FIG. 29E, right panel) on either dietary regimen. A high salt diet induced a mean ~6% increase in mean arterial blood pressure in both WT and mPGES-1 KO groups which was significant ($p<0.01$), but no significant difference was apparent between the KOs and the WT mice. Mean arterial pressure also rose significantly with activity on both dietary regimens (FIG. 29**E).

Figure 29F:
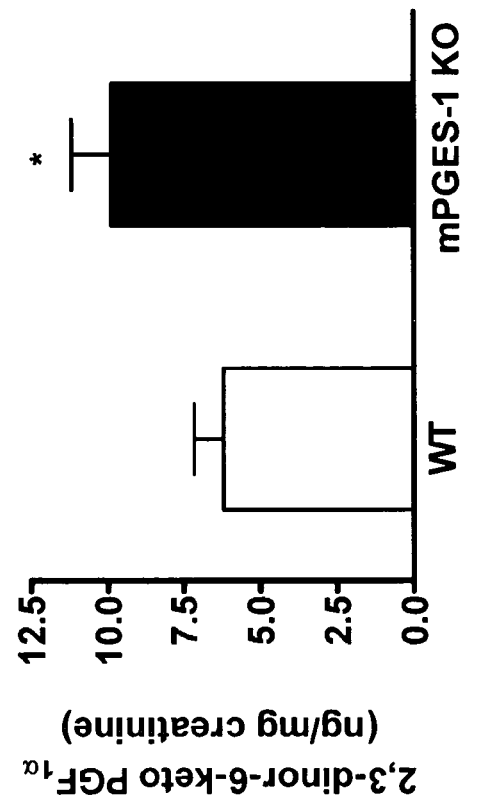
FIG. 29F is a series of graphs depicting the effect of mPGES-1 KO on PGI$_2$ biosynthesis. Both PGE-M (left panel) and 2,3-dinor-6-keto PGF$_1$, (right panel) were measured in male littermates on a normal salt diet. (***p<0.001; *p<0.05; n=8 per group).
Figure 29F:
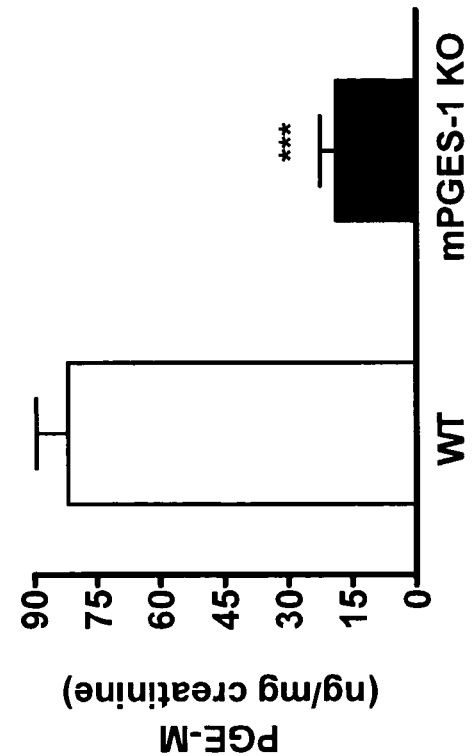

Deletion (or inhibition) of a PG synthase enzyme, such as mPGES-1, may theoretically lead to accumulation of the PGHS product, $PGH_2$, rendering it available for rediversion to other vasoactive PGs. Such a phenomenon has been reported in LPS-stimulated macrophages obtained from mPGES-1 KO mice, in which formation of $TxA_2$ and $PGI_2$ were augmented, coincident with suppression of $PGE_2$ (Trebino et al., 2005, J. Biol. Chem. 280:16579). Here, urinary excretion of 2,3-dinor 6-keto $PGF_{1\alpha}$ and 2,3-dinor $TxB_2$ between mPGES-1 KOs and WT controls was compared to address this possibility in vivo. PGE-M decreased significantly in the KOs compared to WT controls (FIG. 29F, left panel). 2,3-dinor $TxB_2$ was unaltered by mPGES-1 deletion (544.4±135.7 ng/mg creatinine vs. 433.6±68.9 ng/mg creatinine; $n=17$-$20$ mice per group; $p=0.84$). Notably, $PGI_2$ biosynthesis was increased significantly by a mean 60% compared to WT controls (FIG. 29F, right panel).

In summary, selective inhibition, knockout (KO) and mutation of PGHS-2 confirmed that PGHS-2 is the dominant source of $PGI_2$ in mice, as in humans. In addition, KO and knock down (KD) of PGHS-1 established it as the major source of $TxA_2$ in mice, as in humans. Thrombogenesis was accelerated and blood pressure elevated by PGHS-2 inhibition, KO and mutation, an effect replicated by deletion of the $PGI_2$ receptor (IP). Notably, the thrombotic phenotype evoked by the PGHS-2 inhibitor was roughly intermediate between that resulting from hetero- and homozygous deletion of the IP. This observation is consistent with detection of an increase in humans of thrombotic events with selective COX-2 inhibitors which suppress biosynthesis of $PGI_2$ by 60%-80% (McAdam et al., 1999, Proc. Natl. Acad. Sci. U.S.A. 96:272; Catella-Lawson et al., 1999, J. Pharmacol. Exp. Ther. 289:735; Cullen et al., 1998, J. Pharmacol. Exp. Ther. 287:578). Simulating low dose aspirin, PGHS-1 KD attenuates the impact of PGHS-2 inhibition on thrombogenesis and blood pressure. By contrast, deletion of microsomal PGE synthase (mPGES)-1, which depresses $PGE_2$, augments $PGI_2$, and leaves Tx unaltered, affected neither thrombogenesis nor blood pressure. Suppression of $PGI_2$ by PGHS-2 inhibitors predisposes to thrombosis and hypertension, while augmented $PGI_2$ may attenuate the cardiovascular consequences of mPGES-1 deletion.

Thus, inhibition of PGHS-2-derived $PGI_2$ augments the response to thrombogenic stimuli in vivo and may contribute to hypertension on NSAIDs. Deletion of mPGES-1, in contrast to PGHS-2 inhibition, deletion or disruption, does not alter blood pressure or predispose to thrombosis. This may result from diversion of the $PGH_2$ substrate to PGI synthase, augmenting the production of $PGI_2$.

Experimental Example 6

Interindividual Variability in the Response to Selective Inhibitors of Cyclooxygenase-2

The emergence of a cardiovascular signal attributable to coxibs should relate in patients to their underlying risk of cardiovascular disease (FitzGerald, 2004, N. Engl. J. Med. 351:1709-11; FitzGerald, 2003, Nat. Rev. Drug Discov. 2: 879-90). However, the detection of such uncommon drug related adverse effects in patients at lower intrinsic cardiovascular risk might be confounded by multiple factors (FitzGerald, 2004, N. Engl. J. Med. 351:1709-11). Such factors include: the degree of selectivity for inhibition of COX-2 actually attained within an individual and elements of drug exposure, such as dose, half life and duration of action.

In this example, the variability in response, both within and between subjects, to two COX-2 selective inhibitor compounds, celecoxib and rofecoxib, was examined in a placebo controlled, crossover study.

The materials and methods used in the experiments presented in this Experimental Example are now described.

Study Design: This randomized, double-blind, placebo-controlled protocol was approved by the Institutional Review Board of the University of Pennsylvania Health System and by the Advisory Council of the General Clinical Research Center (University of Pennsylvania, Philadelphia). Written informed consent was obtained from all study volunteers. All had an unremarkable medical history, physical examination, routine hematologic and biochemical screen and were within 30 percent of ideal body weight. Subjects were non-smokers and abstained from the use of aspirin and traditional NSAIDs, as assessed by history and platelet aggregometry, for at least two weeks before enrollment (Catella-Lawson et al., 2001, N. Engl. J. Med. 345: 1809-17). Routine hematology, biochemistry, and urinalysis were assessed at time of screening and at 24 hours after administration of the drugs on completion of the study.

Treatments and Assessment: Fifty healthy volunteers (Table 4), aged between 21 and 43 years, received, in random order, a single dose of placebo, celecoxib (200 mg), or rofecoxib (25 mg) under double blind conditions, separated by washout periods of at least two weeks. Inhibition of platelet COX-1 was assessed by measurement of serum $TxB_2$ (Patrignani et al., 1982, J. Clin. Invest. 69: 1366-72). COX-2 inhibition was assessed ex vivo by measurement of lipopolysaccharide-stimulated $PGE_2$ in plasma (Panara et al., 1999, J. Pharmacol. Exp. Ther. 290: 276-80). The coefficients of variation for repeatability and reproducibility were 4.3% and 4.1% respectively for COX-1 inhibition and 1.9% and 4.3% respectively for COX-2 inhibition. Measurements were performed immediately before the administration of drug (0 hrs) and 4 hours thereafter. Urinary 2,3-dinor-6-keto $PGF_{1\alpha}$ (PGI-M), an index of $PGI_2$ biosynthesis (FitzGerald et al., 1983, Circulation 67: 1174-7), and 11-dehydro $TxB_2$ (Tx-M) (Catella and FitzGerald, 1987, Thromb. Res. 47: 647-56), reflective of $TxA_2$ formation in vivo, were assessed at 0 and 4 hours in spot urine samples that were collected 30 minutes after voiding. The coefficients of variation for both assays were <10%. A subset of the volunteers (n=5) progressed through the entire protocol on five occasions, each separated by two weeks, to assess intraindividual variability in drug response in five replicates.

Plasma drug concentrations: Plasma samples were analyzed by liquid chromatography tandem mass spectrometry (Micromass Quattro Ultima, Micromass, Beverly, Mass.) using L755100 (Merck Frosst, Point Claire, Canada) and SC58125 (Cayman, Ann Arbor, Mich.) as internal standards for celecoxib and rofecoxib, respectively. Samples were separated on a Luna 3μ $C_{18}$ (150×2.0 mm) column (Phenomenex, Torrance, Calif.) and quantitated using negative atmospheric pressure ionization and multiple reaction monitoring of m/z 380.2→316.1 (celecoxib), 384.2→305.1 (SC58125), 314.2→215.1 (rofecoxib) and 328.2→313.1 (L755100).

TABLE 4

Characteristics of the Subjects

| | Female (n=22) | Male (n=28) | All (n=50) |
|---|---|---|---|
| Age-yrs | | | |
| (25%, median, 75%) | 23.3, 26.0, 31.8 | 23.0, 29.5, 35.3 | 23.0, 27.5, 34.5 |
| Race-no. (%) | | | |
| White | 12 (54.6) | 17 (60.7) | 29 (58.0) |
| Black | 7 (31-8) | 5 (17.9) | 12 (24.0) |
| Asian | 3 (13.6) | 6 (21.4) | 9 (18.0) |
| Body-mass index | | | |
| (25%, median, 75%) | 21.0, 23.5, 28.2 | 23.3, 25.3, 27.8 | 21.8, 24.8, 28.0 |

Single nucleotide polymorphism (SNP) genotyping: SNP analysis was done using DNA obtained from blood leucocytes. Twenty-six SNP assays (Table 5) were performed, using the Sequenom® MassARRAY® system (Sequenom, San Diego, Calif.) (Wiltshire et al., 2003, Proc. Natl. Acad. Sci. USA 100: 3380-5). These assays robustly detected 1083 out of 1482 genotypes. The additional 399 genotypes were determined by resequencing (ABI 3730x1, Applied Biosystems, Foster City, Calif.).

Statistical analysis: The primary response variables were: i) ex vivo COX-2 inhibition, expressed as the ratio of postdrug to predrug plasma $PGE_2$; ii) ex vivo COX-1 inhibition, expressed as the ratio of postdrug to predrug serum $TxB_2$; iii) urinary PGI-M inhibition, expressed as the ratio of concentration post drug to post placebo administration; iv) urinary Tx-M inhibition, expressed as the ratio of concentration post drug to post placebo administration; and v) plasma drug concentrations four hours post drug administration. Derived variables were ratios of primary measures as estimates of COX-2 selectivity. All variables were log transformed to approximate normality. Three extreme outlying datapoints were removed.

Each subject in the study had either one or five replicate sets of measurements. Hence, the study followed an unbalanced hierarchical design with the repeated factor DRUG nested within measurement REPLICATE nested within study SUBJECT. However, the effects of REPLICATE grouped within SUBJECT were minimal and a regression model was adopted in which the multivariate outcomes were grouped only by SUBJECT. These semiparametric regression models were estimated by Generalized Estimating Equations (GEE) using a robust 'sandwich' variance estimator and identity link functions for the mean and scale models (geepack v0.2-10 in R 2.0-1; The Comprehensive R Archive Network, Vienna University of Technology, Vienna, Austria, http://www(dot)cran(dot)R-project(dot)org) (Yan and Fine, 2004, Stat. Med. 23: 859-74; discussion 75-7, 79-80). The multiple measures grouped by SUBJECT were assumed to have an exchangeable correlation structure: this is equivalent to a hierarchical model with random intercepts grouped within SUBJECT. Variance components estimates were calculated using Bayesian hierarchical linear models of this type, with Markov Chain Monte Carlo estimation in winBUGS 1.4.1. (Win BUGS 1.4.1, MRC Biostatistics Unit, Cambridge, UK, www(dot)mrc-bsu(dot)cam(dot)ac(dot)uk/bugs//winbugs/contents(dot)shtml).

Tests of genetic association on multiple outcome measures were conducted using MANOVA with the dependent variables averaged over replicate measurements for each subject. Analyses were conducted in two ways: with data points unweighted and with data points weighted by the number of replicate sets of measurements.

The results of the experiments presented in this Experimental Example are now described.

Figure 31A:
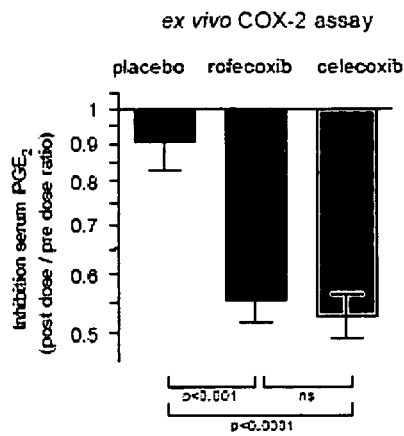
FIGS. 31A-31L are the comparison of four primary drug responses (i) COX-2 inhibition, ii) COX-1 inhibition, iii) urinary excretion of the prostacyclin metabolite (PGI-M) and iv) urinary excretion of the thromboxane metabolite (Tx-M)) to placebo, rofecoxib and celecoxib treatments.
Figure 31B:
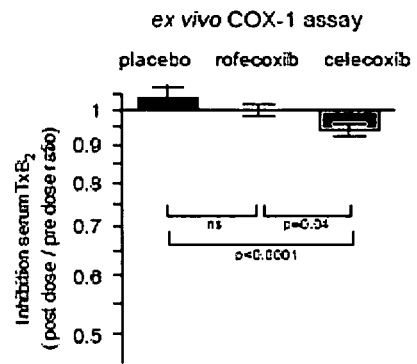
Figure 31C:
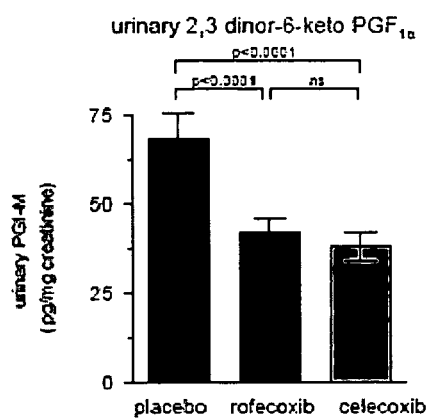
Figure 31D:
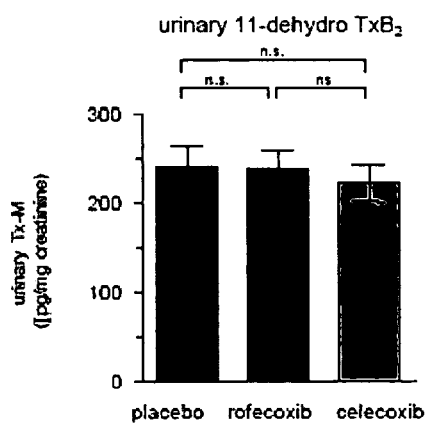
Figure 31E:
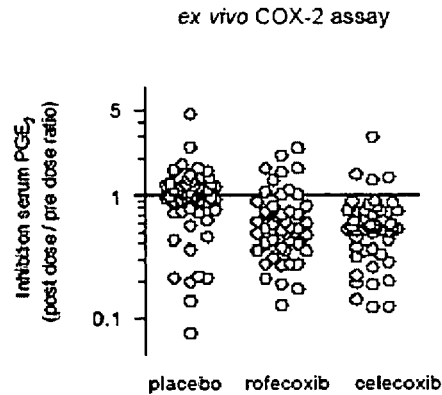
Figure 31F:
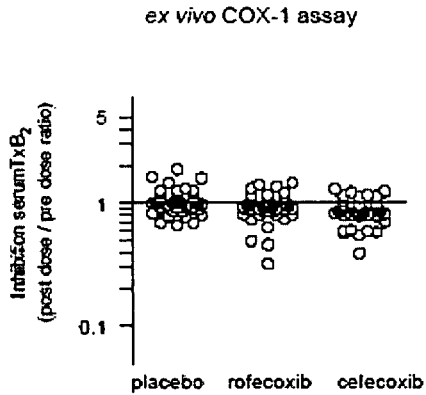
Figure 31G:
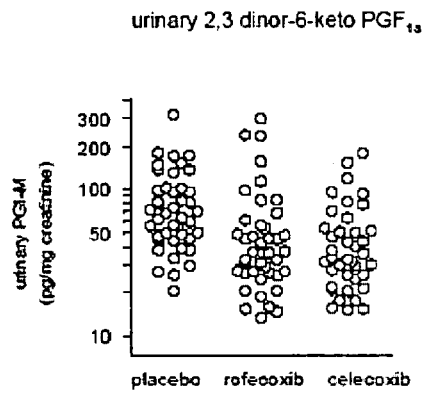
Figure 31H:
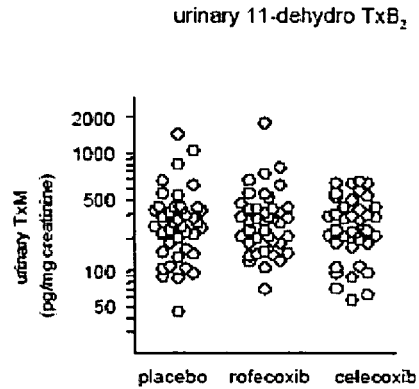
Figure 31I:
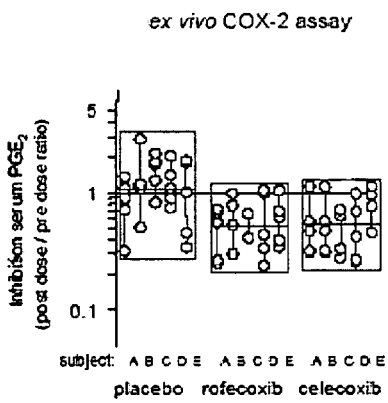
Figure 31J:
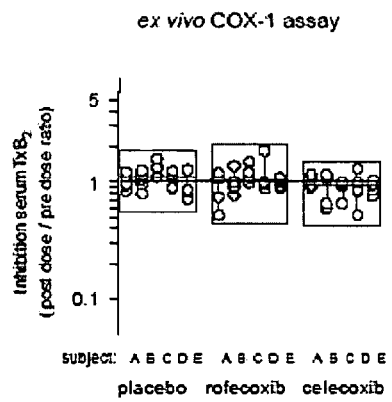
Figure 31K:
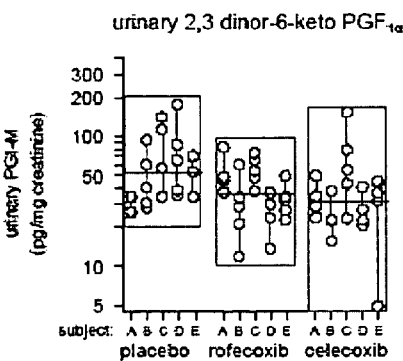
Figure 31L:
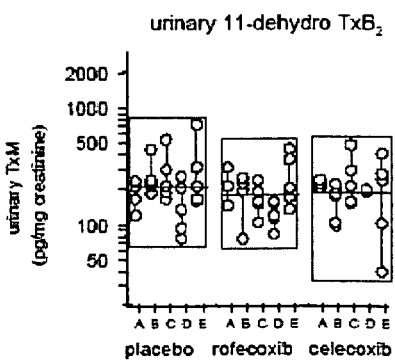
Figure 32A:
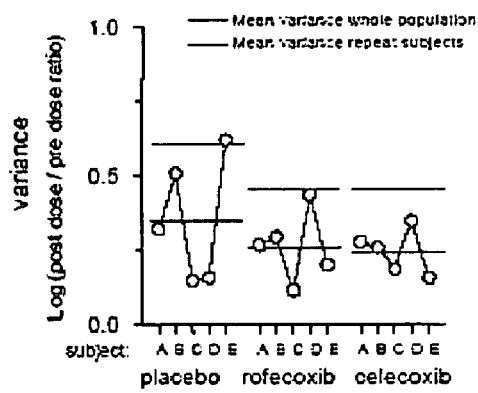
FIGS. 32A-32D depict the comparison of the intraindividual variability with total variability in the study population. Variances of replicate measurements of the four primary drug responses (32A-32D) are plotted for each subject and treatment (dots connected by lines). The lower horizontal lines indicate the average variances of replicate measurements (intraindividual variability). The upper horizontal lines represent the derived variance of all measurements within the whole population (total variability). The variances of replicate measurements (intraindividual variability) are significantly (p<0.05) lower than the variances of the whole population (total variability) for the drug responses COX-2 inhibition ex vivo (32A), depression of urinary prostacyclin metabolite excretion as a marker of COX-2 inhibition in vivo (32C), and depression of urinary thromboxane metabolite excretion as a marker of COX-1 inhibition in vivo (32D).
Figure 32B:
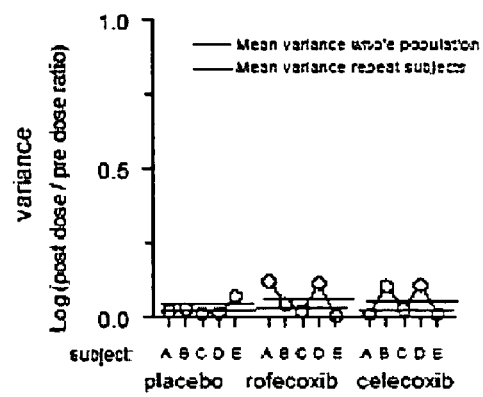
Figure 32C:
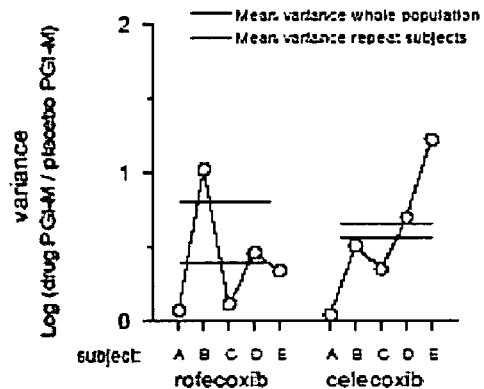
Figure 32D:
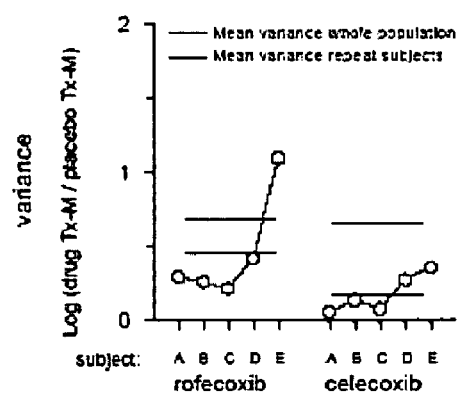

Fifty volunteers received, in random order, placebo and single therapeutic doses of rofecoxib and celecoxib to compare directly the responses to the drugs within the same subjects. Both rofecoxib and celecoxib inhibited COX-2 dependent $PGE_2$ formation ex vivo significantly when compared to placebo (FIG. 31A). However, there was no difference in the degree of inhibition attained by the two drugs (44.8% vs. 47.5%). Celecoxib also depressed serum $TxB_2$, but the effect was small in comparison to the inhibition of $PGE_2$ (FIG. 31B). Rofecoxib failed to inhibit significantly COX-1 derived serum $TxB_2$, consistent with its higher selectivity for inhibition of COX-2 in vitro (FitzGerald and Patrono, 2001, N. Engl. J. Med. 345: 433-42). Small placebo effects may be attributable to diurnal variation as pre drug and post drug measurements were performed consistently at 08:00 and 12:00 hrs. When selectivity was estimated using the ex vivo assays, both drugs differed significantly from placebo, but not from each other at this time point after dosing. A similar pattern was observed assessing selectivity in vivo. Thus, both drugs depressed urinary PGI-M, but not excretion of urinary Tx-M when compared to placebo, but not to each other (FIGS. 31C and 31D).

There was considerable variability in both ex vivo and in vivo indices of inhibition of both COX-2 and COX-1 (FIGS. 31E-H). However, drug response, measured either ex vivo or in vivo, correlated poorly with plasma drug concentrations of rofecoxib (median 215 ng/ml; range 115 to 658 ng/ml) and celecoxib (median 575 ng/ml, range 179 to 1372 ng/ml) at 4 hours after dosing. Plasma drug levels after dosing exhibited a trend towards lower concentrations with increasing body mass index (BMI). However, this attained significance ($p<0.05$) only for rofecoxib: a unit increase in BMI was associated with a drop in plasma concentration of about 2%.

Intra- and interindividual variability in drug response was assessed to determine the likely contribution of random and environmental fluctuations rather than genetic factors to variability. Five replicate sets of measurements were performed in five volunteers (FIGS. 31I-L). The average responses for both drugs in these individuals closely approximate the observations made within the whole population. Variability within these individuals was less than the variation in the population as a whole. This can be visualized by expressing for each individual the variances of the replicate measurements, and comparing the average variance of measurements within the same subject with the total variance (FIGS. 32A-D). The replicate measurements in three out of four response variables exhibited a lower variation within individuals than in the whole population, indicating that interindividual variability, beyond that attributable to random and environmental influences, is potentially detectable within the population. Indeed, variance component analysis suggested that up to about 30% of the total variability may be attributed to interindividual differences.

Genetic variability is a likely contributor to such differences in drug response between individuals. Thus, the study population was genotyped for polymorphisms in the genes encoding COX-1 (PTGS1), COX-2 (PTGS2) and cytochrome P450 2C9 (CYP2C9), the principle metabolizing enzyme of celecoxib, to examine their potential role in drug response (Table 5). Variants potentially affecting either baseline expression or activity of the enzymes or their interaction with the coxibs were targeted (Table 5). Fourteen volunteers (28%) were heterozygous for a variant located in the signal peptide or the catalytic site of COX-1, three (6%) were heterozygous for a variant in the catalytic site of COX-2 and 14 (28%) were heterozygous for a variant of CYP2C9. Thus, the population was genetically quite heterogeneous regarding the enzymes most likely to affect drug response; a total 24 out of 50 individuals had one or more genetic variant. No homozygous variants occurred and they did not associate with gender. This Experimental Example was not designed to address comprehensively the impact of SNPs on drug response, therefore the analyses were confined to those SNPs that occurred in four or more volunteers. Thus, CYP2C9*2 and CYP2C9*3 were tested for their effect on plasma concentrations of celecoxib, and the Lys185Thr, Trp8Arg, and Pro17Leu variants of COX-1, and the Val511Ala variant of COX-2 were tested for their effects on drug response.

Figures 33A, 33B, 33C:
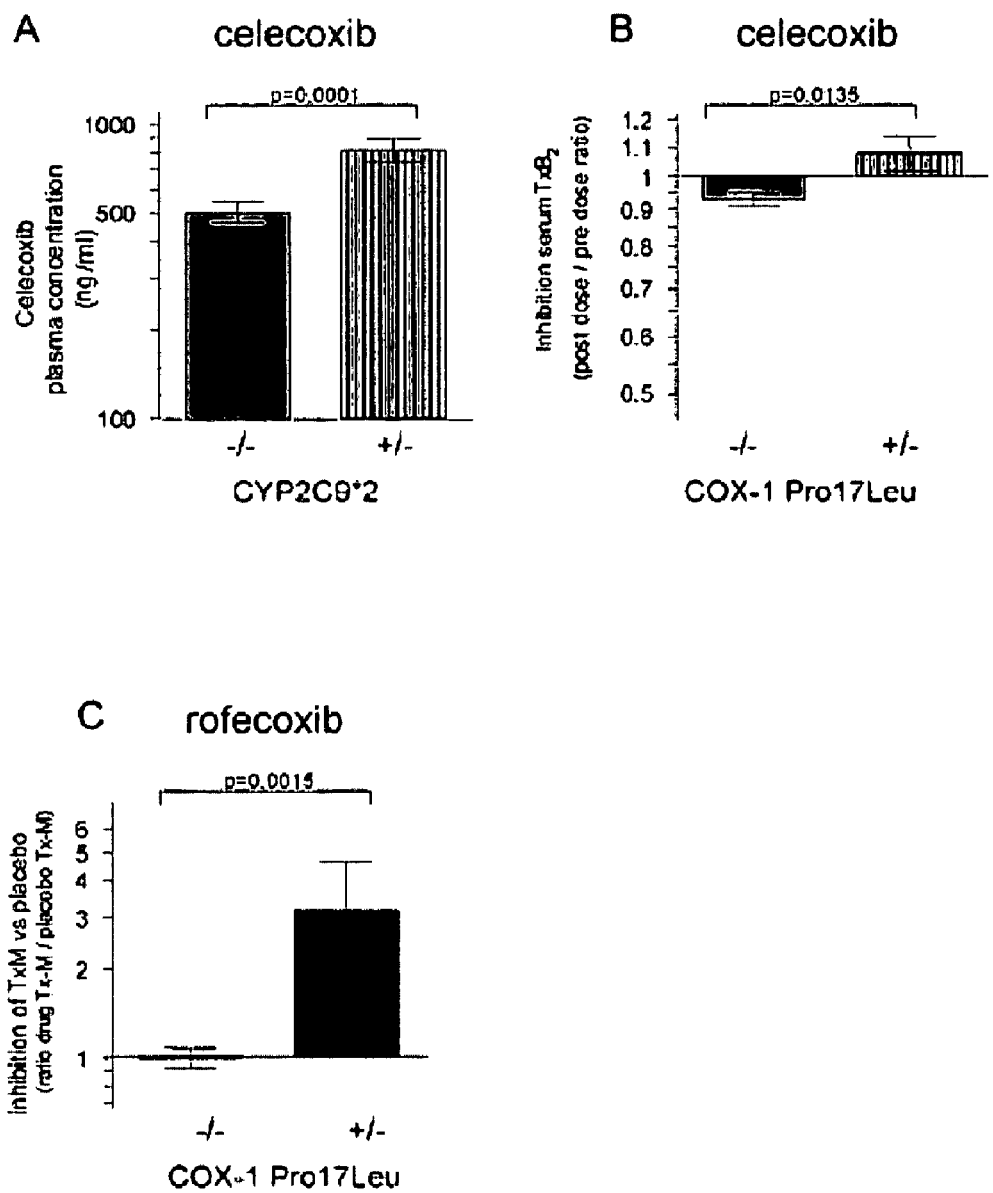
FIGS. 33A-33C depict an association of polymorphisms in CYP2C9 and COX-1 with plasma celecoxib four hours post dosing (33A), COX-1 inhibition ex vivo by celecoxib (33B) and depression of the urinary thromboxane metabolite by rofecoxib (33C). Eight individuals, heterozygous for CYP2C9*2, had higher plasma concentrations of celecoxib than those without this variant (33A). The Pro17Leu variant of COX-1 was associated with a reduction in COX-1 inhibition both ex vivo (33B) and in vivo (33C).

CYP2C9*2 occurred in 8 individuals (5 Caucasian, 3 Asian) and was associated with higher plasma concentrations of celecoxib, after adjusting for the linear effects of age (FIG. 33A). BMI and age were not significant covariates in this model. Effects on the drug responses were not statistically significant. CYP2C9*3 had no effect on plasma concentrations. The Pro17Leu variant of COX-1 was associated with a statistically significant (MANOVA, p=0.009, unweighted; p=0.011, weighted) pharmacodynamic effect—a reduction in COX-1 inhibition both ex vivo and in vivo. Post hoc analysis revealed an association with an absence of the COX-1 inhibition by celecoxib ex vivo (FIG. 33B) and an absence of COX-1 inhibition in vivo by rofecoxib (FIG. 33C). No effects of BMI or age were found in these analyses; males showed greater Tx-M suppression with both rofecoxib and celecoxib than females ($p<0.05$).

In summary, these experiments suggest that individuals respond quite differently to COX-2 selective inhibitor compounds. This variance might confound the detection of cardiovascular events attributable to drug exposure. On the other hand, variability in response might be exploited to identify patients in whom the evolution of cardiovascular risk is accelerated. This may permit definition of the parameters within which these useful drugs (Bombardier et al., 2000, N. Engl. J. Med. 343:1520-8, 2 p following 8; Schnitzer et al., 2004, Lancet 364:665-74) might be administered chronically to patients initially at low risk of cardiovascular disease.

Variability between individuals in their response to drugs is well recognized (Wood, 2001, N. Engl. J. Med. 344: 1394-6; Evans and McLeod, 2003, N. Engl. J. Med. 348: 538-49). Nevertheless, the typical paradigms of drug development and approval infer a common response to a limited number of doses—sometimes just one—within a therapeutic category. Selective inhibitors of COX-2 are no exception. Indeed, considerable interindividual variability in the plasma concentration/enzyme inhibition response relationships were noted as the first member of the class, celecoxib, entered the US market (McAdam et al., 1999, Proc. Natl. Acad. Sci. USA 96: 272-7). Typically, assays in whole human blood have been utilized to compare the selectivity for inhibition of COX-2 amongst members of the class (FitzGerald and Patrono, 2001, N. Engl. J. Med. 345: 433-42). Although the multiple factors which can distort the relationship between the degree of selectivity attained in vitro and in vivo have been noted (FitzGerald and Patrono, 2001, N. Engl. J. Med. 345: 433-42), the implications of this observation have received little attention.

Epidemiological approaches and, indeed, clinical trials have poor precision for detection of uncommon, but serious adverse effects, such as clinical events prevalent in the relevant populations. Thus, this Experimental Example was designed to explore the variability in response to coxibs in more detail. Therapeutic doses of celecoxib and rofecoxib were assessed, using a placebo-controlled, crossover design to investigate variability in plasma drug concentrations and pharmacodynamic responses, as assessed by both ex vivo and in vivo indices of COX-1 and COX-2 activity. Both interindividual and intraindividual variability were determined, the latter to get an impression of whether variation attributable to environment and random effects was sufficient to obscure a contribution from genetic sources.

Significant intraindividual variability was evident in all parameters as five individuals progressed through the entire study on five occasions. Some of the variation, evident on placebo, may have derived from circadian variability, as samples were obtained at discrete time points before (0800 hrs) and after (1200 hrs) dosing. Diurnal variation in the indices of COX activity has not been described, but diurnal variation in the pharmacokinetics of NSAIDs (Markiewicz and Semenowicz, 1979, Int. J. Clin. Pharmacol. Biopharm. 17: 409-11; Clench et al., 1981, Eur. J. Clin. Pharmacol. 20: 359-69), including celecoxib (FDA. New Drug Application 20-998. Clinical Pharmacology and Biopharmaceutics Review Celecoxib. Bethesda, Md.: Food and Drug Administration; 1998), attributable in part to circadian variation in drug-metabolizing enzymes (Hogenesch et al., 2003, Novartis Found. Symp. 253: 171-80; discussion 52-5,02-9, 80-3 passim), is well recognized. Furthermore, although the COX enzymes were not identified in the subset of genes subject to circadian variation in aorta (Rudic et al., 2004, PLoS Biol. 2: e377), liver, kidney or brain (http://expression(dot)gnf(dot) org/cgi-bin/circadian/index(dot)cgi), expression of COX-2 in rat monocytes varies inversely with the rhythm in endogenous steroids (Masferrer et al., 1994, J. Pharmacol. Exp. Ther. 270: 1340-4). The intraindividual variability in response to both drugs is striking. This may reflect in part variability in assays. Sources of variability that may be attenuated under steady state conditions and random environmental effects, despite standardization of certain conditions of dosing (time, posture, environment, fasting/feeding), remain unrecognized. Little comparable information is available with other drugs in which intra-versus interindividual variability in response have been compared so comprehensively (Drazen et al., 2000, Br. Med. Bull. 56: 1054-70; Chladek et al., 2002, Br. J. Clin. Pharmacol. 54: 147-56; Stahle et al., 2004, Ther. Drug Monit. 26: 267-70).

Despite substantial intraindividual variability in response, the variation in the subject population as a whole exceeded it. Thus, the variance of both plasma drug concentrations and three out of four pharmacodynamic parameters were greater in the entire population than for replicate measurements within individuals.

This observation suggests the possibility that genetic sources of variance might contribute detectably to differences in drug response over and above the background "noise" attributable to analytical variability and fluctuating features of the environment. The analysis in this example reveals that almost half of the study population had variants in the target enzymes, some with allelic frequencies of five percent or more. Information is only beginning to emerge on genetic variation in the COX enzymes (Ulrich et al., 2002, Hum. Mutat. 20: 409-10; Papafili et al., 2002, Arterioscler. Thromb. Vasc. Biol. 22: 1631-6; Halushka et al., 2003, Clin. Pharmacol. Ther 73: 122-30) and this example was not designed or sized to afford a comprehensive analysis of genetic variants which may modulate the response to coxibs. Notwithstanding these restrictions, two of the SNPs tested showed evidence of allelic association with elements of drug response. The CYP2C9*2 is an inactivating variant of a major metabolizing variant of celecoxib (Tang et al., 2000, J. Pharmacol. Exp. Ther. 293: 453-9) and was associated with elevated plasma concentrations of the drug four hours after administration. However, while this and other genetic variants of CYP2C9 are thought to affect the metabolic clearance of perhaps twenty percent of all prescribed drugs (Lee et al., 2002, Pharmacogenetics 12: 251-63), acquired or environmental factors may also contribute to variability in drug clearance (Scordo et al., 2002, Clin. Pharmacol. Ther. 72: 702-10).

The Pro17Leu variant of the COX-1 enzyme was observed to be associated with a failure of inhibition of thromboxane formation with both drugs. All COX-2 inhibitors are relatively, as opposed to absolutely selective for COX-2 and, at sufficient concentration, become coincidental inhibitors of both COXs in vitro, like traditional, non-selective NSAIDs (FitzGerald and Patrono, 2001, N. Engl. J. Med. 345: 433-42). The interindividual variability of coincidental inhibition of COX-1 evident four hours after dosing with either coxib was substantial and may be attributable in part to this variant. The greater the coincidental inhibition of COX-1-derived $TxA_2$ in an individual, the more the gastrointestinal and cardiovascular profile of a coxib would be expected to resemble that of a traditional, non-selective NSAID.

In summary, this example demonstrates substantial variability, both within and between individuals in their response to acute dosing with both celecoxib and rofecoxib. SNPs in both COX-1 and CYP2C9 are apparently associated with elements of drug response, although population stratification may confound these findings. It is likely that a more comprehensive approach will shed further light on genetic sources of variation. Validated genetic markers might be usefully combined with biomarkers of atherogenesis, functional (e.g. blood pressure), kinetic and dynamic parameters of drug action to identify individuals who accelerate their development of cardiovascular risk during treatment with coxibs. Such a strategy might conserve the value of extended dosing with selective inhibitors of COX-2 for patients at low risk of cardiovascular diseases who have previously exhibited gastrointestinal intolerance of traditional NSAIDs.

TABLE 5

Single nucleotide polymorphisms.* Accession numbers refer to the NCBI (rs. . .) or the EXPASY (VAR_. . .) SNP database

| | | | | | allele frequency | |
|---|---|---|---|---|---|---|
| gene | domain/ name | accession*/ reference | position | base/amino acid change | major allele | minor allele |
| PTGS1 | promoter | (see note 1) | −842 | G/A | 1 | 0 |
| | signal peptide | rs1236913 | 8 | Trp/Arg | 0.96 | 0.04 |
| | | rs3842787 | 17 | Pro/Leu | 0.95 | 0.05 |
| | EGF domain | rs3842789 | 53 | Arg/His | 1 | 0 |
| | catalytic domain | rs3842792 | 185 | Lys/Thr | 0.97 | 0.03 |
| | | (see note 2) | 230 | Gly/Ser | 1 | 0 |
| | | rs5789 | 237 | Leu/Met | 0.98 | 0.02 |
| | | (see note 2) | 341 | Lys/Arg | 1 | 0 |
| | | rs5791 | 359 | Lys/Arg | 1 | 0 |
| | | rs5792 | 443 | Ile/Val | 1 | 0 |
| | | rs5793 | 467 | Lys/Glu | 1 | 0 |
| | | rs5794 | 481 | Val/Ile | 0.99 | 0.01 |
| PTGS2 | promoter | (see note 3) | −765 | G/C | 1 | 0 |
| | signal pep | rs20426 | 1 | Met/Ile | 1 | 0 |
| | membrane binding | rs4987011 | 61 | Thr/Arg | 1 | 0 |
| | catalytic domain | rs3218622 | 228 | Arg/His | 1 | 0 |
| | | rs4648279 | 428 | Pro/Ala | 1 | 0 |
| | | rs5272 | 488 | Glu/Gly | 1 | 0 |
| | | rs5273 | 511 | Val/Ala | 0.97 | 0.03 |
| | C-terminus | rs3218625 | 587 | Gly/Arg | 1 | 0 |

TABLE 5-continued

Single nucleotide polymorphisms.* Accession numbers refer
to the NCBI (rs. . .) or the EXPASY (VAR_ . . .) SNP database

| gene | domain/ name | accession*/ reference | position | base/amino acid change | allele frequency major allele | allele frequency minor allele |
|---|---|---|---|---|---|---|
| CYP-2C9 | catalytic | rs1799853 (CYP2C9*2) | 144 | Arg/Cys | 0.92 | 0.08 |
| | | rs2256871 (CYP2C9*9) | 251 | His/Arg | 0.99 | 0.01 |
| | | rs1057909 | 358 | Tyr/Cys | 1 | 0 |
| | | rs1057910 (CYP2C9*3) | 359 | Ile/Leu | 0.95 | 0.05 |
| | | VAR_ 013515 (CYP2C9*4) | 359 | Ile/Thr | 1 | 0 |
| | | VAR_ 013516 (CYP2C9*5) | 360 | Asp/Glu | 0.99 | 0.01 |

Note 1: Polymorphism reported in Halushka et al., 2003, Clin. Pharmacol. Ther. 73:122-30.
Note 2: Polymorphism reported in Ulrich et al., 2002, Hum. Mutat. 20:409-410.
Note 3: Polymorphism reported in Papafili et al., 2002, Arterioscler. Thromb. Vasc. Biol. 22:1631-1636.

Experimental Example 7

Case Study of Cardiovascular Risk and Short Term Use of COX-2 Selective Inhibitor Compound Coxibs, selective inhibitors of COX-2, increase the risk of myocardial infarction and stroke (FitzGerald, 2004, N. Engl. J. Med. 351: 1709-11; Furberg et al., 2004, Circulation 111: 249). Their use will be restricted in patients with established cardiovascular disease. Caution may also extend to young individuals, without pre-existing disease, but predisposed to thrombosis by genetic or environmental factors.

The materials and methods used in the experiments presented in this Example are now described.

A ventilation-perfusion scan (VQ scan) was performed according to typical hospital procedure. Inhalation of 20.1 millicurie (mCi) of Xenon-133 gas was used for the ventilation scan. Intravenous injection of 4.1 mCi of Tc-99m-labelled MAA was used for the perfusion scan.

The results of the experiments presented in this example are now described.

A 25-year-old woman presented with pulmonary embolism. She had been taking, without complication, Ortho-Tri-cyclen® (0.180, 0.215, and 0.250 mg norgestimate cycles; 35 microgram (µg) ethinyl estradiol) for two years and Ortho Tri-cyclen® LO (same norgestimate; 25 µg ethinyl estradiol) for 14 months. A non-smoker, she lacked a relevant family history and was vigorously athletic.

Figure 34A:
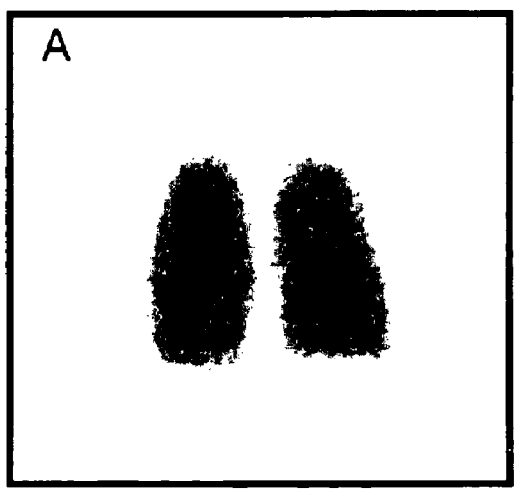
FIG. 34A depicts a scintigraphic image of a ventilation scan to assess the ability of air to reach all portions of the lungs. Image is posterior projection.
Figure 34B:
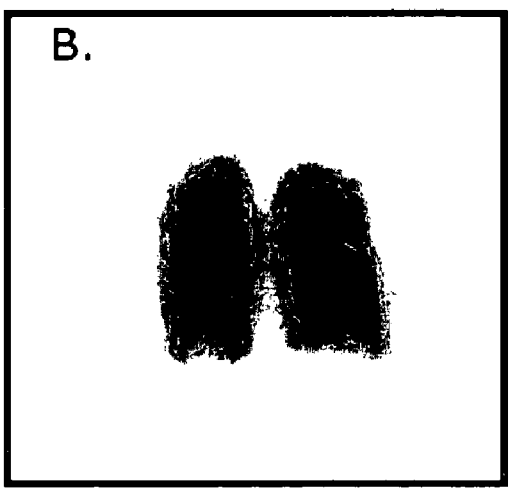
FIG. 34B depicts a scintigraphic image of a perfusion scan to assess the blood supply throughout the lungs. Image is posterior projection.

One month prior to presentation, she developed neck pain. Disc protrusion at C5-C6 was detected by magnetic resonance imaging (MRI). The patient was prescribed valdecoxib 20 mg b.i.d. for two weeks. Her neck pain resolved. However, towards the end of this two-week treatment period, she developed left-sided pleuritic chest and shoulder pain after a 6 hour car ride. She was commenced on cyclobenzaprine 10 mg b.i.d. and continued on valdecoxib. Her left-sided pain abated gradually. However, 18 days later, she developed right-sided chest and shoulder pain. A diagnosis of left iliac vein thrombosis and bilateral pulmonary emboli was based on a computed tomography (CT) scan. She was heparinized and continued on therapy with warfarin 5 mg b.i.d. and enoxaparin 60 mg b.i.d. Despite this treatment regiment, a ventilation-perfusion scan performed 13 days later revealed multiple pulmonary emboli. The ventilation scan revealed uniform ventilation to the lungs (FIG. 34A) The perfusion scan (FIG. 34B) revealed decreased blood flow activity in the following regions: apical segment of right upper lobe, anterior segment of right upper lobe, superior segment of right lower lobe, posterior basal segment of right lower lobe, anteromedial basal segment of left lower lobe, and lateral basal segment of left lower lobe. Abnormalities in lupus anticoagulant, antithrombin III, proteins C and S, plasma homocysteine, anticardiolipin, β2 glycoprotein antibody and prothrombotic mutations in Factor V and prothrombin were excluded.

In summary, suppression of COX-2-derived prostacyclin ($PGI_2$) may explain the cardiovascular hazard attributable to coxibs (FitzGerald, 2004, N. Engl. J. Med. 351: 1709-11). Deletion of the $PGI_2$ receptor in mice does not cause spontaneous thrombosis, but rather enhances the response to thrombotic stimuli (Murata et al., 1997, Nature 388(6643): 678-82). Thus, one would expect to detect a cardiovascular hazard from a coxib most readily in patients with hemostatic activation. Indeed, a three-fold increase in the relative risk of heart attack and stroke was observed in small, short-term studies of cardiopulmonary bypass grafting with valdecoxib (Furberg et al., 2004, Circulation 111: 249). Similarly, thrombotic events on coxibs have been reported in patients with connective tissue disease (Crofford et al., 2000, Arthritis & Rheumatism 43(8): 1891-6).

Without wishing to be bound by theory, both the use of oral contraceptives and the venous stasis of a road trip may, in this case, have interacted with the coxib to enhance the risk of a thrombotic event. Small absolute risks of thrombosis may interact dramatically, such as occurs when patients on oral contraceptives have prothrombotic mutations (Bloemenkamp et al., 2000, Arch. Intern. Med. 160(1):49-52). This case prompts awareness of the need to exclude genetic and environmental factors which predispose to the risk of thrombosis even in younger individuals being considered for treatment with selective inhibitors of COX-2.

The studies presented herein affirm the utility of urinary 8,12-iso-$iPF_{2\alpha}$-VI, urinary $PGI_2$ metabolites and urinary thromboxane metabolites as noninvasive indices of oxidant stress in conditions associated with systemic oxidant stress. These include, but are not limited to, the following conditions: cardiovascular diseases, such as atherosclerosis, ischemic-reperfusion injury, and circulatory system diseases affected by oxidative stress.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of assessing cardiovascular risk in a subject contemplating therapy with a COX-2 selective inhibitor compound the method comprising:
   measuring the level of an isoprostane in a body fluid of the subject prior to administration of the compound,
   measuring the level of the isoprostane in the body fluid of the subject at about four hours after administration of the compound, and
   determining a ratio by dividing the level of the isoprostane in the body fluid of the subject at about four hours after administration of the compound by the level of the isoprostane in the body fluid of the subject prior to administration of the compound,
   comparing the determined ratio to a database of ratios for a representative population, wherein the database is divided into quartiles,
   wherein the subject has not taken a non-steroidal anti-inflammatory drug or a COX-2 selective inhibitor compound for at least two weeks prior to administration of the compound, and
   wherein a ratio of the level of the isoprostane about four hours after compound administration to the level of the isoprostane prior to compound administration in the upper quartile is indicative of increased cardiovascular risk in the subject.

2. The method of claim 1 further comprising:
   measuring the level of at least one of a thromboxane metabolite and a $PGI_2$ metabolite in the urine of the subject.

3. The method of claim 1 further comprising:
   assessing at least one additional parameter of cardiovascular risk in the subject,
   wherein the parameter is selected from the group consisting of: blood pressure, blood level of C-reactive protein, blood level of interleukin-6 (IL-6), blood level of soluble intracellular adhesion molecule-1 (sICAM-1), blood level of monocyte chemoattractant protein-1 (MCP-1), blood level of homocysteine, blood level of $iPF_{2\alpha}$-III, presence or extent of atherosclerotic plaques, and presence of one or more genetic predispositions for elevated cardiovascular risk.

4. The method of claim 1 wherein the isoprostane is selected from the group consisting of 8,12-iso-$iPF_{2\alpha}$-VI, 8-iso-$PGF_{2\alpha}$, and $iPF_{2\alpha}$-VI.

5. The method of claim 1 wherein the body fluid is one of urine and plasma.

6. The method of claim 1 wherein the body fluid is urine.

7. The method of claim 6 Wherein the isoprostane is 8,12-iso-$iPF2\alpha$-VI.

8. The method of claim 7 wherein measuring the level of 8,12-iso-$iPF_{2\alpha}$-VI in the urine comprises:
   assessing the ratio of 8,12-iso-$iPF_{2\alpha}$-VI to a known quantity of a synthetic 8,12-iso-$iPF_{2\alpha}$-VI homologous internal standard added thereto using gas chromatography and mass spectrometry, thereby measuring the level of the 8,12-iso-$iPF_{2\alpha}$-VI in the urine of the subject.

9. A method of assessing cardiovascular risk in a subject contemplating therapy with a COX-2 selective inhibitor compound the method comprising:
   measuring the concentration of a COX-2 selective inhibitor compound in the plasma of the subject contemplating therapy with the compound at about four hours after administration of the compound,
   comparing the measured concentration to a database of COX-2 selective inhibitor compound concentrations for a representative population, wherein the database is divided into quartiles,
   wherein the subject has not taken aspirin, any non-steroidal anti-inflammatory drug or any COX-2 selective inhibitor compound for at least two weeks prior to administration of the compound, and
   wherein a plasma COX-2 selective inhibitor compound concentration level in the upper quartile is indicative of increased cardiovascular risk in the subject.

10. The method of claim 9 further comprising:
    measuring the level of at least one of a $PGI_2$ metabolite, a thromboxane metabolite and 8,12-iso-$iPF_{2\alpha}$ in the urine of the subject.

11. The method of claim 9 further comprising:
    assessing at least one additional parameter of cardiovascular risk in the subject,
    wherein the parameter is selected from the group consisting of: blood pressure, blood level of C-reactive protein, blood level of interleukin-6 (IL-6), blood level of soluble intracellular adhesion molecule-1 (sICAM-1), blood level of monocyte chemoattractant protein-1 (MCP-1), blood level of homocysteine, blood level of $iPF_{2\alpha}$-III, presence or extent of atherosclerotic plaques, and presence of one or more genetic predispositions for elevated cardiovascular risk.

12. The method of claim 9 wherein measuring the level of plasma compound concentration comprises:
    assessing the ratio of the COX-2 selective inhibitor compound to a known quantity of a synthetic COX-2 selective inhibitor compound homologous internal standard added thereto using liquid chromatography and tandem mass spectrometry, thereby measuring the level of the a COX-2 selective inhibitor compound in the plasma of the subject.

* * * * *

SEQUENCE LISTING

<160> NUMBER OF SEQ ID NOS: 4

<210> SEQ ID NO 1
<211> LENGTH: 1800
<212> TYPE: DNA
<213> ORGANISM: Homo sapiens

<400> SEQUENCE: 1

| | |
|---|---|
| atgagccgga gtctcttgct ctggttcttg ctgttcctgc tcctgctccc gccgctcccc | 60 |
| gtcctgctcg cggacccagg ggcgcccacg ccagtgaatc cctgttgtta ctatccatgc | 120 |
| cagcaccagg gcatctgtgt ccgcttcggc cttgaccgct accagtgtga ctgcaccccgc | 180 |
| acgggctatt ccggccccaa ctgcaccatc cctggcctgt ggacctggct ccggaattca | 240 |
| ctgcggccca gcccctcttt cacccacttc ctgctcactc acgggcgctg gttctgggag | 300 |
| tttgtcaatg ccaccttcat ccgagagatg ctcatgcgcc tggtactcac agtgcgctcc | 360 |
| aaccttatcc ccagtccccc cacctacaac tcagcacatg actacatcag ctgggagtct | 420 |
| ttctccaacg tgagctatta cactcgtatt ctgccctctg tgcctaaaga ttgccccaca | 480 |
| cccatgggaa ccaaagggaa gaagcagttg ccagatgccc agctcctggc ccgccgcttc | 540 |
| ctgctcagga ggaagttcat acctgacccc caaggcacca acctcatgtt tgccttcttt | 600 |
| gcacaacact tcacccacca gttcttcaaa acttctggca agatgggtcc tggcttcacc | 660 |
| aaggccttgg gccatggggt agacctcggc cacatttatg gagacaatct ggagcgtcag | 720 |
| tatcaactgc ggctctttaa ggatgggaaa ctcaagtacc aggtgctgga tggagaaatg | 780 |
| tacccgccct cggtagaaga ggcgcctgtg ttgatgcact accccgagg catcccgccc | 840 |
| cagagccaga tggctgtggg ccaggaggtg tttgggctgc ttcctgggct catgctgtat | 900 |
| gccacgctct ggctacgtga gcacaaccgt gtgtgacc tgctgaaggc tgagcacccc | 960 |
| acctggggcg atgagcagct tttccagacg acccgcctca tcctcatagg ggagaccatc | 1020 |
| aagattgtca tcgaggagta cgtgcagcag ctgagtggca atttcctgca gctgaaattt | 1080 |
| gacccagagc tgctgttcgg tgtccagttc caataccgca accgcattgc catggagttc | 1140 |
| aaccatctct accactggca cccctcatg cctgactcct tcaaggtggg ctcccaggag | 1200 |
| tacagctacg agcagttctt gttcaacacc tccatgttgg tggactatgg ggttgaggcc | 1260 |
| ctggtggatg ccttctctcg ccagattgct ggccggatcg gtggggcag gaacatggac | 1320 |
| caccacatcc tgcatgtggc tgtggatgtc atcagggagt ctcgggagat gcggctgcag | 1380 |
| cccttcaatg agtaccgcaa gaggtttggc atgaaaccct acacctcctt ccaggagctc | 1440 |
| gtaggagaga aggagatggc agcagagttg gaggaattgt atggagacat tgatgcgttg | 1500 |
| gagttctacc ctggactgct tcttgaaaag tgccatccaa actctatctt tggggagagt | 1560 |
| atgatagaga ttggggctcc cttttccctc aagggtctcc tagggaatcc catctgttct | 1620 |
| ccggagtact ggaagccgag cacatttggc ggcgaggtgg gctttaacat tgtcaagacg | 1680 |
| gccacactga gaagctggt ctgcctcaac accaagacct gtccctacgt ttccttccgt | 1740 |
| gtgccggatg ccagtcagga tgatgggcct gctgtggagc gaccatccac agagctctga | 1800 |

<210> SEQ ID NO 2
<211> LENGTH: 1473
<212> TYPE: DNA
<213> ORGANISM: Homo sapiens

<400> SEQUENCE: 2

```
atggattctc ttgtggtcct tgtgctctgt ctctcatgtt tgcttctcct ttcactctgg      60
agacagagct ctgggagagg aaaactccct cctggcccca ctcctctccc agtgattgga     120
aatatcctac agataggtat taaggacatc agcaaatcct taaccaatct ctcaaaggtc     180
tatggccctg tgttcactct gtattttggc ctgaaaccca tagtggtgct gcatggatat     240
gaagcagtga aggaagccct gattgatctt ggagaggagt ttctggaag aggcattttc     300
ccactggctg aaagagctaa cagaggattt ggaattgttt tcagcaatgg aaagaaatgg     360
aaggagatcc ggcgtttctc cctcatgacg ctgcggaatt tgggatggg gaagaggagc     420
attgaggacc gtgttcaaga ggaagcccgc tgccttgtgg aggagttgag aaaaaccaag     480
gcctcaccct gtgatcccac tttcatcctg ggctgtgctc cctgcaatgt gatctgctcc     540
attatttttcc ataaacgttt tgattataaa gatcagcaat tcttaactt aatggaaaag     600
ttgaatgaaa acatcaagat tttgagcagc ccctggatcc agatctgcaa taatttttct     660
cctatcattg attacttccc gggaactcac aacaaattac ttaaaaacgt tgcttttatg     720
aaaagttata ttttggaaaa agtaaaagaa caccaagaat caatggacat gaacaaccct     780
caggacttta ttgattgctt cctgatgaaa atggagaagg aaaagcacaa ccaaccatct     840
gaatttacta ttgaaagctt ggaaaacact gcagttgact tgtttggagc tgggacagag     900
acgacaagca caaccctgag atatgctctc cttctcctgc tgaagcaccc agaggtcaca     960
gctaaagtcc aggaagagat tgaacgtgtg attggcagaa accggagccc ctgcatgcaa    1020
gacaggagcc acatgcccta cacagatgct gtggtgcacg aggtccagag atacattgac    1080
cttctcccca ccagcctgcc ccatgcagtg acctgtgaca ttaaattcag aaactatctc    1140
attcccaagg gcacaaccat attaatttcc ctgacttctg tgctacatga caacaaagaa    1200
tttcccaacc cagagatgtt tgaccctcat cactttctgg atgaaggtgg caattttaag    1260
aaaagtaaat acttcatgcc tttctcagca ggaaaacgga tttgtgtggg agaagccctg    1320
gccggcatgg agctgttttt attcctgacc tccattttac agaactttaa cctgaaatct    1380
ctggttgacc caaagaacct tgacaccact ccagttgtca atggatttgc ctctgtgccg    1440
cccttctacc agctgtgctt cattcctgtc tga                                 1473
```

<210> SEQ ID NO 3
<211> LENGTH: 19
<212> TYPE: DNA
<213> ORGANISM: Artificial sequence
<220> FEATURE:
<223> OTHER INFORMATION: PCR sense primer for murine COX-2 cDNA

<400> SEQUENCE: 3
ccgggttgct gggggaaga                                                   19

<210> SEQ ID NO 4
<211> LENGTH: 24
<212> TYPE: DNA
<213> ORGANISM: Artificial sequence
<220> FEATURE:
<223> OTHER INFORMATION: PCR antisense primer for murine COX-2 cDNA

<400> SEQUENCE: 4
gtggctgttt tggtaggctg tgga                                             24